(12) United States Patent
Lin et al.

(10) Patent No.: US 7,470,701 B2
(45) Date of Patent: Dec. 30, 2008

(54) SUBSTITUTED 2,5-HETEROCYCLIC DERIVATIVES

(75) Inventors: Xiaodong Lin, Walnut Creek, CA (US); Alice Rico, Berkeley, CA (US); Xiaojing Michael Wang, Livermore, CA (US); Yasheen Zhou, Moraga, CA (US); Ann B. Jefferson, Oakland, CA (US); Annette Walter, Mill Valley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 11/095,993

(22) Filed: Mar. 30, 2005

(65) Prior Publication Data
US 2005/0256121 A1    Nov. 17, 2005

Related U.S. Application Data

(60) Provisional application No. 60/558,342, filed on Mar. 30, 2004.

(51) Int. Cl.
*A61K 31/506* (2006.01)
*C07D 401/04* (2006.01)
*C07D 239/42* (2006.01)

(52) U.S. Cl. ..................... 514/275; 544/331
(58) Field of Classification Search .................. 544/238
See application file for complete search history.

(56) References Cited

U.S. PATENT DOCUMENTS

| 3,908,012 | A | * | 9/1975 | De Angelis et al. | 514/256 |
| 6,034,093 | A | * | 3/2000 | Ewing et al. | 514/301 |
| 6,897,220 | B2 | * | 5/2005 | Delorme et al. | 514/275 |

FOREIGN PATENT DOCUMENTS

| WO | WO 00/75129 | 12/2000 |
| WO | WO 01/62233 | 8/2001 |
| WO | WO 02/083667 | 10/2002 |
| WO | WO 03/004472 | 1/2003 |
| WO | WO 03/008405 | 1/2003 |
| WO | WO 03/037886 | 5/2003 |
| WO | WO 03/086279 | 10/2003 |
| WO | WO 2004/013130 | 2/2004 |
| WO | WO 2004/041813 | 5/2004 |
| WO | WO 2004076412 A2 | * | 9/2004 |
| WO | WO 2004/089913 | 10/2004 |
| WO | WO 2005066139 A2 | * | 7/2005 |
| WO | WO 2005074642 A2 | * | 8/2005 |

OTHER PUBLICATIONS

CAS Abstracts provided.*
Fisera et al., "Furan Derivatives LXXIX. Synthesis andMas Spectra of Some Pydridylfuran Derivatives . . . " Data Accession No. 1977 171213 Abstract (Chemical Abstracts Service).
Zhao et al., "Arotinololis a Weak Partial Agonist on beta 3-Adrenergic Receptors in Brown Adipocytes" Data Accession No. 2001:547115 and *Canadian J. of Physiology and Pharmacology* 79(7):585-593.

* cited by examiner

*Primary Examiner*—Rebecca L Anderson
*Assistant Examiner*—Jason M Nolan
(74) *Attorney, Agent, or Firm*—Vinit Kathardekar; Lorna Tanner; Alisa A. Harbin

(57) ABSTRACT

The present invention relates to new substituted five-membered compounds and pharmaceutically acceptable salts, esters or prodrugs thereof, compositions of the new compounds together with pharmaceutically acceptable carriers, and uses of the new compounds. The compounds of the invention have the following general formula:

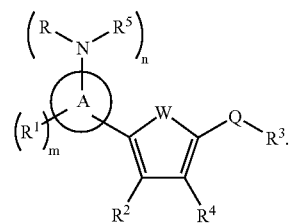

38 Claims, No Drawings

SUBSTITUTED 2,5-HETEROCYCLIC DERIVATIVES

This application claims the benefit under 35 U.S.C. §119 (e) of U.S. Provisional Application Ser. No. 60/558,342, filed Mar. 30, 2004, which is hereby incorporated by reference in its entirety.

BACKGROUND OF THE INVENTION

Field of the Invention

The present invention relates to substituted five-membered heterocyclic compounds and pharmaceutically acceptable salts, esters or prodrugs thereof, compositions of these compounds together with pharmaceutically acceptable carriers, and uses of these compounds.

REFERENCES

The following literature publications are cited in this application:

Alessi, D. R.; Caudwell, F. B.; Andjelkovic, M.; Hemmings, B. A.; Cohen, P. (1996) Molecular basis for the substrate specificity of protein kinase B; comparison with MAPKAP kinase-1 and p70 S6 kinase. *FEBS Lett.* 399:333-38.

Brazil, D. P. and Hemmings, B. A. (2001) Ten years of protein kinase B signalling: a hard Akt to follow. *Trends Biochem. Sci.* 26:657-64.

Don, J., Stelzer, G. (2002) The expanding family of CREB/CREM transcription factors that are involved with spermatogenesis. 187:115-24.

Harris, T. K. (2003) PDK1 and PKB/Akt: ideal targets for development of new strategies to structure-based drug design. *IUBMB Life.* 55:117-26.

Lewin, B. ed. (1997) *Genes VI*, Oxford University Press.

Lawlor, M. A. and Alessi, D. R. (2001) PKB/Akt: a key mediator of cell proliferation, survival and insulin responses. *J. Cell Sci.* 114:2903-10.

Luo, J.; Manning, B. D.; Cantley, L. C. (2003) Targeting the PI3K-Akt pathway in human cancer: rationale and promise. *Cancer Cell.* 4:257-62.

Obata, T.; Yaffe, M. B.; Leparc, G. G.; Piro, E. T.; Maegawa, H.; Kashiwagi, A.; Kikkawa, R.; Cantley, L. C. (2000) Peptide and protein library screening defines optimal substrate motifs for AKT/PKB. *J. Biol. Chem.* 275:36108-15.

Powell, D. J.; Hajduch, E.; Kular, G.; Hundal, H. S. (2003) Ceramide disables 3-phosphoinositide binding to the pleckstrin homology domain of protein kinase B (PKB)/Akt by a PKCzeta-dependent mechanism. *Mol. Cell. Biol.* 23:7794-808.

Radin, N. S. (2003) Killing tumours by ceramide-induced apoptosis: a critique of available drugs. *Biochem. J.* 371:243-56.

Scheid, M. P. and Woodgett, J. R. (2003) Unravelling the activation mechanisms of protein kinase B/Akt. *FEBS Lett.* 546:108-12.

Staal, S. P. and Hartley, J. W. (1988) Thymic lymphoma induction by the AKT8 murine retrovirus. *J. Exp. Med.* 167:1259-64.

Tierney, E. P., Tulac, S., Huang, S. T., and Giudice, L. C. (2003) Activation of the protein kinase A pathway in human endometrial stromal cells reveals sequential categorical gene regulation. *Physiol. Genomics.* 16:47-66.

Vitari, A. C.; Deak, M.; Collins, B. J.; Morrice, N.; Prescott, A. R.; Phelan, A.; Humphreys, S.; Alessi, D. R.; (2003) WNK1, the kinase mutated in an inherited high blood pressure syndrome, is a novel PKB/Akt substrate. *Biochem. J* (Nov. 11, 2003, electronic publication ahead of printed version).

Watson, J. D. et al., eds. (1987) Molecular Biology of the Gene, Benjamin/Cummings Pub. Co., Inc.

Montagnoli, A. et al. (2004) Cdc7 inhibition reveals a p53-dependent replication checkpoint that is defective in cancer cells. *Cancer Res.* 64:7110-16.

Woo, R. A. and Poon, R. Y. (2003) Cyclin-dependent kinases and S phase control in mammalian cells. *Cell Cycle* 2:316-24.

Semple, J. W. and Duncker, B. P. (2004) *Biotechnol. Adv.* 22:621-31.

Walker, M. G. (2001) Drug target discovery by gene expression analysis: cell cycle genes. *Curr. Cancer Drug Targets.* 1:73-83.

All of the above identified publications are herein incorporated by reference in their entirety to the same extent as if each individual publication was specifically and individually incorporated by reference in its entirety.

STATE OF THE ART

Akt Kinase vAkt was first identified as a cell-derived, viral oncogene present in the transforming murine leukemia retrovirus, AKT8 (Staal and Hartley, 1988). The virus was unusual in its ability to transform mink lung epithelial cells but not other cells, such as NIH3T3 fibroblasts, suggesting the presence of a novel, cell-type specific oncogene. The human homolog of the viral Akt kinase is a serine/threonine protein kinase belonging to the AGC protein kinase superfamily, was named protein kinase B for its similarity to protein kinases A and C, giving rise to the current "PKB/Akt" nomenclature system (Brazil and Hemmings, 2001; and references within).

Akt was later shown to mediate downstream events associated with phosphatidylinositol 3-kinase (PI3K), which is recruited to the plasma membrane in response to growth factors (including platelet-derived growth factor (PDGF), epidermal growth factor (EGF), basic fibroblast growth factor (bFGF), insulin-like growth factor (IGF-1), nerve growth factor (NGF), stem cell factor, and vascular endothelial growth factor), cytokines (including interleukins 2, 3, 4, 5, and 8), insulin, bradykinin, RANTES, and endothelin, as well as attachment to the extracellular matrix (ECM) and various forms of cell stress (e.g., hypoxia and heat shock) (Lawlor and Alessi, 2001; Brazil and Hemmings, 2001; Scheid and Woodgett, 2003).

At the plasma membrane, PI3K converts phosphatidylinositol 4,5-bisphosphate (PtdIns(4,5)$P_2$; PIP2) to the lipid second-messenger, phosphatidylinositol 3,4,5-triphosphate (PtdIns(3,4,5)$P_3$; PIP3). PIP3, or its breakdown product, phosphatidylinositol 3,4-bisphosphate (PtdIns(3,4)$P_3$; PI(3,4)P2), recruits Akt to the plasma membrane via the N-terminal, pleckstrin homology (PH) region of PKB.

Membrane bound PKB is activated by multi-site phosphorylation, particularly within the activation T-loop of the central catalytic domain. Phosphorylated PKB then participates in a number of downstream signaling events related to cell cycle regulation, survival, motility and growth (Lawlor and Alessi, 2001; Scheid and Woodgett, 2003). These processes are essential for normal cell function. In addition, mutations and/or aberrant expression of polypeptides affecting the activity and/or production of phosphorylated PKB have been implicated in human cancer (Luo et al., 2003). In particular, Akt has been found in ovarian, breast, and colon cancers (Id.).

At least three cellular homologues have now been identified (i.e., Akt1/PKBα, Akt2/PKBβ, and Akt3/PKBγ) (Lawlor and Alessi, 2001; Scheid and Woodgett, 2003). In addition to the PH region, these proteins are known to possess a docking domain (HM) for their upstream activating kinase, 3-phosphoinoside-dependent kinase (PDK1), also an AGC family kinase. The HM domain also appears to function as a site for other means of allosteric regulation (Scheid and Woodgett, 2003). Phosphorylation at Thr308, situated within the activation T-loop, appears to be performed by PDK1, and is necessary for PKB function. Phosphorylation at Ser473, located at the C-terminal hydrophobic domain of PKB, is also important for maximum PKB activity, although the mechanism of phosphorylation is not clear (Brazil and Hemmings, 2001; Scheid and Woodgett, 2003).

Numerous Akt substrates have been identified or proposed, including Bcl-2 pro-apoptotic family member (BAD); the FOXO family of fork-head transcription factors, which mediate apoptosis through FasL and Bim; the cancer-associated 3'-phosphatase, PTEN; breast cancer susceptibility gene product 1 (BRCA-1); cAMP responsive element binding protein (CREB); endothelial nitric oxide synthase (eNOS); NFκB inhibitor (I-κB); with No K (Lys) protein kinase-1 (WNK1), a hypertension-related gene linked to pseudohypoaldosteronism type II (PHAII) (Vitari et al. 2003); and others, suggesting that Akt plays a fundamental role in the regulation of cell growth (Brazil and Hemmings, 2001; Luo et al., 2003).

One common alteration seen in a range of different advanced cancers is mutation of the PTEN gene, a gene which is linked with cell regulation and apoptosis (programmed cell death). PTEN is the lipidphosphatase that inactivates PIP3 and turns off PDK1 and Akt. Mutations in the PTEN gene are documented in cancers of the breast, prostate, endometrium, ovary, colon, melanoma, glioblastoma, and lymphoma. Animal models have shown that the loss of just one copy of the PTEN gene is enough to interrupt cell signalling and begin the process of uncontrolled cell growth. All of these PTEN-mutated cancers have activated AKT and are natural indications for an Akt therapeutic.

A PKB-binding consensus sequence has been predicted by Alessi and colleagues (Alessi et al., 1996); however, a flanking sequence significantly affects the ability of PKB to phosphorylate peptide substrates harboring the consensus sequence (Obata et al., 2000). Accordingly, PKB/Akt substrate specificity must depend on protein-protein interactions in addition to primary amino acid sequence recognition (Luo et al., 2003); underscoring the specificity of PKB/Akt substrate recognition.

Successful kinase inhibitors have been developed for clinical use, including inhibitors that interfere with receptor tyrosine kinase (RTK)-phosphorylation of Erb2/HER2, PDGF, BCR-Abl, and c-KIT receptors. PI3K inhibitors are also available, for research use, and have been shown to inhibit tumor growth (Luo et al., 2003; and references within). Unfortunately, the targets of such inhibitors lie upstream of PKB/Akt and inhibition of these targets produces wide-ranging effects on cellular biochemical pathways.

The high degree of structural similarity among the AGC kinases, including PKB/Akt and PDK1, has thwarted efforts to identify kinase inhibitors that target such downstream kinases, which would presumably affect only a subset of the biochemical pathways modulated by the downstream kinases. Partial X-ray structures of the PKB/Akt and PDK1 kinase domains have been reported; however, such structures do not reveal the structures of the respective PH domains, which are likely to be a preferred target site for PKB/Akt and/or PDK1-specific inhibitors (Harris, 2003).

While the naturally-occurring sphingolipid, ceramide, appears to prevent the interaction of PIP3 with the PH region of PKB/Akt (Powell et al., 2003), and has been used as an anti-cancer drug, the observed effects of ceramide are sometimes contradictory, potentially short-lived, and poorly understood (Radin, 2003).

Accordingly, the need exists for specific inhibitors of kinases such as PKB/Akt.

Protein Kinase A

Many peptide hormones, for example follicle-stimulating hormone (FSH), function by modulating the activity of adenylate cyclase, which is bound to the inner surface of the plasma membrane. The relative level of adenylate cyclase activity in a cell controls the amount of cyclic AMP (cAMP), which serves as a "second messenger" for downstream transduction of the peptide hormone signal (Watson et al., 1987 at p. 982). Protein kinase A (PKA) normally localizes to the plasma membrane via the regulatory "R" subunit of PKA. However, when present at elevated intracellular concentrations, cAMP binds to the regulatory R subunit of PKA and releases the catalytic portion of the protein kinase. Activated PKA then translocates to the nucleus where it activates a number of substrates, including the cAMP-response element binding protein (CREB), cAMP-responsive element modulator (CREM), and activating transcription factor (ATF) (Lewin, 1996 at pp. 1081-82; Don and Stelzer, 2002).

In the case of CREB, phosphorylation at even one Ser residue (typically Ser-133) increases its affinity for the cAMP responsive element (CRE), found in a number of genes, including but not limited to cell cycle regulators, extracellular matrix proteases (ECM), cholesterol trafficking proteins, neuropeptides, immune genes, insulin-like growth factor (IGF) family members, hormone signaling proteins, signal transduction proteins and other protein associated with cell growth, differentiation, reproduction, and spermatogenesis. Proteins that are down-regulated by cAMP include cyclins B and E2, insulin-like growth factor binding protein-5 (IGFBP-5), α1 type XVI collagen, lipocortin III, 1-kynurenine hydrolase, frizzle-related protein, NF-κB, and actin/tropomyosin/calmodulin binding protein (Tierney et al., 2003).

CDC7

CDC7 kinase, in a complex with a DBF4 regulatory subunit, is required for the initiation of DNA replication in eukaryotes. CDC7 appears to be necessary for the "triggering" or "firing" of origins of replication initiation by recruiting the appropriate enzymes to the initiation sites. CDC7 has been implicated in S-phase checkpoint signaling downstream of the ATR and Chk1 kinases.

The biological role of CDC7 has been studied in several model systems. In yeast, inactivation of CDC7 results in growth arrest after completion of ongoing DNA replication. Studies in yeast also suggest a role for CDC7 in meiosis, checkpoint responses, and chromosome structure maintenance and repair. In contrast, conditional inactivation of CDC7 in undifferentiated mouse embryonic stem cells leads to growth arrest accompanied by cessation of ongoing DNA synthesis, suggesting that CDC7 is required even after initiation of DNA synthesis. Loss of CDC7 function also induces recombinational repair and inhibition of CDC2 kinase, eventually resulting in p53-dependent apoptosis. Minichromosome maintanance proteins (MCM) appear to be the major physiological substrates of CDC7.

Partial loss of CDC7 kinase expression results in retarded growth at both cellular and whole body levels, while elevated levels of CDC7 kinase are observed in cancer cells. The latter observation makes CDC7 kinase an attractive target for small-molecule kinase inhibitors (Montagnoli, A. et al., 2004; Woo, R. A. and Poon, R. Y., 2003; Semple, J. W. and Duncker, B. P., 2004). Gene expression analysis using microarrays has also identified CDC7 as a drug target (Walker, M. G., 2001).

It is therefore well-known that PKB/Akt, PKA, and CDC7 are inextricably tied to cell growth, differentiation, dysfunction, and survival. Accordingly, the need exists for specific inhibitors of kinases such as PKB/Akt, PKA and CDC7.

SUMMARY OF THE INVENTION

This invention is directed to substituted five-membered heterocyclic derivative compounds represented by formula I:

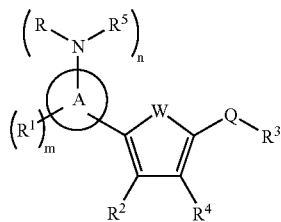

wherein:
ring A is a nitrogencontaining heteroaryl comprising 5 or 6 ring atoms wherein from 1 to 4 ring atoms are nitrogen atoms;
n is an integer selected from zero or one;
R is selected from the group consisting of:
  a) hydrogen,
  b) hydroxy,
  c) alkyl,
  d) substituted alkyl,
  e) cycloalkyl,
  f) substituted cycloalkyl,
  g) —SO$_2$R$^7$ where R$^7$ is C$_1$ to C$_5$ alkyl or substituted alkyl,
  h) alkoxy,
  i) carboxyl,
  j) carboxyl ester,
  k) nitro,
  l) aryl,
  m) substituted aryl,
  n) heteroaryl,
  o) substituted heteroaryl,
  p) heterocyclyl,
  q) substituted heterocyclyl,
  r) acylamino, and
  s) acyl;
R$^5$ is selected from the group consisting of:
  a) hydrogen,
  b) alkyl, and
  c) substituted alkyl;
each R$^1$ is independently selected from the group consisting of:
  a) halo,
  b) cyano,
  c) nitro,
  d) hydroxy,
  e) thiol,
  f) amino,
  g) substituted amino,
  h) alkoxy,
  i) substituted alkoxy,
  j) aryloxy,
  k) substituted aryloxy,
  l) heteroaryloxy,
  m) substituted heteroaryloxy,
  n) alkylthio,
  o) substituted alkylthio,
  p) —C(=O)NR$^8$R$^8$, wherein each R$^8$ is independently selected from the group consisting of hydrogen, alkyl, substituted alkyl, aryl, substituted aryl, heteroaryl, substituted heteroaryl, heterocyclyl, substituted heterocyclyl, or each R$^8$ can be optionally joined together with the nitrogen atom pendent thereto to form a heterocyclyl or substituted heterocyclyl,
  q) —NHC(=O)—R$^9$, wherein R$^9$ is selected from the group consisting of hydrogen, alkyl, substituted alkyl, aryl, substituted aryl, heteroaryl, substituted heteroaryl, heterocyclyl, substituted heterocyclyl,
  r) aryl or heteroaryl, each of which may be optionally substituted with optionally substituted alkyl or aryl,
  s) heterocyclyl, each of which may be optionally substituted with optionally substituted alkyl or aryl, and
  t) C$_1$ to C$_5$ alkyl optionally substituted with 1 to 3 substituents selected from halo, hydroxy, amino, aryl, C$_1$ to C$_5$ alkyl monosubstituted amino, and C$_1$ to C$_5$ alkyl disubstituted amino wherein each alkyl group is independent from the other alkyl group;
m is an integer equal to 0, 1 or 2;
R$^2$ and R$^4$ are independently selected from the group consisting of:
  a) hydrogen,
  b) cycloalkyl,
  c) substituted cycloalkyl,
  d) heterocyclyl,
  e) substituted heterocyclyl,
  f) aryl,
  g) substituted aryl,
  h) heteroaryl,
  i) substituted heteroaryl,
  j) optionally substituted C$_1$ to C$_5$ substituted alkyl,
  k) optionally substituted C$_2$ to C$_5$ alkenyl,
  l) optionally substituted C$_2$ to C$_5$ alkynyl,
  m) optionally substituted C$_1$ to C$_5$ alkoxy,
  n) hydroxy,
  o) amino,
  p) C$_1$ to C$_5$ alkyl monosubstituted amino, and
  q) C$_1$ to C$_5$ alkyl disubstituted amino wherein each alkyl group is independent from the other alkyl group,
with the proviso that when one of R$^2$ or R$^4$ is cycloalkyl, substituted cycloalkyl, heterocyclyl, substituted heterocyclyl, aryl substituted aryl, heteroaryl, substituted heteroaryl, then the other of R$^2$ or R$^4$ is hydrogen;
R$_3$ is selected from the group consisting of:
  a) hydrogen,
  b) C$_1$ to C$_5$ alkyl, and
  c) —(C$_1$ to C$_5$ alkylene)$_p$-Z optionally substituted on the alkylene chain with 1 to 2 substituents selected from the group consisting of:
    i. C$_1$ to C$_5$ alkyl optionally substituted with 1 to 3 substituents selected from hydroxy, carboxyl, carboxyl esters, amino, C$_1$ to C$_5$ alkyl monosubstituted amino, and $C_1$ to $C_5$ alkyl disubstituted amino wherein each alkyl group is independent from the other alkyl group, ii. $C_2$ to $C_5$ alkenyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group with the proviso that said hydroxy substitution is not pendent to a vinyl carbon atom of the substituted alkenyl, iii. $C_2$ to $C_5$ alkynyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group with the proviso that said hydroxyl substitution is not pendent to a acetylene carbon atom of the substituted alkynyl, iv. $C_3$ to $C_6$ cycloalkyl, v. $C_3$ to $C_6$ spirocycloalkyl, vi. carboxyl, vii. carboxyl esters, viii. halo, ix. hydroxy, x. $C_1$ to $C_5$ alkoxy, xi. amino, xii. $C_1$ to $C_5$ alkyl monosubstituted amino, xiii. $C_1$ to $C_5$ alkyl disubstituted amino, xiv. aryl, and xv. heterocyclyl;

Z is selected from the group consisting of:
a) alkyl,
b) substituted alkyl,
c) alkylamino,
d) alkoxy,
e) substituted alkoxy,
f) cycloalkyl,
g) heterocyclyl,
h) substituted heterocyclyl,
i) aryl,
j) substituted aryl,
k) heteroaryl, and
l) substituted heteroaryl;

p is an integer selected from zero or one;

Q is selected from the group consisting of:
a) $-C(X')NR_6-$,
b) $-CH_2NR_6-$,
c) $-NR^6C(X')-$,
d) $-NR^6C(X')O-$,
e) $-NR^6C(X')NR^6-$,
f) $-OC(X')NR^6-$,
g) $-C(X')O-$,
h) $-CR^6=CR^6-$,
i) $-C\equiv C-$,
j) $-S(O)_2NR^6-$, and
k) $-S(O)NR^6-$, where X' is selected from the group consisting of oxygen and sulfur and each $R^6$ is independently selected from the group consisting of hydrogen and $C_1$-$C_3$ alkyl and $C_1$-$C_3$ substituted alkyl, or $R^6$ together with Q and the carbon atom attached thereto and together with $R_4$ and the carbon atom attached thereto join to form a heterocyclyl or substituted heterocyclyl, with the proviso that when Q is $-C(O)NH-$, then $R^3$ is not $C_2$ alkyl further substituted with at least a $-C(O)$ group at the beta position to the $-C(O)NH-$, with the further proviso that when Q is $-S(O)_2NH-$, then $R^3$ is not $C_2$ alkyl further substituted with at least a $-C(O)$ group;

W is selected from the group consisting of $-O-$, $-S-$, $-SO-$, and $-SO_2-$;

with the proviso that when ring A is pyrimidine and Q is $-C(O)NR_6-$, then $R^4$ is not aryl or heteroaryl;

or pharmaceutically acceptable salts, esters or prodrugs thereof.

Also provided is a pharmaceutical composition comprising a compound of formula I and a pharmaceutically acceptable excipient or carrier.

In another aspect, the present invention provides methods of treating a mammalian patient suffering from a disorder mediated, at least in part, by CDC7, PKA and/or Akt. Thus, the present invention provides methods of treating a mammalian patient in need of such treatment comprising administering to the patient a therapeutically effective amount of a compound of formula I (including mixtures thereof).

In one embodiment, the disorder mediated, at least in part, by CDC7, PKA and/or Akt is a cellular proliferative disorder. The cellular proliferative disorder can be cancer. In another embodiment, cancer can be a tumor or a neoplasm, selected from the group consisting of carcinomas, adenocarcinomas and sarcomas.

In another embodiment, cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In still yet another embodiment, cancer is selected from the group consisting of angiogenesis-mediated diseases, benign tumors, acoustic neuromas, neurofibromas, pyogenic granulomas, biliary tract cancer, choriocarcinoma, esophageal cancer, gastric cancer, intraepithelial neoplasms, lung cancer, neuroblastomas, chronic myelogenous leukemia, acute myelogenous leukemia, and multiple myeloma.

In yet other aspects, the present invention provides methods for treating a disorder mediated, at least in part by, Akt in a mammalian patient comprising administering to said patient an amount of compound of formula I effective to reduce or prevent tumor growth in the patient either alone or in combination with at least one additional anticancer agent.

In still yet another aspect, the present invention provides methods for treating a disorder mediated, at least in part, by PKA in a mammalian patient comprising administering to said patient an amount of compound of formula I effective to reduce or prevent tumor growth in the patient either alone or in combination with at least one additional anticancer agent.

In still other aspects, the present invention provides methods for treating a disorder mediated, at least in part, by CDC7 in a mammalian patient comprising administering to said patient an amount of compound of formula I effective to reduce or prevent tumor growth in the patient either alone or in combination with at least one additional anticancer agent.

A compound or composition of this invention may be administered to the mammal by a suitable route, such as orally, intravenously, parenterally, transdermally, topically, rectally, or intranasally.

Mammalian patients include, for example, humans and other primates, pet or companion animals, such as dogs and cats, laboratory animals, such as rats, mice and rabbits, and farm animals, such as horses, pigs, sheep, and cattle.

PREFERRED EMBODIMENTS

In a preferred embodiment, ring A is selected from the group consisting of:

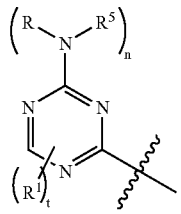
IA

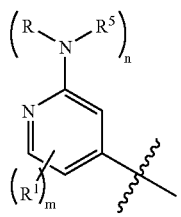
IB

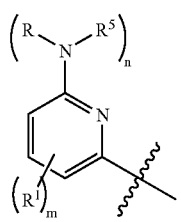
IC

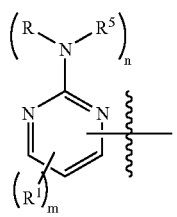
ID

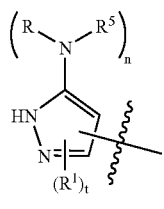
IE

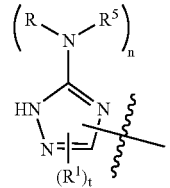
IF wherein R, $R^1$, $R^5$, n and m are as defined herein and t is 0 or 1.

Preferably, W is sulfur.

Preferred R groups are selected from the groups consisting of hydrogen, alkyl, substituted alkyl, cycloalkyl, substituted cycloalkyl, acylamino, heteroaryl, nitro, aryl, —$SO_2R^7$, carboxyl ester, and acyl.

Particularly preferred R groups are selected from the group consisting of:
  2-(methylamino)eth-1-yl,
  2-(N-methylpiperazin-N'-yl)eth-1-yl,
  2-(N-methylpyrrol-2-yl)eth-1-yl,
  2-(N-morpholino)eth-1-yl,
  2-(piperidin-N-yl)eth-1-yl,
  2-(pyridin-2-yl)eth-1-yl,
  2-(pyridin-3-yl)eth-1-yl,
  2-(pyridin-4-yl)eth-1-yl,
  2-(S)-phenylcyclopropyl,
  2-aminoeth-1-yl,
  2-hydroxyeth-1-yl,
  2-phenyleth-1-yl,
  2-spirocyclopropyl-2-(4-chlorophenyl)eth-1-yl,
  3-(imidazol-N-yl)prop-1-yl,
  3-(N-methylpiperazin-N'-yl)prop-1-yl,
  3-(N-morpholino)prop-1-yl,
  3-aminobut-1-yl,
  3-aminoprop-1-yl,
  5-carboxy-4-(R,S)-aminopent-1-yl,
  aminocarbonyl,
  benzyl,
  benzylaminocarbonyl,
  butyl,
  cyclobutyl,
  cyclopentyl,
  cyclopropyl,
  cyclopropylmethyl,
  dimethylaminocarbonyl,
  ethyl,
  ethylaminocarbonyl,
  hydrogen,
  methyl,
  methoxycarbonyl,
  methylaminocarbonyl,
  methylcarbonyl,
  neopentyl,
  nitro,
  phenyl,
  phenylaminocarbonyl,
  propyl,
  propylaminocarbonyl,
  pyridin-2-ylmethyl,
  pyridin-3-ylmethyl, pyridin-4-yl,
pyridin-4-ylmethyl, and
SO$_2$CH$_3$.
Preferably R$^5$ is hydrogen or methyl.
Preferred R$^1$ groups are selected from the group consisting of hydrogen, C$_{1-5}$ alkyl, —C(=O)NR$^9$, and —NHC(=O)—R$^9$ wherein R$^9$ is selected from hydrogen or methyl. More preferably, R$^1$ is selected from the group consisting of hydrogen, methyl, aminocarbonyl, and methylcarbonylamino.
Preferably R$^2$ and R$^4$ are selected from the group consisting of hydrogen, hydroxy, amino, and C$_1$ to C$_5$ alkoxy optionally substituted with aryl or amino. More preferably R$^2$ and R$^4$ are selected from the group consisting of hydrogen, amino, hydroxy, methoxy, benzyloxy, and 2-aminoethoxy.
Preferably R$^3$ is —(C$_1$ to C$_5$ alkylene)$_p$-Z where p is 0 or 1. When p is 1, the alkylene chain is preferably unsubstituted or substituted with a substituent selected from the group consisting of C$_1$ to C$_5$ alkyl, C$_1$ to C$_5$ alkyl substituted with hydroxy, amino, monosubstituted amino, or disubstituted amino, C$_2$ to C$_5$ alkenyl, C$_2$ to C$_5$ alkynyl, C$_3$ to C$_6$ spirocycloalkyl, carboxyl, carboxyl esters, hydroxy, amino, heterocyclyl and aryl. Still more preferably when p is 1, the alkylene chain is unsubstituted or substituted with a substituent selected from the group consisting of:
  2-aminoethyl,
  2-dimethylaminoethyl, and
  2-hydroxyethyl,
  2-methylaminoethyl,
  3-methylaminopropyl,
  amino,
  aminomethyl,
  carboxyl,
  dimethylamino,
  dimethylaminomethyl,
  ethyl,
  methyl,
  methylcarboxyl,
  morpholino,
  hydroxymethyl,
  phenyl,
  prop-2-enyl,
  prop-2-ynyl,
  propyl,
  spirocyclobutyl, and
  spirocyclopropyl.
In other preferred embodiments, Z is selected from the group consisting of cycloalkyl, substituted cycloalkyl, heterocyclyl, substituted heterocyclyl, aryl, substituted aryl, heteroaryl, substituted heteroaryl, alkyl, amino, alkylamino, and dialkylamino.
Particularly preferred R$^3$ are selected from the group consisting of:
  (2-fluoro-4-methoxyphenyl)eth-1-yl,
  (2-fluoro-4-methylphenyl)eth-1-yl,
  [1-(4-chlorophenyl)cyclobut-1-yl]methyl,
  [1-(4-chlorophenyl)cycloprop-1-yl]methyl,
  1-(1-aminoethyl)-4-chloro-1H-benzoimidazol-2-yl,
  1-(2-aminoethyl)-1H-benzoimidazol-2-yl,
  1-(2-aminoethyl)-4-chloro-1H-benzimidazol-2-yl,
  1-(2-aminoethyl)-4-methoxy-1H-benzimidazol-2-yl,
  1-(2-aminoethyl)-4-phenyl-1H-benzimidazol-2-yl,
  1-(2-aminoethyl)-7-chloro-1H-benzimidazol-2-yl,
  1-(2-methylpropyl)-4-chloro-1H-benzimidazol-2-yl,
  1-(3,3-dimethylbutyl)-4-chloro-1H-benzimidazol-2-yl,
  1-(3-aminopropyl)-4-chloro-1H-benzimidazol-2-yl,
  1-(4-chlorophenyl)-3-(N-methylamino)prop-1-yl,
  1-(4-chlorophenyl)-3-(N,N-dimethylamino)prop-1-yl,
  1-(4-chlorophenyl)-3-hydroxyprop-1-yl,
  1-(aminomethyl)-2-(2,4-dichlorophenyl)eth-1-yl,
  1-(R)-1-(2,4-dichlorobenzyl)-4-(dimethylamino)but-2-yl,
  1-(R)-1-(2,4-dichlorobenzyl)-4-(methylamino)but-2-yl,
  1-(R)-1-(2,4-dichlorobenzyl)-4-aminobut-2-yl,
  1-(R)-2-(2,4-dichlorophenyl)-1-methyleth-1-yl,
  1-(R)-4-fluorophenyl)eth-1-yl,
  1-(R)-amino-1-(2,4-dichlorobenzyl)eth-1-yl,
  1-(R)-aminomethyl-2-(2,4-dichlorophenyl)eth-1-yl,
  1-(R)-hydroxymethyl-2-(4-chlorophenyl)eth-1-yl,
  1-(R,S)-carboxyl-2-(2,4-dichlorophenyl)eth-1-yl,
  1-(R,S)-hydroxymethyl-1-phenylmethyl,
  1-(R,S)-hydroxymethyl-2-(2,4-dichlorophenyl)eth-1-yl,
  1-(R,S)-hydroxymethyl-2-phenyleth-1-yl,
  1-(R,S)-methylcarboxyl-2-(2,4-dichlorophenyl)eth-1-yl,
  1-(R,S)-phenyl-2-phenyleth-1-yl,
  1-(S)-1-(2,4-dichlorobenzyl)-4-(dimethylamino)but-2-yl,
  1-(S)-1-(2,4-dichlorobenzyl)-4-(methylamino)but-2-yl,
  1-(S)-1-(2,4-dichlorobenzyl)-4-amino-but-2-yl,
  1-(S)-amino-1-(2,4-dichlorobenzyl)eth-1-yl,
  1-(S)-aminomethyl-2-(1H-indol-3yl)eth-1-yl,
  1-(S)-aminomethyl-2-(2,4-dichlorophenyl)eth-1-yl,
  1-(S)-aminomethyl-2-(indol-3-yl)eth-1-yl,
  1-(S)-dimethylamino-2-(2,4-dichlorophenyl)eth-1-yl,
  1-(S)-dimethylaminomethyl-2-(2,4-dichlorophenyl)eth-1-yl,
  1,2,3,4-tetrahydronaphthalen-1-yl,
  1-aminoethyl-4-methoxybenzoimidazol-2-yl,
  1-aminomethyl-2-(2,4-dichlorophenyl)eth-1-yl,
  1-aminomethyl-2-(4-chlorophenyl)eth-1-yl,
  1-aminomethyl-4-chloro-1H-benzimidazole-2-yl,
  1-benzylpyrrolidin-3-yl,
  1-dimethylamino-3-(2,4-dichlorophenyl)prop-2-yl,
  1-ethyl-4-chlorobenzoimidazol-2-yl,
  1-hydroxymethyl-2-(2,4-dichlorophenyl)eth-1-yl,
  1-hydroxymethyl-2-methylprop-1-yl,
  1-isobutyl-4-chlorobenzoimidazol-2-yl,
  1-methyl-2-hydroxyeth-1-yl,
  1-methyl-4-chlorobenzoimidazol-2-yl,
  1-methylbenzoimidazol-2-yl,
  1-phenyl-1-(4-chlorophenyl)methyl,
  1-phenyl-2-hydroxyeth-1-yl,
  2-(2,4-dichlorophenyl)but-1-yl,
  2-(2,4-dichlorophenyl)eth-1-yl,
  2-(2,4-dichlorophenyl)pent-1-yl,
  2-(2,4-dichlorophenyl)pent-4-en-1-yl,
  2-(2,4-dichlorophenyl)pent-4-yn-1-yl,
  2-(2,4-dichlorophenyl)prop-1-yl,
  2-(2,5-dimethoxyphenyl)eth-1-yl,
  2-(2,6-dichlorophenyl)eth-1-yl,
  2-(2-chlorophenyl)eth-1-yl,
  2-(3,4-dichlorophenyl)eth-1-yl,
  2-(3,4-dimethoxyphenyl)eth-1-yl,
  2-(3-chlorophenyl)eth-1-yl,
  2-(3-fluorophenyl)eth-1-yl,
  2-(3-methoxyphenyl)eth-1-yl,
  2-(4-aminophenyl)eth-1-yl,
  2-(4-aminosulfonylphenyl)eth-1-yl,
  2-(4-biphenyl)eth-1-yl,
  2-(4-bromophenyl)eth-1-yl,
  2-(4-chlorophenyl)eth-1-yl,
  2-(4-ethoxyphenyl)eth-1-yl,
  2-(4-ethylphenyl)eth-1-yl,
  2-(4-fluorophenyl)eth-1-yl,
  2-(4-methoxyphenyl)eth-1-yl,
  2-(4-methylphenyl)eth-1-yl,
  2-(4-phenoxyphenyl)eth-1-yl, 2-(N-methylpiperazin-N'-yl)eth-1-yl,
2-(N-methylpyrrol-2-yl)eth-1-yl,
2-(N-morpholino)eth-1-yl,
2-(piperidin-1-yl)eth-1-yl,
2-(piperidin-3-yl)eth-1-yl,
2-(pyridin-2-yl)eth-1-yl,
2-(pyridin-4-yl)eth-1-yl,
2-(R)-(N-morpholino)-2-phenyleth-1-yl,
2-(R)-amino-3-(indol-3-yl)prop-1-yl,
2-(R)-hydroxyindan-1-yl,
2-(R)-methyl-2-phenyleth-1-yl,
2-(R,S)-amino-2-phenyleth-1-yl,
2-(R,S)-hydroxy-2-(4-chlorophenyl)eth-1-yl,
2-(R,S)-methyl-2-phenyleth-1-yl,
2-(S)-amino-3-(indol-3-yl)prop-1-yl,
2-(S)-methyl-2-phenyleth-1-yl,
2-(trifluoromethyl)-4-fluorophenylmethyl,
2,4-dichlorobenzyl,
2,4-dichlorophenylmethyl,
2,2-dimethyl-5-benzyltetrahydropyran-4-yl,
2,2-diphenyleth-1-yl,
2,4-dichlorobenzyl,
2,4-difluorobenzyl,
2,5-difluorobenzyl,
2-aminobenzothiazol-4-yl,
2-aminoeth-1-yl,
2-chlorobenzyl,
2-dimethylaminoeth-1-yl,
2-fluoro-4-chlorobenzyl,
2-fluoro-6-aminobenzyl,
2-methoxybenzyl,
2-methyl-4-chlorophenylnethyl,
2-methylbenzyl,
2-phenethyl,
2-phenylbenzyl,
2-piperidin-N-ylbenzyl,
3-(4-fluorophenyl)prop-1-yl,
3-(pyrrol-N-yl)prop-1-yl,
3,4-dichlorobenzyl,
3,5-dichlorobenzyl,
3,5-difluorobenzyl,
3-amino-1-(4-chlorophenyl)prop-1-yl,
3-bromobenzyl,
3-chlorobenzyl,
3-methoxybenzyl,
4-(2-chlorophenyl)thiazol-2-yl,
4-(3,4-difluorophenyl)thiazol-2-yl,
4-(3-chlorophenyl)thiazol-2-yl,
4-(4-methoxyphenyl)thiazol-2-yl,
4-(aminomethyl)benzothiazol-2-yl,
4-(pyridin-2-yl)thiazol-2-yl,
4-(pyridin-3-yl)thiazol-2-yl,
4-(trifluoromethoxy)-6-(aminomethyl)benzothiazol-2-yl,
4-(trifluoromethyl)-6-(aminomethyl)benzothiazol-2-yl,
4,6-dichlorobenzothiazol-2-yl,
4,6-difluorobenzothiazol-2-yl,
4-amino-2-(4-chlorophenyl)but-1-yl,
4-aminobenzyl,
4-aminosulfonylbenzyl,
4-bromo-6-(aminomethyl)benzothiazol-2-yl,
4-bromo-6-isopropyl-benzothiazol-2-yl,
4-bromobenzothiazol-2-yl,
4-bromobenzyl,
4-chloro-[2-(S)-2-(aminopropanoyl)aminomethyl]benzothiazol-2-yl,
4-chloro-1,3-benzothiazol-2-yl,
4-chloro-5-methylcarboxyl-benzothiazol-2-yl,
4-chloro-6-({[2-(S)-2-amino-3-phenylpropanoyl]amino}methyl)benzothiazol-2-yl,
4-chloro-6-(2-aminoethyl)benzothiazol-2-yl,
4-chloro-6-(2-nitroethyl)benzothiazol-2-yl,
4-chloro-6-(dimethylaminomethyl)benzothiazol-2-yl,
4-chloro-6-(methylaminomethyl)benzothiazol-2-yl,
4-chloro-6-(methylcarbonylaminomethyl)benzothiazol-2-yl,
4-chloro-6-(trifluoromethoxy)benzothiazol-2-yl,
4-chloro-6-(trifluoromethyl)benzothiazol-2-yl,
4-chloro-6-[(2-amino)ethylaminocarbonyl]benzothiazol-2-yl,
4-chloro-6-{[(aminomethylcarbonyl)amino]methyl}benzothiaozl-2-yl,
4-chloro-6-aminomethylbenzothiazol-2-yl,
4-chloro-6-hydroxymethylbenzothiazol-2-yl,
4-chloro-6-methylaminomethylbenzothiazol-2-yl,
4-chloro-6-methylthiazol-2-yl,
4-chloro-6-N-morpholinomethyl-benzothiazol-2-yl,
4-chloro-7-aminomethyl-benzothiazol-2-yl,
4-chloro-7-hydroxymethyl-benzothiazol-2-yl,
4-chlorobenzothiazol-2-yl,
4-chlorobenzoxazol-2-yl,
4-chlorobenzyl,
4-dimethylaminobenzyl,
4-fluorobenzyl,
4-fluorobenzothiazol-2-yl,
4-fluorobenzyl,
4-fluorophenyl,
4-fluorophenylmethyl,
4-hydroxy-2-(4-chlorophenyl)but-1-yl,
4-hydroxybenzothiazol-2-yl,
4-hydroxybenzothiazol-4-yl,
4-methoxy-6-(methylaminomethyl)benzothiazol-1-yl,
4-methoxybenzothiazol-2-yl,
4-methoxythiazol-2-yl,
4-methyl-6-aminomethyl-benzothiazol-2-yl,
4-methylbenzyl,
4-methylthiazol-2-yl,
4-phenylthiazol-2-yl,
5-(2-bromothiophen-5-yl)thiazol-2-yl,
5-(3-bromo-4-methoxyphenyl)thiazol-2-yl,
5-chlorobenzoimidazol-2-yl,
5-chlorobenzothiazol-2-yl,
6-aminomethyl-8-chloroquinolin-2-yl,
6-aminomethyl-benzothiazol-2-yl,
6-chlorobenzothiazol-2-yl,
6-fluorobenzothiazol-2-yl,
7-chlorobenzothiazol-2-yl,
benzoimidazol-2-yl,
benzothiazol-2-yl,
benzothiazol-6-yl,
benzothiophen-2-yl,
benzyl,
hydrogen,
indan-1-yl,
naphthalen-1-ylmethyl,
pyridin-2-ylmethyl,
pyridin-3-ylmethyl,
pyridin-4-ylmethyl,
pyrimidin-3-yl,
pyrrolidin-3-yl,
quinolin-2-yl,
quinolin-3-yl,
quinolin-6-yl, and
thiophen-2-ylmethyl.

Preferred Q groups include, —C(O)NH—, —NHC(O)—, —NHC(O)NH—, —NHC(O)O—, —CH₂NH—, —C(O)N(CH₂CH₂NH₂)—, —C(O)N(CH₃)—, —SO₂NH—, —C(O)O—, —CH=CH—, and —C≡C—.

In another preferred embodiment, $R^6$ together with Q and the carbon atom attached thereto and together with $R^4$ and the carbon atom attached thereto join to form a substituted heterocyclyl, more preferably, join to form a 5,6-dihydropyrimidin-4-one.

Preferably, $R^6$ is hydrogen or $C_{1-3}$ substituted alkyl, optionally substituted with amino.

Alternative Embodiments

This invention is directed to substituted five-membered heterocyclic derivative compounds represented by the formula IA':

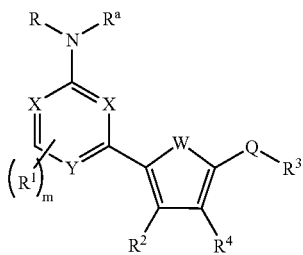

IA' wherein:
R is selected from the group consisting of:
  a) hydrogen,
  b) hydroxy,
  c) alkyl,
  d) substituted alkyl,
  e) cycloalkyl,
  f) substituted cycloalkyl,
  g) —SO₂R⁵ where $R_5$ is $C_1$ to $C_5$ alkyl or substituted alkyl,
  h) alkoxy,
  i) carboxyl ester,
  j) nitro,
  k) aryl,
  l) substituted aryl,
  m) heteroaryl,
  n) substituted heteroaryl,
  o) acylamino, and
  p) acyl;
$R^a$ is selected from the group consisting of hydrogen, alkyl and substituted alkyl;
each $R^1$ is independently selected from the group consisting of:
  a) halo,
  b) cyano,
  c) nitro,
  d) hydroxy,
  e) thiol,
  f) amino,
  g) substituted amino,
  h) alkoxy,
  i) substituted alkoxy,
  j) aryloxy,
  k) substituted aryloxy,
  l) heteroaryloxy,
  m) substituted heteroaryloxy,
  n) alkylthio,
  o) substituted alkylthio,
  p) —C(=O)NR"R", wherein each R" is independently selected from the group consisting of hydrogen, alkyl, substituted alkyl, aryl, substituted aryl, heteroaryl, substituted heteroaryl, or each R" can be optionally joined together with the nitrogen atom pendent thereto to form a heterocyclyl,
  q) —NHC(=O)—R", wherein R" is as defined above,
  r) aryl or heteroaryl, each of which may be optionally substituted with optionally substituted alkyl or aryl, and
  s) $C_1$ to $C_5$ alkyl optionally substituted with 1 to 3 substituents selected from halo, hydroxy, amino, $C_1$ to $C_5$ alkyl monosubstituted amino, and $C_1$ to $C_5$ alkyl disubstituted amino wherein each alkyl group is independent from the other alkyl group;
m is an integer equal to 0, 1 or 2;
$R^2$ and $R^{2'}$ are independently selected from the group consisting of:
  a) hydrogen,
  b) cycloalkyl,
  c) heterocyclyl,
  d) aryl,
  e) heteroaryl,
  f) $C_1$ to $C_5$ alkyl optionally substituted with 1 to 3 substituents selected from halo, hydroxy, amino, $C_1$ to $C_5$ alkyl monosubstituted amino, and $C_1$ to $C_5$ alkyl disubstituted amino wherein each alkyl group is independent from the other alkyl group,
  g) $C_1$ to $C_5$ alkenyl optionally substituted with 1 to 3 substituents selected from halo, hydroxy, amino, $C_1$ to $C_5$ alkyl monosubstituted amino, and $C_1$ to $C_5$ alkyl disubstituted amino wherein each alkyl group is independent from the other alkyl group,
  h) $C_1$ to $C_5$ alkynyl optionally substituted with 1 to 3 substituents selected from halo, hydroxy, amino, $C_1$ to $C_5$ alkyl monosubstituted amino, and $C_1$ to $C_5$ alkyl disubstituted amino wherein each alkyl group is independent from the other alkyl group,
  i) $C_1$ to $C_5$ alkoxy optionally substituted with 1 to 3 substituents selected from halo, hydroxy, amino, $C_1$ to $C_5$ alkyl monosubstituted amino, and $C_1$ to $C_5$ alkyl disubstituted amino wherein each alkyl group is independent from the other alkyl group,
  j) hydroxy,
  k) amino,
  l) $C_1$ to $C_5$ alkyl monosubstituted amino, and
  m) $C_1$ to $C_5$ alkyl disubstituted amino wherein each alkyl group is independent from the other alkyl group,
with the proviso that when one of $R^2$ or $R^{2'}$ is cycloalkyl, heterocyclyl, aryl or heteroaryl, then the other of $R^2$ or $R^{2'}$ is hydrogen;
$R^3$ selected from the group consisting of:
  a) $C_1$ to $C_5$ alkyl, and
  b) —($C_1$ to $C_5$ alkylene)$_p$-Z optionally substituted on the alkylene chain with 1 to 2 substituents selected from the group consisting of:
    i. $C_1$ to $C_5$ alkyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group,
    ii. $C_2$ to $C_5$ alkenyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group, iii. $C_2$ to $C_5$ alkynyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group, iv. $C_3$ to $C_6$ cycloalkyl, v. $C_3$ to $C_6$ spirocycloalkyl, vi. carboxyl, vii. carboxyl esters, viii. halo, ix. hydroxy, x. $C_1$ to $C_5$ alkoxy, xi. amino, xii. $C_1$ to $C_5$ alkyl monosubstituted amino, xiii. $C_1$ to $C_5$ alkyl disubstituted amino wherein each alkyl group is independent from the other alkyl group, and xiv. heterocyclyl;

Z is selected from the group consisting of:
a) alkyl,
b) substituted alkyl,
c) alkylamino,
d) alkoxy,
e) substituted alkoxy,
f) cycloalkyl,
g) heterocyclyl,
h) substituted heterocyclyl,
i) aryl,
j) substituted aryl,
k) heteroaryl, and
l) substituted heteroaryl;

p is zero or one;

Q is selected from the group consisting of:
a) —C(X')$NR^6$—,
b) —$CH_2NR^6$—,
c) —$NR^6$C(X')—,
d) —$NR^6$C(X')O—,
e) —$NR^6$C(X')$NR^6$—, and
f) —OC(X')$NR^6$—, where X' is selected from the group consisting of oxygen and sulfur and $R^6$ is selected from the group consisting of hydrogen and $C_1$-$C_3$ alkyl and $C_1$-$C_3$ substituted alkyl, with the proviso that when Q is —C(O)NH—, then $R^2$ is not $C_2$ alkyl further substituted with at least a —C(O) group;

W is selected from the group consisting of —O—, —S—, —SO—, and —$SO_2$—;

each X is independently selected from the group consisting of —CH—, —$CR^1$ wherein $R^1$ is as defined above, or nitrogen with the proviso that at least one X is nitrogen; and Y is selected from the group consisting of —CH—, —$CR^1$ wherein $R^1$ is as defined above, and nitrogen with the proviso that when Y is nitrogen, both X are nitrogen, with the further proviso that when Y is —CH— or —$CR^1$ and Q is —C(O)$NR^6$—, then $R^{2'}$ is not aryl or heteroaryl;

or pharmaceutically acceptable salts, esters or prodrugs thereof.

Exemplary Compounds of the Invention

Substituted five-membered heterocyclic derivatives within the scope of this invention are exemplified by those set forth in Tables 1 through 5 as follows. In the following tables "Me" refers to methyl, "Et" refers to ethyl, and "Ph" refers to phenyl.

TABLE 1

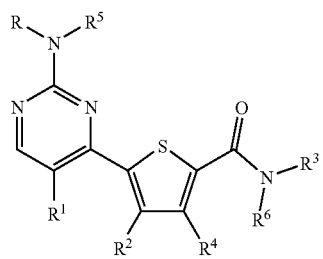

| No | $R^5$ | R | $R^1$ | $R^2$ | $R^4$ | $R^3$ | $R^6$ |
|---|---|---|---|---|---|---|---|
| 1. | H | Me | H | H | H | 2-(4-fluorophenyl)eth-1-yl | H |
| 2. | H | Me | H | H | H | 2-phenethyl | H |
| 3. | H | Me | H | H | H | 4-fluorobenzyl | H |
| 4. | H | $SO_2Me$ | H | H | H | 2-(4-fluorophenyl)eth-1-yl | H |
| 5. | H | Me | H | H | H | 2-(4-chlorophenyl)eth-1-yl | H |
| 6. | H | Me | H | H | H | 2-(4-bromophenyl)eth-1-yl | H |
| 7. | H | Me | H | H | H | 2-(4-aminosulfonylphenyl)eth-1-yl | H |
| 8. | H | Me | H | H | H | 2-(2-fluorophenyl)eth-1-yl | H |
| 9. | H | Me | H | H | H | 2-(4-methoxyphenyl)eth-1-yl | H |
| 10. | H | Me | H | H | H | 2-(3-fluorophenyl)eth-1-yl | H |

TABLE 1-continued

| No  | R⁵ | R                | R¹ | R² | R⁴ | R³ | R⁶ |
|-----|----|------------------|----|----|----|----|----|
| 11. | H  | Me               | H  | H  | H  | 2-(3-methoxyphenyl)eth-1-yl | H |
| 12. | H  | Me               | H  | H  | H  | 2-(R)-methyl-2-phenyleth-1-yl | H |
| 13. | H  | Me               | H  | H  | H  | 2-(2,4-dichlorophenyl)eth-1-yl | H |
| 14. | H  | Me               | H  | H  | H  | 2-(2,6-dichlorophenyl)eth-1-yl | H |
| 15. | H  | Me               | H  | H  | H  | 2-(3,4-dichlorophenyl)eth-1-yl | H |
| 16. | H  | Me               | H  | H  | H  | 3-(4-fluorophenyl)prop-1-yl | H |
| 17. | H  | Et               | H  | H  | H  | 2-(2,4-dichlorophenyl)eth-1-yl | H |
| 18. | H  | H                | H  | H  | H  | 2-(2,4-dichlorophenyl)eth-1-yl | H |
| 19. | H  | neopentyl        | H  | H  | H  | 2-(2,4-dichlorophenyl)eth-1-yl | H |
| 20. | H  | cyclopropyl      | H  | H  | H  | 2-(2,4-dichlorophenyl)eth-1-yl | H |
| 21. | H  | cyclobutyl       | H  | H  | H  | 2-(2,4-dichlorophenyl)eth-1-yl | H |
| 22. | H  | Me               | H  | H  | H  | 4-chlorobenzothiazol-2-yl | H |
| 23. | H  | Me               | H  | H  | H  | 4-aminosulfonylbenzyl | H |
| 24. | H  | Me               | H  | H  | H  | thiophen-2-ylmethyl | H |
| 25. | H  | Me               | H  | H  | H  | [1-(4-chlorophenyl)cycloprop-1-yl]methyl | H |
| 26. | H  | Me               | H  | H  | H  | 2-(N-methylpyrrol-2-yl)eth-1-yl | H |
| 27. | H  | 2-hydroxyeth-1-yl| H  | H  | H  | 2-(2,4-dichlorophenyl)eth-1-yl | H |
| 28. | H  | Me               | Me | H  | H  | 2-(4-fluorophenyl)eth-1-yl | H |
| 29. | H  | Me               | H  | H  | H  | 1-(R)-4-fluorophenyl)eth-1-yl | H |
| 30. | H  | Me               | H  | H  | H  | 2-chlorobenzyl | H |
| 31. | H  | Me               | H  | H  | H  | 3-chlorobenzyl | H |
| 32. | H  | Me               | H  | H  | H  | 4-chlorobenzyl | H |
| 33. | H  | Me               | H  | H  | H  | 2,4-difluorobenzyl | H |
| 34. | H  | Me               | H  | H  | H  | 2,4-dichlorobenzyl | H |
| 35. | H  | Me               | H  | H  | H  | 2-(R)-(N-morpholino)-2-phenyleth-1-yl | H |
| 36. | H  | Me               | H  | H  | H  | naphthalen-1-ylmethyl | H |
| 37. | H  | Me               | H  | H  | H  | 2-(R)-methyl-2-phenyleth-1-yl | H |
| 38. | H  | Me               | H  | H  | H  | 2-(2-chlorophenyl)eth-1-yl | H |
| 39. | H  | Me               | H  | H  | H  | 2-(3-chlorophenyl)eth-1-yl | H |
| 40. | H  | Me               | H  | H  | H  | 1-(R)-hydroxymethyl-2-(4-chlorophenyl)eth-1-yl | H |
| 41. | H  | Me               | H  | H  | H  | 2-(R,S)-methyl-2-phenyleth-1-yl | H |
| 42. | H  | Me               | H  | H  | H  | 2-(R,S)-amino-2-phenyleth-1-yl | H |
| 43. | H  | H                | H  | H  | H  | 2-chlorobenzyl | H |
| 44. | H  | H                | H  | H  | H  | 3-chlorobenzyl | H |
| 45. | H  | H                | H  | H  | H  | 4-chlorobenzyl | H |
| 46. | H  | H                | H  | H  | H  | 2,4-difluorobenzyl | H |
| 47. | H  | H                | H  | H  | H  | 2,5-difluorobenzyl | H |
| 48. | H  | H                | H  | H  | H  | 3,5-difluorobenzyl | H |
| 49. | H  | H                | H  | H  | H  | 2-fluoro-4-chlorobenzyl | H |
| 50. | H  | H                | H  | H  | H  | 2,4-dichlorobenzyl | H |
| 51. | H  | H                | H  | H  | H  | 3,4-dichlorobenzyl | H |
| 52. | H  | H                | H  | H  | H  | 3,5-dichlorobenzyl | H |
| 53. | H  | H                | H  | H  | H  | 2-(2-chlorophenyl)eth-1-yl | H |
| 54. | H  | H                | H  | H  | H  | 2-(3-chlorophenyl)eth-1-yl | H |
| 55. | H  | H                | H  | H  | H  | 2-(4-chlorophenyl)eth-1-yl | H |
| 56. | H  | H                | H  | H  | H  | 2-(3,4-dichlorophenyl)eth-1-yl | H |
| 57. | H  | H                | H  | H  | H  | 2-(2,6-dichlorophenyl)eth-1-yl | H |
| 58. | H  | H                | H  | H  | H  | 2-(S)-methyl-2-phenyleth-1-yl | H |
| 59. | H  | H                | H  | H  | H  | 2-(R)-methyl-2-phenyleth-1-yl | H |
| 60. | H  | H                | H  | H  | H  | 2-(R,S)-methyl-2-phenyleth-1-yl | H |
| 61. | H  | H                | H  | H  | H  | [1-(4-chlorophenyl)cycloprop-1-yl]methyl | H |
| 62. | H  | H                | H  | H  | H  | 2-(N-methylpyrrol-2-yl)eth-1-yl | H |
| 63. | H  | Me               | H  | H  | H  | 1-(R,S)-hydroxymethyl-2-(2,4-dichlorophenyl)eth-1-yl | H |
| 64. | H  | Me               | H  | H  | H  | 4-hydroxy-2-(4-chlorophenyl)but-1-yl | H |
| 65. | H  | H                | H  | H  | H  | 2-(R,S)-amino-2-phenyleth-1-yl | H |
| 66. | H  | H                | H  | H  | H  | 2-methylbenzyl | H |
| 67. | H  | H                | H  | H  | H  | 4-methylbenzyl | H |

TABLE 1-continued

| No | R⁵ | R | R¹ | R² | R⁴ | R³ | R⁶ |
|---|---|---|---|---|---|---|---|
| 68. | H | H | H | H | H | 2-methoxybenzyl | H |
| 69. | H | H | H | H | H | 3-methoxybenzyl | H |
| 70. | H | H | H | H | H | 3-bromobenzyl | H |
| 71. | H | H | H | H | H | 4-bromobenzyl | H |
| 72. | H | H | H | H | H | 1-phenyl-2-hydroxyeth-1-yl | H |
| 73. | H | H | H | H | H | (2-fluoro-4-methylphenyl)eth-1-yl | H |
| 74. | H | H | H | H | H | (2-fluoro-4-methoxyphenyl)eth-1-yl | H |
| 75. | H | H | H | H | H | 2-(R,S)-hydroxy-2-(4-chlorophenyl)eth-1-yl | H |
| 76. | H | H | H | H | H | 2-(2,4-dichlorophenyl)prop-1-yl | H |
| 77. | H | H | H | H | H | 2-(2,4-dichlorophenyl)but-1-yl | H |
| 78. | H | H | H | H | H | 2-(2,4-dichlorophenyl)pent-1-yl | H |
| 79. | H | H | H | H | H | 2-(2,4-dichlorophenyl)pent-4-en-1-yl | H |
| 80. | H | H | H | H | H | 2-(2,4-dichlorophenyl)pent-4-yn-1-yl | H |
| 81. | H | H | H | H | H | benzothiazol-2-yl | H |
| 82. | H | H | H | H | H | 4-chlorobenzothiazol-2-yl | H |
| 83. | H | H | H | H | H | [1-(4-chlorophenyl)cyclobut-1-yl]methyl | H |
| 84. | H | H | H | H | H | 1-(R,S)-hydroxymethyl-2-(2,4-dichlorophenyl)eth-1-yl | H |
| 85. | H | Me | H | H | H | 1-(R,S)-methylcarboxyl-2-(2,4-dichlorophenyl)eth-1-yl | H |
| 86. | H | Me | H | H | H | 1-(R,S)-hydroxymethyl-2-phenyleth-1-yl | H |
| 87. | H | Me | H | H | H | 1-(R,S)-hydroxymethyl-1-phenylmethyl | H |
| 88. | H | Me | H | H | H | 4-amino-2-(4-chlorophenyl)but-1-yl | H |
| 89. | H | Me | H | H | H | 1-(4-chlorophenyl)-3-hydroxyprop-1-yl | H |
| 90. | H | Me | H | H | H | 1-hydroxymethyl-2-(2,4-dichlorophenyl)ethyl-1-yl | H |
| 91. | H | H | H | H | H | 1-hydroxymethyl-2-(2,4-dichlorophenyl)eth-1-yl | H |
| 92. | H | Me | H | H | H | 1-(R,S)-carboxyl-2-(2,4-dichlorophenyl)eth-1-yl | H |
| 93. | H | Me | H | H | H | 2-methyl-4-chlorophenylmethyl | H |
| 94. | H | H | H | H | H | 2-methyl-4-chlorophenylmethyl | H |
| 95. | H | Me | H | H | H | 1-aminomethyl-2-(4-chlorophenyl)eth-1-yl | H |
| 96. | H | Me | H | H | H | 1-(4-chlorophenyl)-3-(N,N-dimethylamino)prop-1-yl | H |
| 97. | H | H | H | H | H | 1-(4-chlorophenyl)-3-(N-methylamino)prop-1-yl | H |
| 98. | H | H | H | H | H | 1-(4-chlorophenyl)-3-(N,N-dimethylamino)prop-1-yl | H |
| 99. | H | H | H | H | H | 2-phenylbenzyl | H |
| 100. | H | H | H | H | H | 3-amino-1-(4-chlorophenyl)prop-1-yl | H |
| 101. | H | Me | H | H | H | 1-aminomethyl-2-(2,4-dichlorophenyl)eth-1-yl | H |
| 102. | H | Me | H | H | H | 4-methylthiazol-2-yl | H |
| 103. | H | Me | H | H | H | 4-methoxythiazol-2-yl | H |
| 104. | H | H | H | H | H | 2-(4-fluorophenyl)eth-1-yl | H |
| 105. | H | Et | H | H | H | 2-(4-fluorophenyl)eth-1-yl | H |
| 106. | H | Me | H | H | H | 2-(4-fluorophenyl)eth-1-yl | Me |
| 107. | H | H | H | H | H | 1-(R)-2-(2,4-dichlorophenyl)-1-methyleth-1-yl | H |
| 108. | H | Me | H | H | H | 1-(aminomethyl)-2-(2,4-dichlorophenyl)eth-1-yl | H* |
| 109. | H | Me | H | H | H | 1-(2-aminoethyl)-1H-benzoimidazol-2-yl | H |
| 110. | H | Me | H | H | H | 1-(2-aminoethyl)-7-chloro-1H-benzimidazol-2-yl | H |

TABLE 1-continued

| No | R⁵ | R | R¹ | R² | R⁴ | R³ | R⁶ |
|---|---|---|---|---|---|---|---|
| 111. | H | Me | H | H | H | 1-(R)-amino-1-(2,4-dichlorobenzyl)eth-1-yl | H |
| 112. | H | Me | H | H | H | 1-(S)-amino-1-(2,4-dichlorobenzyl)eth-1-yl | H |
| 113. | H | Me | H | H | H | 1-(R)-1-(2,4-dichlorobenzyl)-4-(methylamino)but-2-yl | H |
| 114. | H | Me | H | H | H | 1-(R)-1-(2,4-dichlorobenzyl)-4-(dimethylamino)but-2-yl | H |
| 115. | H | Me | H | H | H | 1-(S)-1-(2,4-dichlorobenzyl)-4-(methylamino)but-2-yl | H |
| 116. | H | Me | H | H | H | 1-(S)-1-(2,4-dichlorobenzyl)-4-(dimethylamino)but-2-yl 1 | H |
| 117. | H | Me | H | H | H | 1-(R)-1-(2,4-dichlorobenzyl)-4-amino but-2-yl | H |
| 118. | H | Me | H | H | H | 1-(S)-1-(2,4-dichlorobenzyl)-4-amino but-2-yl | H |
| 119. | H | Me | H | H | H | 4-chloro-1,3-benzothiazol-2-yl | 2-NH₂Et |
| 120. | H | Me | H | H | H | 1-(1-aminoethyl)-4-chloro-1H-benzoimidazol-2-yl | H |
| 121. | H | Me | H | H | H | 1-(S)-aminomethyl-2-(2,4-dichlorophenyl)eth-1-yl | H |
| 122. | H | Me | H | H | H | 1-(R)-aminomethyl-2-(2,4-dichlorophenyl)eth-1-yl | H |
| 123. | H | Me | H | H | H | 1-(S)-dimethylamino-2-(2,4-dichlorophenyl)eth-1-yl | H |
| 124. | H | H | H | H | H | 1-(S)-dimethylamino-2-(2,4-dichlorophenyl)eth-1-yl | H |
| 125. | H | Me | H | H | H | 4-chlorobenzothiazol-2-yl | Me |
| 126. | H | Me | H | H | H | 4,6-difluorobenzothiazol-2-yl | H |
| 127. | H | H | H | H | H | 4,6-difluorobenzothiazol-2-yl | H |
| 128. | H | H | H | H | H | 1-aminopropyl-4-chlorobenzoimidazol-2-yl | H |
| 129. | H | Me | H | H | H | 1-aminoethyl-4-methoxybenzoimidazol-2-yl | H |
| 130. | H | H | H | H | H | 1-aminoethyl-4-methoxybenzoimidazol-2-yl | H |
| 131. | H | Me | H | H | H | quinolin-2-yl | H |
| 132. | H | H | H | H | H | 4-methoxybenzothiazol-2-yl | H |
| 133. | H | Me | H | H | NH₂ | 1-(S)-dimethylaminomethyl-(2,4-dichlorophenyl)eth-1-yl | H |
| 134. | H | Me | H | H | OMe | 1-(S)-dimethylaminomethyl-2-(2,4-dichlorophenyl)eth-1-yl | H |
| 135. | H | H | H | H | H | 4-methoxybenzothiazol-2-yl | H |
| 136. | H | Me | H | H | NH₂ | 4-chlorobenzothiazol-2-yl | H |
| 137. | H | Me | H | H | H | 1-hydroxymethyl-2-methylprop-1-yl | H |
| 138. | H | Me | H | H | H | 1-methyl-2-hydroxyeth-1-yl | H |
| 139. | H | Me | H | H | H | 2-dimethylaminoeth-1-yl | H |
| 140. | H | Me | H | H | H | 2-aminoeth-1-yl | H |
| 141. | H | Me | H | H | H | pyrrolidin-3-yl | H |
| 142. | H | Me | H | H | H | pyrimidin-3-yl | H |
| 143. | H | Me | H | H | H | 2-(S)-amino-3-(indol-3-yl)prop-1-yl | H |
| 144. | H | Me | H | H | H | 1-(S)-aminomethyl-2-(indol-3-yl)eth-1-yl | H |
| 145. | H | Me | H | H | H | 2-(2,4-dichlorophenyl)eth-1-yl | H* |
| 146. | H | Me | H | R⁴/R⁶ together with the thiophene and the carboxamide = thieno[3,2-d]pyrimidin-4-one | H | 2-(2,4-dichlorophenyl)eth-1-yl | — |

TABLE 1-continued

| No | R⁵ | R | R¹ | R² | R⁴ | R³ | R⁶ |
|---|---|---|---|---|---|---|---|
| 147. | H | H | H | R⁴/R⁶ together with the thiophene and the carboxamide = thieno[3,2-d]pyrimidin-4-one | H | 2-(2,4-dichlorophenyl)eth-1-yl | — |
| 148. | H | H | H | H | H | 1-(2-aminoethyl)-4-chloro-1H-benzimidazol-2-yl | H |
| 149. | H | Me | H | H | H | 1-(3-aminopropyl)-4-chloro-1H-benzimidazol-2-yl | H |
| 150. | H | Me | H | H | H | 1-ethyl-4-chloro-1H-benzimidazol-2-yl | H |
| 151. | H | Me | H | H | H | 1-(3,3-dimethylbutyl)-4-chloro-1H-benzimidazol-2-yl | H |
| 152. | H | Me | H | NH₂ | H | 2-(2,4-dichlorophenyl)eth-1-yl | H |
| 153. | H | Me | H | H | H | 1-(2-methylpropyl)-4-chloro-1H-benzimidazol-2-yl | H |
| 154. | H | Me | H | H | H | 1-(2-aminoethyl)-4-methoxy-1H-benzimidazol-2-yl | H |
| 155. | H | H | H | H | H | 1-(2-aminoethyl)-4-methoxy-1H-benzimidazol-2-yl | H |
| 156. | H | Me | H | H | H | 1-(2-aminoethyl)-4-phenyl-1H-benzimidazol-2-yl | H |
| 157. | H | H | H | H | H | 1-(2-aminoethyl)-4-phenyl-1H-benzimidazol-2-yl | H |
| 158. | H | H | H | H | H | 4-hydroxy-benzothiazol-4-yl | H |
| 159. | H | Me | H | H | H | 2-fluoro-6-aminobenzyl | H |
| 160. | H | Me | H | OH | H | 1-dimethylamino-3-(2,4-dichlorophenyl)prop-2-yl | H |
| 161. | H | Me | H | OMe | H | 1-(S)-aminomethyl-2-(1H-indol-3yl)eth-1-yl | H |
| 162. | H | Me | H | H | H | 1-benzylpyrrolidin-3-yl | H |
| 163. | H | Me | H | OCH₂Ph | H | 1-dimethylamino-3-(2,4-dichlorophenyl)prop-2-yl | H |
| 164. | H | Me | H | H | H | 4-chloro-6-aminomethylbenzothiazol-2-yl | H |
| 165. | H | H | H | H | H | 4-chloro-6-aminomethylbenzothiazol-2-yl | H |
| 166. | H | Me | H | H | H | 4-chloro-6-methylaminomethyl-benzothiazol-2-yl | H |
| 167. | H | H | H | H | H | 4-chloro-6-hydroxymethyl-benzothiazol-2-yl | H |
| 168. | H | Me | H | H | H | 4-chloro-7-hydroxymethyl-benzothiazol-2-yl | H |
| 169. | H | Me | H | H | H | 6-aminomethyl-benzothiazol-2-yl | H |
| 170. | H | H | H | H | H | 6-aminomethyl-benzothiazol-2-yl | H |
| 171. | H | Me | H | H | H | H | H |
| 172. | H | H | H | H | H | H | H |
| 173. | H | Me | H | H | H | 4-methyl-6-aminomethyl-benzothiazol-2-yl | H |
| 174. | H | Me | H | H | H | 4-chloro-7-aminomethyl-benzothiazol-2-yl | H |
| 175. | H | Me | H | H | H | 4-bromobenzothiazol-2-yl | H |
| 176. | H | Me | H | H | H | 4-chloro-6-N-morpholinomethyl-benzothiazol-2-yl | H |
| 177. | H | H | H | H | H | 4-chloro-6-N-morpholinomethyl-benzothiazol-2-yl | H |

TABLE 1-continued

| No | R⁵ | R | R¹ | R² | R⁴ | R³ | R⁶ |
|---|---|---|---|---|---|---|---|
| 178. | H | Me | H | H | H | 4-phenylthiazol-2-yl | H |
| 179. | H | H | H | H | H | 4-phenylthiazol-2-yl | H |
| 180. | H | Me | H | H | H | 5-chlorobenzothiazol-2-yl | H |
| 181. | H | Me | H | H | H | 4-(3-chlorophenyl)thiazol-2-yl | H |
| 182. | H | Me | H | H | H | 4-(4-methoxyphenyl)thiazol-2-yl | H |
| 183. | H | Me | H | H | H | 4-(3,4-difluorophenyl)thiazol-2-yl | H |
| 184. | H | Me | H | H | H | 5-(3-bromo-4-methoxyphenyl)thiazol-2-yl | H |
| 185. | H | H | H | H | H | 5-chlorobenzothiazol-2-yl | H |
| 186. | H | H | H | H | H | 4-(3-chlorophenyl)thiazol-2-yl | H |
| 187. | H | H | H | H | H | 4-(4-methoxyphenyl)thiazol-2-yl | H |
| 188. | H | H | H | H | H | 4-(3,4-difluorophenyl)thiazol-2-yl | H |
| 189. | H | H | H | H | H | 5-(3-bromo-4-methoxyphenyl)thiazol-2-yl | H |
| 190. | H | Me | H | H | H | 4-(2-chlorophenyl)thiazol-2-yl | H |
| 191. | H | H | H | H | H | 4-(2-chlorophenyl)thiazol-2-yl | H |
| 192. | H | Me | H | H | H | 4-chloro-6-(dimethylaminomethyl)-benzothiazol-2-yl | H |
| 193. | H | H | H | H | H | 4-chloro-6-(dimethylaminomethyl)-benzothiazol-2-yl | H |
| 194. | H | H | H | H | H | 4-bromobenzothiazol-2-yl | H |
| 195. | H | H | H | H | H | 4-fluorobenzothiazol-2-yl | H |
| 196. | H | H | H | H | H | 4,6-dichlorobenzothiazol-2-yl | H |
| 197. | H | H | H | H | H | 7-chlorobenzothiazol-2-yl | H |
| 198. | H | H | H | H | H | 4-chloro-6-(2-aminoethyl)benzothiazol-2-yl | H |
| 199. | H | H | H | H | H | 4-chloro-6-(2-nitroethyl)benzothiazol-2-yl | H |
| 200. | H | Me | H | H | H | 4-(pyridin-2-yl)thiazol-2-yl | H |
| 201. | H | H | H | H | H | 4-(pyridin-2-yl)thiazol-2-yl | H |
| 202. | H | Me | H | H | H | 4-(pyridin-3-yl)thiazol-2-yl | H |
| 203. | H | H | H | H | H | 4-(pyridin-3-yl)thiazol-2-yl | H |
| 204. | H | Me | H | H | H | 4-chloro-6-(2-aminoethyl)benzothiazol-2-yl | H |
| 205. | H | Me | H | H | H | 4-chloro-6-(2-nitroethyl)benzothiazol-2-yl | H |
| 206. | H | Me | H | H | H | 4-chloro-6-(methylaminocarbonyl)benzothiazol-2-yl | H |
| 207. | H | Me | H | H | H | 4-chloro-6-[(2-amino)ethylaminocarbonyl]benzothiazol-2-yl | H |
| 208. | H | H | H | H | H | 4-chloro-6-[(2-amino)ethylaminocarbonyl]benzothiazol-2-yl | H |
| 209. | H | Me | H | H | H | 4-chloro-6-(methylaminomethyl)benzothiazol-2-yl | H |
| 210. | H | H | H | H | H | 4-chloro-6-(methylaminomethyl)benzothiazol-2-yl | H |
| 211. | H | Me | H | H | H | 4-chloro-5-methylcarboxyl-benzothiazol-2-yl | H |
| 212. | H | H | H | H | H | 4-chloro-5-methylcarboxyl-benzothiazol-2-yl | H |
| 213. | H | Me | H | H | H | 4-chloro-6-methylthiazol-2-yl | H |
| 214. | H | H | H | H | H | 4-chloro-6-methylthiazol-2-yl | H |
| 215. | H | H | H | H | H | 4-chlorobenzoxazol-2-yl | H |
| 216. | H | H | H | H | H | 4-chloro-[2-(S)-2-(aminopropanoyl)aminomethyl]benzothiazol-2-yl | H |

TABLE 1-continued

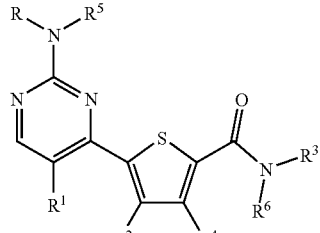

| No | R⁵ | R | R¹ | R² | R⁴ | R³ | R⁶ |
|---|---|---|---|---|---|---|---|
| 217. | H | Me | H | H | H | 4-bromo-6-(aminomethyl)benzothiazol-2-yl | H |
| 218. | H | Me | H | H | H | 4-methoxy-6-(methylaminomethyl)benzothiazol-1-yl | H |
| 219. | H | H | H | H | H | 4-methoxy-6-(methylaminomethyl)benzothiazol-1-yl | H |
| 220. | H | Me | H | H | H | 4-chlorobenzoxazol-2-yl | H |
| 221. | H | H | H | H | H | 4-chloro-6-({[2-(S)-2-amino-3-phenylpropanoyl]amino}methyl)benzothiazol-2-yl | H |
| 222. | H | H | H | H | H | 4-chloro-6-{[(aminomethylcarbonyl)amino]methyl}benzothiaozl-2-yl | H |
| 223. | H | H | H | H | H | 4-chloro-6-(methylcarbonylaminomethyl)benzothiazol-2-yl | H |
| 224. | H | Me | H | H | H | 4-(trifluoromethyl)-6-(aminomethyl)benzothiazol-2-yl | H |
| 225. | H | H | H | H | H | 4-(trifluoromethyl)-6-(aminomethyl)benzothiazol-2-yl | H |
| 226. | H | Me | H | H | H | 4-(trifluoromethoxy)-6-(aminomethyl)benzothiazol-2-yl | H |
| 227. | H | H | H | H | H | 4-(trifluoromethoxy)-6-(aminomethyl)benzothiazol-2-yl | H |
| 228. | H | Me | H | H | H | 4-chloro-6-(trifluoromethyl)-6-benzothiazol-2-yl | H |
| 229. | H | H | H | H | H | 4-chloro-6-(trifluoromethyl)-6-benzothiazol-2-yl | H |
| 230. | H | Me | H | H | H | 4-chloro-6-(trifluoromethoxy)benzothiazol-2-yl | H |
| 231. | H | H | H | H | H | 4-chloro-6-(trifluoromethoxy)benzothiazol-2-yl | H |
| 232. | H | H | H | H | H | 4-bromo-6-(aminomethyl)benzothiazol-2-yl | H |
| 233. | H | Me | H | H | H | 4-bromo-6-isopropyl-benzothiazol-2-yl | H |
| 234. | H | H | H | H | H | 4-bromo-6-isopropyl-benzothiazol-2-yl | H |
| 235. | H | H | H | H | H | 4-(aminomethyl)benzothiazol-2-yl | H |
| 236. | H | Me | H | H | H | 4-(aminomethyl)benzothiazol-2-yl | H |
| 237. | H | H | H | H | H | 6-aminomethyl-8-chloroquinolin-2-yl | H |
| 238. | H | H | H | OMe | H | 1-(S)-aminomethyl-2-(2,4-dichlorophenyl)eth-1-yl | H |
| 239. | H | Me | H | H | H | 2,2-dimethyl-5-benzyltetrahydropyran-4-yl | H |
| 240. | H | Me | Me | H | H | 2-(4-fluorophenyl)eth-1-yl | H |
| 241. | H | NO₂ | H | H | H | 2-(4-fluorophenyl)eth-1-yl | H |
| 242. | H | Ph | H | H | H | 2-(4-fluorophenyl)eth-1-yl | H |
| 243. | H | C(O)OMe | H | H | H | 2-(4-fluorophenyl)eth-1-yl | H |
| 244. | H | C(O)N(Me)₂ | H | H | H | 2-(4-fluorophenyl)eth-1-yl | H |
| 245. | H | C(O)NH(Me) | H | H | H | 2-(4-fluorophenyl)eth-1-yl | H |
| 246. | H | C(O)Me | H | H | H | 2-(4-fluorophenyl)eth-1-yl | H |
| 247. | H | Me | H | H | H | 2-(4-methylphenyl)eth-1-yl | H |
| 248. | H | Me | H | H | H | 2-(4-ethylphenyl)eth-1-yl | H |
| 249. | H | Me | H | H | H | 2-(4-methoxyphenyl)eth-1-yl | H |
| 250. | H | Me | H | H | H | 2-(4-biphenyl)eth-1-yl | H |
| 251. | H | Me | H | H | H | 2-(4-ethoxyphenyl)eth-1-yl | H |
| 252. | H | Me | H | H | H | 2-(4-phenoxyphenyl)eth-1-yl | H |
| 253. | H | Me | H | H | H | 2-(2,5-dimethoxyphenyl)eth-1-yl | H |

TABLE 1-continued

| No | R⁵ | R | R¹ | R² | R⁴ | R³ | R⁶ |
|---|---|---|---|---|---|---|---|
| 254. | H | Me | H | H | H | 2-(3,4-dimethoxyphenyl)eth-1-yl | H |
| 255. | Me | Me | H | H | H | 2-(4-fluorophenyl)eth-1-yl | H |
| 256. | H | Me | H | H | H | 4-fluorophenyl | H |
| 257. | Me | Me | H | H | H | 2-(2,4-dichlorophenyl)eth-1-yl | H |
| 258. | H | C(O)NH₂ | H | H | H | 2-(2,4-dichlorophenyl)eth-1-yl | H |
| 259. | H | propyl | H | H | H | 2-(2,4-dichlorophenyl)eth-1-yl | H |
| 260. | H | butyl | H | H | H | 2-(2,4-dichlorophenyl)eth-1-yl | H |
| 261. | H | cyclopropylmethyl | H | H | H | 2-(2,4-dichlorophenyl)eth-1-yl | H |
| 262. | H | benzyl | H | H | H | 2-(2,4-dichlorophenyl)eth-1-yl | H |
| 263. | H | cyclopentyl | H | H | H | 2-(2,4-dichlorophenyl)eth-1-yl | H |
| 264. | H | 2-(N-morpholino)eth-1-yl | H | H | H | 2-(2,4-dichlorophenyl)eth-1-yl | H |
| 265. | H | 3-(N-morpholino)prop-1-yl | H | H | H | 2-(2,4-dichlorophenyl)eth-1-yl | H |
| 266. | H | 3-(N-methylpiperazin-N'-yl)prop-1-yl | H | H | H | 2-(2,4-dichlorophenyl)eth-1-yl | H |
| 267. | H | 2-(piperidin-N-yl)eth-1-yl | H | H | H | 2-(2,4-dichlorophenyl)eth-1-yl | H |
| 268. | H | 2-phenyleth-1-yl | H | H | H | 2-(2,4-dichlorophenyl)eth-1-yl | H |
| 269. | H | Me | H | H | H | benzoimidazol-2-yl | H |
| 270. | H | Me | H | H | H | benzothiazol-2-yl | H |
| 271. | H | Me | H | H | H | 6-chlorobenzothiazol-2-yl | H |
| 272. | H | Me | H | H | H | 6-fluorobenzothiazol-2-yl | H |
| 273. | H | Me | H | H | H | benzothiazol-6-yl | H |
| 274. | H | Me | H | H | H | quinolin-3-yl | H |
| 275. | H | Me | H | H | H | quinolin-6-yl | H |
| 276. | H | Me | H | H | H | 5-(2-bromothiophen-5-yl)thiazol-2-yl | H |
| 277. | H | Me | H | H | H | pyridin-2-ylmethyl | H |
| 278. | H | Me | H | H | H | pyridin-3-ylmethyl | H |
| 279. | H | Me | H | H | H | pyridin-4-ylmethyl | H |
| 280. | H | Me | H | H | H | 2-(pyridin-2-yl)eth-1-yl | H |
| 281. | H | Me | H | H | H | 2-(pyridin-4-yl)eth-1-yl | H |
| 282. | H | Me | H | H | H | 2-(piperidin-1-yl)eth-1-yl | H |
| 283. | H | Me | H | H | H | 2-(N-methylpiperazin-N'-yl)eth-1-yl | H |
| 284. | H | Me | H | H | H | 2-(N-morpholino)eth-1-yl | H |
| 285. | H | Me | H | H | H | 3-(pyrrol-N-yl)prop-1-yl | H |
| 286. | H | aminocarbonyl | H | H | H | 2-(4-fluorophenyl)eth-1-yl | H |
| 287. | H | 2-aminoeth-1-yl | H | H | H | 2-(2,4-dichlorophenyl)eth-1-yl | H |
| 288. | H | 3-aminoprop-1-yl | H | H | H | 2-(2,4-dichloropenyl)eth-1-yl | H |
| 289. | H | 3-aminobut-1-yl | H | H | H | 2-(2,4-dichlorophenyl)eth-1-yl | H |
| 290. | H | 5-carboxy-4-(R,S)-aminopent-1-yl | H | H | H | 2-(2,4-dichlorophenyl)eth-1-yl | H |
| 291. | H | pyridin-4-yl | H | H | H | 2-(2,4-dichlorophenyl)eth-1-yl | H |
| 292. | H | 2-(S)-phenylcyclopropyl | H | H | H | 2-(2,4-dichlorophenyl)eth-1-yl | H |
| 293. | H | pyridin-2-ylmethyl | H | H | H | 2-(2,4-dichlorophenyl)eth-1-yl | H |
| 294. | H | pyridin-3-ylmethyl | H | H | H | 2-(2,4-dichlorophenyl)eth-1-yl | H |
| 295. | H | pyridin-4-ylmethyl | H | H | H | 2-(2,4-dichlorophenyl)eth-1-yl | H |
| 296. | H | 2-(pyridin-2-yl)eth-1-yl | H | H | H | 2-(2,4-dichlorophenyl)eth-1-yl | H |
| 297. | H | 2-(pyridin-3-yl)eth-1-yl | H | H | H | 2-(2,4-dichlorophenyl)eth-1-yl | H |
| 298. | H | 2-(pyridin-4-yl)eth-1-yl | H | H | H | 2-(2,4-dichlorophenyl)eth-1-yl | H |
| 299. | H | 2-spirocyclopropyl-2-(4-chlorophenyl)eth-1-yl | H | H | H | 2-(2,4-dichlorophenyl)eth-1-yl | H |
| 300. | H | 2-(N-methylpyrrol-2-yl)eth-1-yl | H | H | H | 2-(2,4-dichlorophenyl)eth-1-yl | H |

TABLE 1-continued

| No | R⁵ | R | R¹ | R² | R⁴ | R³ | R⁶ |
|---|---|---|---|---|---|---|---|
| 301. | H | 2-(N-methylpiperazin-N'-yl)eth-1-yl | H | H | H | 2-(2,4-dichlorophenyl)eth-1-yl | H |
| 302. | H | 3-(imidazol-N-yl)prop-1-yl | H | H | H | 2-(2,4-dichlorophenyl)eth-1-yl | H |
| 303. | H | Me | H | H | H | 1-(R,S)-phenyl-2-phenyleth-1-yl | H |
| 304. | H | Me | H | H | H | 2,2-diphenyleth-1-yl | H |
| 305. | H | Me-NHC(O) | H | H | H | 2-(2,4-dichlorophenyl)eth-1-yl | H |
| 306. | H | Et-NHC(O) | H | H | H | 2-(2,4-dichlorophenyl)eth-1-yl | H |
| 307. | H | propyl-NHC(O) | H | H | H | 2-(2,4-dichlorophenyl)eth-1-yl | H |
| 308. | H | H | H | H | H | 2-(piperidin-3-yl)eth-1-yl | H |
| 309. | H | phenyl-NHC(O) | H | H | H | 2-(2,4-dichlorophenyl)eth-1-yl | H |
| 310. | H | benzyl-NHC(O) | H | H | H | 2-(2,4-dichlorophenyl)eth-1-yl | H |
| 311. | H | H | H | H | H | 4-aminobenzyl | H |
| 312. | H | H | H | H | H | 4-dimethylaminobenzyl | H |
| 313. | H | H | H | H | H | 2-(4-aminophenyl)eth-1-yl | H |
| 314. | H | H | H | H | H | benzoimidazol-2-yl | H |
| 315. | H | H | H | H | H | 1-methylbenzoimidazol-2-yl | H |
| 316. | H | Me | H | H | H | 2-(R)-hydroxyindan-1-yl | H |
| 317. | H | Me | H | H | H | indan-1-yl | H |
| 318. | H | Me | H | H | H | 1,2,3,4-tetrahydronaphthalen-1-yl | H |
| 319. | H | Me | H | H | H | 1-phenyl-1-(4-chlorophenyl)methyl | H |
| 320. | H | H | H | H | H | 2-(trifluoromethyl)-4-fluorophenylmethyl | H |
| 321. | H | H | H | H | H | benzoimidazol-2-yl | H |
| 322. | H | H | H | H | H | benzothiophen-2-yl | H |
| 323. | H | Me | H | H | H | 5-chlorobenzoimidazol-2-yl | H |
| 324. | H | H | H | H | H | 1-methyl-4-chlorobenzoimidazol-2-yl | H |
| 325. | H | Me | H | H | H | 1-methyl-4-chlorobenzoimidazol-2-yl | H |
| 326. | H | H | H | H | H | 1-ethyl-4-chlorobenzoimidazol-2-yl | H |
| 327. | H | H | H | H | H | 1-(3,3-dimethylbutyl)-4-chlorobenzoimidazol-2-yl | H |
| 328. | H | H | H | H | H | 1-isobutyl-4-chlorobenzoimidazol-2-yl | H |
| 329. | H | Me | H | H | H | 4-hydroxybenzothiazol-2-yl | H |
| 330. | H | Me | H | H | H | 2-piperidin-N-ylbenzyl | H |
| 331. | H | Me | H | H | OMe | 4-chlorobenzothiazol-2-yl | H |
| 332. | H | Me | H | H | OH | 4-chlorobenzothiazol-2-yl | H |
| 333. | H | Me | H | H | OEtNH₂ | 4-chlorobenzothiazol-2-yl | H |

*Compound 108 is a 2,4-thiophene.
*Compound 145 contains a 1,3,5-triazine in place of the pyrimidine.

TABLE 2

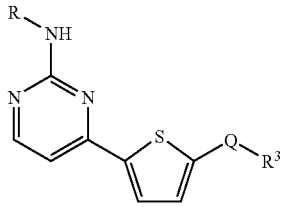

| No. | R | Q | R³ |
|---|---|---|---|
| 334. | Me | —NHC(O)— | 2-(4-fluorophenyl)eth-1-yl |
| 335. | Me | —NHC(O)— | 2-(2,4-dichlorophenyl)eth-1-yl |
| 336. | H | —NHC(O)— | 2-(2,4-dichlorophenyl)eth-1-yl |
| 337. | Me | —NHC(O)O— | benzyl |
| 338. | Me | —NHC(O)O— | 4-fluorobenzyl |
| 339. | Me | —NHC(O)O— | -2-(R)-amino-3-(indol-3-yl)prop-1-yl |
| 340. | Me | —NHC(O)O— | -2-(S)-amino-3-(indol-3-yl)prop-1-yl |
| 341. | Me | —NHC(O)NH— | 4-fluorobenzyl |
| 342. | Me | —NHC(O)NH— | 2,4-dichlorobenzyl |
| 343. | Me | —CH₂NH— | 2-(4-fluorophenyl)eth-1-yl |
| 344. | Me | —CH₂NH— | 2-(4-chlorophenyl)eth-1-yl |
| 345. | Me | —CH₂NH— | 2-(2,4-dichlorophenyl)eth-1-yl |
| 346. | H | —CH₂NH— | 2-(4-chlorophenyl)eth-1-yl |
| 347. | Me | —CH₂NH— | 4-chlorobenzothiazol-2-yl |
| 348. | H | —CH₂NH— | 4-chlorobenzothiazol-2-yl |

TABLE 2-continued

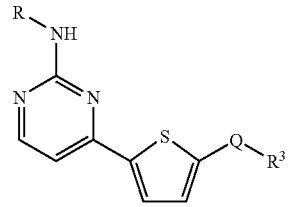

| No. | R | Q | R³ |
|---|---|---|---|
| 349. | Me | —SO₂NH— | 2-(4-fluorophenyl)eth-1-yl |
| 350. | Me | —SO₂NH— | 2-(4-chlorophenyl)eth-1-yl |
| 351. | Me | —SO₂NH— | 2-(2,4-dichlorophenyl)eth-1-yl |
| 352. | Me | —SO₂NH— | 4-fluorophenylmethyl |
| 353. | Me | —SO₂NH— | 2,4-dichlorophenylmethyl |
| 354. | H | —SO₂NH— | 2-(4-fluorophenyl)eth-1-yl |
| 355. | H | —SO₂NH— | 2-(2,4-dicholorophenyl)eth-1-yl |
| 356. | H | —SO₂NH— | 4-fluorophenylmethyl |
| 357. | H | —SO₂NH— | 2,4-dichiorophenylmethyl |
| 358. | Me | —C(O)O— | 2-aminobenzothiazol-4-yl |
| 359. | H | —C(O)O— | 2-aminobenzothiazol-4-yl |
| 360. | H | —CH═CH— | 4-chlorobenzothiazol-2-yl |
| 361. | H | —C≡C— | 4-chlorobenzothiazol-2-yl |

TABLE 3

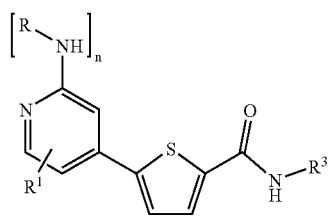

| No. | n | R | R¹ | R³ |
|---|---|---|---|---|
| 362. | 1 | Me | H | 2-(4-fluorophenyl)eth-1-yl |
| 363. | 1 | Me | H | 2-(2,4-dichlorophenyl)eth-1-yl |
| 364. | 1 | 2-(methylamino)eth-1-yl | H | 2-(4-fluorophenyl)eth-1-yl |
| 365. | 1 | C(O)Me | H | 1-(S)-aminomethyl-2-(2,4-dichlorophenyl)eth-1-yl |
| 366. | 0 | — | H | 2-(4-fluorophenyl)eth-1-yl |
| 367. | 0 | — | 2-NH₂C(O)— | 2-(4-fluorophenyl)eth-1-yl |
| 368. | 0 | — | H | 1-(S)-aminomethyl-2-(2,4-dichlorophenyl)eth-1-yl |

TABLE 4

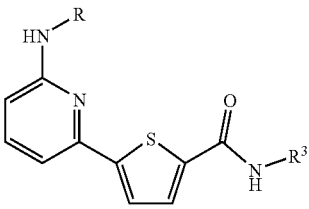

| No. | R | R³ |
|---|---|---|
| 369. | Me | 2-(4-fluorophenyl)eth-1-yl |

TABLE 5

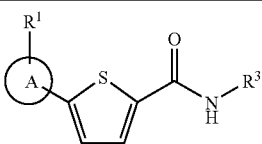

| No. | A and R¹ | R³ |
|---|---|---|
| 370. | 1H-pyrazol-3-yl | 2-(4-fluorophenyl)eth-1-yl |
| 371. | 1H-pyrazol-4-yl | 1-(S)-aminomethyl-2-(2,4-dichlorophenyl)eth-1-yl |
| 372. | 1H-2-amino-imidazol-4-yl | 1-(S)-aminomethyl-2-(2,4-dichlorophenyl)eth-1-yl |
| 373. | 2-methylcarbonylamino-1H-imidazol-4-yl | 1-(S)-aminomethyl-2-(2,4-dichlorophenyl)eth-1-yl |
| 374. | pyrimidin-4-yl | 2-(2,4-dichlorophenyl)eth-1-yl |

Specific compounds within the scope of this invention may be found in Table 6 in the Example section.

DETAILED DESCRIPTION OF THE INVENTION

Definitions and Overview

As discussed above, the present invention is directed to new substituted five-membered heterocyclic compounds.

It is also to be understood that the terminology used herein is for the purpose of describing particular embodiments only and is not intended to limit the scope of the present invention. It must be noted that as used herein and in the claims, the singular forms "a," "and" and "the" include plural referents unless the context clearly dictates otherwise. In this specification and in the claims which follow, reference will be made to a number of terms which shall be defined to have the following meanings:

Unless otherwise defined herein, the following terms have the following meanings.

The term "alkyl" refers to monovalent saturated aliphatic hydrocarbyl groups having from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, spirocycloalkyl, heteroaryl, substituted heteroaryl, heterocyclic, and substituted heterocyclic.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) and the like.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NR¹⁰R¹⁰ where each $R^{10}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each $R^{10}$ is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to an acetylene (unsaturated) carbon atom.

"Amino" refers to the group —$NH_2$.

"Cyano" refers to the group —CN.

"Substituted amino" refers to the group —$NR^{10}R^{10}$ where each $R^{10}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each $R^{10}$ are joined, together with the nitrogen bound thereto to form a heterocyclic or substituted heterocyclic group provided that both $R^{10}$ are not hydrogen. When $R^{10}$ is hydrogen and the other $R^{10}$ is alkyl, the substituted amino group is sometimes referred to herein as alkylamino. When both of $R^{10}$ are alkyl, the substituted amino group is sometimes referred to herein as dialkylamino. When referring to a monosubstituted amino, it is meant that either $R^{10}$ is hydrogen but not both. When referring to a disubstituted amino, it is meant that neither $R^{10}$ is hydrogen.

"Aminoacyl" refers to the groups —$NR^{11}C(O)$alkyl, —$NR^{11}C(O)$substituted alkyl, —$NR^{11}C(O)$cycloalkyl, —$NR^{11}C(O)$substituted cycloalkyl, —$NR^{11}C(O)$alkenyl, —$NR^{11}C(O)$substituted alkenyl, —$NR^{11}C(O)$alkynyl, —$NR^{11}C(O)$substituted alkynyl, —$NR^{11}C(O)$aryl, —$NR^{11}C(O)$substituted aryl, —$NR^{11}C(O)$heteroaryl, —$NR^{11}C(O)$substituted heteroaryl, —$NR^{11}C(O)$heterocyclic, and —$NR^{11}C(O)$substituted heterocyclic where $R^{11}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Nitro" refers to the group —$NO_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl ($NH_2$—$SO_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Spirocycloalkyl" refers to cyclic groups from 3 to 10 carbon atoms having a cycloalkyl ring with a spiro union (the union formed by a single atom which is the only common member of the rings) as exemplified by the following structure:

"Substituted cycloalkyl" refers to a cycloalkyl, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridinyl, pyrrolyl, indolyl, thiophenyl, and furanyl.

The term "nitrogen-containing heteroaryl" as used herein refers to a heteroaryl group wherein at least one ring atom is a nitrogen and preferably, wherein from 1 to 6 ring atoms are nitrogens. In some embodiments, from 1 to 4 ring atoms are nitrogen.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" or "heterocyclyl" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

It should be noted that when referring to heteroaryl, substituted heteroaryl, heterocyclic, and substituted heterocyclic, any nitrogen or sulfur atoms that might be present may optionally be oxidized.

"Thiol" refers to the group —SH.

"Alkylthio" or "alkylthioether" or "alkoxythio" refers to the group —S-alkyl.

"Substituted alkylthio" or "substituted alkylthioether" or "substituted alkoxythio" refers to the group —S-substituted alkyl.

"Arylthio" refers to the group —S-aryl, where aryl is defined above.

"Substituted arylthio" refers to the group —S-substituted aryl, where substituted aryl is defined above.

"Heteroarylthio" refers to the group —S-heteroaryl, where heteroaryl is as defined above.

"Substituted heteroarylthio" refers to the group —S-substituted heteroaryl, where substituted heteroarylthio is defined above.

"Heterocyclicthio" refers to the group —S-heterocyclic and "substituted heterocyclicthio" refers to the group —S-substituted heterocyclic, where heterocyclic and substituted heterocyclic.

"Heterocyclyloxy" refers to the group heterocyclyl-O— and "substituted heterocyclyl-O— refers to the group substituted heterocyclyl-O— where heterocyclyl and substituted heterocyclyl are as defined above.

"Cycloalkylthio" refers to the group —S-cycloalkyl and "substituted cycloalkylthio" refers to the group —S-substituted cycloalkyl, where cycloalkyl and substituted cycloalkyl are as defined above.

"Biological activity" as used herein refers to an inhibition concentration when tested in at least one of the assays outlined in Examples 22 through 25.

As used herein, the term "pharmaceutically acceptable salts" refers to the nontoxic acid or alkaline earth metal salts of the compounds of formula I. These salts can be prepared in situ during the final isolation and purification of the compounds of formula I, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quatemized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula I, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which may hydrolyze in vivo and include those that break down in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "Recommendations for Section E, Fundamental Stereochemistry," Pure Appl. Chem. 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometric isomers include the cis and trans forms of compounds of the invention having alkenyl or alkenylenyl moieties. The present invention comprises the individual geometrical isomers and stereoisomers and mixtures thereof.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Unless otherwise indicated, the reagents used in the following examples are commercially available and may be purchased, for example, from Sigma-Aldrich Company, Inc. (Milwaukee, Wis., USA).

Compounds of the invention may be synthesized according to Scheme 1 below. Compound 1B may be formed by coupling carboxylic acid 1A with an amine of the formula $NH_2R^3$, under a variety of known amide-forming conditions. Exposure of methyl ketone 1B to 1.5 eq. of dimethylformamide dimethyl acetal in refluxing toluene at 110° C. yields vinylogous amide 1C. The amide 1C may then be further treated at 80° C. for about 16 hours with 2 eq. of the HCl salt of the guanidine of the formula $H_2NC(=NR)NH_2$, under basic conditions with a suitable base such as 2.1 eq. of NaOEt/EtOH to give 5-(2-aminopyrimidin-4-yl)thiophene-2-carboxamides.

Scheme 1
Synthesis of 5-(2-aminopyrimidin-4-yl)
thiophene-2-carboxamides

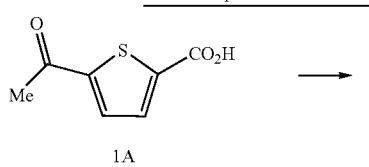

1A

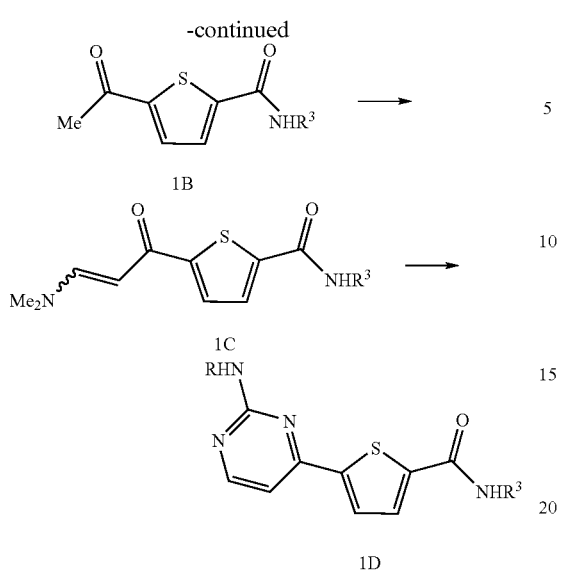

wherein R and R³ are as defined herein

Alternatively, the pyrimidine ring may be functionalized via activated pyrimidine 2B as shown in Scheme 2. Vinylogous amide 1C is condensed in a suitable solvent such as pyridine at 100° C. for 3 days with S-methyl isothiourea hemisulfate (3 eq. of H₂NC(=NH)SMe in 0.5 eq. of H₂SO₄) to form sulfide 2A, that is then oxidized at room temperature for 14 hours to sulfone 2B with 2 eq. of m-chloroperoxybenzoic acid in solvent, such as methylene chloride, and reacted with the appropriate amine of formula RNH₂ in 1,4-dioxane at 110° C. from about 4 to about 14 hours to give 1D.

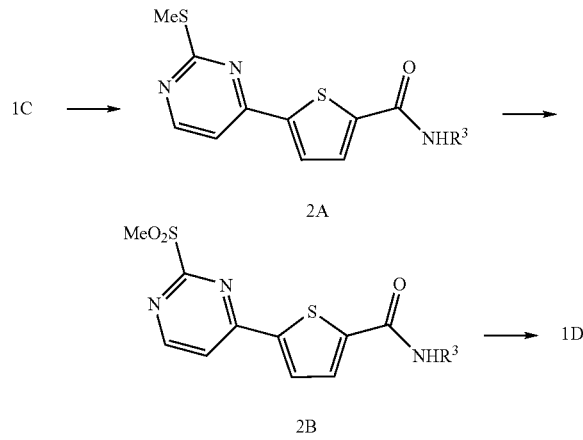

wherein R and R³ are as defined herein

Additionally, compounds of the type 1D may also be synthesized by assembling the pyrimidine ring first followed by introduction of the carboxamide moiety as shown in Scheme 3. 1A is treated with 2.5 eq. of dimethylformamide dimethyl acetal in refluxing toluene at 110° C. for 15 hours which produced 3A. The vinylogous amide 3A is reacted with 2 eq. of the HCl salt of a guanidine of the formula H₂NC(=NR) NH₂ under basic conditions using a suitable base such as NaOEt/EtOH at 70° C. for about 15 hours to form the ethyl ester 3B. The product of the previous reaction is then condensed with the amine NH₂R³ in 0.5 eq. of NaOMe in MeOH at 70° C. for 2 days to give amide 1D.

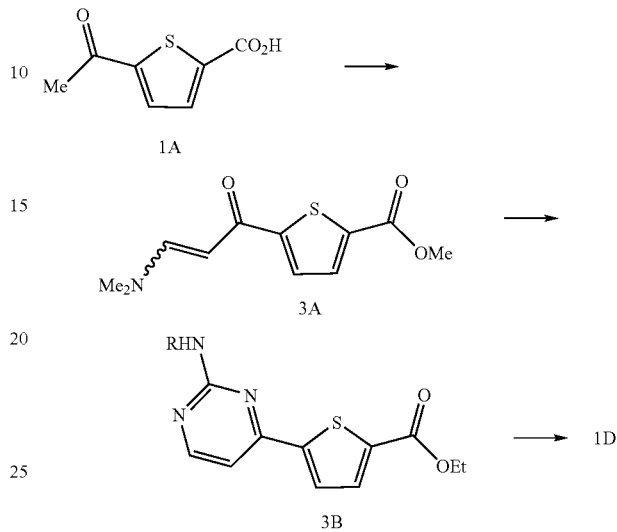

wherein R and R³ are as defined herein

Thiophene carboxamides may also be synthesized as shown in Scheme 4. Bistriflate 4B, formed by reacting 4A with NaH and triflic anhydride in DCM at room temperature for 60 hours. Carboxylic acid 4C is reacted with 1 eq. of carbonyl diimidazole in THF at room temperature for about 12 hours and then coupled with an appropriate amine, NH₂R³ to yield the amide 4D. Suitable amine starting materials include hydroxyl amine, alkyl amine, nitroamine, H₂N—CN, and the like. 1.1 eq. of Bistriflate 4B is coupled to boronic acid 4D via a palladium (0.05 eq. Pd(dppf)₂) catalyzed Suzuki reaction (2 eq. DIEA, THF at 80° C. for 12 hours) to yield triflate 4E. Addition of an amine (5 eq. of RNH₂ or RR'ᵃNH in THF) to 4E under refluxing conditions for about 16 hours gives pyrimidine 4F.

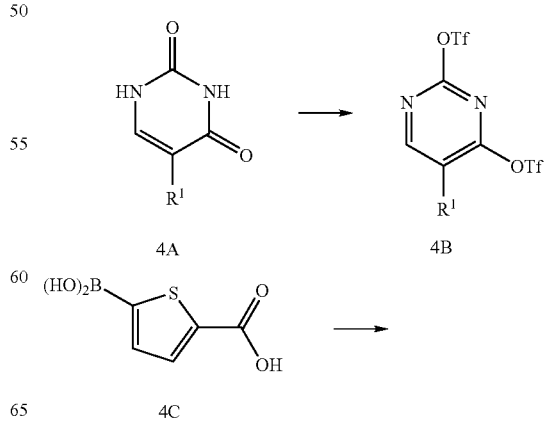

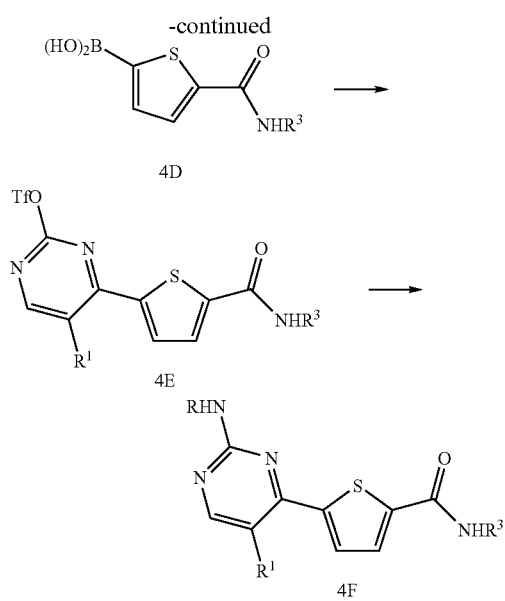

wherein R, R¹, R³ are as defined herein

The palladium mediated coupling to form the pyrimidine-thiophene bond also allows access to pyridinyl substituted thiophenes as shown in Scheme 5, wherein 1 eq. of boronic acid 4D is coupled utilizing a Palladium catalyst, such as Pd(PPh$_3$)$_4$ in 2.6 eq. Na$_2$CO$_3$ (2M aq.) to 2-choloro-4-iodo pyridine, 5A for 18 hours at 70° C. Displacement of the resulting chloride with an excess (5-45 eq.) of the amine, RR$^a$NH in THF at 150° C. for 2 days gives 5-(2-aminopyridin-4-yl)thiophene-2-carboxamides.

Scheme 5
Synthesis of 5-(2-aminopyridin-4-yl)
thiophene-2-carboxamides

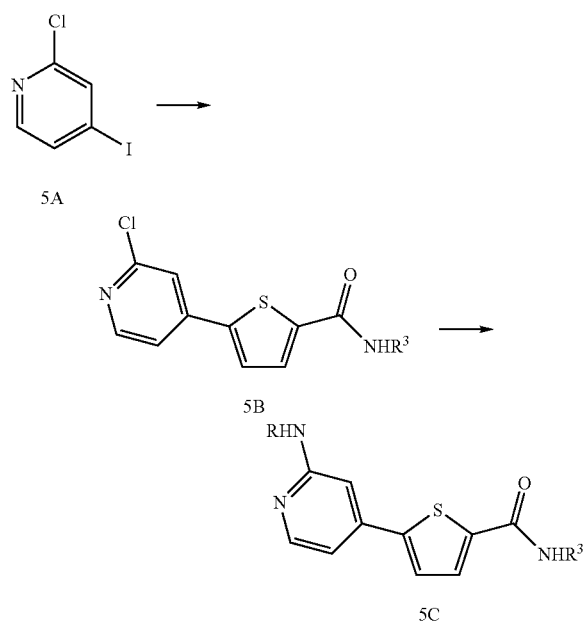

wherein R and R³ are defined herein

Compounds of the invention containing a 4-(5-aminothien-2-yl)pyrimidin-2-amine core may be synthesized as shown in Scheme 6. Ester 6A is treated with 10 eq. of hydrazine in a solvent such as methanol at 70° C. for 16 hours to form acyl hydrazine 6B. The acyl hydrazine is then converted to acyl azide 6C using 1.05 eq. of HCl (0.6 M aq.) and 1 eq. NaNO$_2$ (4.0 M aq.) in acetic acid at 0° C. for 30 min. Compound 6C undergoes a rearrangement when heated to form an isocyanate that may be reacted with an amine (xylenes at 130° C. for 30 minutes, followed by 3 eq. of R³NH$_2$ for 1 hour at 130° C.), alcohol (xylenes at 130° C. for 30 minutes, followed by 3 eq. of R³OH at 130° C. for 1 hour), or acid (6 eq. of HCl 1.5 M aq. at 100° C. for 16 hours) to produce the respective urea 6D, carbamate 6E, or amine 6F. Compound 6F may further be further acylated, such as with R³C(=O)OC(=O)-imidazole to produce amide 6G.

Scheme 6
Synthesis of 4-(5-aminothien-2-yl)
pyrimidin-2-amine derivatives.

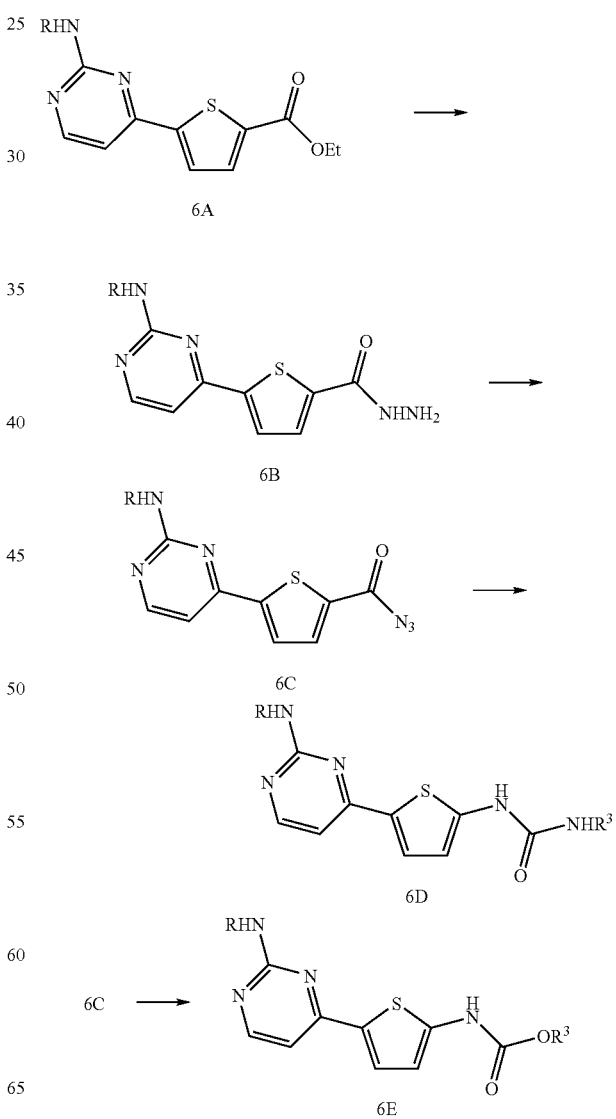

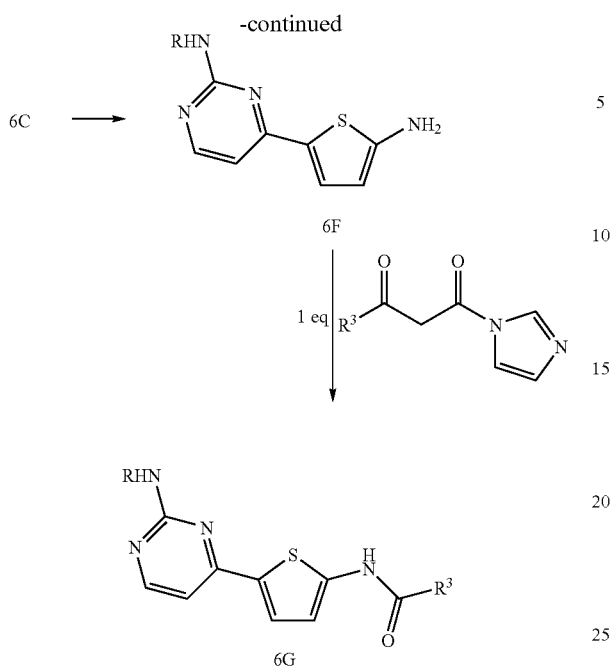

wherein R and R³ are as defined herein

Compounds of the invention containing a 5-(2-aminopyrimidin-4-yl)thiophene-3-carboxamide core may be synthesized as shown in Scheme 7, wherein 3-bromothiophene 7C is lithiated and quenched with carbon dioxide. The resulting acid 7D may further be coupled with an amine to produce the corresponding amide 7E.

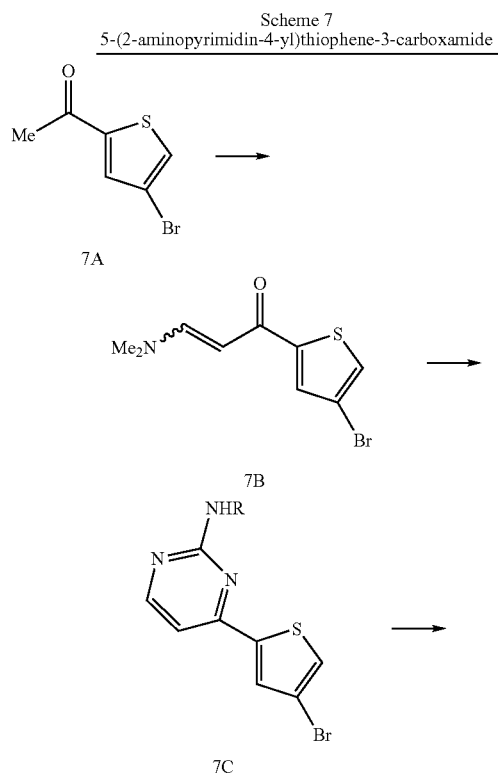

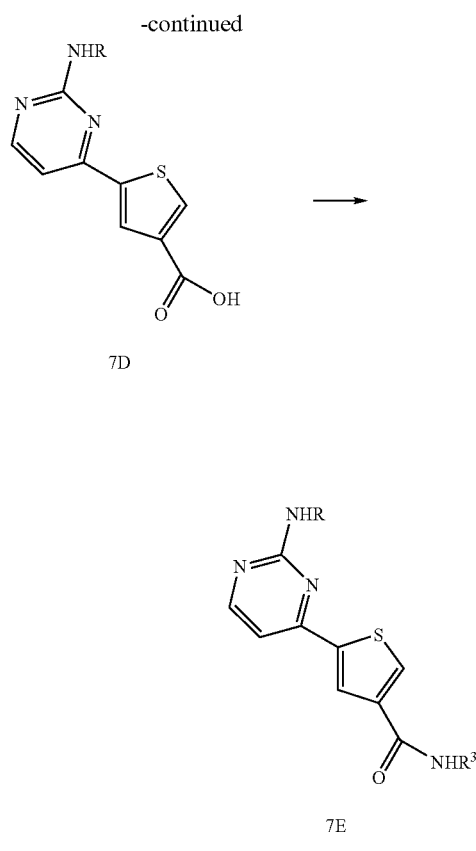

wherein R and R³ are as defined herein

Compounds of the invention containing a 5-(2-aminopyrimidin-4-yl)thiophene-2-aminomethyl core may be synthesized as shown below in Scheme 8. Following functionalization of nucleophile 8A with 2,4-dichloropyrimidine using (PPh₃)Pd(0), in THF at 70° C., the acetal group is removed under acidic conditions and then exposed to an amine to form the corresponding imine via aldehyde 8C. The imine of aldehyde 8C is converted to amine 8D under reductive amination conditions. Displacement of chloride 8D leads to the desired amine 8E.

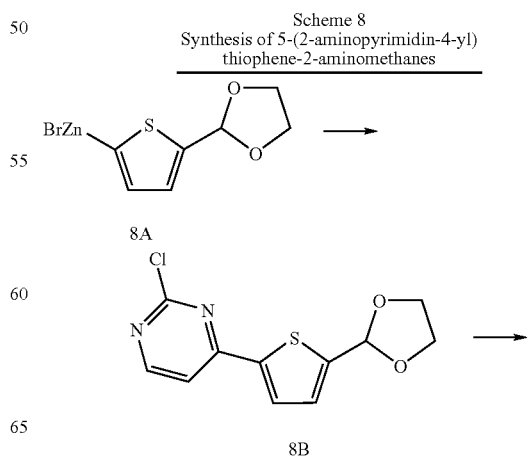

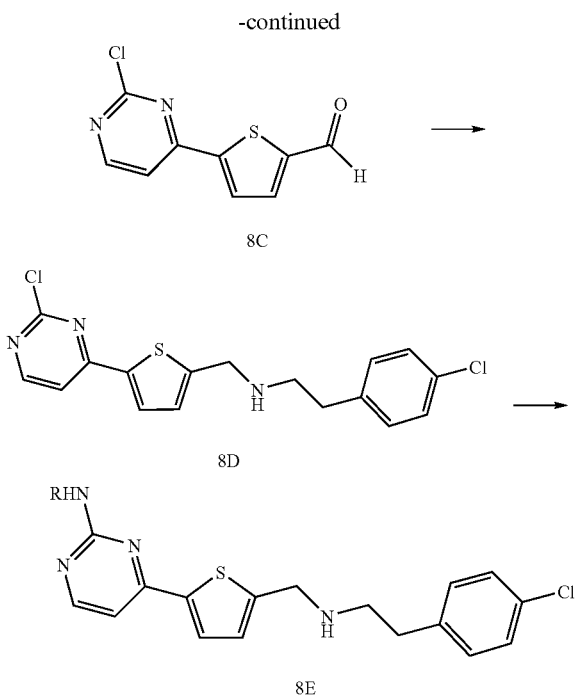

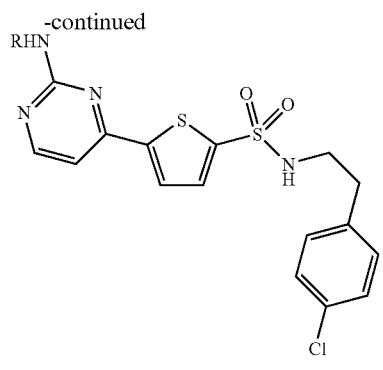

Compounds of the invention containing a 5-(2-aminopyrimidin-4-yl)thiophene-2-sulfonamide core may be synthesized as shown below in Scheme 9. Sulphonyl chloride 9A, commercially available from Maybridge (Maybridge, Trevillett, Tintagel, Cornwall, PL34 OHW, England), is contacted with an amine $R^3NH_2$, where $R^3$=4-chlorophenethyl, followed with oxidation with meta-chloroperoxybenzoic acid to give compound 9B. Displacement of the sulphonate with an amine gives sulphonamide 9C.

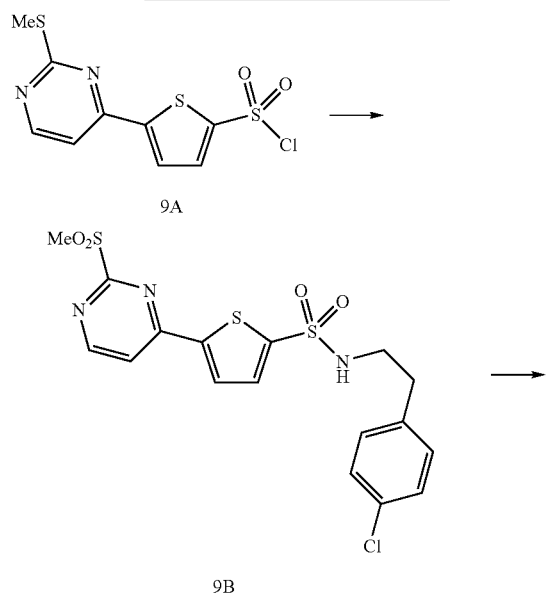

Further exemplification of synthetic protocols for making the compounds are provided in the examples.

Pharmaceutical Formulations

When employed as pharmaceuticals, the compounds of the subject invention are usually administered in the form of pharmaceutical compositions. These compounds can be administered by a variety of routes including oral, parenteral, transdermal, topical, rectal, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, inflammation in warm-blooded animals, the compounds or pharmaceutical compositions thereof will be administered by any appropriate route, such as orally, topically, transdermally, and/or parenterally at a dosage to obtain and maintain a concentration, that is, an amount, or blood-level of active component in the animal undergoing treatment that will be therapeutically effective. Generally, such therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone(as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No.20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
| --- | --- |
| Active Ingredient | 5.0 mg |
| Corn Oil | 1.0 mL |

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

An intravenous formulation may be prepared as follows:

| Ingredient | Quantity |
| --- | --- |
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17$^{th}$ ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Administration

Compounds of the instant invention are useful for inhibiting the activity of Akt in eukaryotic cells. Activation of Akt is associated with a number of upstream events, including those mediated by phosphatidylinositol 3-kinase (PI3K), which is recruited to the plasma membrane in response to various growth factors, cytokines, insulin, bradykinin, RANTES, and endothelin. Akt activation is also associated with attachment to the extracellular matrix (ECM) and various forms of cell stress (e.g., hypoxia and heat shock).

Known PKB substrates include, but are not limited to, the Bcl-2 pro-apoptotic family member (BAD); the FOXO family of fork-head transcription factors, which mediate apoptosis through FasL and Bim; the cancer-associated 3'-phosphatase, PTEN; breast cancer susceptibility gene product 1 (BRCA-1); cAMP responsive element binding protein (CREB); endothelial nitric oxide synthase (eNOS); NFκB inhibitor (I-κB); with No K (Lys) protein kinase-1 (WNK1), a hypertension-related gene linked to pseudohypoaldosteronism type II (PHAII) (Vitari et al. 2003); and other proteins associated with cell growth and cancer. In view of the number of Akt substrates already identified, and the prevalence of these substrates in cell proliferative disorders such as cancer, it is expected that additional cancer-associated Akt substrates will also be identified.

The ability to inhibit the activity of Akt will allow the modulation of activity of Akt substrates, including those listed herein. Since Akt substrates are known to be associated with specific forms of cancer, such as BRCA-1, or believed to be generally associated with inhibition of apoptosis, such as Bcl-2, the ability to inhibit Akt will have beneficial effects in preventing or treating uncontrolled cellular proliferation, including cancer. The invention will be useful for treating cancers that occur in mammals using the compounds and/or compositions of the present invention. Mammals include, for example, humans and other primates, pet or companion animals, such as dogs and cats, laboratory animals, such as rats, mice and rabbits, and farm animals, such as horses, pigs, sheep, and cattle.

Similarly, PKA is known to activate expression of genes associated with cell cycle regulation, cholesterol trafficking, hormone signaling, and signal transduction, and known to activate extracellular matrix proteases (ECM), neuropeptides, immune genes, insulin-like growth factor (IGF) family members, and other protein associated with spermatogenesis, cell growth, differentiation, and reproduction (Tierney et al., 2003). The ability to modulate PKA activity will allow the modulation of activity of PKA substrates, including those listed herein.

Additionally, compounds of the present invention may be used in the treatment of disorders mediated, at least in part, by CDC7. CDC7 is found in elevated levels in cancer cells. As such, it is contemplated that compounds of the invention modulate the activity CDC7, for example, by inhibiting the enzyme.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Tumors or neoplasms which are expected to be treatable by the compounds and/or compositions of the present invention include, but are not limited to, solid tumors, i.e., carcinomas, adenocarcinomas and sarcomas. Carcinomas include those malignant neoplasms derived from epithelial cells which infiltrate (invade) the surrounding tissues and give rise to metastases. Adenocarcinomas are carcinomas derived from granular tissue, or from tissues which form recognizable glandular structures. Another broad category of cancers includes sarcomas, which are tumors whose cells are embedded in a fibrillar or homogenous substance like embryonic connective tissue.

In particular, the invention is useful for treating breast cancer, prostate cancer, ovarian cancer, pancreatic cancer, glioblastoma, melanoma, etc.

Compounds of the invention may be delivered to an animal, such as a human patient, by one or more methods, and/or using one or more pharmaceutical compositions, some of which are described herein. Other methods of delivering beneficial pharmacological agents to humans and other animals are well known in then art.

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17$^{th}$ ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose" or "therapeutically effective amount." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 10 μg to about 20 mg per kilogram body weight per day, preferably about 1 mg to about 10 mg per kilogram body weight per day. In the alternative, for intravenous administration, the dose will typically be in the range of about 5 μg to about 10,000 μg per kilogram body weight, preferably about 500 μg to about 5000 μg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a-circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention. Unless otherwise stated, all temperatures are in degrees Celsius.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) aceton in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 µL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.)

Melting points are determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Unless otherwise stated all temperatures are in degrees Celsius. Also, in these examples and elsewhere, abbreviations have the following meanings:

| | |
|---|---|
| aq = | aqueous |
| $Boc_2O$ = | di-tertbutyl dicarbonate |
| BuLi = | butyl lithium |
| CDI = | N,N'-carbonyldiimidazole |
| d = | day |
| DCM = | dichloromethane |
| DIEA = | diisopropylethylamine |
| DMAP = | dimethylaminopyridine |
| DMF-DMA = | dimethylformamide-dimethylacetal |
| DMSO = | dimethylsulfoxide |
| EDTA = | ethylenediaminetetraacetic acid |
| eq. = | equivalence |
| ES/MS = | electrospray mass spectroscopy |
| $Et_3N$ = | triethyl amine |
| EtOH = | Ethanol |
| g = | gram |
| GCMS = | gas chromatograph mass spectroscopy |
| h = | hour |
| HOAc = | acetic acid |
| HOBt = | 1-hydroxybenzotriazole |
| HPLC = | high performance liquid chromatography |
| kg = | kilogram |
| L = | liter |
| M = | molar |
| m/z = | mass/charge ratio |
| mCPBA = | m-chloroperoxybenzoic acid |
| MeOH = | methanol |
| mg = | milligram |
| mL = | milliliter |
| mol = | mole |
| N = | normal |
| nM = | nanomolar |
| NaOEt = | sodium ethoxide |
| NaOMe = | sodium methoxide |
| nBuLi = | n-butyl lithium |
| Pd $(dppf)_2$ = | palladium 1,1'-bis(diphenylphosphino) ferrocene |
| Pd $(PPh_3)_4$ = | Tetrakis (triphenylphosphine) palladium (0) |
| PyBrop = | bromotripyrrolidinophosphonium hexafluorophosphate |
| rt = | room temperature |
| Tf = | triflate |
| THF = | tetrahydrofuran |
| v/v | volume/volume |
| µM = | micromolar |

The following examples contain numbered compounds. The numbers employed in the examples do not correspond to the numbers in Tables 1-6.

Example 1

Synthesis of N-[2-(4-fluorophenyl)ethyl]-5-[2-(methylamino)pyrimidin-4-yl]thiophene-2-carboxamide

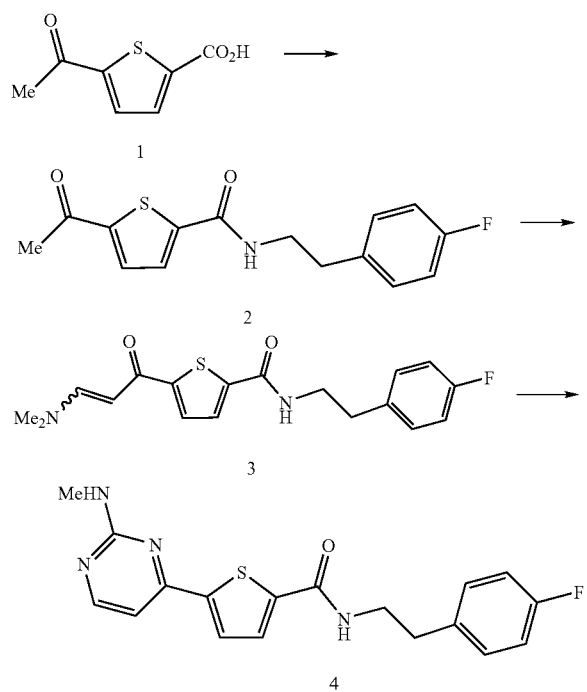

Step 1: Condensation to Amide (2)

N,N'-Carbonyldiimidazole (1.00 eq.) was added to a 0.25 M solution of compound 1 in anhydrous tetrahydrofuran. The mixture was stirred for 2 h at ambient temperature. 4-fluorophenethylamine (1.00 eq.) was added, and the reaction was stirred an additional 4 h at ambient temperature. Volatiles were removed under reduced pressure. The material was redissolved in dichloromethane and washed successively with water and brine. The organic phase was dried over sodium sulfate, filtered, and concentrated to give compound 2. ES/MS m/z 292 (MH$^+$), $C_{15}H_{14}FNO_2S=291$ g/mol.

Step 2: Formation of Vinylogous Amide (3)

Dimethylformamide dimethyl acetal (1.50 eq.) was added to a 0.30 M solution of compound 1 (1.00 eq.) in anhydrous toluene. The reaction was refluxed for 15 h and then returned to ambient temperature. The product was precipitated by the addition of 1:1 ether: hexanes and isolated by vacuum filtration. The filter cake was rinsed with additional 1:1 ether: hexanes and then dried under reduced pressure to give compound 3 as a tan solid. ES/MS m/z 347 (MH$^+$), $C_{18}H_{19}FN_2O_2S=346$ g/mol.

Step 3: Formation of Pyrimidine Ring (4)

Sodium ethoxide (2.10 eq.) and methylguanidine hydrochloride (2.00 eq.) were added to a 0.2 M suspension of compound 3 (1.00 eq.) in absolute ethanol. The reaction was stirred at 80° C. for 2 days and then returned to ambient temperature. The mixture was diluted with dichloromethane and washed successively with water and brine. The organic phase was dried over sodium sulfate, filtered, and concentrated. The crude material was purified by flash chromatography over silica gel (96:4 dichloromethane: methanol) to give compound 4. ES/MS m/z 357 (MH$^+$), $C_{18}H_{17}FN_4OS=356$ g/mol.

Example 2

Synthesis of N-[2-(2,4-dichlorophenyl)ethyl]-5-{2-[(2-hydroxyethyl)amino]pyrimidin-4-yl}thiophene-2-carboxamide

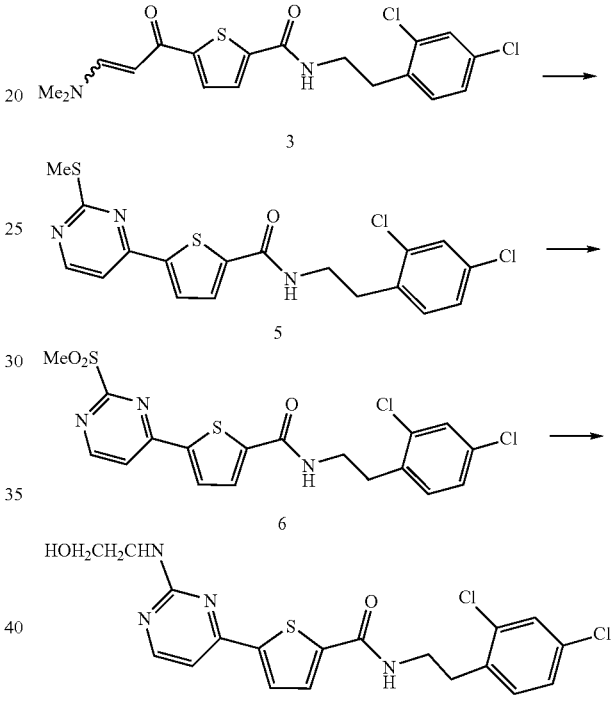

Step 1: Formation of Pyrimidine Ring (5)

NOTE: "Compound 3" as listed here was prepared in a similar fashion to N-[2-(4-fluorophenyl)ethyl]-5-[2-(methylamino)pyrimidin-4-yl]thiophene-2-carboxamide except that: (1) in Step 1 2,4-dichlorophenethylamine was used in the place of 4-fluorophenethylamine and (2) the reaction was stirred at 50° C. after the addition of the amine to the intermediate acylimidazolide.

Compound 3 (1.00 eq.) was added to a 1.2 M solution of S-methyl isothiourea hemisulfate (3.00 eq.) in 4:1 water: pyridine at 100° C. The mixture was stirred at 100° C. for three days. After being cooled to ambient temperature, the mixture was diluted with dichloromethane and washed sequentially with water and brine. The organic phase was dried over sodium sulfate, filtered, and concentrated. The crude material was purified by flash chromatography over silica gel (1:1:1 hexanes:ethyl acetate:dichloromethane) to give compound 5. ES/MS m/z 424, 426 (MH$^+$), $C_{18}H_{15}Cl_2N_3OS_2=424$ g/mol.

Step 2: Oxidation to Sulfone (6)

Meta-chloroperoxybenzoic acid (2.00 eq.) was added to a 0.25 M solution of compound 5 in dichloromethane at ambient temperature. The mixture was stirred for 16 h at ambient temperature. The mixture was diluted with dichloromethane and washed sequentially with 1 M aqueous sodium carbonate and brine. The organic phase was dried over sodium sulfate, filtered, and concentrated. The crude material was purified by flash chromatography over silica gel (1:1:1 hexanes:ethyl acetate:dichloromethane) to give compound 6. ES/MS m/z 456, 458 (MH+), $C_{18}H_{15}Cl_2N_3O_3S_2$=456 g/mol.

Step 3: Displacement of Sulfone by Amine (4)

Ethanolamine (R=$CH_2CH_2OH$, 2.00 eq.) was added to a 0.5 M solution of compound 6 (1.00 eq.) in 1,4-dioxane. The reaction was refluxed for 4 h and then returned to ambient temperature. Volatiles were removed under reduced pressure. Purification by reverse-phase HPLC gave compound 4. ES/MS m/z 437,439 (MH+), $C_{19}H_{18}Cl_2N_4O_2S$=437 g/mol.

Example 3

Synthesis of 5-[2-(methylamino)pyrimidin-4-yl]-N-(2-phenylethyl)thiophene-2-carboxamide

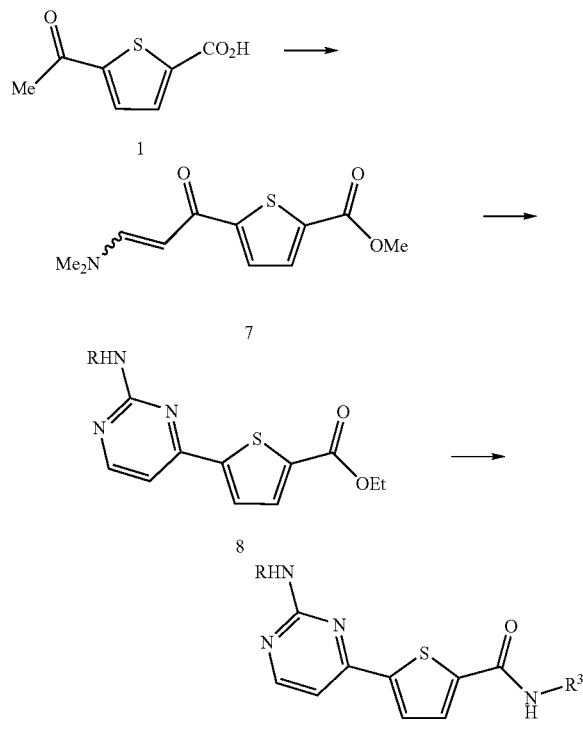

Step 1: Formation of Vinylogous Amide (7)

Dimethylformamide dimethyl acetal (2.50 eq.) was added to a 0.30 M solution of compound 1 (1.00 eq.) in anhydrous toluene. The reaction was refluxed for 15 h and then returned to ambient temperature. The product was precipitated by the addition of 1:1 ether: hexanes and isolated by vacuum filtration. The filter cake was rinsed with additional 1:1 ether: hexanes and then dried under reduced pressure to give compound 7 as a tan solid. ES/MS m/z 240 (MH+), $C_{11}H_{13}NO_3S$=239 g/mol.

Step 2: Cyclization to Aminopyrimidine (8)

Sodium ethoxide (2.10 eq.) and methylguanidine hydrochloride (R=Me, 2.00 eq.) were added to a 0.2 M solution of compound 7 (1.00 eq.) in absolute ethanol at ambient temperature. The mixture was stirred at 70° C. for 16 h. Volatiles were removed under reduced pressure. The slurry was diluted with dichloromethane and washed sequentially with water and brine. The organic phase was dried over sodium sulfate, filtered, and concentrated to give compound 8. ES/MS m/z 264 (MH+), $C_{12}H_{13}N_3O_2S$=263 g/mol.

Step 3: Condensation to Amide (9)

Method A

Phenethylamine ($R^3$=phenethyl, 2.50 eq.) and sodium methoxide (0.500 eq.) were added to a 0.2 M solution of compound 8 (R=Me, 1.00 eq.) in methanol. The reaction was refluxed for 2 days and then returned to ambient temperature. Volatiles were removed under reduced pressure. Purification by reverse-phase HPLC gave compound 9. ES/MS m/z 339 (MH+), $C_{18}H_{18}N_4OS$=338 g/mol.

Method B

Sodium hydride (2.00 eq.) was added to a 1.1 M solution of 2-amino-4-chlorobenzothiazole ($R^3$=4-chlorobenzothiazol-2-yl, 2.20 eq.) in N,N'-dimethylformamide. The mixture was stirred 15 min. A 0.5 M solution of compound 8 (R=Me, 1.00 eq.) in N,N'-dimethylformamide was added drop wise over 20 min. The reaction was stirred 2 h at ambient temperature and them quenched by the addition of water. Purification by reverse-phase HPLC gave compound 9. ES/MS m/z 402, 404 (MH+), $C_{17}H_{12}ClN_5OS_2$=402 g/mol.

Example 4

Synthesis of N-(4-methoxy-1,3-benzothiazol-2-yl)-5-[2-(methylamino)pyrimidin-4-yl]thiophene-2-carboxamide

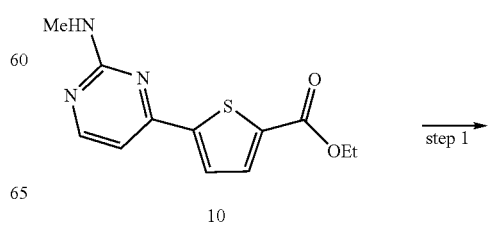

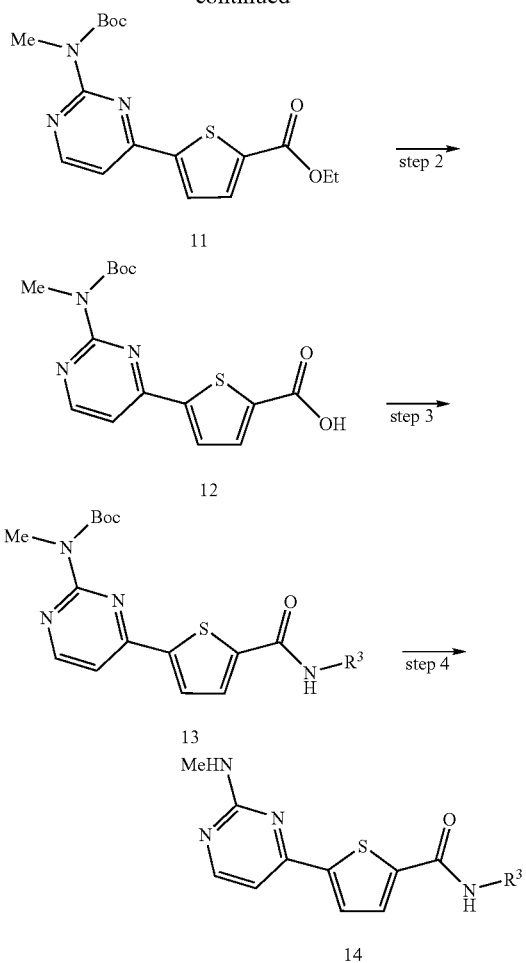

filtered, and concentrated to give compound 11 which was used without further purification. ES/MS m/z 364 (MH+), $C_{17}H_{21}N_3O_4S$=363 g/mol.

Step 2: Saponification to Carboxylic Acid (12)

Aqueous sodium hydroxide (2.00 eq.) was added to a 0.2 M solution of compound 11 in ethanol. The mixture was stirred for 16 h at ambient temperature. Volatiles were removed under reduced pressure. The residue was re-dissolved in dichloromethane and washed sequentially with dilute aqueous hydrochloric acid and brine. The organic phase was dried over sodium sulfate, filtered, and concentrated to give compound 11 which was used without further purification. ES/MS m/z 336 (MH+), $C_{15}H_{17}N_3O_4S$=335 g/mol.

Step 3: Condensation to Amide (13)

N,N'-Carbonyldiimidazole (1.00 eq.) was added to a 0.2 M solution of compound 12 in anhydrous tetrahydrofuran. The mixture was stirred for 1 h at 50° C. The solution was returned to ambient temperature, and 2-amino-4-methoxybenzothiazole ($R^3$=4-methoxybenzothiazol-2-yl, 1.10 eq.) was added. The solution was stirred an additional 15 h at 50° C. Volatiles were removed under reduced pressure. The residue was re-dissolved in dichloromethane and washed sequentially with water and brine. The organic phase was dried over sodium sulfate, filtered, and concentrated to give compound 13 which could be purified further by flash chromatography. ES/MS m/z 498 (MH+), $C_{23}H_{23}N_5O_4S_2$=497 g/mol.

Step 4: Deprotection to Free Amine (14)

Aqueous hydrochloric acid (30 eq.) was added to a 0.1 M solution of compound 13 in methanol. The mixture was stirred at 50° C. for 4 h. The mixture was diluted with dichloromethane and washed successively with 1 M aqueous sodium carbonate and brine. The organic phase was dried over sodium sulfate, filtered, and concentrated. The crude material was purified by reverse-phase HPLC to give compound 14. ES/MS m/z 398 (MH+), $C_{18}H_{15}N_5O_2S_2$=397 g/mol.

Example 5

Synthesis of N-(4-fluorobenzyl)-N'-{5-[2-(methylamino)pyrimidin-4-yl]thien-2-yl}urea, 4-fluorobenzyl 5-[2-(methylamino)pyrimidin-4-yl]thien-2-ylcarbamate and 3-(4-fluorophenyl)-N-{5-[2-(methylamino)pyrimidin-4-yl]thien-2-yl}propanamide Step 1: Protection as t-butyl Carbamate (11)

Di-tert-butyldicarbonate (1.20 eq.), 4-dimethylaminopyridine (0.200 eq.), and triethylamine (1.20 eq.) were added to a 0.5 M solution of compound 10 in tetrahydrofuran. The mixture was stirred 16 h at ambient temperature. The mixture was diluted with ethyl acetate and washed sequentially with water and brine. The organic phase was dried over sodium sulfate,

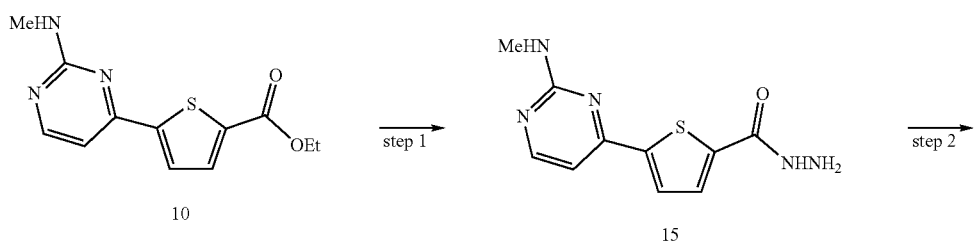

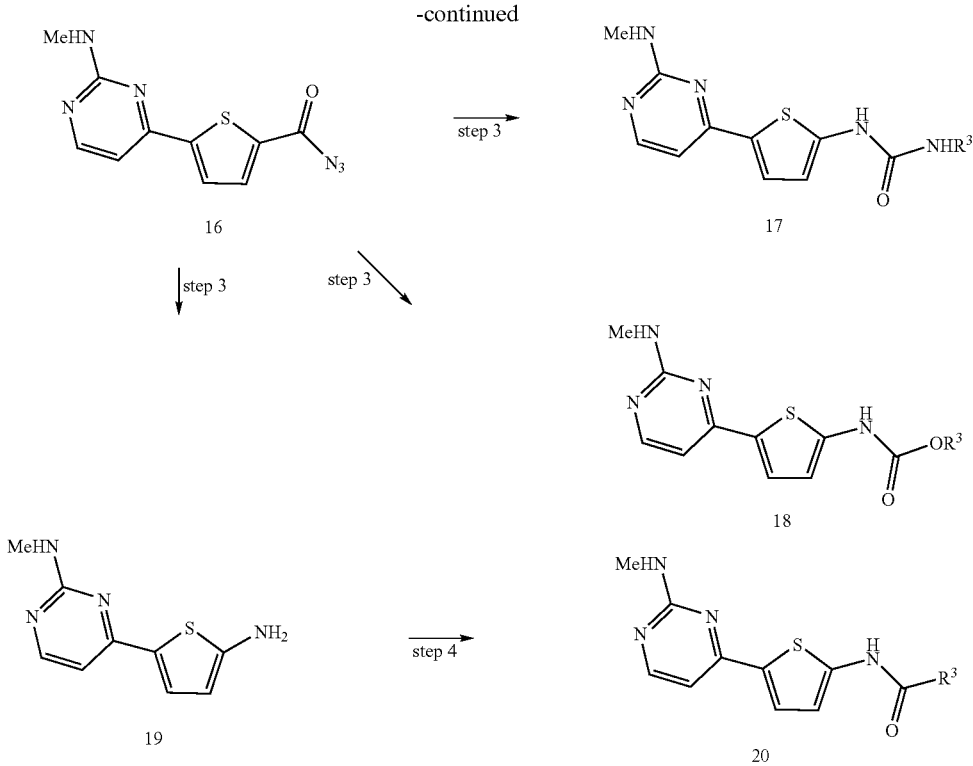

Step 1: Conversion to Acyl Hydrazide (15)

Hydrazine hydrate (10.0 eq.) was added to a 0.5 M suspension of compound 10 in methanol. The mixture was refluxed for 14 h and returned to ambient temperature. The product was precipitated by the addition of water and collected by vacuum filtration. The filter cake was rinsed with methanol and dried in a desiccator to give compound 15. ES/MS m/z 250 (MH$^+$), $C_{10}H_{11}N_5OS$=249 g/mol.

Step 2: Conversion of Acyl Hydrazide to Carbonyl Azide (16)

A 0.6 M aqueous solution of hydrochloric acid (1.05 eq.) was added to a 1.1 M suspension of compound 15 in glacial acetic acid. A 4.0 M aqueous solution of sodium nitrite (1.00 eq.) was added drop wise over 30 min. The slurry was diluted with one volume of water and filtered. The solid was suspended in water, and the pH was adjusted to 7-8 with 6 M aqueous sodium hydroxide. The precipitate was collected by vacuum filtration and rinsed with water. The yellow solid was dried in a desiccator to give compound 16. ES/MS m/z 261 (MH$^+$), $C_{10}H_8N_6OS$=260 g/mol.

Step 3a: Conversion of Carbonyl Azide to Urea (17) N-(4-fluorobenzyl)-N'-{5-[2-(methylamino)pyrimidin-4-yl]thien-2-yl}urea A 0.2 M solution of compound 16 (1.00 eq.) in xylenes was stirred at 130° C. for 30 min. 4-fluorobenzylamine ($R^3$=4-fluorobenzyl, 2.00 eq.) was added, and the mixture was stirred an additional 1 h at 130° C. Volatiles were removed under reduced pressure. The crude material was purified by reverse-phase HPLC to give compound 17. ES/MS m/z 358 (MH$^+$), $C_{17}H_{16}FN_5OS$=357 g/mol.

Step 3b: Conversion of Carbonyl Azide to Carbamate (18) 4-fluorobenzyl 5-[2-(methylamino)pyrimidin-4-yl]thien-2-ylcarbamate A 0.2 M solution of compound 16 (1.00 eq.) in xylenes was stirred at 130° C. for 30 min. 4-fluorobenzylalcohol ($R^3$=4-fluorobenzyl, 2.00 eq.) was added, and the mixture was stirred an additional 1 h at 130° C. Volatiles were removed under reduced pressure. The crude material was purified by reverse-phase HPLC to give compound 18. ES/MS m/z 359 (MH$^+$), $C_{17}H_{15}FN_4O_2S$=358 g/mol.

Step 3c: Rearrangement of Carbonyl Azide to Amine (19)

A 0.25 M suspension of compound 16 (1.00 eq.) in 1.5 M aqueous hydrochloric acid was stirred at 100° C. for 14 h. The pH of the mixture was adjusted to 9 with 6 N aqueous sodium hydroxide. The aqueous phase was extracted with dichloromethane. The organic phase was dried over sodium sulfate, filtered, and concentrated. The crude material was purified by flash chromatography over silica gel (94:6 dichloromethane:methanol) to give compound 19. ES/MS m/z 207 (MH$^+$), $C_9H_{10}N_4S$=206 g/mol.

Step 4: Condensation to amide (20) 3-(4-fluorophenyl)-N-{5-[2-(methylamino)pyrimidin-4-yl]thien-2-yl}propanamide N,N'-Carbonyldiimidazole (1.00 eq.) was added to a 0.25 M solution of 4-fluorophenylpropionic acid ($R^3$=4-fluorophenethyl, 1.00 eq.) in anhydrous tetrahydrofuran. The mixture was stirred for 1 h at 50° C. Compound 19 (1.00 eq.) was added, and the reaction was stirred an additional 2 h at 50° C. Volatiles were removed under reduced pressure. The material was re-dissolved in dichloromethane and washed successively with water and brine. The organic phase was dried over sodium sulfate, filtered, and concentrated. The crude material was purified by reverse-phase HPLC to give compound 20. ES/MS m/z 357 (MH$^+$), $C_{18}H_{17}FN_4OS$=356 g/mol.

Example 6

Synthesis of N-[2-(4-fluorophenyl)ethyl]-5-[5-methyl-2-(methylamino)pyrimidin-4-yl]thiophene-2-carboxamide

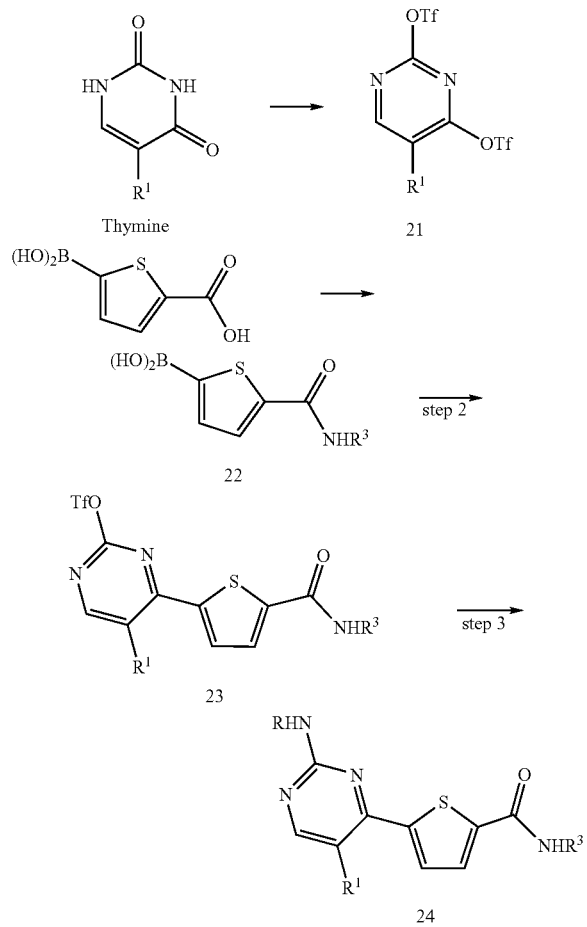

Step 1: Condensation to Amides (22)

N,N'-Carbonyldiimidazole (1.00 eq.) was added to a 0.28 M solution of 5-(dihydroxyboryl)-2-thiophene carboxylic acid in anhydrous tetrahydrofuran. The mixture was stirred for 1 h at ambient temperature. 4-Fluorophenethylamine ($R^3$=4-fluorophenethyl, 1.00 eq.) was added, and the reaction was stirred an additional 12 hr at ambient temperature. Volatiles were removed under reduced pressure. The material was re-dissolved in ethyl acetate and washed successively with water and brine. The organic phase was dried over sodium sulfate, filtered, and concentrated to give compound 22. ES/MS m/z 294 (MH$^+$), $C_{13}H_{13}BFNO_3S$=293 g/mol.

Step 2: Suzuki Coupling to Amides (23)

Pd(dppf)$_2$ (0.05 eq.) was added to a 0.34 M solution of compound 22 ($R^3$=4-fluorophenethyl, 1.00 eq.) and compound 21 ($R^1$=Me, 1.1 eq.) in anhydrous tetrahydrofuran, followed by the addition of diisopropylethylamine (2.0 eq.). The reaction mixture was purged with Argon and was heated to 80° C. for 12 hr. Volatiles were removed under reduced pressure. The material was re-dissolved in ethyl acetate and washed successively with water, saturated sodium metabisulfite and brine. The organic phase was dried over sodium sulfate, filtered, and concentrated. The crude product was purified by Biotage using 20% ethyl acetate in hexane to give compound 23. ES/MS m/z 490 (MH$^+$), $C_{19}H_{15}F_4N_3O_4S_2$=489 g/mol.

Step 3: Formation of the Aminopyrimidine Ring to give N-[2-(4-fluorophenyl)ethyl]-5-[5-methyl-2-(methylamino)pyrimidin-4-yl]thiophene-2-carboxamide (24)

The mixture of methylamine (R=Me, 2.0 M in tetrahydrofuran, 5.0 eq.) and compound 23 ($R^1$=Me; $R^3$=4-fluorophenethyl, 1.0 eq.) was heated in an oil bath to 150° C. for 16 hr. Volatiles were removed under reduced pressure. The crude material was purified by Biotage using 60% ethyl acetate in hexane to give compound 24. ES/MS m/z 371 (MH$^+$), $C_{19}H_{19}FN_4OS$=370 g/mol.

Example 7

Synthesis of N-[2-(4-fluorophenyl)ethyl]-5-[2-(methylamino)pyridin-4-yl]thiophene-2-carboxamide

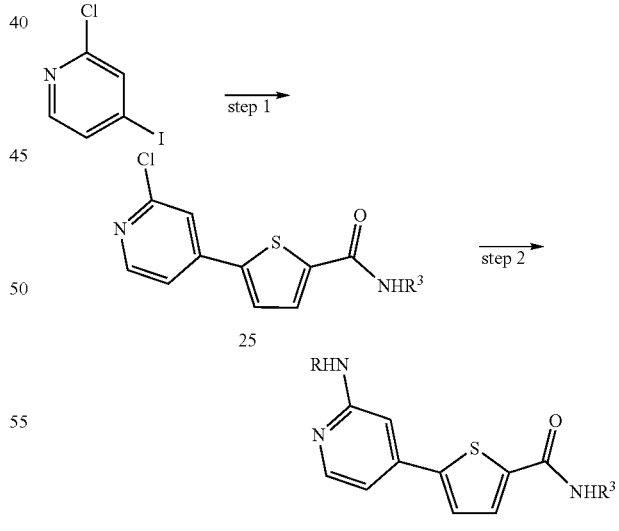

Step 1: Suzuki Coupling to Amides (25)

Pd(PPh$_3$)$_4$ (0.05 eq.) was added to a 0.37 M solution of compound 22 ($R^3$=4-fluorophenethyl, 1.0 eq.), 2-chloro-4- iodopyridine (1.2 eq.), and sodium carbonate (2.0 M in water, 2.6 eq.) in tetrahydrofuran. The reaction mixture was purged with Argon and was heated to 70° C. for 18 h. Volatiles were removed under reduced pressure. The material was re-dissolved in ethyl acetate and washed successively with water and brine. The organic phase was dried over sodium sulfate, filtered, and concentrated. The material was purified by Biotage using 40% ethyl acetate in hexane to give compound 25. ES/MS m/z 361 (MH$^+$), $C_{18}H_{14}ClFN_2OS$=360 g/mol.

Step 3: Formation of Aminopyrimidine Ring (26)

The mixture of methylamine (2.0 M in tetrahydrofuran, 45 eq.) and compound 25 (1.0 eq.) was heated in an oil bath to 150° C. for 2 days. Volatiles were removed under reduced pressure. The material was re-dissolved in ethyl acetate and washed successively with 5% NaOH and brine. The organic phase was dried over sodium sulfate, filtered, and concentrated. The crude material was purified by Biotage using 90% ethyl acetate in hexane to give compound 26. ES/MS m/z 356 (MH$^+$), $C_{19}H_{18}FN_3OS$=355 g/mol.

Example 8

Synthesis of N-[2-(2,4-dichlorophenyl)ethyl]-5-[2-(methylamino)pyrimidin-4-yl]thiophene-3-carboxamide

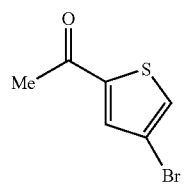

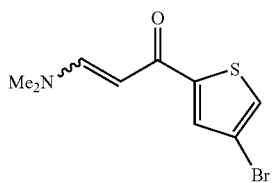

27

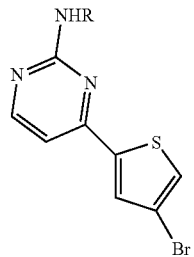

28

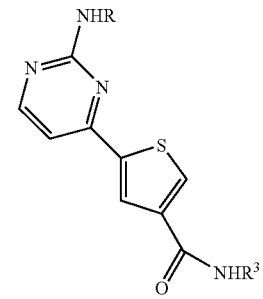

29

Step 1: Formation of Vinylogous Amide (27)

Dimethylformamide dimethyl acetal (2.50 eq.) was added to a 0.48 M solution of 2-acetyl-4-bromothiophene (1.00 eq.) in anhydrous toluene. The reaction was refluxed for 20 h and then returned to ambient temperature. The product was precipitated by the addition of 1:1 ether:hexanes and isolated by vacuum filtration. The filter cake was rinsed with additional 1:1 ether:hexanes and then dried under reduced pressure to give compound 27. ES/MS m/z 260 (MH$^+$).

Step 2: Formation of Pyrimidine Ring (28)

Sodium ethoxide (2.0 eq.) and methylguanidine hydrochloride (R=Me, 2.00 eq.) were added to a 0.25 M suspension of compound 27 (1.00 eq.) in absolute ethanol. The reaction was stirred at 75° C. for 18 h and then returned to ambient temperature. The mixture was diluted with ethyl acetate and washed successively with water and brine. The organic phase was dried over sodium sulfate, filtered, and concentrated. The crude material was triturated with hexane and was filtered to give compound 28. ES/MS m/z 270 (MH$^+$).

Step 3: Formation of Carboxylic Acid (29)

BuLi (2.5 M in hexane, 2.5 eq.) was added to a mixture of compound 28 (R=Me, 1.0 eq.) in THF/ether (1:1) at −78° C., in 10 min. The reaction mixture was stirred at −78° C. for another 10 min. CO$_2$ was purged into the reaction solution in a period of 40 min. The reaction was then returned to ambient temperature and stirred for 12 h. Reaction mixture was quenched with cold acetic acid (5.0 eq.) aqueous solution. Volatiles were removed under reduced pressure. The material was re-dissolved in ethyl acetate and washed with brine. The organic phase was dried over sodium sulfate, filtered, and concentrated to give desired product 29. ES/MS m/z 236 (MH$^+$).

Step 4: Formation of the Amide Bond to give N-[2-(2,4-dichlorophenyl)ethyl]-5-[2-(methylamino)pyrimidin-4-yl]thiophene-3-carboxamide (30)

Diisopropylethylamine (3.0 eq.) was added to a mixture of compound 29 (R=Me, 1.0 eq.) PyBrop (1.2 eq.), HOBt (1.2 eq.) in tetrahydrofuran. The mixture was stirred at ambient temperature for 1 hr. 2,4-dichlorophenethylamine ($R^3$=2,4-dichlorophenethyl, 1.2 eq.) was added to the solution. The reaction solution was stirred for 18 h at ambient temperature. Volatiles were removed under reduced pressure. The material was re-dissolved in ethyl acetate and washed with water and brine. The organic phase was dried over sodium sulfate, filtered, and concentrated. Purification by reverse phase HPLC gave compound 30. ES/MS m/z 407 ($MH^+$), $C_{18}H_{16}Cl_2N_4OS$=406 g/mol.

Example 9

Synthesis of 4-[5-({[2-(4-chlorophenyl)ethyl]amino}methyl)thien-2-yl]-N-methylpyrimidin-2-amine

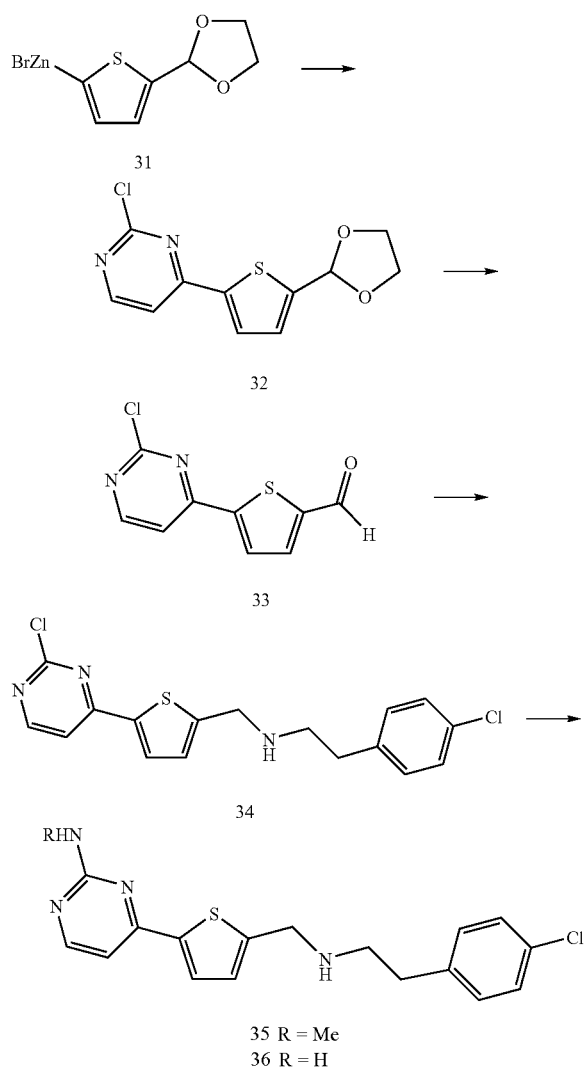

Step 1: Negishi Coupling to 4-(2-thienyl)pyrimidine (32)

To a degassed 0.50 M solution of 2,4-dichloropyrimidine (1.0 eq.) and 5-(1,3-dioxolan-2-yl)-2-thienylzinc bromide 31 (1.0 eq.) in tetrahydrofuran was added tetrakis(triphenylphosphine)palladium(0) (0.050 eq.). The mixture was stirred for 16 h at 70° C. and then returned to ambient temperature and diluted with ether. The solution was washed sequentially with a 0.5 M aqueous pH 9 solution of EDTA and brine. The organic phase was dried over sodium sulfate, filtered, and concentrated. The crude material was purified by flash chromatography over silica gel (1:1:1 hexanes:ethyl acetate:dichloromethane) to give compound 32. ES/MS m/z 269 ($MH^+$), $C_{11}H_9ClN_2O_2S$=269 g/mol.

Step 2: Deprotection of Dioxolane to Aldehyde (33)

Aqueous hydrochloric acid (6.0 eq.) was added to a 0.10 M suspension of compound 32 in acetone. The mixture was stirred 16 h at ambient temperature. Volatiles were removed under reduced pressure. The residue was re-dissolved in ether and washed sequentially with saturated aqueous sodium bicarbonate and brine. The organic phase was dried over sodium sulfate, filtered, concentrated, and the crude aldehyde 33 used without further purification. ES/MS m/z 225 ($MH^+$), $C_9H_5ClN_2OS$=225 g/mol.

Step 3: Reductive Amination to Amine (34)

4-Chlorophenethylamine (1.1 eq.) was added to a 0.15 M solution of compound 33 (1.0 eq.) in toluene. The mixture was refluxed for 4.5 h. Volatiles were removed under reduced pressure. The residue was re-dissolved in methanol to make a 0.15 M solution. Sodium borohydride (1.3 eq.) was added. The mixture was stirred 2 h at ambient temperature. Volatiles were removed under reduced pressure. The crude material was purified by flash chromatography over silica gel (96:4 dichloromethane:methanol) to give compound 34. ES/MS m/z 364 ($MH^+$), $C_{17}H_{15}Cl_2N_3S$=364 g/mol.

Step 4: Nucleophilic Substitution to 2-Aminopyrimidine (35) and (36)

A 0.05 M solution of compound 34 (1.0 eq.) in a 2.0M solution of methylamine (R=Me) in tetrahydrofuran (40 eq.) was refluxed overnight. Volatiles were removed under reduced pressure. The crude material was purified by reversed-phase HPLC to give compound 35, 4-[5-({[2-(4-chlorophenyl)ethyl]amino}methyl)thien-2-yl]-N-methylpyrimidin-2-amine. ES/MS m/z 359 ($MH^+$), $C_{18}H_{19}ClN_4S$=359 g/mol.

Alternatively, a 0.05 M solution of compound 34 (1.0 eq.) in 1:1 1,4-dioxane:ammonium hydroxide was refluxed overnight. Volatiles were removed under reduced pressure. The crude material was purified by reversed-phase HPLC to give compound 36, 4-[5-({[2-(4-chlorophenyl)ethyl]amino}methyl)thien-2-yl]pyrimidin-2-amine. ES/MS m/z 345 ($MH^+$), $C_{17}H_{17}ClN_4S$=345 g/mol.

Example 10

Synthesis of 5-(2-aminopyrimidin-4-yl)-N-[2-(2,4-dichlorophenyl)ethyl]thiophene-2-sulfonamide and N-[2-(4-chlorophenyl)ethyl]-5-[2-(methylamino)pyrimidin-4-yl]thiophene-2-sulfonamide

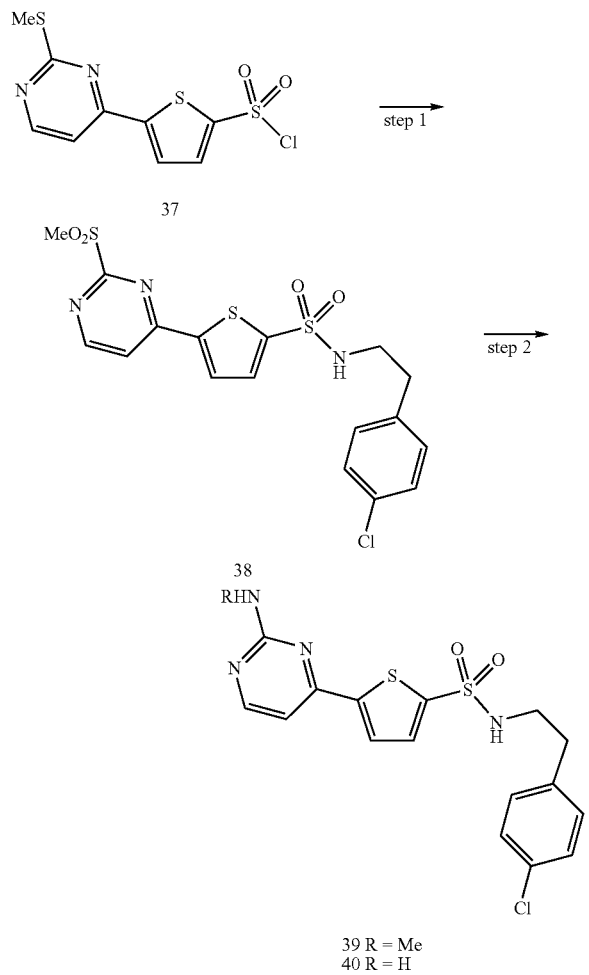

39 R = Me
40 R = H

Step 1: Formation of Sulfonamide (38)

4-Chlorophenethylamine (1.0 eq.) and triethylamine (1.0 eq.) were added to a 0.20 M solution of 5-[2-(methylthio)pyrimidin-4-yl]thiophene-2-sulphonyl chloride 37 (1.0 eq.) in dichloromethane. The reaction was stirred at ambient temperature for 3 h. Meta-chloroperoxybenzoic acid (3.0 eq.) was added and the reaction was stirred at ambient temperature for an additional 4 h. The reaction mixture was diluted with dichloromethane, washed sequentially with 1 M aqueous sodium carbonate and brine, dried over sodium sulfate, filtered, and concentrated. The crude material 38 was used without further purification. ES/MS m/z 458 (MH+), $C_{17}H_{16}ClN_3O_4S_3$=458 g/mol.

Step 2: Nucleophilic Substitution to Aminopyrimidine (39) and (40)

A 2.0M solution of methylamine (5.0 eq., R=Me) was added to a 0.20M solution of compound 38 (1.0 eq.) in 1,4-dioxane and stirred at 70° C. overnight. Volatiles were removed under reduced pressure. The crude material was purified by reversed-phase HPLC to give compound 39, N-[2-(4-chlorophenyl)ethyl]-5-[2-(methylamino)pyrimidin-4-yl]thiophene-2-sulfonamide. ES/MS m/z 409 (MH+), $C_{17}H_{17}ClN_4O_2S_2$=409 g/mol.

Alternatively, ammonium hydroxide (15 eq., R=H) was added to a 0.20 M solution of compound 38 (1.0 eq.) in 1,4-dioxane and refluxed overnight. Volatiles were removed under reduced pressure. The crude material was purified by reversed-phase HPLC to give compound 40, 5-(2-aminopyrimidin-4-yl)-N-[2-(2,4-dichlorophenyl)ethyl]thiophene-2-sulfonamide. ES/MS m/z 395 (MH+), $C_{16}H_{15}ClN_4O_2S_2$=395 g/mol.

Example 11

Synthesis of 3-[2-(2,4-dichlorophenyl)ethyl]-6-[2-(methylamino)pyrimidin-4-yl]thieno[3,2-d]pyrimidin-4(3H)-one and 6-(2-aminopyrimidin-4-yl)-3-[2-(2,4-dichlorophenyl)ethyl]thieno[3,2-d]pyrimidin-4(3H)-one

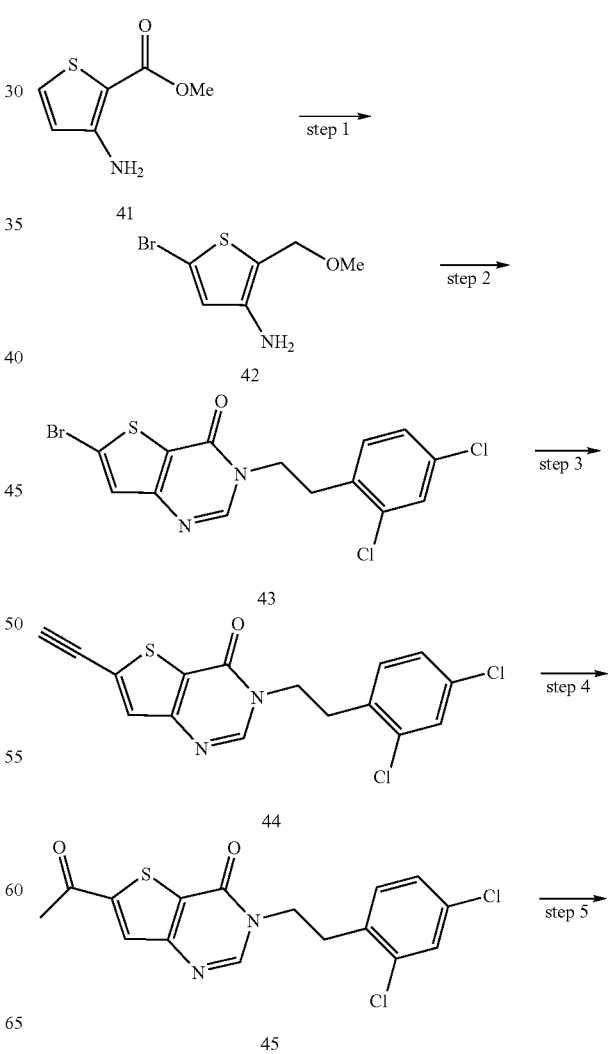

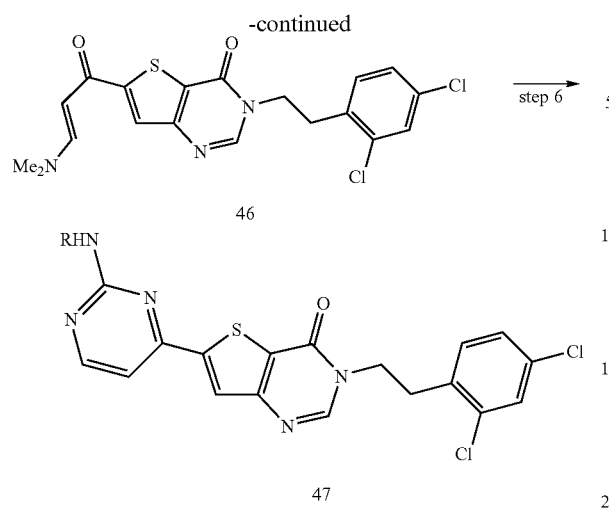

Step 1: Bromination of Thiophene (42)

Phenyltrimethylammonium tribromide (3.00 eq.) and calcium carbonate (4.00 eq.) were added to a 0.3 M solution of 3-aminothiophene-2-carboxylic acid methyl ester 41. The mixture was stirred at ambient temperature for 16 h and filtered. The filtrate was concentrated and chromatographed (1:1 hexanes:ethyl acetate) to give the desired bromide 43. ES/MS m/z 236, 238 (MH$^+$), $C_6H_6BrNO_2S$=236 g/mol.

Step 2: Cyclization to Amide (43)

Dimethylformamide dimethyl acetal (2.00 eq.) was added to a 0.5 M solution of compound 42 in xylenes. The mixture was stirred for 2 d at 130-135° C. Volatiles were removed under reduced pressure. The residue was redissolved in 1,4-dioxane to make a 0.3 M solution. 2,4-Dichlorophenethylamine (1.00 eq.) and p-toluenesulfonic acid (0.2 eq.) were added, and the reaction was stirred an additional 21 h at 100° C. The reaction mixture was returned to ambient temperature, diluted with ethyl acetate, and washed sequentially with saturated sodium bicarbonate and brine. The organic phase was dried over sodium sulfate, filtered, concentrated, and chromatographed (1:1 hexanes:ethyl acetate) to give compound 43. ES/MS m/z 403, 405 (MH$^+$), $C_{14}H_9BrCl_2N_2OS$=404 g/mol.

Step 3: Sonogashira and Deprotection to Alkyne (44)

Trimethylsilyl acetylene (1.2 eq.), dichlorobis(triphenylphosphine)palladium (0.04 eq.), and copper iodide (0.06 eq.) were added to a degassed solution of the bromide 43 in 2:1 tetrahydrofuran:triethylamine. The mixture was stirred for 16 h at 70° C. and then cooled to ambient temperature, diluted with ethyl acetate, and filtered through a silica gel plug. The filtrate was concentrated and re-dissolved to make a 0.05 M solution in methanol. Potassium carbonate (2.0 eq.) was added, and the mixture was stirred 16 h at ambient temperature. Volatiles were removed under reduced pressure. The residue was redissolved in dichloromethane, washed sequentially with water and brine, dried over sodium sulfate, filtered, concentrated to give the desired alkyne 44. ES/MS m/z 349 (MH$^+$), $C_{16}H_{10}Cl_2N_2OS$=349 g/mol.

Step 4: Hydration to Ketone (45)

A 2.0 N aqueous solution of sulfuric acid (20 eq.) was added to a 0.05 M solution of the alkyne 44 in 1,4-dioxane. The mixture was refluxed 16 h and returned to ambient temperature. Volatiles were removed under reduced pressure. Ethyl acetate was added. The organic layer was dried over sodium sulfate, filtered, concentrated, and chromatographed to give the desired ketone 45. ES/MS m/z 367 (MH$^+$), $C_{16}H_{12}Cl_2N_2O_2S$=367 g/mol.

Step 5: Formation of Vinylogous Amide (46)

Dimethylformamide dimethyl acetal (2.0 eq.) was added to a 0.20 M solution of compound 45 (1.0 eq.) in anhydrous toluene. The reaction was refluxed for 40 h and then returned to ambient temperature. Volatiles were removed under reduced pressure. The amide 46 was used without further purification. ES/MS m/z 422 (MH$^+$), $C_{19}H_{17}Cl_2N_3O_2S$=422 g/mol.

Step 6: Formation of Pyrimidine Ring (47)

Sodium ethoxide (3.0 eq.) and methylguanidine hydrochloride (R=Me, 3.0 eq.) or guanidine hydrochloride (R=H, 3.0 eq.) were added to a 0.2 M suspension of compound 46 in absolute ethanol. The reaction was stirred at 70° C. for 2 days and then returned to ambient temperature. The crude material was purified by reverse-phase HPLC to give 47. The following data is for R=Me. ES/MS m/z 432 (MH$^+$), $C_{19}H_{15}Cl_2N_5OS$=432 g/mol.

Example 12

Synthesis of 3-amino-N-[2-(2,4-dichlorophenyl)ethyl]-5-[2-(methylamino)pyrimidin-4-yl]thiophene-2-carboxamide

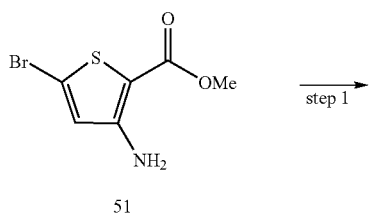

51

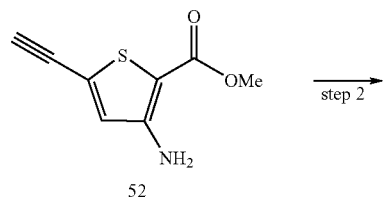

52

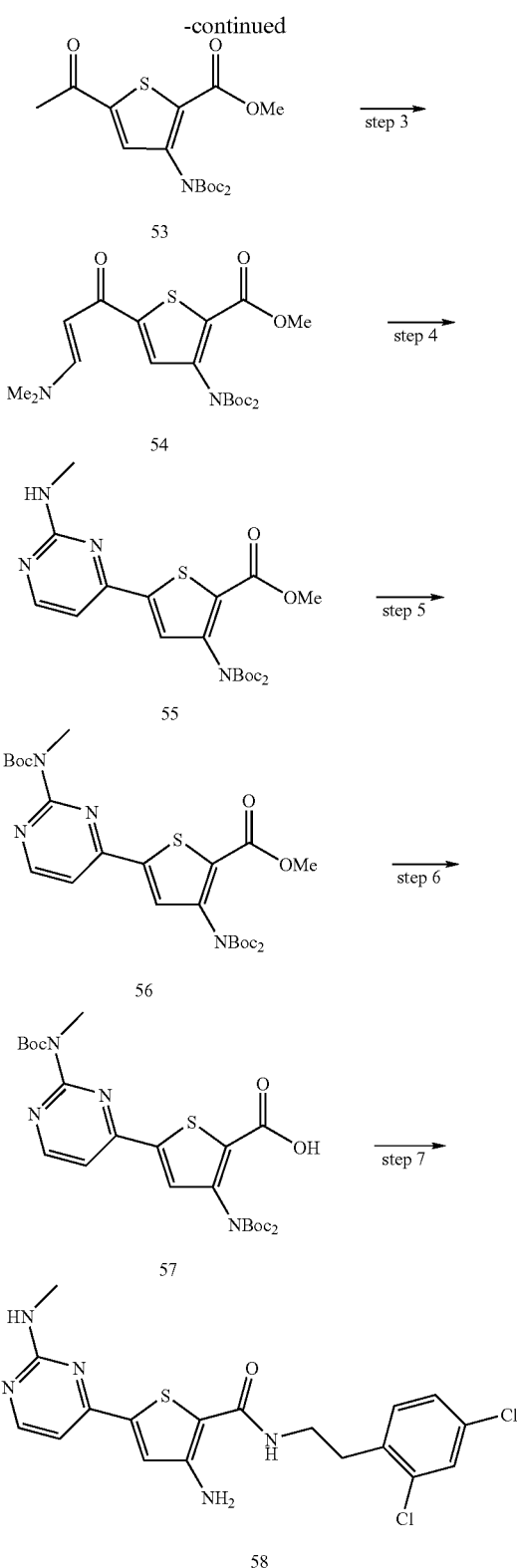

eq.) were added to a degassed solution of the bromide 51 in 2:1 tetrahydrofuran:triethylamine. The mixture was stirred for 16 h at 70° C. and then cooled to ambient temperature, diluted with ethyl acetate, and filtered through a silica gel plug. The filtrate was concentrated and re-dissolved to make a 0.05 M solution in methanol. Potassium carbonate (2.0 eq.) was added, and the mixture was stirred 16 h at ambient temperature. Volatiles were removed under reduced pressure. The residue was redissolved in dichloromethane, washed sequentially with water and brine, dried over sodium sulfate, filtered, concentrated to give the desired alkyne 52. ES/MS m/z 182 (MH$^+$), $C_8H_7N_2OS=181$ g/mol.

Step 2: Hydration to Ketone and Protection as t-Butyl Carbamate (53)

A 2.0 N aqueous solution of sulfuric acid (20 eq.) was added to a 0.05 M solution of the alkyne 52 in 1,4-dioxane. The mixture was stirred at 80° C. for 16 h and returned to ambient temperature. Volatiles were removed under reduced pressure. Ethyl acetate and saturated aqueous sodium bicarbonate were added. The organic layer was dried over sodium sulfate, filtered, and concentrated.

Di-tert-butyldicarbonate (2.50 eq.) and 4-dimethylaminopyridine (0.200 eq.) were added to a 0.3 M solution of the crude material in tetrahydrofuran. The mixture was stirred 16 h at ambient temperature. Volatiles were removed under reduced pressure. The residue was purified by flash chromatography (2:1 hexanes:ethyl acetate) to give the desired ketone 53. ES/MS m/z 400 (MH$^+$), $C_{18}H_{25}NO_7S=399$ g/mol.

Step 3: Formation of Vinylogous Amide (54)

Dimethylformamide dimethyl acetal (2.5 eq.) was added to a 0.20 M solution of compound 53 (1.0 eq.) in anhydrous toluene. The reaction was refluxed for 18 h and then returned to ambient temperature. Volatiles were removed under reduced pressure. The amide 54 was used without further purification. ES/MS m/z 455 (MH$^+$), $C_{21}H_{30}N_2O_7S=454$ g/mol.

Step 4: Formation of Aminopyrimidine (55)

Sodium ethoxide (4.1 eq.) and methylguanidine hydrochloride (4.0 eq.) were added to a 0.2 M suspension of compound 54 in absolute ethanol. The reaction was stirred at 70° C. for 3 days and then returned to ambient temperature. Volatiles were removed under reduced pressure. Ethyl acetate and saturated aqueous sodium bicarbonate were added. The organic layer was dried over sodium sulfate, filtered, and concentrated. The aminopyrimidine 55 was used without further purification. ES/MS m/z 465 (MH$^+$), $C_{21}H_{28}N_4O_6S=464$ g/mol.

Step 5: Protection as t-Butyl Carbamate (56)

Di-tert-butyldicarbonate (3.0 eq.), triethylamine (2.0 eq.), and 4-dimethylaminopyridine 55 (0.20 eq.) were added to a 0.2 M solution of the crude material in tetrahydrofuran. The mixture was stirred 16 h at ambient temperature. Volatiles Step 1: Sonogashira and Deprotection to Alkyne (52)

Trimethylsilyl acetylene (1.2 eq.), dichlorobis(triphenylphosphine)palladium (0.04 eq.), and copper iodide (0.06 were removed under reduced pressure. The residue was purified by flash chromatography (1:1 hexanes:ethyl acetate) to give the desired product 56. ES/MS m/z 565 (MH+), $C_{26}H_{36}N_4O_8S$=564 g/mol.

Step 6: Saponification to Carboxylic Acid (57)

A 1.0 M aqueous solution of sodium hydroxide (3.0 eq.) was added to a 0.1 M solution of the t-butyl carbamate 56 in ethanol. The mixture was stirred for 16 h at ambient temperature. The reaction mixture was diluted with dichloromethane and washed sequentially with dilute aqueous HCl and brine. The organic layer was dried over sodium sulfate, filtered, and concentrated. The carboxylic acid 57 was used without further purification. ES/MS m/z 551 (MH+), $C_{23}H_{34}N_4O_8S$=550 g/mol.

Step 7: Condensation to Amide (58)

N,N'-Carbonyldiimidazole (1.0 eq.) was added to a 0.1 M solution of the carboxylic acid 57 in anhydrous THF. The mixture was stirred for 3 h at 60° C. The solution was returned to ambient temperature; and 2,4-dichlorophenethylamine (1.1 eq.) was added. The solution was stirred 3 d at 60° C. The mixture was returned to ambient temperature and diluted with one volume of methanol and 2 volumes of 3M aqueous hydrochloric acid. The mixture was stirred at 60° C. for 3 h. Volatiles were removed under reduced pressure, and the residue was purified by reverse-phase HPLC to give the final product 58. ES/MS m/z 422 (MH+), $C_{18}H_{17}Cl_2N_5OS$=422 g/mol.

Example 13

Synthesis of 4-{5-[(E)-2-(4-chloro-1,3-benzothiazol-2-yl)vinyl]thien-2-yl}pyrimidin-2-amine and 4-{5-[(4-chloro-1,3-benzothiazol-2-yl)ethynyl]thien-2-yl}pyrimidin-2-amine

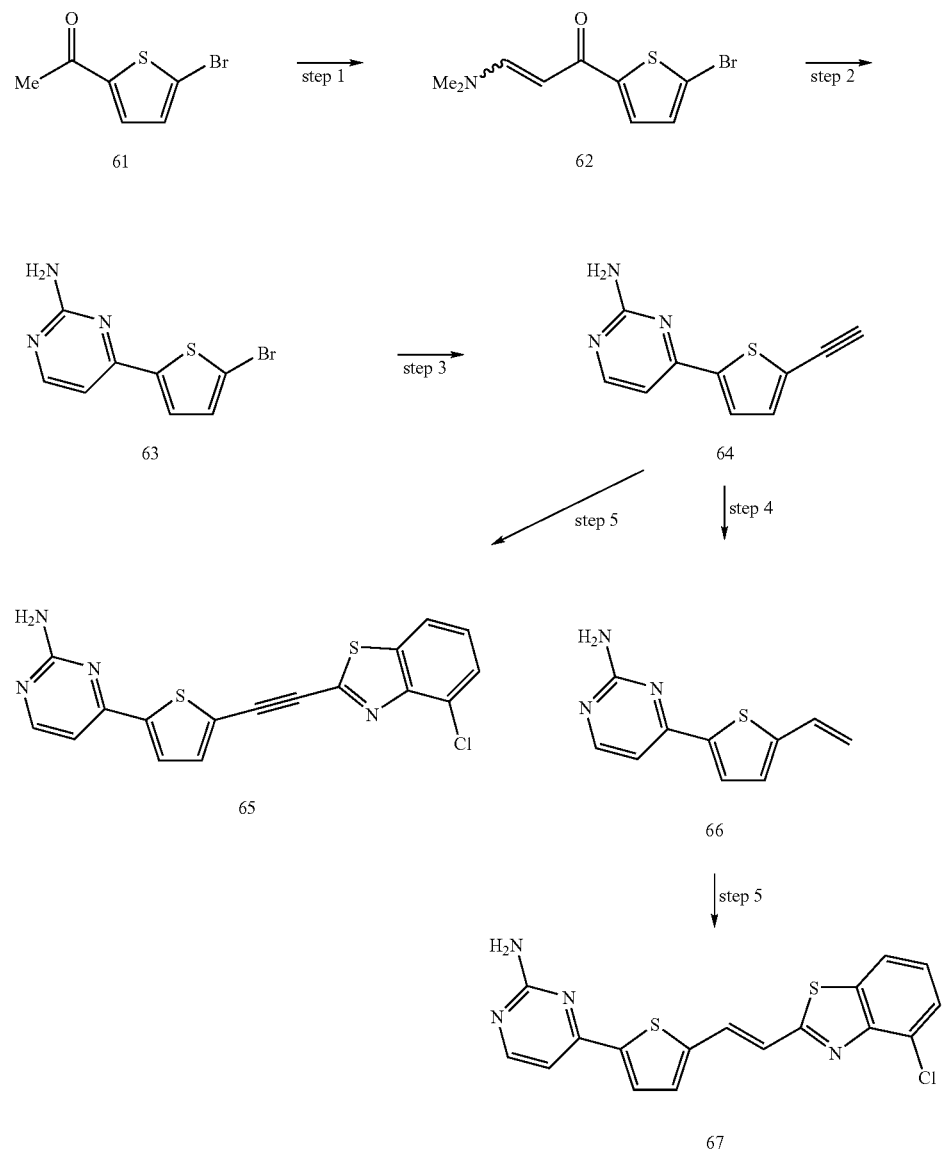

Step 1: Formation of Vinylogous Amide (62)

Dimethylformamide dimethyl acetal (2.50 eq.) was added to a 0.30 M solution of compound 61 (1.00 eq.) in anhydrous toluene. The reaction was refluxed for 15 h and then returned to ambient temperature. The product was precipitated by the addition of 1:1 ether:hexanes and isolated by vacuum filtration. The filter cake was rinsed with additional 1:1 ether:hexanes and then dried under reduced pressure to give compound 62 as a tan solid. ES/MS m/z 260,262 (MH$^+$), $C_9H_{10}BrNOS=260$ g/mol.

Step 2: Cyclization to Aminopyrimidine (63)

Sodium ethoxide (2.10 eq.) and methylguanidine hydrochloride (2.00 eq.) were added to a 0.2 M solution of compound 62 (1.00 eq.) in absolute ethanol at ambient temperature. The mixture was stirred at 70° C. for 16 h. Volatiles were removed under reduced pressure. The slurry was diluted with dichloromethane and washed sequentially with water and brine. The organic phase was dried over sodium sulfate, filtered, and concentrated to give compound 63. ES/MS m/z 256, 258 (MH$^+$), $C_{12}H_{13}N_3O_2S=256$ g/mol.

Step 3: Sonogashira and Deprotection to Alkyne (64)

Trimethylsilyl acetylene (1.5 eq.), dichlorobis(triphenylphosphine)palladium (0.04 eq.), and copper iodide (0.06 eq.) were added to a degassed solution of the bromide 63 in 2:1 tetrahydrofuran:triethylamine. The mixture was stirred for 16 h at 70° C. and then cooled to ambient temperature, diluted with ethyl acetate, and filtered through a silica gel plug. The filtrate was concentrated and re-dissolved to make a 0.07 M solution in methanol. Potassium carbonate (2.0 eq.) was added, and the mixture was stirred 3 h at ambient temperature. Volatiles were removed under reduced pressure. The residue was chromatographed to give the desired alkyne 64. ES/MS m/z 202 (MH$^+$), $C_{10}H_7N_3S=201$ g/mol.

Step 4: Reduction to Alkene (66)

Quinoline (0.20 eq by mass) and Lindlar's catalyst (0.10 eq by mass) were added to a 0.05 M suspension of alkyne 64 in ethyl acetate. The mixture was stirred under a hydrogen balloon overnight, filtered, and concentrated. The alkene 66 was used without further purification. ES/MS m/z 204 (MH$^+$), $C_{10}H_7N_3S=203$ g/mol.

Step 5: Palladium-Catalyzed Coupling (65 and 67)

Either the alkyne 64 from step 3 or the alkene 66 from step 4 was mixed with 2-bromo-4-chloro benzothiazole (1.0 eq.), dicyclohexylmethylamine (1.1 eq.), tri-t-butylphosphine (0.03 eq.), and tris(dibenzylideneacetone)dipalladium(0) (0.015 eq.) and dioxane in a microwave vial. The mixture was microwaved at 190° C. for 8 min. The mixture was diluted with ethyl acetate, filtered through a silica plug, concentrated, and purified by reverse-phase HPLC to give the desired product 65 or 67.

Example 14

Synthesis of N-[(1S)-2-amino-1-(2,4-dichlorobenzyl)ethyl]-5-(2-amino-1H-imidazol-4-yl)thiophene-2-carboxamide

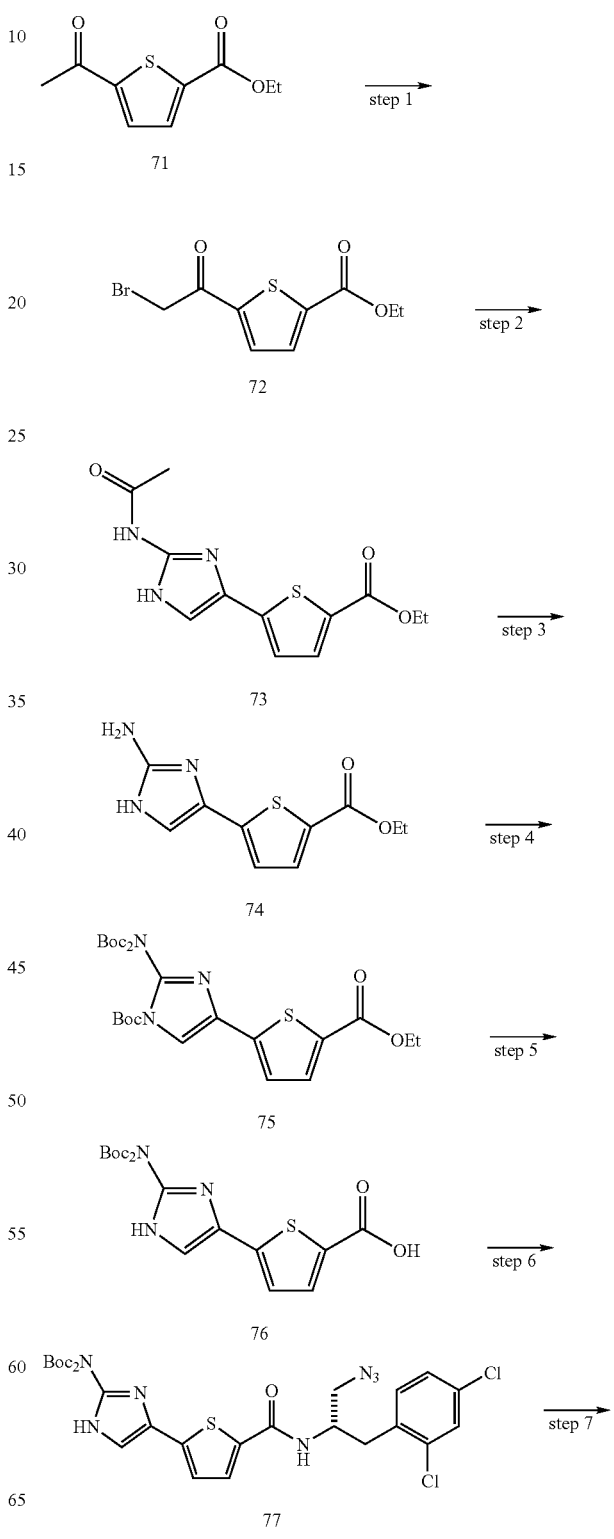

-continued

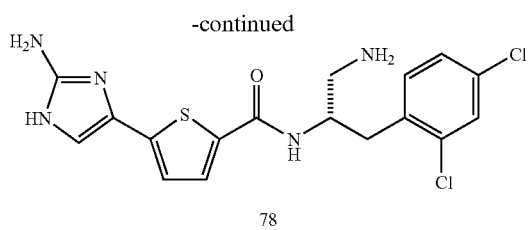

78

Step 1: Bromination to alpha-Bromoketone (72)

To a 0.75 M solution of 5-acetylthiophene-2-carboxylic acid ethyl ester 71 (1.0 eq.) in 1,4-dioxane was added bromine (1.0 eq.). The mixture was stirred for 16 h at ambient temperature. Ether was added. The solution was washed with water, dried over sodium sulfate, filtered, and concentrated to provide the alpha-bromoketone 72. The crude material was used without further purification.

Step 2: Cyclization to Acetamidoimidazole (73)

The alpha-bromoketone 72 was dissolved in acetonitrile. 1-Acetylguanidine (2.50 eq.) was added. The mixture was stirred at 80° C. for 6 h. Volatiles were removed under reduced pressure. The residue was redissolved in DCM, washed with saturated aqueous sodium bicarbonate, dried over sodium sulfate, filtered, and concentrated to provide the acetamidoimidazole 73. The material was purified by flash chromatography (1:1 acetone:hexanes). ES/MS m/z 280 (MH+), $C_{12}H_{13}N_3O_3S$=279 g/mol.

Step 3: Cleavage of Acetyl Group (74)

2.0 N aqueous sulfuric acid (3.0 eq.) was added to a 0.3M solution of compound 73 in methanol. The mixture was stirred 18 h at 70° C. Volatiles were removed under reduced pressure. The residue was redissolved in DCM, washed with saturated aqueous sodium bicarbonate, dried over sodium sulfate, filtered, and concentrated to provide compound 74. The crude material was used without further purification. ES/MS m/z 238 (MH+), $C_{10}H_{11}N_3O_2S$=237 g/mol.

Step 4: Protection as t-Butyl Carbamate (75)

Di-tert-butyldicarbonate (3.0 eq.) and 4-dimethylaminopyridine (0.20 eq.) were added to a 0.3 M solution of compound 74 in tetrahydrofuran. The mixture was stirred 16 h at ambient temperature, concentrated, and purified by flash chromatography (2:1 hexanes:ethyl acetate) to provide the t-butyl carbamate 75. ES/MS m/z 538 (MH+), $C_{25}H_{35}N_3O_8S$=537 g/mol.

Step 5: Saponification to Carboxylic Acid (76)

Aqueous potassium hydroxide (4.0 eq.) was added to a 0.2 M solution of the t-butyl carbamate 75 in ethanol. The mixture was stirred for 5 d at ambient temperature. Volatiles were removed under reduced pressure. The pH was adjusted to about 3 with aqueous HCl. Dichloromethane was added. The precipitate was filtered off, washed with water, and dried in a desiccator to give the carboxylic acid 76 which was used without further purification. ES/MS m/z 410 (MH+), $C_{18}H_{23}N_3O_6S$=409 g/mol.

Step 6: Condensation to Amide (77)

N,N'-Carbonyldiimidazole (1.0 eq.) was added to a 0.2 M solution of the carboxylic acid 76 in anhydrous N,N-dimethylformamide. The mixture was stirred for 16 h at ambient temperature. 1-Azidomethyl-2-(2,4-dichlorophenyl)ethanamine (1.1 eq.) was added. The solution was stirred an additional 16 h at 50° C. to provide the amide 77. The mixture was purified by flash chromatography (1:2 hexanes:ethyl acetate). ES/MS m/z 636, 638 (MH+), $C_{27}H_{31}ClN_7O_5S$=636 g/mol.

Step 7: Hydrogenation and Deprotection (78)

To a degassed 0.05 M solution of the amide 77 in methanol was added 10% palladium on carbon (0.10 eq by mass). The mixture was stirred under a hydrogen atmosphere for 2 h. The mixture was filtered and treated with an equal volume of 3.0M aqueous hydrochloric acid at 50° C. for 3 h. The material was concentrated and purified by HPLC to give the desired product 78.

Example 15

Synthesis of 2-Amino-4-Thiophenyl-Pyrimidine Derivatives

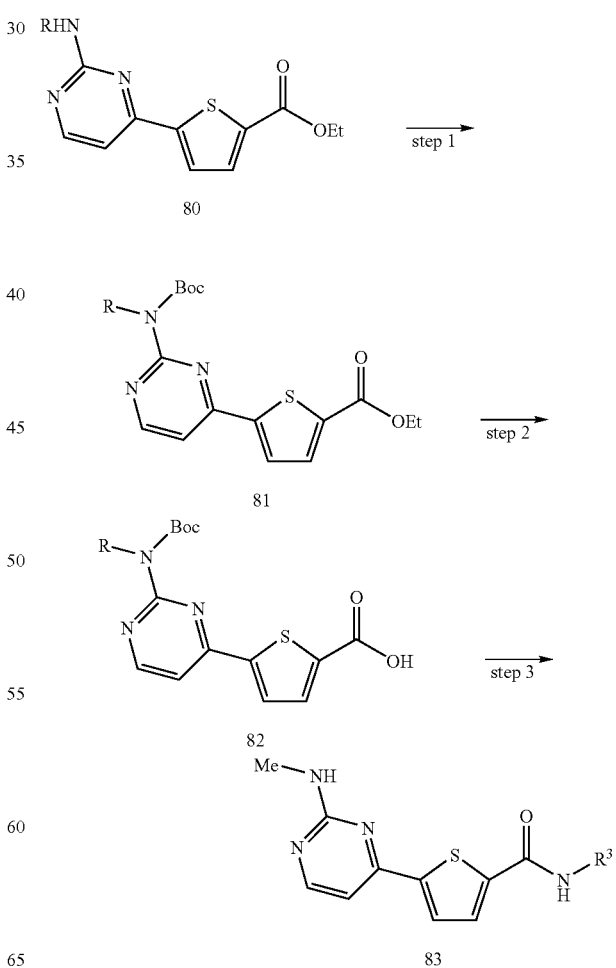

Step 1: Protection as t-butyl Carbamate (81)

Di-tert-butyldicarbonate (1.20 eq.), 4-dimethylaminopyridine (0.200 eq.), and triethylamine (1.20 eq.) were added to a 0.5 M solution of 80 (R=H, Me) in tetrahydrofuran. The mixture was stirred 16 h at ambient temperature. The mixture was diluted with ethyl acetate and washed sequentially with water and brine. The organic phase was dried over sodium sulfate, filtered, and concentrated to give compound 81 which was used without further purification. ES/MS m/z 364 (MH$^+$), $C_{17}H_{21}N_3O_4S$=363 g/mol.

Step 2: Saponification to Carboxylic Acid (82)

Aqueous sodium hydroxide (2.00 eq.) was added to a 0.2 M solution of the t-butyl carbamate 81 in ethanol. The mixture was stirred for 16 h at ambient temperature. Volatiles were removed under reduced pressure. The pH was adjusted to 3-4 with aqueous HCl. The precipitate was filtered off, washed with water, and dried in a desiccator to give the carboxylic acid 82 which was used without further purification. ES/MS m/z 336 (MH$^+$), $C_{15}H_{17}N_3O_4S$=335 g/mol.

Step 3: Condensation to Amide (83)

N,N'-Carbonyldiimidazole (1.00 eq.) was added to a 0.2 M solution of the carboxylic acid in anhydrous 1,4-dioxane. The mixture was stirred for 3 h at 60° C. The solution was returned to ambient temperature and the appropriate amine (1.1 eq.) was added. The solution was stirred an additional 16 h at 60 to 100° C. The mixture was returned to ambient temperature and diluted with one volume of methanol and 2 volumes of 3M aqueous hydrochloric acid. The mixture was stirred at 60° C. for 18 h. Volatiles were removed under reduced pressure, and the residue was purified by reverse-phase HPLC to give the final product (83) (R$^3$ is as defined herein).

Step 4: Optional Additional Step

When R$^3$ was the aminomethyldichlorophenethyl substituent, an additional step was needed. The material from the previous step was not purified. Instead it was re-dissolved in methanol and flushed with inert gas. Palladium on carbon (0.1 eq by mass) was added, and the mixture was stirred under hydrogen for 2 h. The mixture was filtered and concentrated then purified by HPLC. The aminomethyl was protected as the azidomethyl. This step reduced the azide to the primary amine.

Example 16

Synthesis of N-[(1S)-2-amino-1-(2,4-dichlorobenzyl)ethyl]-5-pyridin-4-ylthiophene-2-carboxamide

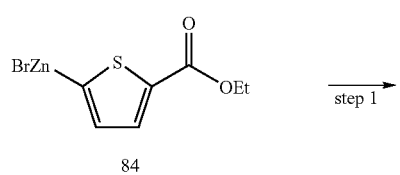

84

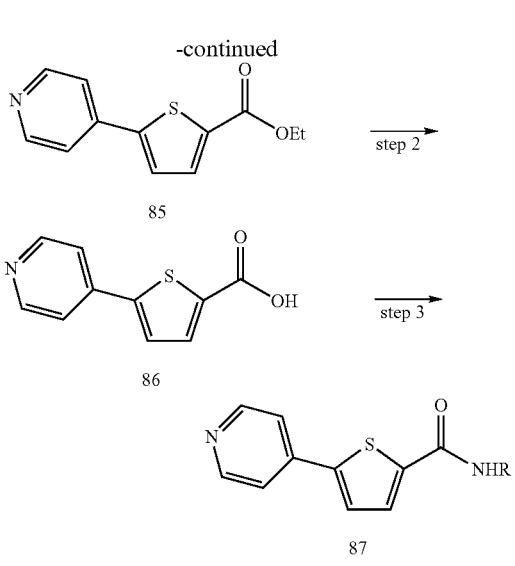

R = (1S)-2-amino-1-(2,4-dichlorobenzyl)ethyl

In addition to synthesizing the title compound, this synthesis was employed to synthesize other 2-heteroarylthiophenes, pyrazoles, aminopyridines, and acylaminopyeridines of this invention.

Step 1: Negishi Coupling to 4-(2-thienyl)pyridine (85)

To a degassed 0.50 M solution of 4-bromopyridine (1.0 eq.) and 5-ethoxycarbonyl-2-thienylzinc bromide 84 (1.0 eq.) in tetrahydrofuran was added tetrakis(triphenylphosphine)palladium(0) (0.050 eq.). The mixture was stirred for 16 h at 70° C. and then returned to ambient temperature and diluted with ether. The solution was washed sequentially with a 0.5 M aqueous pH 9 solution of EDTA and brine. The organic phase was dried over sodium sulfate, filtered, and concentrated. The crude material was purified by flash chromatography over silica gel (1:1:1 hexanes:ethyl acetate:dichloromethane) to give compound 2. ES/MS m/z 234 (MH$^+$), $C_{12}H_{11}NO_2S$=233 g/mol.

Step 2: Saponification to Carboxylic Acid (86)

Aqueous sodium hydroxide (2.00 eq.) was added to a 0.2 M solution of the ester 85 in ethanol. The mixture was stirred for 16 h at ambient temperature. Volatiles were removed under reduced pressure. The pH was adjusted to 3-4 with aqueous HCl. The precipitate was filtered off, washed with water, and dried in a desiccator to give the carboxylic acid 86 which was used without further purification. ES/MS m/z 206 (MH$^+$), $C_{10}H_7NO_2S$=205 g/mol.

Optional Step 2': Use for Synthesis of 5-[2-(acetylamino)pyridin-4-yl]-N-[(1S)-2-amino-1-(2,4-dichlorobenzyl)ethyl]thiophene-2-carboxamide To 2-fluoro-4-(thien-2-yl-5-carboxylic acid) was added a 0.5 M solution of NH$_3$ in dioxane (2.0 eq.) and an equal volume of concentrated ammonium hydroxide. The mixture was stirred in a sealed vessel at 120° C. for 3 d. The mixture was concentrated and used without further purification. To a 0.1 M solution of the crude material was added acetic anhydride (1.5 eq.) and diisopropylethylamine (2.5 eq.). The mixture was refluxed 4 d at 100° C. The mixture was returned to ambient temperature and diluted with water. The pH of the mixture was adjusted to 3-4 and ethyl acetate was added. The organic layer was dried over sodium sulfate, filtered, and concentrated. The crude material was used without further purification.

Step 3: Condensation to Amide (87)

N,N'-Carbonyldiimidazole (1.00 eq.) was added to a 0.2 M solution of the carboxylic acid 86 in anhydrous 1,4-dioxane. The mixture was stirred for 3 h at 60° C. The solution was returned to ambient temperature; and the appropriate amine (1.1 eq.) was added. The solution was stirred an additional 16 h at 60 to 100° C. The mixture was returned to ambient temperature and diluted with 5 volumes of methanol. The reaction vessel was flushed with argon. Catalytic 10% Pd on C was added. The mixture was stirred under $H_2$ for 2 h, flushed with argon, and filtered. Volatiles were removed under reduced pressure, and the residue was purifed by reverse-phase HPLC to give the final product 87. ES/MS m/z 406 (MH$^+$), $C_{19}H_{17}Cl_2N_3OS$=406 g/mol.

Example 17

Synthesis of 2-amino-4-chlorobenzo[d]thiazole-6-carbonitrile slurry was concentrated to about half of its original volume and then filtered. The precipitate was rinsed with ether and then dried in a desiccator while under reduced pressure to give compound 93. ES/MS m/z 212 (MH$^+$), $C_8H_6ClN_3S$=211 g/mol.

Step 3: Cyclization to 6-cyanobenzthiazole (94)

A 0.6 M solution of bromine (1.5 eq.) in chloroform was added over 15 min to a 0.4 M suspension of compound 93 (1.0 eq.) in chloroform at ambient temperature. The mixture was stirred at 75° C. for 16 h and then returned to ambient temperature. The precipitate was collected and crushed to a fine powder. This material was returned to the filtrate. Additional bromine (0.5 eq.) was added; and the mixture was stirred at 75° C. for 46 h. The reaction mixture was returned to ambient temperature and filtered. The precipitate was rinsed with ether and dried under reduced pressure to give compound 94 as its HBr salt. ES/MS m/z 210 (MH$^+$), $C_8H_4ClN_3S$=209 g/mol.

Step 4: Reduction to 6-aminomethylbenzthiazole (95)

Compound 94 (1.00 eq.) was added to a 0.4M suspension of lithium aluminum hydride (4.00 eq.) in ether at 0° C. The slurry was stirred overnight at ambient temperature. The mixture was returned to 0° C. and quenched with water. The

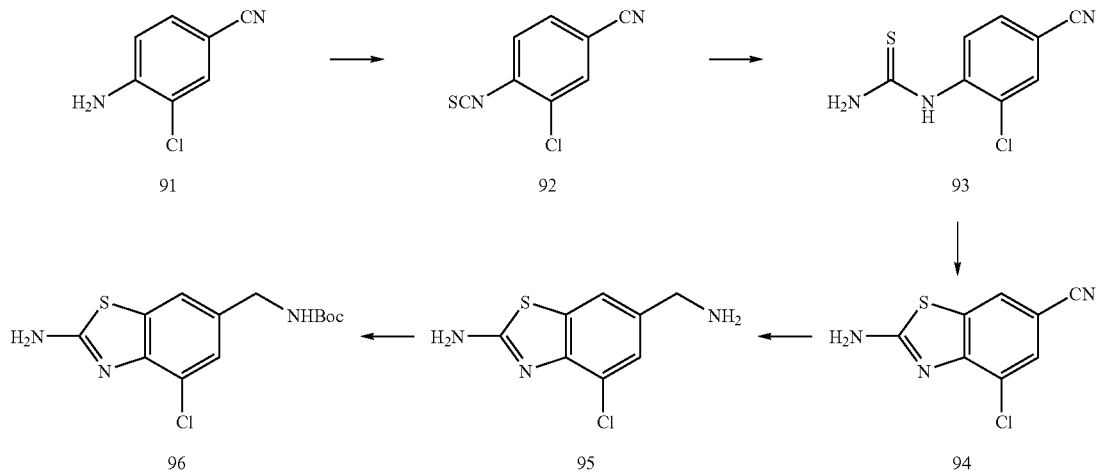

The title compound was a useful intermediate in preparing compounds of the invention.

Step 1: Synthesis of Isothiocyanate (92)

Thiophosgene (1.1 eq.) was added to a 0.5 M suspension of 4-amino-3-chlorobenzthiazole 91 (1.00 eq.) in toluene. The mixture was stirred at 110° C. for 16 h. Volatiles were removed under reduced pressure to give compound 92 which was used without further purification. ES/MS m/z 195 (MH$^+$), $C_8H_3ClN_2S$=194 g/mol.

Step 2: Synthesis of Thiourea (93)

Compound 92 (1.0 eq.) was suspended in 1,4-dioxane. Concentrated ammonium hydroxide (2.0 eq.) was added. The mixture was stirred for 30 min at ambient temperature. The layers were separated. The aqueous phase was adjusted to pH 10-11 and then extracted with dichloromethane. The combined organic phases were dried over sodium sulfate, filtered, and concentrated to give compound 95 which was used without further purification. ES/MS m/z 214 (MH$^+$), $C_8H_8ClN_3S$=213 g/mol.

Step 5: Conversion to N-Boc-aminomethylbenzthiazole (96)

Di-tertbutyl-dicarbonate (1.0 eq.) was added to a 0.1 M suspension of compound 95 in tetrahydrofuran and stirred for 1 h at ambient temperature. Volatiles were removed under reduced pressure. The material was purified by flash chromatography over silica gel (48:48:4 dichloromethane:ethyl acetate:methanol) to give compound 96. ES/MS m/z 314 (MH$^+$), $C_{13}H_{16}ClN_3O_2S$=313 g/mol.

Example 18

Synthesis of 5-(2-aminopyrimidin-4-yl)-N-(4-chloro-1-methyl-1H-benzimidazol-2-yl)thiophene-2-carboxamide

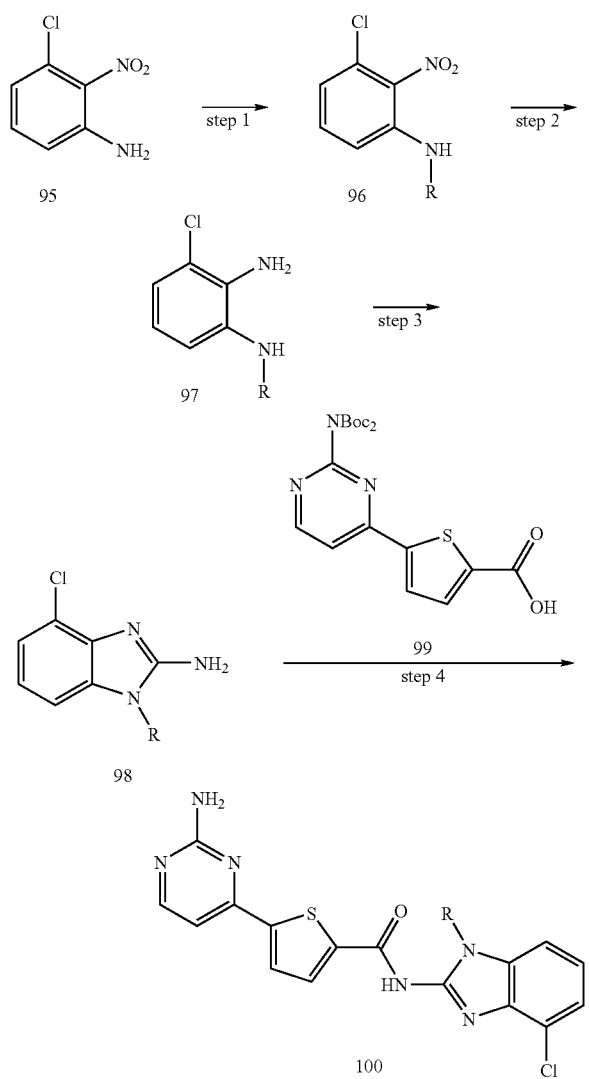

This synthesis was also employed to make the following compounds:
- 5-(2-aminopyrimidin-4-yl)-N-(4-chloro-1-ethyl-1H-benzimidazol-2-yl)thiophene-2-carboxamide;
- 5-(2-aminopyrimidin-4-yl)-N-[4-chloro-1-(3,3-dimethylbutyl)-1H-benzimidazol-2-yl]thiophene-2-carboxamide; and
- 5-(2-aminopyrimidin-4-yl)-N-(4-chloro-1-isobutyl-1H-benzimidazol-2-yl)thiophene-2-carboxamide.

Step 1: Reductive Amination (96)

The mixture of 3-chloro-2-nitroaniline 95 (1.0 eq.) and aldehyde (1.2 eq.) in dichloromethane was stirred for 2 h at ambient temperature. Sodium triacetoxyborohydride (1.2 eq.) was added, followed by the addition of acetic acid (1.2 eq.). The reaction was stirred an additional 3 h at ambient temperature. The mixture was washed with saturated sodium bicarbonate and brine. The organic phase was dried over sodium sulfate, filtered, and concentrated. The crude compound was purified by Biotage using 15% ethyl acetate in hexane to give compound 96.

Step 2: Hydrogenation (97)

Raney-Ni (25% w/w, rinsed with water and methanol) was added to a solution of compound 96 in methanol. Then hydrogen was bubbled into the reaction mixture for 3 h at ambient temperature. The reaction suspension was filtered through Celite. The filter cake was rinsed with methanol and the combined methanol solution was concentrated under reduced pressure to give desired product 97.

Step 3: Formation of 4-chloro-1-alkyl-1H-benzimidazol (98)

To a solution of cyanogens bromide in acetonitrile and water (1:10 v/v) was added compound 97 in methanol. The reaction mixture was stirred at ambient temperature for 15 h. Saturated sodium bicarbonate was added to the solution to adjust pH=8. The reaction mixture was extracted with ethyl acetate. The organic phase was washed with brine and dried with sodium sulfate, filtered and concentrated. The crude product was treaturated with hexane and was filtered to give desired product 98.

Step 4: Condensation to Amide (100)

N,N'-Carbonyldiimidazole (1.1 eq.) was added to a 0.1 M solution of the carboxylic acid 99 (1.0 eq) in anhydrous THF. The mixture was stirred for 1.5 h at 50° C. The solution was returned to ambient temperature; and 4-chloro-1-alkyl-1H-benzimidazol 98 (1.1 eq.) was added. The solution was stirred 15 h at 50° C. The mixture was returned to ambient temperature and diluted with ethyl acetate, and washed with saturated sodium bicarbonate and brine. The organic phase was dried over sodium sulfate, filtered, and concentrated. The crude compound was purified by Biotage using 60% ethyl acetate in hexane to give N-Boc protected product, which was treated with 60% trifluoroacetic acid in dichloromethane 1 h at ambient temperature. Volatiles were removed under reduced pressure, and the residue was purified by reverse-phase HPLC to give final product 100.

Example 19

Synthesis of N-(4-chloro-1,3-benzothiazol-2-yl)-3-hydroxy-5-[2-(methylamino)pyrimidin-4-yl]thiophene-2-carboxamide

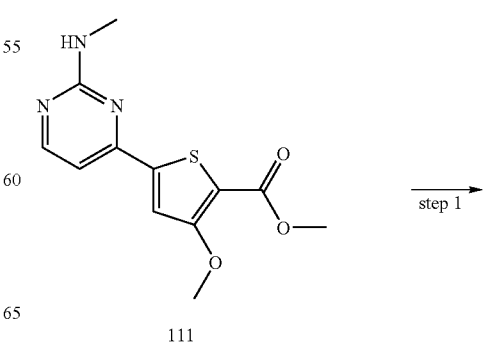

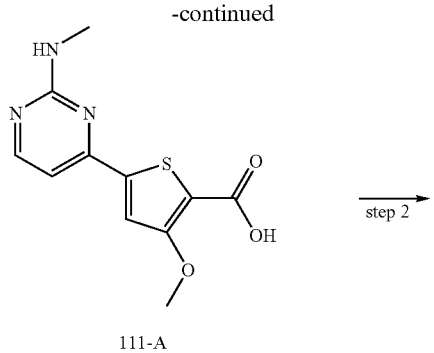

111-A

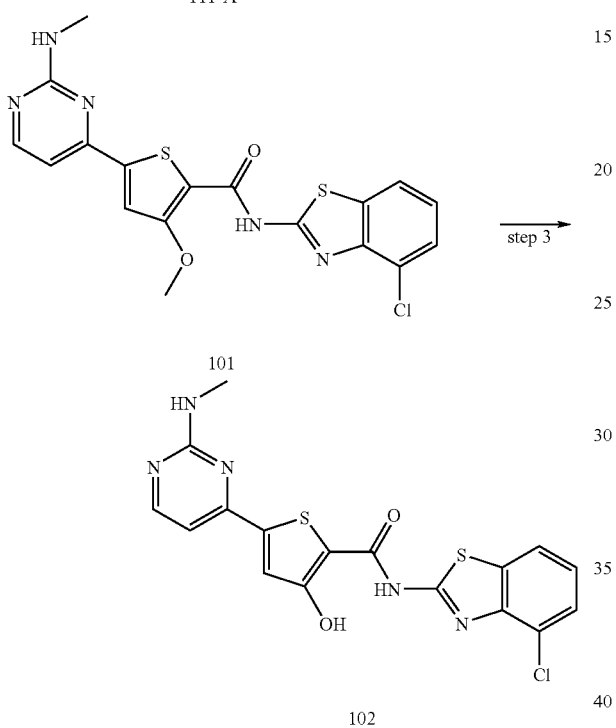

101

102

Step 1: Formation of the Carboxylic Acid (111-A)

Compound 111 underwent the reaction outlined in Step 7 of Example 20 to provide the corresponding carboxylic acid 111-A.

Step 2: Condensation to Amide (101)

Bromo-tris-pyrrolidino-phosphonium hexafluorophosphate (PyBrop, 1.5 eq.) and N-Hydroxybenzotriazole (HOBt, 1.5 eq.) were added to a 0.2 M solution of the carboxylic acid 111-A (1.0 eq.), 2-amino-4-chlorobenzothiozole (4.0 eq.), N,N-diisopropylethylamine (2.0 eq.) in anhydrous THF. The mixture was stirred 12 h at ambient temperature and was diluted with ethyl acetate, washed with saturated sodium bicarbonate and brine. The organic phase was dried over sodium sulfate, filtered, and concentrated. The crude compound was triturated with ethyl acetate and hexane (1:1, v/v) and was filtered to give product 101. ES/MS m/z 432/434 (MH$^+$), $C_{18}H_{14}ClN_5O_2S_2$=431 g/mol.

Step 3: De-methylation (102)

To a 0.1 M solution of aluminum trichloride (12 eq.) in ethanethiol at 0° C. was added a suspension of 101 in dichloromethane. The reaction was stirred at ambient temperature for 5 h. The mixture was diluted with dichloromethane and was washed sequentially with water, brine. The organic phase was dried over sodium sulfate, filtered, and concentrated to give yellow solid product 102. ES/MS m/z 418/420 (MH$^+$), $C_{17}H_{12}ClN_5O_2S_2$=418 g/mol.

Example 20

Synthesis of Various Intermediates Useful in Compounds of the Invention

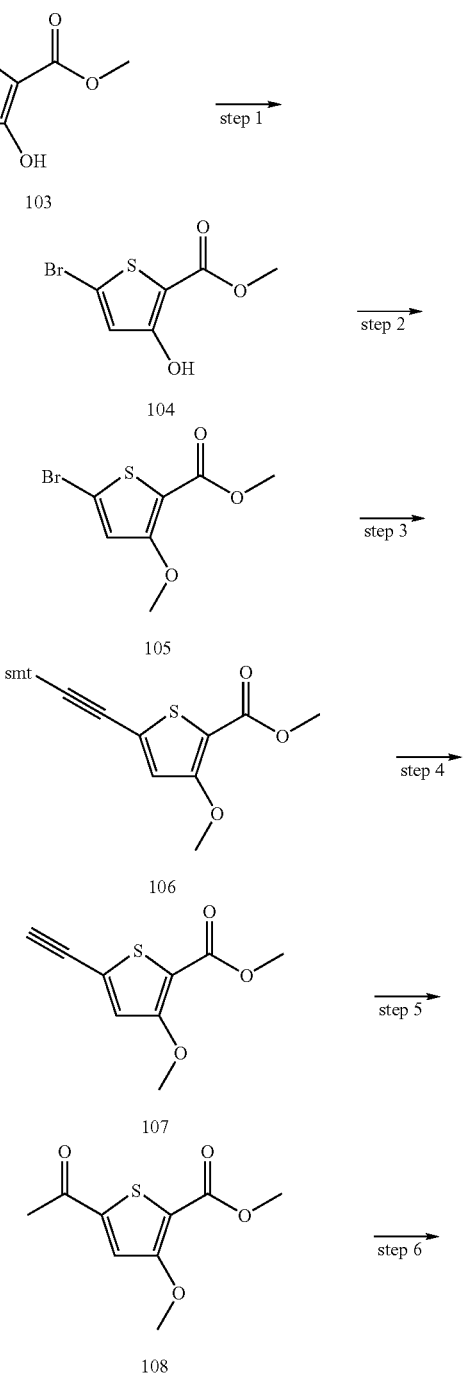

103

104

105

106

107

108

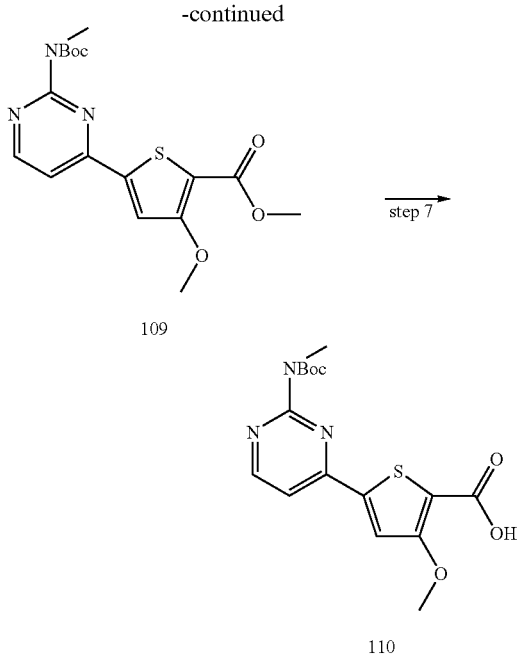

109

110

Step 1: Bromination (104)

Phenyl trimethylammonium tribromide (3.0 eq.) was added to a solution of methyl-3-hydroxythiophene-2-carboxylate 103 (1.0 eq.) in methanol and dichloromethane (1:1, v/v). This was followed by the addition of calcium carbonate (4.0 eq.). The mixture was stirred at ambient temperature for 20 h. The reaction suspension was filtered and filtrate was concentrated under reduced pressure. The residue was redissolved in ethyl acetate and washed successively with saturated sodium bicarbonate and brine. The organic phase was dried over sodium sulfate, filtered, and concentrated. The crude product was purified by Biotage using 10% ethyl acetate in hexane to give compound 104. GC/MS 237 ($M^+$), $C_6H_5BrO_3S$=237 g/mol.

Step 2: Mitsunobu Reaction to Methoxythiophene (105)

Triphenylphosphine (1.5 eq.) was added to a solution of methanol (1.5 eq.) in THF at 0° C. under Argon. This was stirred at 0° C. for 30 min and a clear solution was formed. Diethyl azodicarboxylate (1.5 eq.) was slowly added to the reaction solution at 0° C. and the resulting yellow solution was stirred at 0° C. for 1 h. Compound 104 (1.0 eq.) in THF was added and the reaction was stirred at 0° C. for 1 h and at ambient temperature for 10 h. Volatiles were removed under reduced pressure. The crude product was purified by Biotage using 5% ethyl acetate in hexane to give compound 105. ES/MS m/z 250/252 ($MH^+$), $C_7H_7BrO_3S$=251 g/mol.

Step 3: Sonogashira Reaction to TMS Acetylene (106)

To a solution of 105 (1.0 eq.) in THF and triethylamine (2:1, v/v), at ambient temperature under Argon, was added dichlorobis(triphenylphosphine) palladium(II) (0.12 eq.) and copper(I) iodide (0.2 eq.), respectively. The reaction was stirred at ambient temperature for 10 min. (Trimethylsilyl) acetylene (6.0 eq.) was slowly added. The mixture was heated in an oil bath to 70° C. for 15 h. The reaction mixture was diluted with THF, and was filtered through Silica gel. Volatiles were removed under reduced pressure. The crude material was purified by Biotage using 4% ethyl acetate in hexane to give compound 106. GC/MS 268 ($M^+$), $C_{12}H_{16}O_3SSi$=268 g/mol.

Step 4: De-Trimethylsilylation (107)

Tetrabutylammonium fluoride (1.0 M in THF, 2.0 eq.) was added to a solution of 106 (1.0 eq.) in THF at 0° C. The mixture was stirred at 0° C. for 24 h and GCMS data indicated completion of the reaction. Volatiles were removed under reduced pressure. The crude material was dissolved in dichloromethane and was washed with water, brine. The organic phase was dried over sodium sulfate, filtered, and concentrated. The crude product was purified by Biotage using 5% ethyl acetate in hexane to give compound 107.

GC/MS 196 ($M^+$), $C_9H_8O_3S$=196 g/mol.

Step 5: Replacement of Alkyne (108)

A solution of 107 (1.0 eq.) in 25% trifluoroacetic acid in dichloromethane was stirred at ambient temperature for 4 h. Volatiles were removed under reduced pressure. Tetrabutylammonium chloride (0.1 eq.) and dichloromethane/water (3:1) were added to the residue, followed by the addition of 1.0 M KOH to make aqueous phase pH=10. The reaction was stirred at ambient temperature for 30 min. Dichloromethane and water were added to reaction mixture. The organic phase was washed with brine, dried over sodium sulfate, filtered, and concentrated. The crude product was purified by Biotage using 8% ethyl acetate in hexane to give compound 108. GC/MS 214 ($M^+$), $C_9H_{10}O_4S$=214 g/mol.

Step 6: Addition of the Pyrimidine Ring (109)

Compound 109 was synthesized following Step 1 and Step 2 of Example 3 and Step 1 in Example 4.

Step 7: Saponification to Carboxylic Acid (110)

A 1.0 M aqueous solution of sodium hydroxide (3.0 eq.) was added to a solution of 109 (1.0 eq.) in ethanol. The mixture was stirred for 4 h at ambient temperature. Volatiles were removed under reduced pressure. The residue was taken into ethyl acetate and washed sequentially with dilute aqueous HCl and brine. The organic layer was dried over sodium sulfate, filtered, and concentrated to provide compound 110. The material was used without further purification. ES/MS m/z 366 ($MH^+$), $C_{16}H_{19}N_3O_5S$=365 g/mol.

Example 21

Synthesis of 3-Hydroxythiopene Derivatives

This scheme was useful for making intermediates wherein the 3-position of the thiophene was substituted.

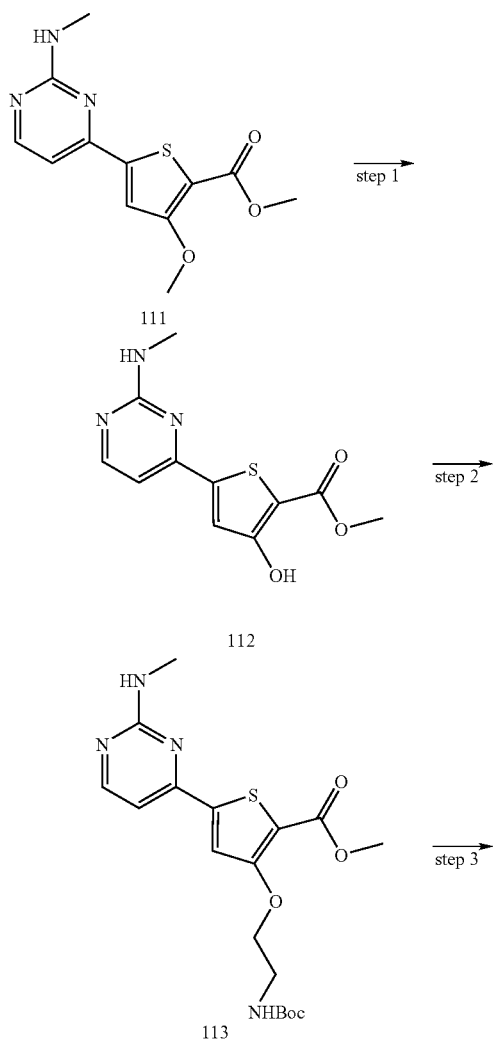

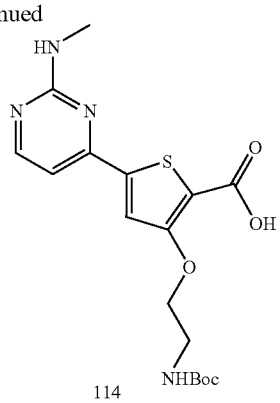

Step 1: Reduction of the Ether (112)

Following the procedure in Example 19, compound 111 is reduced to the corresponding alcohol 112.

Step 2: Mitsunobu Rection (113)

Compound 112 underwent the reaction outlined in Step 2 of Example 20 to provide the corresponding ether 113.

Step 3: Saponification to Carboxylic Acid (114)

Compound 113 underwent the saponification outlined in Step 7 of Example 20 to provide compound 114.

The compounds in Table 6 below may be prepared using the methodology described in the previous Examples. The starting materials used in the synthesis are recognizable to one of skill in the art and are commercially available or may be prepared using known methods. The compounds were named using ACD/Name Batch Version 5.04 (Advanced Chemistry Development Inc.; Toronto, Ontario; www.acd-labs.com).

TABLE 6

| No. | Structure | MH+ | Name |
|---|---|---|---|
| 1 | (structure shown) | 357 | N-[2-(4-fluorophenyl)ethyl]-5-[2-(methylamino)pyrimidin-4-yl]thiophene-2-carboxamide |
| 2 | (structure shown) | 339 | 5-[2-(methylamino)pyrimidin-4-yl]-N-(2-phenylethyl)thiophene-2-carboxamide |

TABLE 6-continued

| No. | Structure | MH+ | Name |
|---|---|---|---|
| 3 | 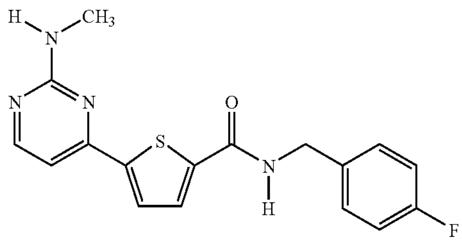 | 343 | N-(4-fluorobenzyl)-5-[2-(methylamino)pyrimidin-4-yl]thiophene-2-carboxamide |
| 4 | 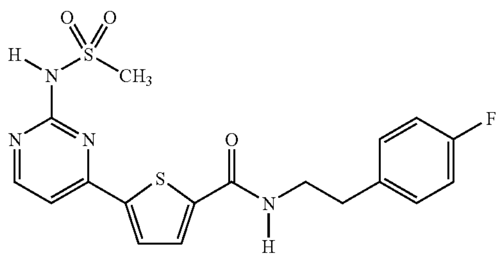 | 421 | N-[2-(4-fluorophenyl)ethyl]-5-{2-[(methylsulfonyl)amino]pyrimidin-4-yl}thiophene-2-carboxamide |
| 5 | 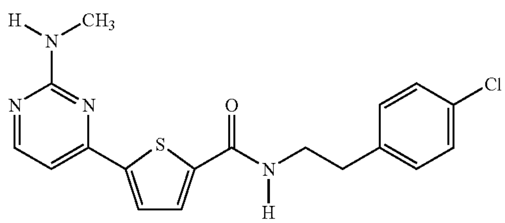 | 373 | N-[2-(4-chlorophenyl)ethyl]-5-[2-(methylamino)pyrimidin-4-yl]thiophene-2-carboxamide |
| 6 | 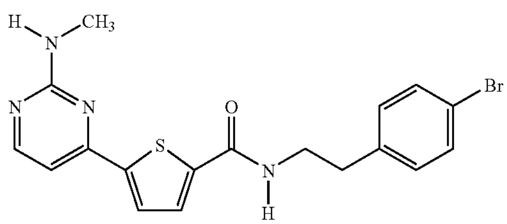 | 417 | N-[2-(4-bromophenyl)ethyl]-5-[2-(methylamino)pyrimidin-4-yl]thiophene-2-carboxamide |
| 7 | 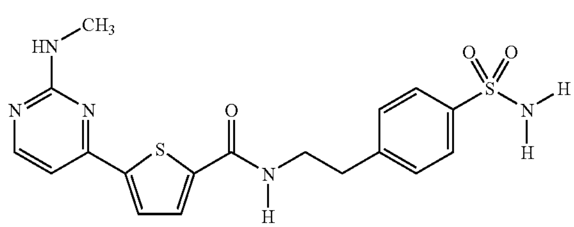 | 418 | N-{2-[4-(aminosulfonyl)phenyl]ethyl}-5-[2-(methylamino)pyrimidin-4-yl]thiophene-2-carboxamide |
| 8 | 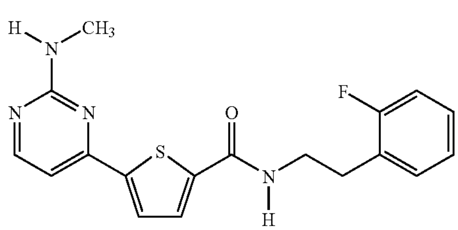 | 357 | N-[2-(2-fluorophenyl)ethyl]-5-[2-(methylamino)pyrimidin-4-yl]thiophene-2-carboxamide |

TABLE 6-continued

| No. | Structure | MH+ | Name |
|---|---|---|---|
| 9 | 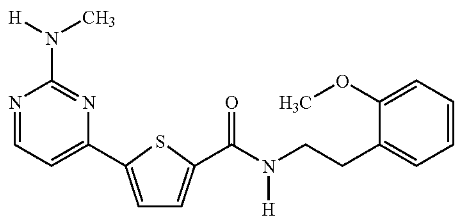 | 369 | N-[2-(2-methoxyphenyl)ethyl]-5-[2-(methylamino)pyrimidin-4-yl]thiophene-2-carboxamide |
| 10 | 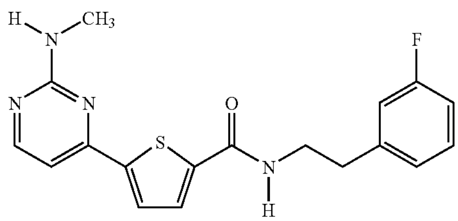 | 357 | N-[2-(3-fluorophenyl)ethyl]-5-[2-(methylamino)pyrimidin-4-yl]thiophene-2-carboxamide |
| 11 | 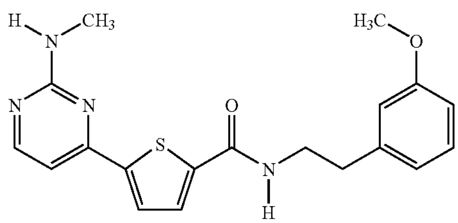 | 369 | N-[2-(3-methoxyphenyl)ethyl]-5-[2-(methylamino)pyrimidin-4-yl]thiophene-2-carboxamide |
| 12 | 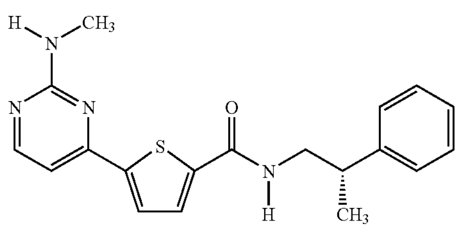 | 353 | 5-[2-(methylamino)pyrimidin-4-yl]-N-[(2S)-2-phenylpropyl]thiophene-2-carboxamide |
| 13 | 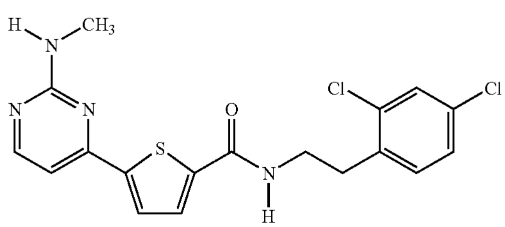 | 407 | N-[2-(2,4-dichlorophenyl)ethyl]-5-[2-(methylamino)pyrimidin-4-yl]thiophene-2-carboxamide |
| 14 | 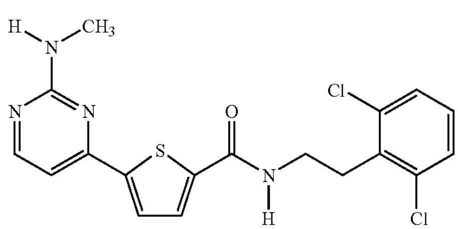 | 407 | N-[2-(2,6-dichlorophenyl)ethyl]-5-[2-(methylamino)pyrimidin-4-yl]thiophene-2-carboxamide |
| 15 | 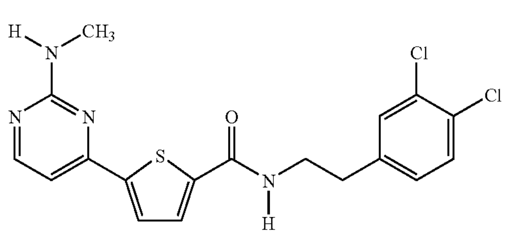 | 407 | N-[2-(3,4-dichlorophenyl)ethyl]-5-[2-(methylamino)pyrimidin-4-yl]thiophene-2-carboxamide |

TABLE 6-continued

| No. | Structure | MH+ | Name |
|---|---|---|---|
| 16 | 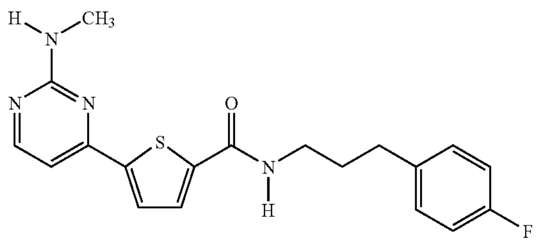 | 371 | N-[3-(4-fluorophenyl)propyl]-5-[2-(methylamino)pyrimidin-4-yl]thiophene-2-carboxamide |
| 17 | 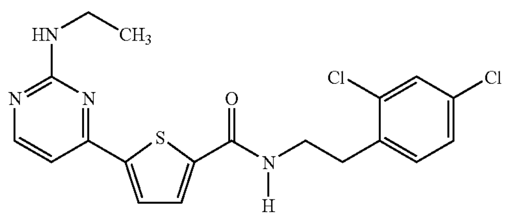 | 421 | N-[2-(2,4-dichlorophenyl)ethyl]-5-[2-(ethylamino)pyrimidin-4-yl]thiophene-2-carboxamide |
| 18 | 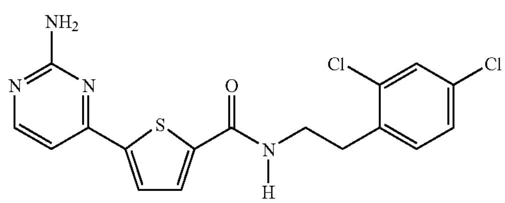 | 393 | 5-(2-aminopyrimidin-4-yl)-N-[2-(2,4-dichlorophenyl)ethyl]thiophene-2-carboxamide |
| 19 | 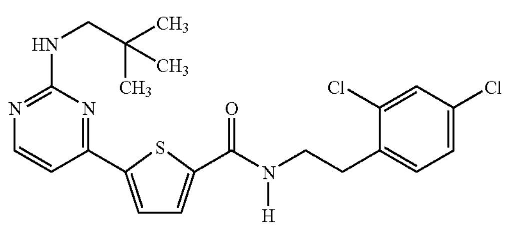 | 463 | N-[2-(2,4-dichlorophenyl)ethyl]-5-[2-(neopentylamino)pyrimidin-4-yl]thiophene-2-carboxamide |
| 20 | 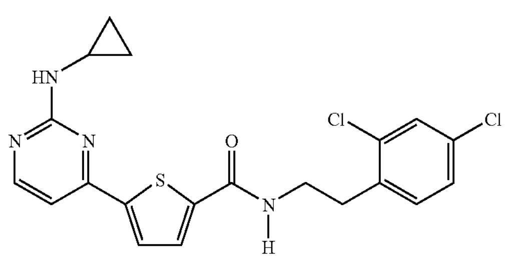 | 433 | 5-[2-(cyclopropylamino)pyrimidin-4-yl]-N-[2-(2,4-dichlorophenyl)ethyl]thiophene-2-carboxamide |
| 21 | 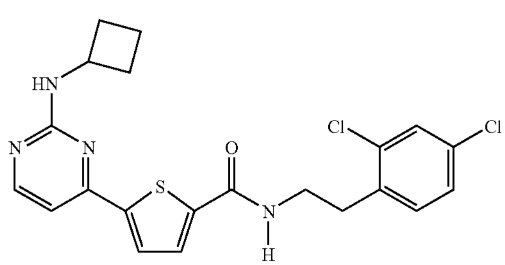 | 447 | 5-[2-(cyclobutylamino)pyrimidin-4-yl]-N-[2-(2,4-dichlorophenyl)ethyl]thiophene-2-carboxamide |

TABLE 6-continued

| No. | Structure | MH+ | Name |
|---|---|---|---|
| 22 | 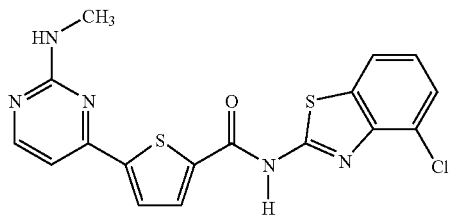 | 402 | N-(4-chloro-1,3-benzothiazol-2-yl)-5-[2-(methylamino)pyrimidin-4-yl]thiophene-2-carboxamide |
| 23 | 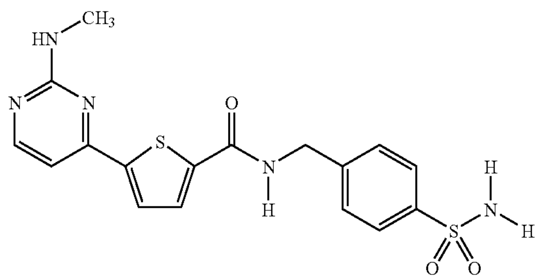 | 404 | N-[4-(aminosulfonyl)benzyl]-5-[2-(methylamino)pyrimidin-4-yl]thiophene-2-carboxamide |
| 24 | 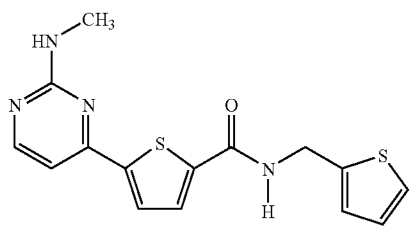 | 331 | 5-[2-(methylamino)pyrimidin-4-yl]-N-(thien-2-ylmethyl)thiophene-2-carboxamide |
| 25 | 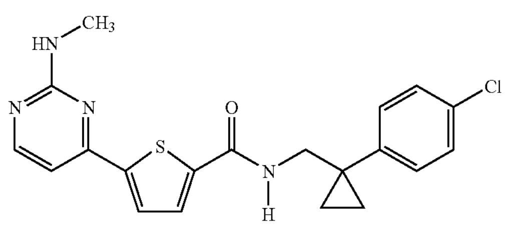 | 399 | N-{[1-(4-chlorophenyl)cyclopropyl]methyl}-5-[2-(methylamino)pyrimidin-4-yl]thiophene-2-carboxamide |
| 26 | 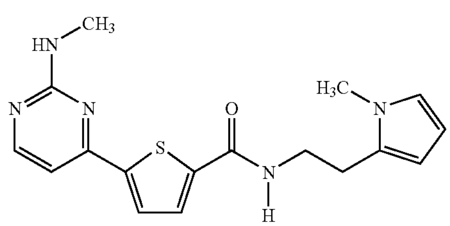 | 342 | 5-[2-(methylamino)pyrimidin-4-yl]-N-[2-(1-methyl-1H-pyrrol-2-yl)ethyl]thiophene-2-carboxamide |
| 27 | 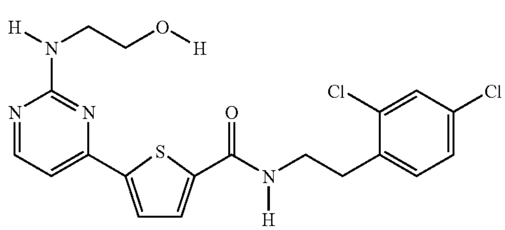 | 437 | N-[2-(2,4-dichlorophenyl)ethyl]-5-{2-[(2-hydroxyethyl)amino]pyrimidin-4-yl}thiophene-2-carboxamide |

TABLE 6-continued

| No. | Structure | MH+ | Name |
|---|---|---|---|
| 28 | 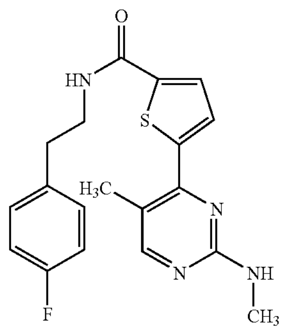 | 371 | N-[2-(4-fluorophenyl)ethyl]-5-[5-methyl-2-(methylamino)pyrimidin-4-yl]thiophene-2-carboxamide |
| 29 | 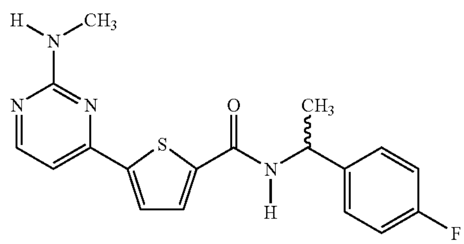 | 357 | N-[1-(4-fluorophenyl)ethyl]-5-[2-(methylamino)pyrimidin-4-yl]thiophene-2-carboxamide |
| 30 | 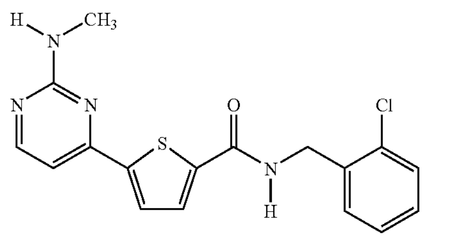 | 359 | N-(2-chlorobenzyl)-5-[2-(methylamino)pyrimidin-4-yl]thiophene-2-carboxamide |
| 31 | 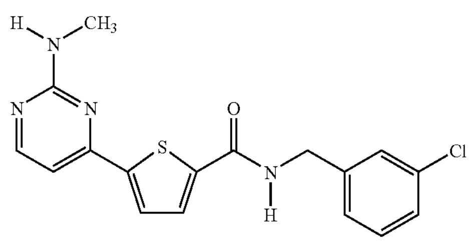 | 359 | N-(3-chlorobenzyl)-5-[2-(methylamino)pyrimidin-4-yl]thiophene-2-carboxamide |
| 32 | 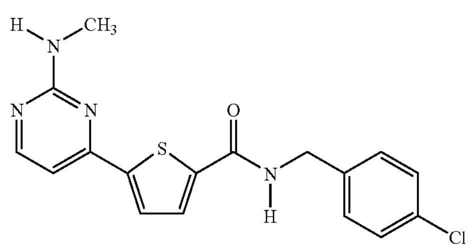 | 359 | N-(4-chlorobenzyl)-5-[2-(methylamino)pyrimidin-4-yl]thiophene-2-carboxamide |
| 33 | 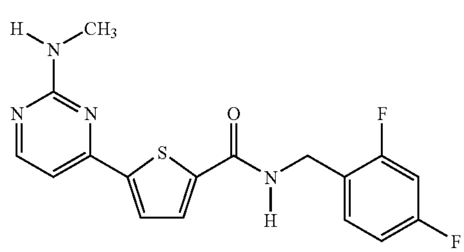 | 361 | N-(2,4-difluorobenzyl)-5-[2-(methylamino)pyrimidin-4-yl]thiophene-2-carboxamide |

TABLE 6-continued

| No. | Structure | MH+ | Name |
|---|---|---|---|
| 34 | 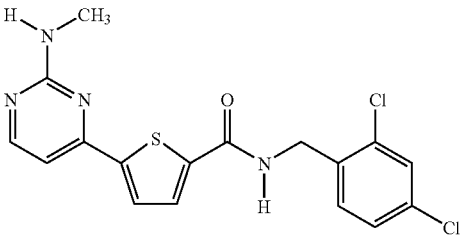 | 393 | N-(2,4-dichlorobenzyl)-5-[2-(methylamino)pyrimidin-4-yl]thiophene-2-carboxamide |
| 35 | 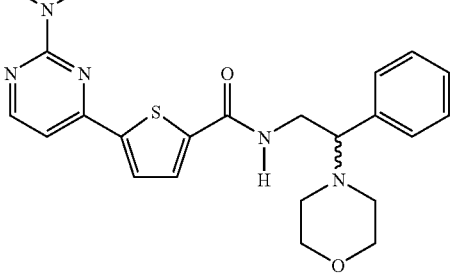 | 424 | 5-[2-(methylamino)pyrimidin-4-yl]-N-(2-morpholin-4-yl-2-phenylethyl)thiophene-2-carboxamide |
| 36 | 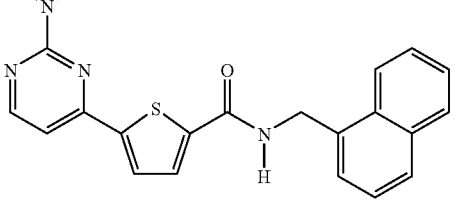 | 375 | 5-[2-(methylamino)pyrimidin-4-yl]-N-(1-naphthylmethyl)thiophene-2-carboxamide |
| 37 | 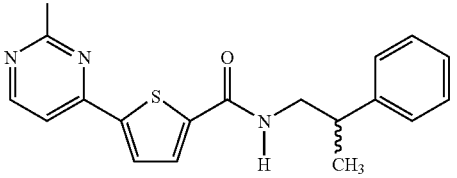 | 353 | 5-[2-(methylamino)pyrimidin-4-yl]-N-(2-phenylpropyl)thiophene-2-carboxamide |
| 38 | 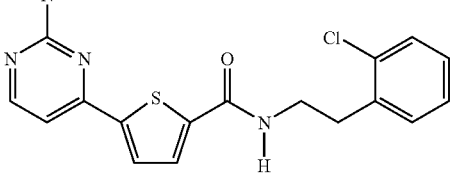 | 373 | N-[2-(2-chlorophenyl)ethyl]-5-[2-(methylamino)pyrimidin-4-yl]thiophene-2-carboxamide |
| 39 | 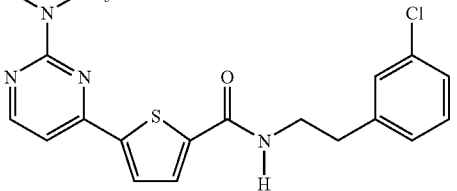 | 373 | N-[2-(3-chlorophenyl)ethyl]-5-[2-(methylamino)pyrimidin-4-yl]thiophene-2-carboxamide |

TABLE 6-continued

| No. | Structure | MH+ | Name |
|---|---|---|---|
| 40 | 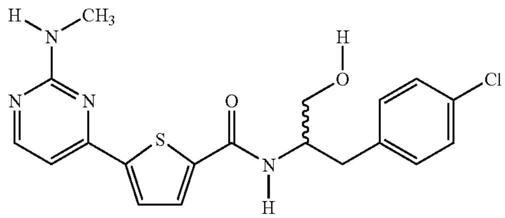 | 403 | N-[1-(4-chlorobenzyl)-2-hydroxyethyl]-5-[2-(methylamino)pyrimidin-4-yl]thiophene-2-carboxamide |
| 41 | 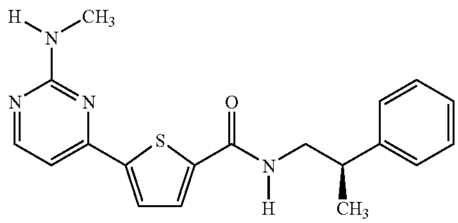 | 353 | 5-[2-(methylamino)pyrimidin-4-yl]-N-[(2R)-2-phenylpropyl]thiophene-2-carboxamide |
| 42 | 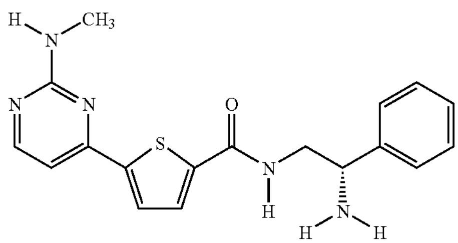 | 354 | N-[(2S)-2-amino-2-phenylethyl]-5-[2-(methylamino)pyrimidin-4-yl]thiophene-2-carboxamide |
| 43 | 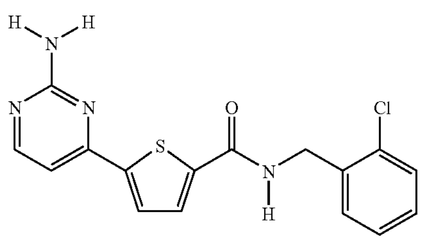 | 345 | 5-(2-aminopyrimidin-4-yl)-N-(2-chlorobenzyl)thiophene-2-carboxamide |
| 44 | 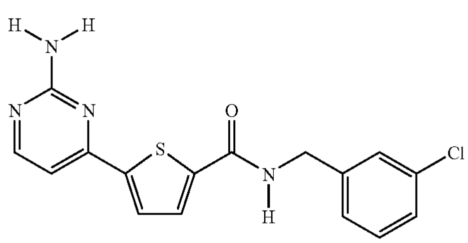 | 345 | 5-(2-aminopyrimidin-4-yl)-N-(3-chlorobenzyl)thiophene-2-carboxamide |
| 45 | 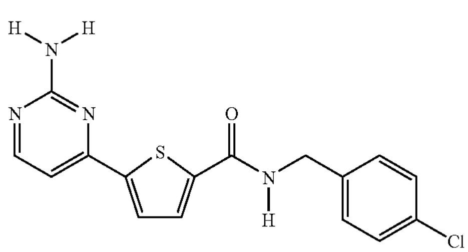 | 345 | 5-(2-aminopyrimidin-4-yl)-N-(4-chlorobenzyl)thiophene-2-carboxamide |

TABLE 6-continued

| No. | Structure | MH+ | Name |
|---|---|---|---|
| 46 | 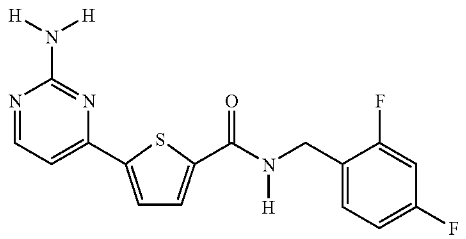 | 347 | 5-(2-aminopyrimidin-4-yl)-N-(2,4-difluorobenzyl)thiophene-2-carboxamide |
| 47 | 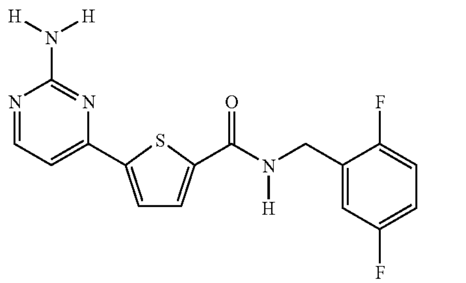 | 347 | 5-(2-aminopyrimidin-4-yl)-N-(2,5-difluorobenzyl)thiophene-2-carboxamide |
| 48 | 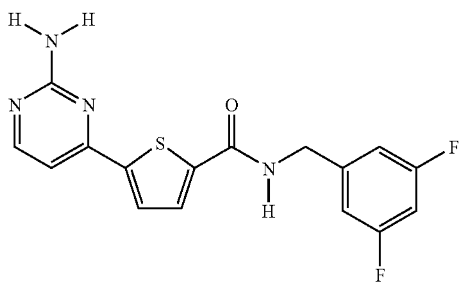 | 347 | 5-(2-aminopyrimidin-4-yl)-N-(3,5-difluorobenzyl)thiophene-2-carboxamide |
| 49 | 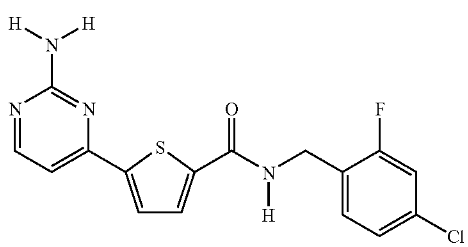 | 363 | 5-(2-aminopyrimidin-4-yl)-N-(4-chloro-2-fluorobenzyl)thiophene-2-carboxamide |
| 50 | 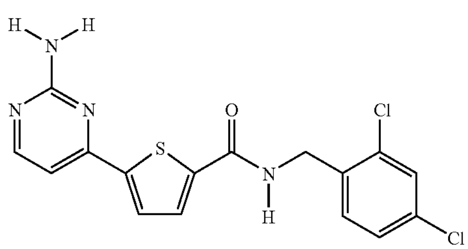 | 379 | 5-(2-aminopyrimidin-4-yl)-N-(2,4-dichlorobenzyl)thiophene-2-carboxamide |
| 51 | 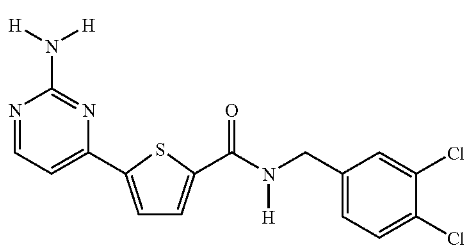 | 379 | 5-(2-aminopyrimidin-4-yl)-N-(3,4-dichlorobenzyl)thiophene-2-carboxamide |

TABLE 6-continued

| No. | Structure | MH+ | Name |
|---|---|---|---|
| 52 | 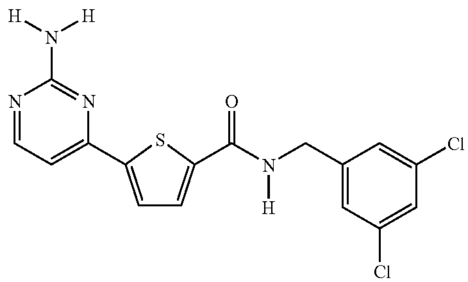 | 379 | 5-(2-aminopyrimidin-4-yl)-N-(3,5-dichlorobenzyl)thiophene-2-carboxamide |
| 53 | 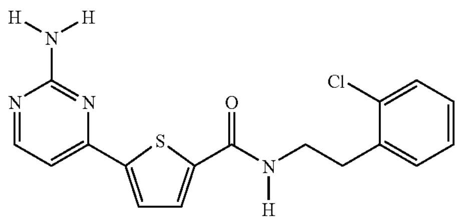 | 359 | 5-(2-aminopyrimidin-4-yl)-N-[2-(2-chlorophenyl)ethyl]thiophene-2-carboxamide |
| 54 | 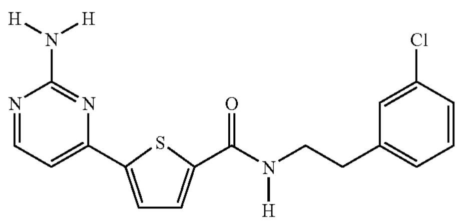 | 359 | 5-(2-aminopyrimidin-4-yl)-N-[2-(3-chlorophenyl)ethyl]thiophene-2-carboxamide |
| 55 | 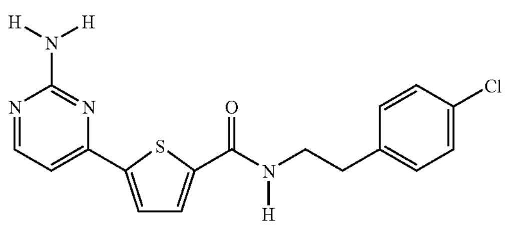 | 359 | 5-(2-aminopyrimidin-4-yl)-N-[2-(4-chlorophenyl)ethyl]thiophene-2-carboxamide |
| 56 | 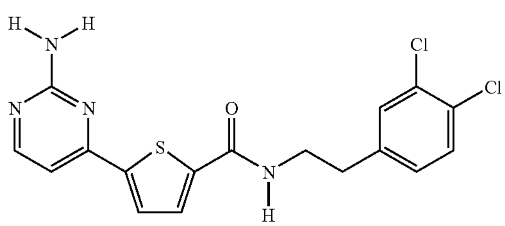 | 393 | 5-(2-aminopyrimidin-4-yl)-N-[2-(3,4-dichlorophenyl)ethyl]thiophene-2-carboxamide |
| 57 | 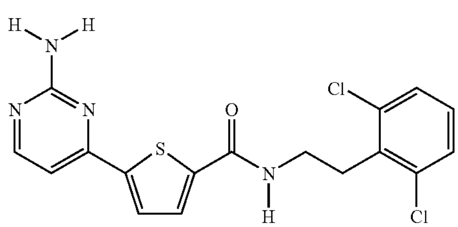 | 393 | 5-(2-aminopyrimidin-4-yl)-N-[2-(2,6-dichlorophenyl)ethyl]thiophene-2-carboxamide |

TABLE 6-continued

| No. | Structure | MH+ | Name |
|---|---|---|---|
| 58 | 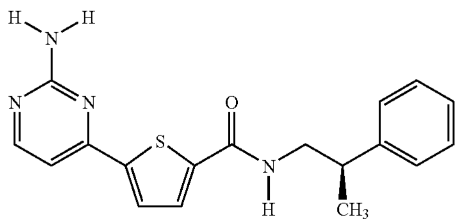 | 339 | 5-(2-aminopyrimidin-4-yl)-N-[(2R)-2-phenylpropyl]thiophene-2-carboxamide |
| 59 | 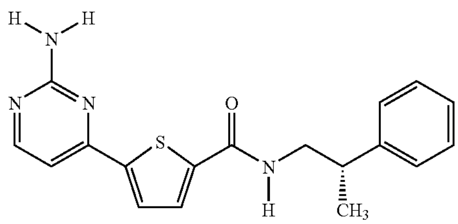 | 339 | 5-(2-aminopyrimidin-4-yl)-N-[(2S)-2-phenylpropyl]thiophene-2-carboxamide |
| 60 | 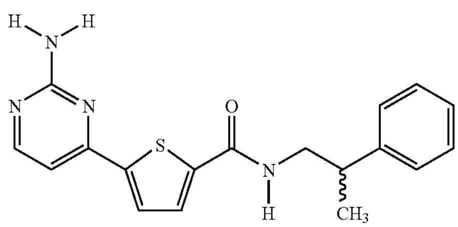 | 339 | 5-(2-aminopyrimidin-4-yl)-N-(2-phenylpropyl)thiophene-2-carboxamide |
| 61 | 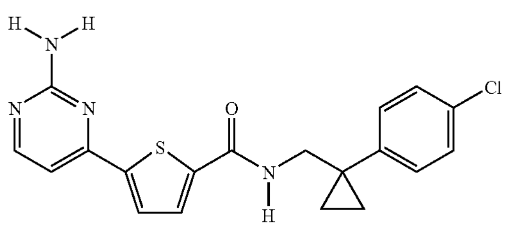 | 385 | 5-(2-aminopyrimidin-4-yl)-N-{[1-(4-chlorophenyl)cyclopropyl]methyl}thiophene-2-carboxamide |
| 62 | 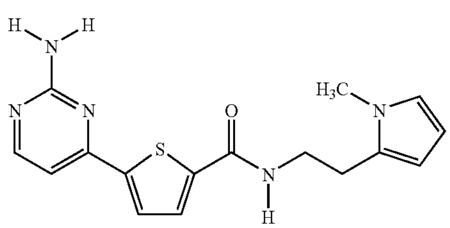 | 328 | 5-(2-aminopyrimidin-4-yl)-N-[2-(1-methyl-1H-pyrrol-2-yl)ethyl]thiophene-2-carboxamide |
| 63 | 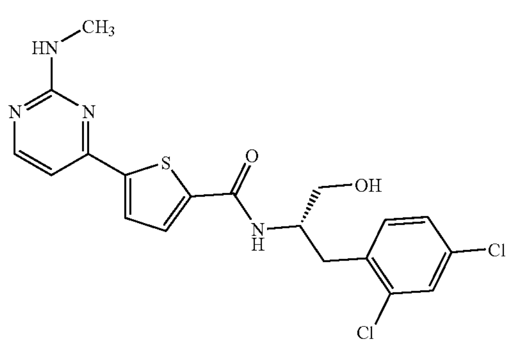 | 438 | N-[(1S)-1-(2,4-dichlorobenzyl)-2-hydroxyethyl]-5-[2-(methylamino)pyrimidin-4-yl]thiophene-2-carboxamide |

TABLE 6-continued

| No. | Structure | MH+ | Name |
|---|---|---|---|
| 64 | 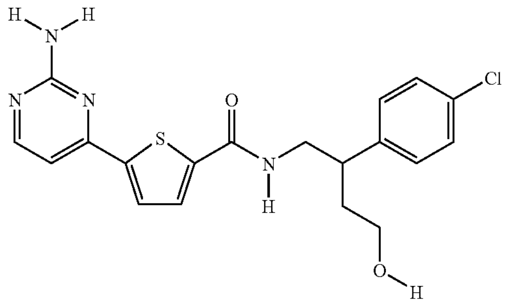 | 417 | N-[2-(4-chlorophenyl)-4-hydroxybutyl]-5-[2-(methylamino)pyrimidin-4-yl]thiophene-2-carboxamide |
| 65 | 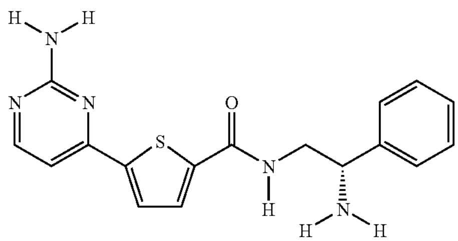 | 340 | N-[(2S)-2-amino-2-phenylethyl]-5-(2-aminopyrimidin-4-yl)thiophene-2-carboxamide |
| 66 | 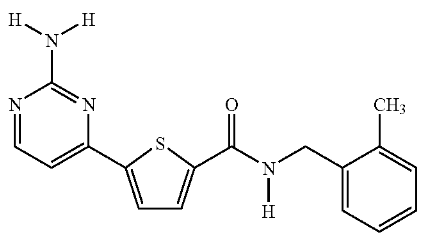 | 325 | 5-(2-aminopyrimidin-4-yl)-N-(2-methylbenzyl)thiophene-2-carboxamide |
| 67 | 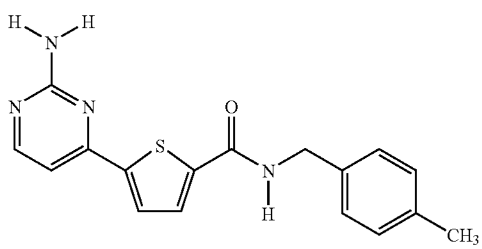 | 325 | 5-(2-aminopyrimidin-4-yl)-N-(4-methylbenzyl)thiophene-2-carboxamide |
| 68 | 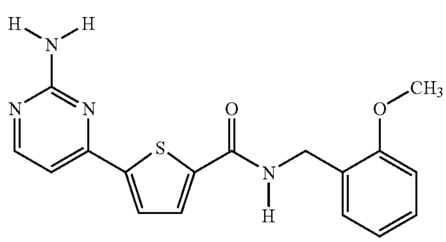 | 341 | 5-(2-aminopyrimidin-4-yl)-N-(2-methoxybenzyl)thiophene-2-carboxamide |
| 69 | 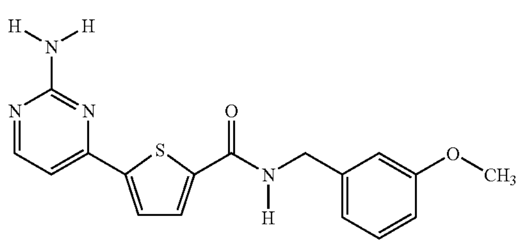 | 341 | 5-(2-aminopyrimidin-4-yl)-N-(3-methoxybenzyl)thiophene-2-carboxamide |

TABLE 6-continued

| No. | Structure | MH+ | Name |
|---|---|---|---|
| 70 | 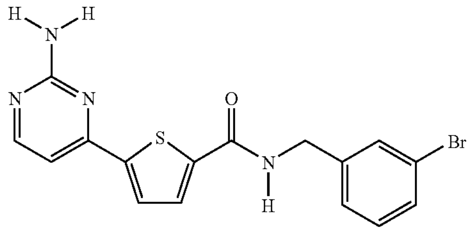 | 389 | 5-(2-aminopyrimidin-4-yl)-N-(3-bromobenzyl)thiophene-2-carboxamide |
| 71 | 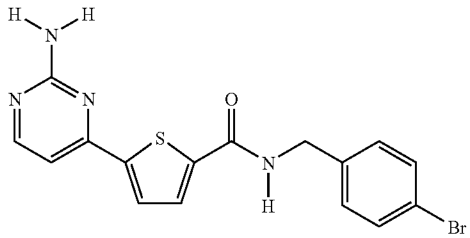 | 389 | 5-(2-aminopyrimidin-4-yl)-N-(4-bromobenzyl)thiophene-2-carboxamide |
| 72 | 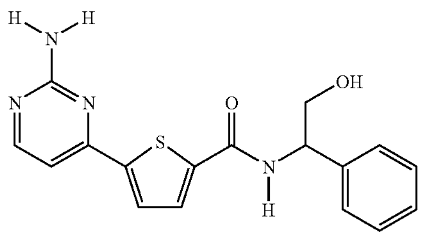 | 341 | 5-(2-aminopyrimidin-4-yl)-N-(2-hydroxy-1-phenylethyl)thiophene-2-carboxamide |
| 73 | 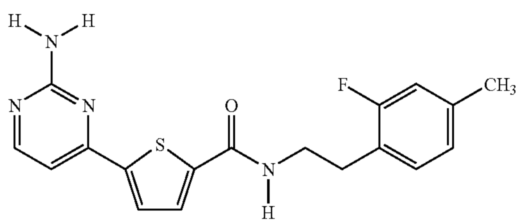 | 357 | 5-(2-aminopyrimidin-4-yl)-N-[2-(2-fluoro-4-methylphenyl)ethyl]thiophene-2-carboxamide |
| 74 | 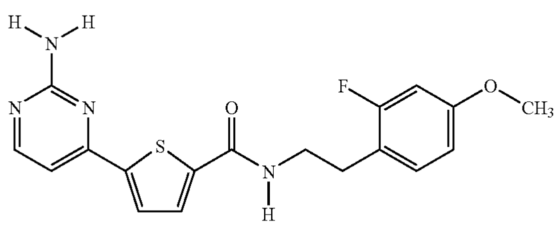 | 373 | 5-(2-aminopyrimidin-4-yl)-N-[2-(2-fluoro-4-methylphenyl)ethyl]thiophene-2-carboxamide |
| 75 | 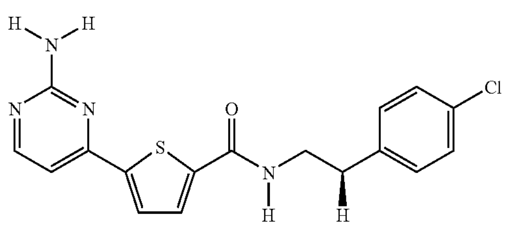 | 375 | 5-(2-aminopyrimidin-4-yl)-N-[(2R)-2-(4-chlorophenyl)-2-hydroxyethyl]thiophene-2-carboxamide |

TABLE 6-continued

| No. | Structure | MH+ | Name |
|---|---|---|---|
| 76 | 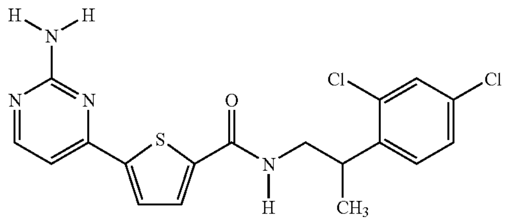 | 407 | 5-(2-aminopyrimidin-4-yl)-N-[2-(2,4-dichlorophenyl)propyl]thiophene-2-carboxamide |
| 77 | 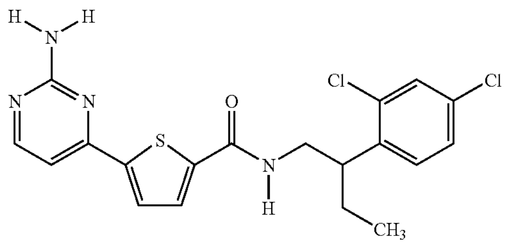 | 421 | 5-(2-aminopyrimidin-4-yl)-N-[2-(2,4-dichlorophenyl)butyl]thiophene-2-carboxamide |
| 78 | 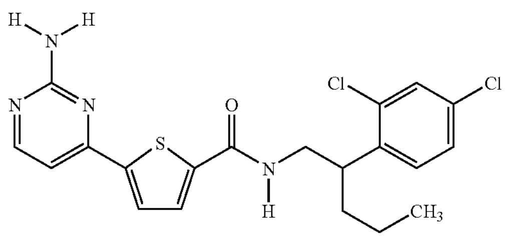 | 435 | 5-(2-aminopyrimidin-4-yl)-N-[2-(2,4-dichlorophenyl)pentyl]thiophene-2-carboxamide |
| 79 | 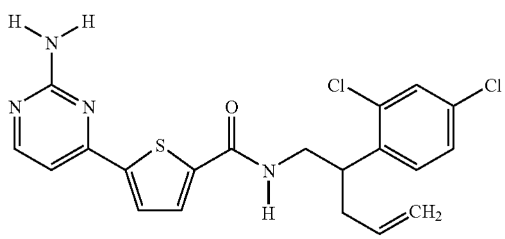 | 433 | 5-(2-aminopyrimidin-4-yl)-N-[2-(2,4-dichlorophenyl)pent-4-enyl]thiophene-2-carboxamide |
| 80 | 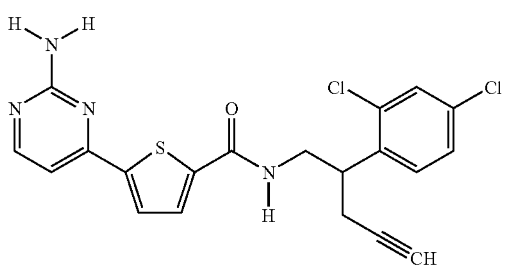 | 431 | 5-(2-aminopyrimidin-4-yl)-N-[2-(2,4-dichlorophenyl)pent-4-ynyl]thiophene-2-carboxamide |
| 81 | 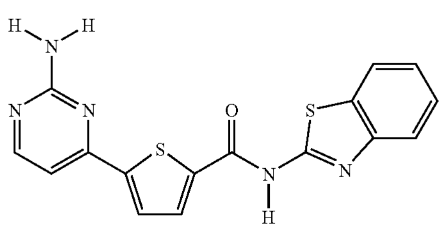 | 354 | 5-(2-aminopyrimidin-4-yl)-N-1,3-benzothiazol-2-ylthiophene-2-carboxamide |

TABLE 6-continued

| No. | Structure | MH+ | Name |
|---|---|---|---|
| 82 | 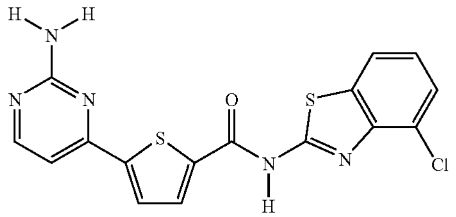 | 388 | 5-(2-aminopyrimidin-4-yl)-N-(4-chloro-1,3-benzothiazol-2-yl)thiophene-2-carboxamide |
| 83 | 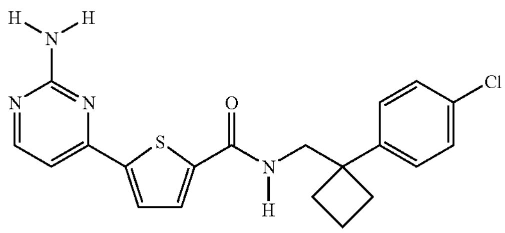 | 399 | 5-(2-aminopyrimidin-4-yl)-N-{[1-(4-chlorophenyl)cyclobutyl]methyl}thiophene-2-carboxamide |
| 84 | 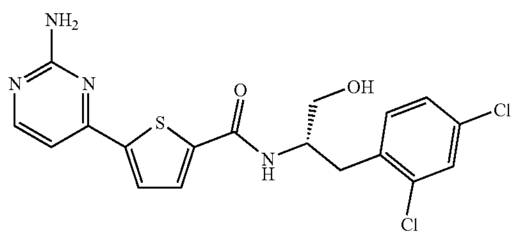 | 424 | 5-(2-aminopyrimidin-4-yl)-N-[(1S)-1-(2,4-dichlorobenzyl)-2-hydroxyethyl]thiophene-2-carboxamide |
| 85 | 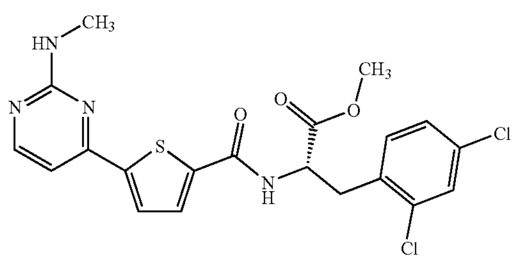 | 466 | methyl 2,4-dichloro-N-({5-[2-(methylamino)pyrimidin-4-yl]thien-2-yl}carbonyl)-L-phenylalaninate |
| 86 | 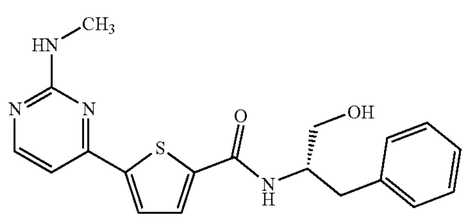 | 369 | N-[(1S)-1-benzyl-2-hydroxyethyl]-5-[2-(methylamino)pyrimidin-4-yl]thiophene-2-carboxamide |
| 87 | 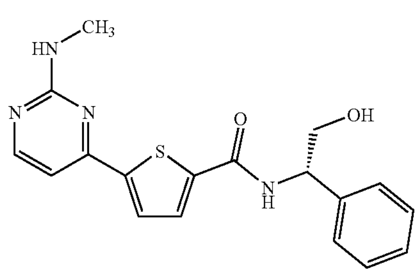 | 355 | N-[(1S)-2-hydroxy-1-phenylethyl]-5-[2-(methylamino)pyrimidin-4-yl]thiophene-2-carboxamide |

TABLE 6-continued

| No. | Structure | MH+ | Name |
|---|---|---|---|
| 88 | 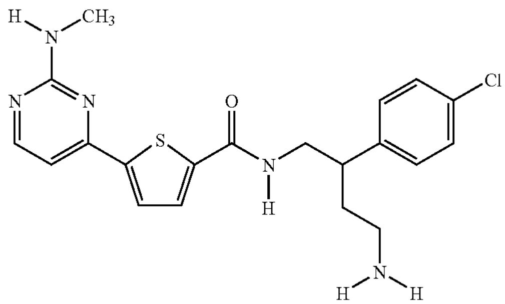 | 416 | N-[4-amino-2-(4-chlorophenyl)butyl]-5-[2-(methylamino)pyrimidin-4-yl]thiophene-2-carboxamide |
| 89 | 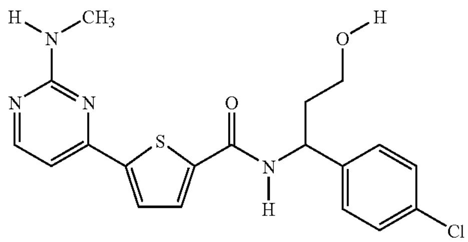 | 403 | N-[1-(4-chlorophenyl)-3-hydroxypropyl]-5-[2-(methylamino)pyrimidin-4-yl]thiophene-2-carboxamide |
| 90 | 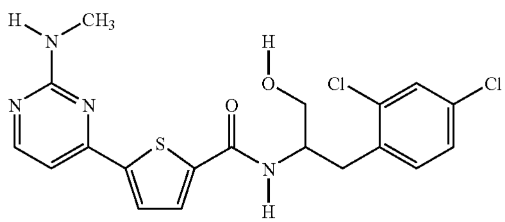 | 437 | N-[1-(2,4-dichlorobenzyl)-2-hydroxyethyl]-5-[2-(methylamino)pyrimidin-4-yl]thiophene-2-carboxamide |
| 91 | 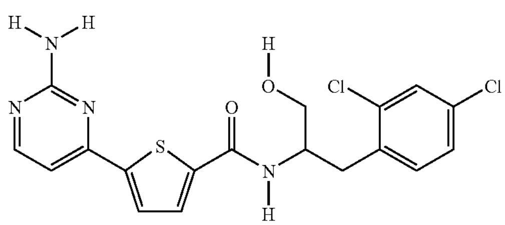 | 423 | 5-(2-aminopyrimidin-4-yl)-N-[1-(2,4-dichlorobenzyl)-2-hydroxyethyl]thiophene-2-carboxamide |
| 92 | 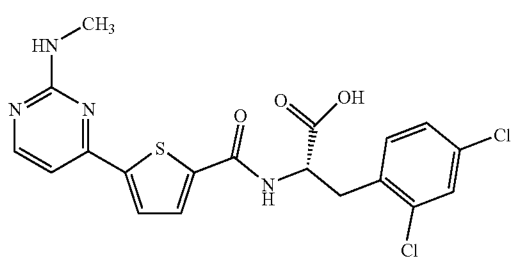 | 452 | 2,4-dichloro-N-({5-[2-(methylamino)pyrimidin-4-yl]thien-2-yl}carbonyl)-L-phenylalanine |
| 93 | 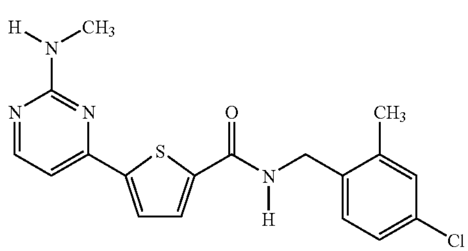 | 373 | N-(4-chloro-2-methylbenzyl)-5-[2-(methylamino)pyrimidin-4-yl]thiophene-2-carboxamide |

TABLE 6-continued

| No. | Structure | MH+ | Name |
|---|---|---|---|
| 94 | 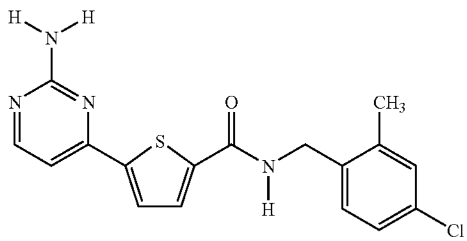 | 359 | 5-(2-aminopyrimidin-4-yl)-N-(4-chloro-2-methylbenzyl)thiophene-2-carboxamide |
| 95 | 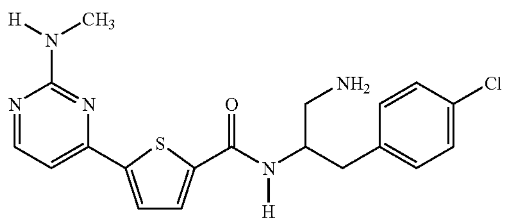 | 402 | N-[2-amino-1-(4-chlorobenzyl)ethyl]-5-[2-(methylamino)pyrimidin-4-yl]thiophene-2-carboxamide |
| 96 | 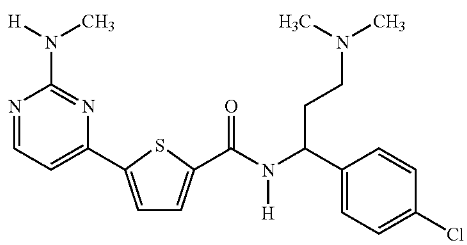 | 430 | N-[1-(4-chlorophenyl)-3-(dimethylamino)propyl]-5-[2-(methylamino)pyrimidin-4-yl]thiophene-2-carboxamide |
| 97 | 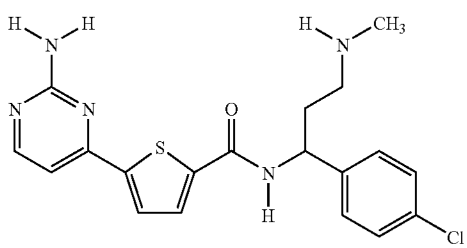 | 402 | 5-(2-aminopyrimidin-4-yl)-N-[1-(4-chlorophenyl)-3-(methylamino)propyl]thiophene-2-carboxamide |
| 98 | 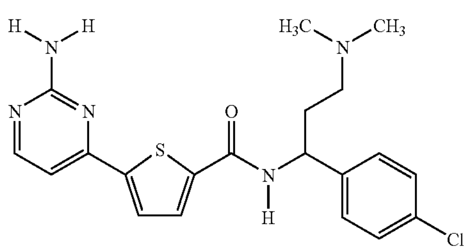 | 416 | 5-(2-aminopyrimidin-4-yl)-N-[1-(4-chlorophenyl)-3-(dimethylamino)propyl]thiophene-2-carboxamide |
| 99 | 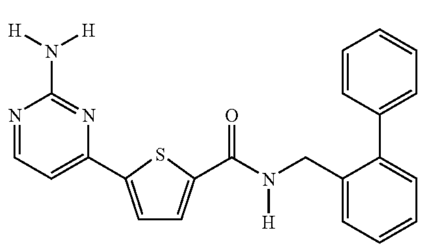 | 387 | 5-(2-aminopyrimidin-4-yl)-N-[1,1'-biphenyl-2-ylmethyl)thiophene-2-carboxamide |

TABLE 6-continued

| No. | Structure | MH+ | Name |
|---|---|---|---|
| 100 | 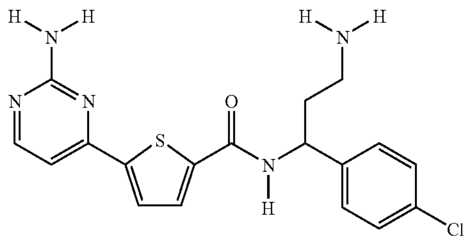 | 388 | N-[3-amino-1-(4-chlorophenyl)propyl]-5-(2-aminopyrimidin-4-yl)thiophene-2-carboxamide |
| 101 | 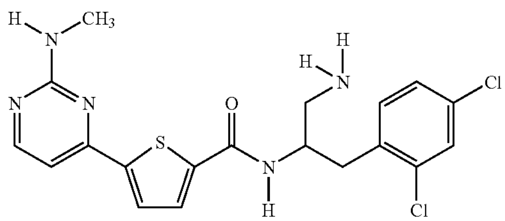 | 436 | N-[2-amino-1-(2,4-dichlorobenzyl)ethyl]-5-[2-(methylamino)pyrimidin-4-yl]thiophene-2-carboxamide |
| 102 | 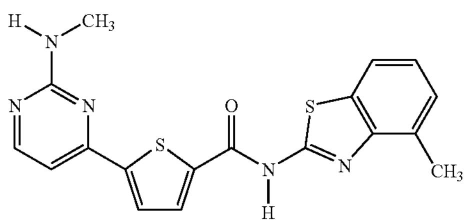 | 382 | 5-[2-(methylamino)pyrimidin-4-yl]-N-(4-methyl-1,3-benzothiazol-2-yl)thiophene-2-carboxamide |
| 103 | 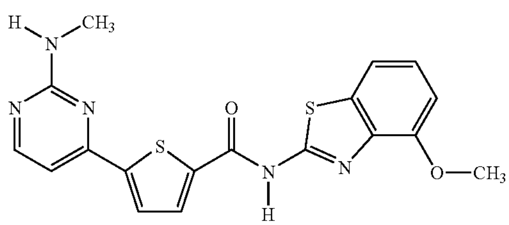 | 398 | N-(4-methoxy-1,3-benzothiazol-2-yl)-5-[2-(methylamino)pyrimidin-4-yl]thiophene-2-carboxamide |
| 104 | 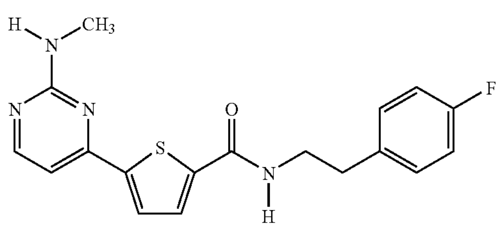 | 343 | 5-(2-aminopyrimidin-4-yl)-N-[2-(4-fluorophenyl)ethyl]thiophene-2-carboxamide |
| 105 | 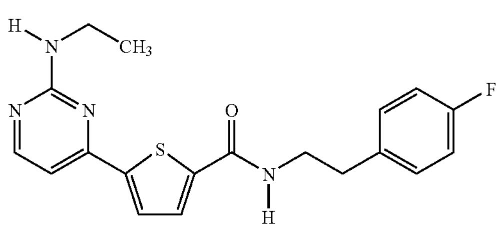 | 371 | 5-[2-(ethylamino)pyrimidin-4-yl]-N-[2-(4-fluorophenyl)ethyl]thiophene-2-carboxamide |

TABLE 6-continued

| No. | Structure | MH+ | Name |
|---|---|---|---|
| 106 | 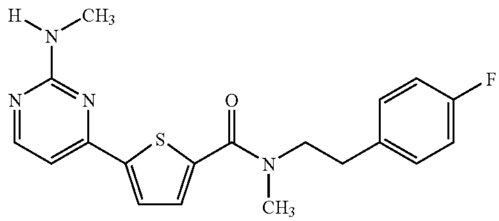 | 371 | N-[2-(4-fluorophenyl)ethyl]-N-methyl-5-[2-(methylamino)pyrimidin-4-yl]thiophene-2-carboxamide |
| 107 | 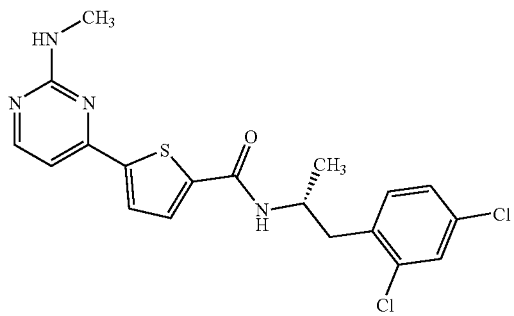 | 422 | N-[(1R)-2-(2,4-dichlorophenyl)-1-methylethyl]-5-[2-(methylamino)pyrimidin-4-yl]thiophene-2-carboxamide |
| 108 | 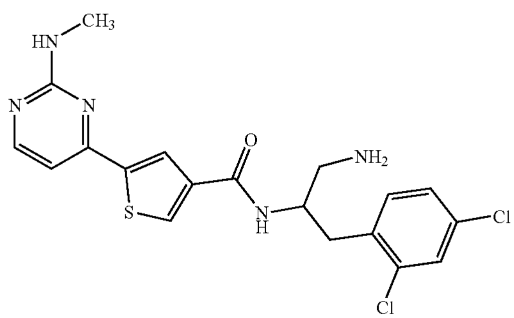 | 437 | N-[2-amino-1-(2,4-dichlorobenzyl)ethyl]-5-[2-(methylamino)pyrimidin-4-yl]thiophene-3-carboxamide |
| 109 | 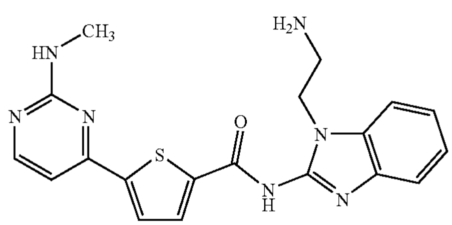 | 394 | N-[1-(2-aminoethyl)-1H-benzimidazol-2-yl]-5-[2-(methylamino)pyrimidin-4-yl]thiophene-2-carboxamide |
| 110 | 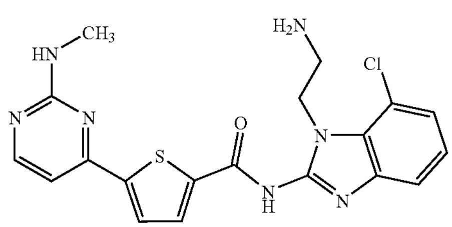 | 428 | N-[1-(2-aminoethyl)-7-chloro-1H-benzimidazol-2-yl]-5-[2-(methylamino)pyrimidin-4-yl]thiophene-2-carboxamide |
| 111 | 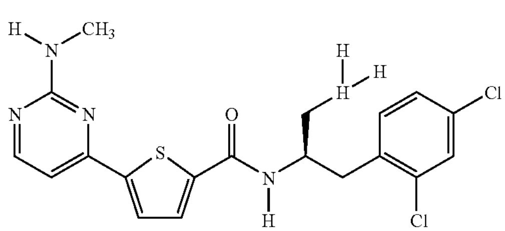 | 436 | N-[(1R)-2-amino-1-(2,4-dichlorobenzyl)ethyl]-5-[2-(methylamino)pyrimidin-4-yl]thiophene-2-carboxamide |

TABLE 6-continued

| No. | Structure | MH+ | Name |
|---|---|---|---|
| 112 | 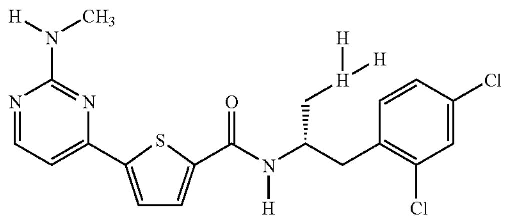 | 436 | N-[(1S)-2-amino-1-(2,4-dichlorobenzyl)ethyl]-5-[2-(methylamino)pyrimidin-4-yl]thiophene-2-carboxamide |
| 113 | 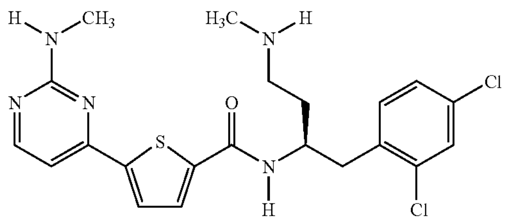 | 464 | N-[(1R)-1-(2,4-dichlorobenzyl)-3-(methylamino)propyl]-5-[2-(methylamino)pyrimidin-4-yl]thiophene-2-carboxamide |
| 114 | 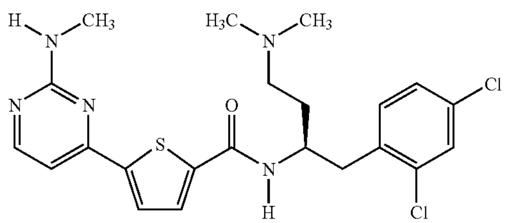 | 478 | N-[(1R)-1-(2,4-dichlorobenzyl)-3-(dimethylamino)propyl]-5-[2-(methylamino)pyrimidin-4-yl]thiophene-2-carboxamide |
| 115 | 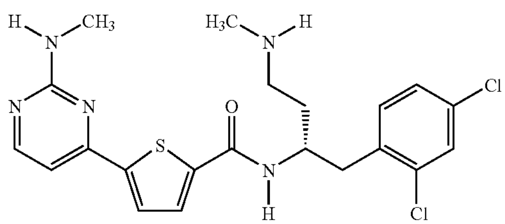 | 464 | N-[(1S)-1-(2,4-dichlorobenzyl)-3-(methylamino)propyl]-5-[2-(methylamino)pyrimidin-4-yl]thiophene-2-carboxamide |
| 116 | 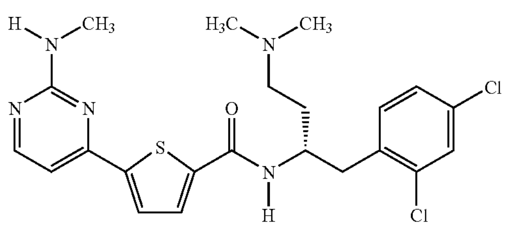 | 478 | N-[(1S)-1-(2,4-dichlorobenzyl)-3-(dimethylamino)propyl]-5-[2-(methylamino)pyrimidin-4-yl]thiophene-2-carboxamide |
| 117 | 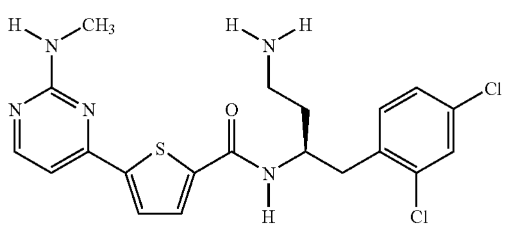 | 450 | N-[(1R)-3-amino-1-(2,4-dichlorobenzyl)propyl]-5-[2-(methylamino)pyrimidin-4-yl]thiophene-2-carboxamide |
| 118 | 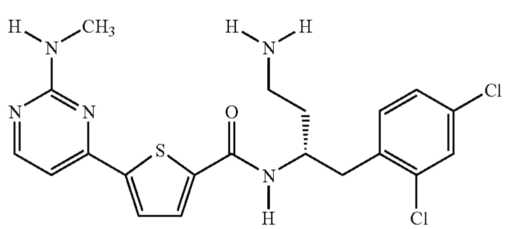 | 450 | N-[(1S)-3-amino-1-(2,4-dichlorobenzyl)propyl]-5-[2-(methylamino)pyrimidin-4-yl]thiophene-2-carboxamide |

US 7,470,701 B2

139 140

TABLE 6-continued

| No. | Structure | MH+ | Name |
|---|---|---|---|
| 119 | 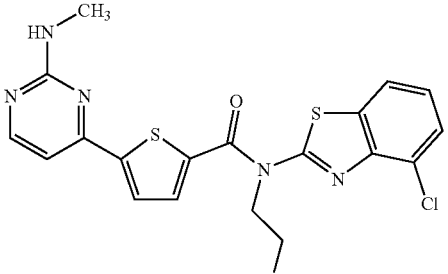 | 445 | N-(2-aminoethyl)-N-(4-chloro-1,3-benzothiazol-2-yl)-5-[2-(methylamino)pyrimidin-4-yl]thiophene-2-carboxamide |
| 120 | 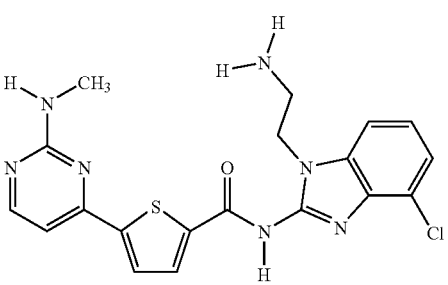 | 428 | N-[1-(2-aminoethyl)-4-chloro-1H-benzimidazol-2-yl]-5-[2-(methylamino)pyrimidin-4-yl]thiophene-2-carboxamide |
| 121 | 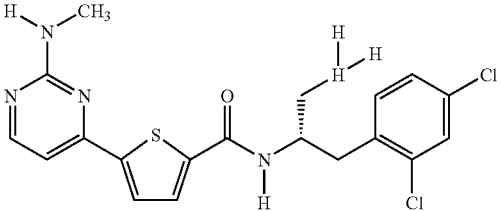 | 436 | N-[(1S)-2-amino-1-(2,4-dichlorobenzyl)ethyl]-5-[2-(methylamino)pyrimidin-4-yl]thiophene-2-carboxamide |
| 122 | 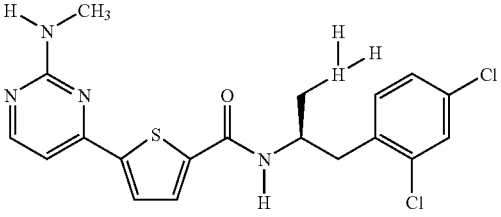 | 436 | N-[(1R)-2-amino-1-(2,4-dichlorobenzyl)ethyl]-5-[2-(methylamino)pyrimidin-4-yl]thiophene-2-carboxamide |
| 123 | 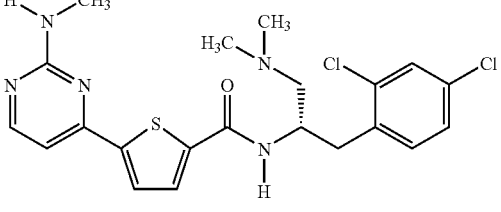 | 464 | N-[(1S)-1-(2,4-dichlorobenzyl)-2-(dimethylamino)ethyl]-5-[2-(methylamino)pyrimidin-4-yl]thiophene-2-carboxamide |
| 124 | 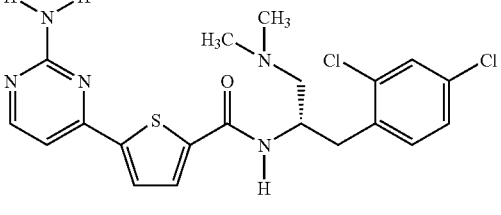 | 450 | 5-(2-aminopyrimidin-4-yl)-N-[(1S)-1-(2,4-dichlorobenzyl)-2-(dimethylamino)ethyl]thiophene-2-carboxamide |

TABLE 6-continued

| No. | Structure | MH+ | Name |
|---|---|---|---|
| 125 | 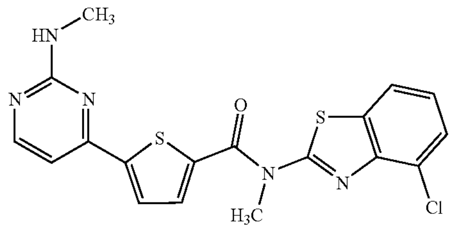 | 416 | N-(4-chloro-1,3-benzothiazol-2-yl)-N-methyl-5-[2-(methylamino)pyrimidin-4-yl]thiophene-2-carboxamide |
| 126 | 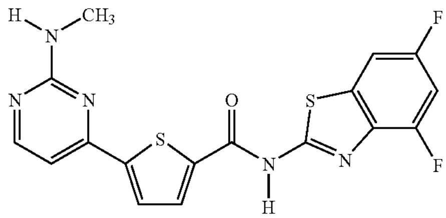 | 404 | N-(4,6-difluoro-1,3-benzothiazol-2-yl)-5-[2-(methylamino)pyrimidin-4-yl]thiophene-2-carboxamide |
| 127 | 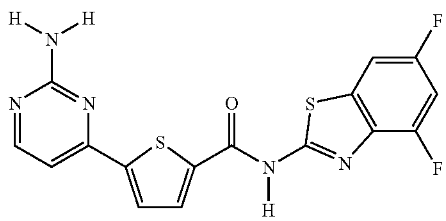 | 390 | 5-(2-aminopyrimidin-4-yl)-N-(4,6-difluoro-1,3-benzothiazol-2-yl)thiophene-2-carboxamide |
| 128 | 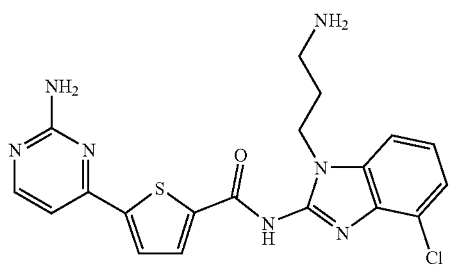 | 428 | N-[1-(3-aminopropyl)-4-chloro-1H-benzimidazol-2-yl]-5-(2-aminopyrimidin-4-yl)thiophene-2-carboxamide |
| 129 | 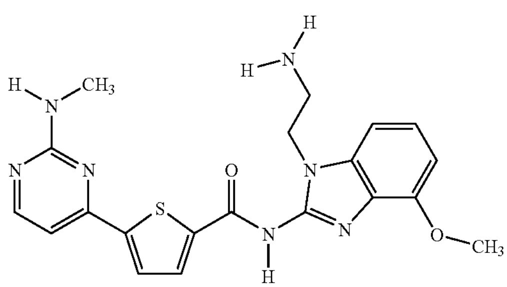 | 424 | N-[1-(2-aminoethyl)-4-methoxy-1H-benzimidazol-2-yl]-5-[2-(methylamino)pyrimidin-4-yl]thiophene-2-carboxamide |
| 130 | 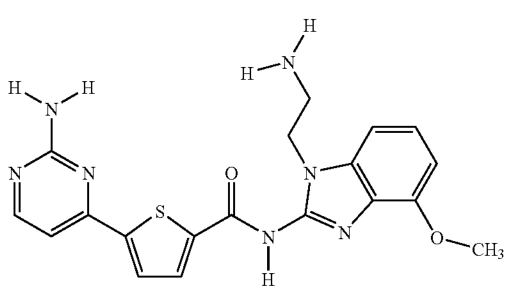 | 410 | N-[1-(2-aminoethyl)-4-methyl-1H-benzimidazol-2-yl]-5-(2-aminopyrimidin-4-yl)thiophene-2-carboxamide |

TABLE 6-continued

| No. | Structure | MH+ | Name |
|---|---|---|---|
| 131 | 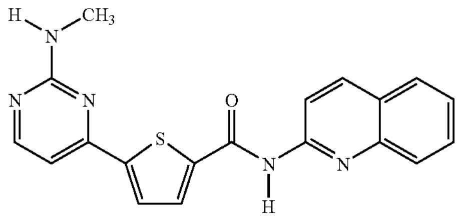 | 362 | 5-[2-(methylamino)pyrimidin-4-yl]-N-quinolin-2-ylthiophene-2-carboxamide |
| 132 | 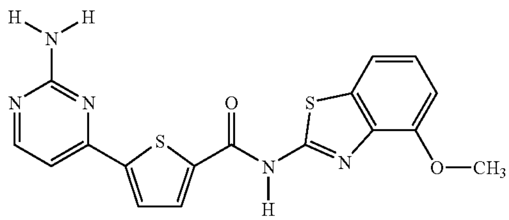 | 384 | 5-(2-aminopyrimidin-4-yl)-N-(4-methoxy-1,3-benzothiazol-2-yl)thiophene-2-carboxamide |
| 133 | 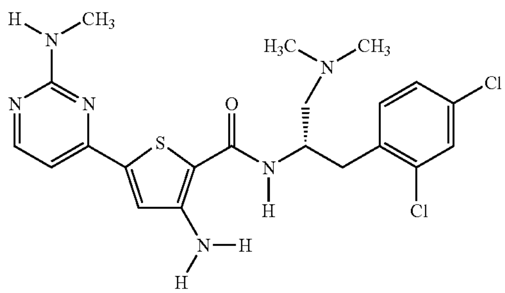 | 479 | 3-amino-N-[(1S)-1-(2,4-dichlorobenzyl)-2-(dimethylamino)ethyl]-5-[2-(methylamino)pyrimidin-4-yl]thiophene-2-carboxamide |
| 134 | 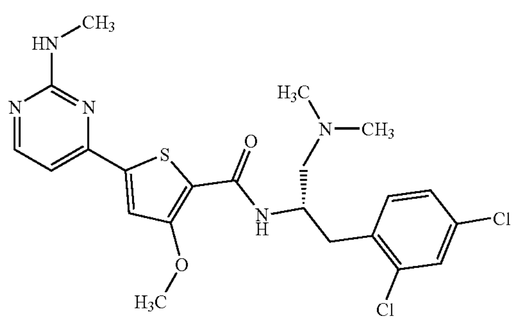 | 495 | N-[(1S)-1-(2,4-dichlorobenzyl)-2-(dimethylamino)ethyl]-3-methoxy-5-[2-(methylamino)pyrimidin-4-yl]thiophene-2-carboxamide |
| 135 | 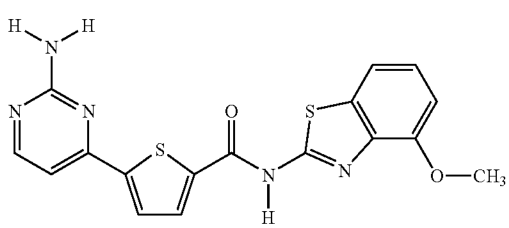 | 384 | 5-(2-aminopyrimidin-4-yl)-N-(4-methoxy-1,3-benzothiazol-2-yl)thiophene-2-carboxamide |
| 136 | 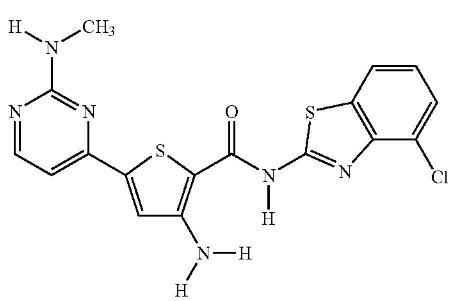 | 417 | 3-amino-N-(4-chloro-1,3-benzothiazol-2-yl)-5-[2-(methylamino)pyrimidin-4-yl]thiophene-2-carboxamide |

TABLE 6-continued

| No. | Structure | MH+ | Name |
|---|---|---|---|
| 137 | 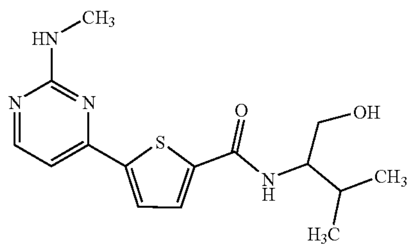 | 321 | N-[1-(hydroxymethyl)-2-methylpropyl]-5-[2-(methylamino)pyrimidin-4-yl]thiophene-2-carboxamide |
| 138 | 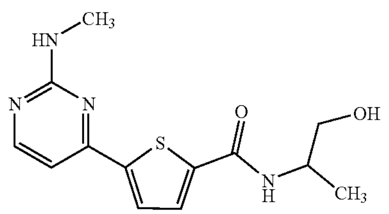 | 293 | N-(2-hydroxy-1-methylethyl)-5-[2-(methylamino)pyrimidin-4-yl]thiophene-2-carboxamide |
| 139 | 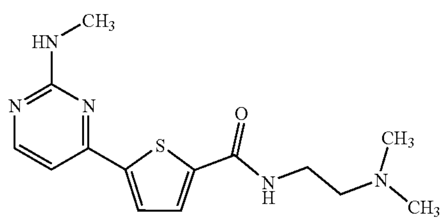 | 306 | N-[2-(dimethylamino)ethyl]-5-[2-(methylamino)pyrimidin-4-yl]thiophene-2-carboxamide |
| 140 | 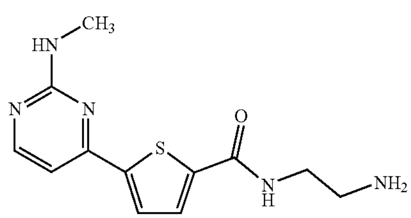 | 278 | N-(2-aminoethyl)-5-[2-(methylamino)pyrimidin-4-yl]thiophene-2-carboxamide |
| 141 | 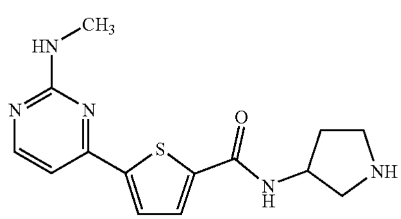 | 304 | 5-[2-(methylamino)pyrimidin-4-yl]-N-pyrrolidin-3-ylthiophene-2-carboxamide |
| 142 | 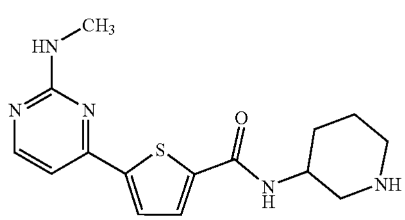 | 318 | 5-[2-(methylamino)pyrimidin-4-yl]-N-piperidin-3-ylthiophene-2-carboxamide |

TABLE 6-continued

| No. | Structure | MH+ | Name |
|---|---|---|---|
| 143 | 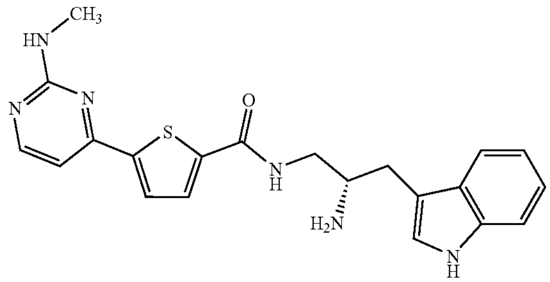 | 407 | N-[(2S)-2-amino-3-(1H-indol-3-yl)propyl]-5-[2-(methylamino)pyrimidin-4-yl]thiophene-2-carboxamide |
| 144 | 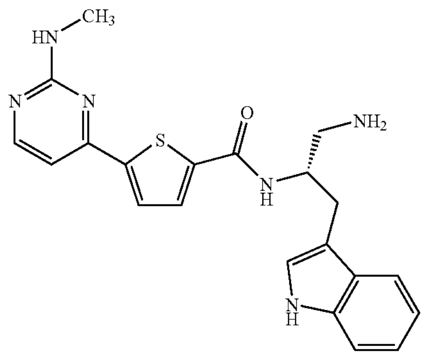 | 404 | N-[(1S)-2-amino-1-(1H-indol-3-ylmethyl)ethyl]-5-[2-(methylamino)pyrimidin-4-yl]thiophene-2-carboxamide |
| 145 | 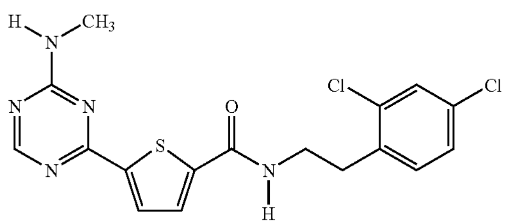 | 408 | N-[2-(2,4-dichlorophenyl)ethyl]-5-[4-(methylamino)-1,3,5-triazin-2-yl]thiophene-2-carboxamide |
| 146 | 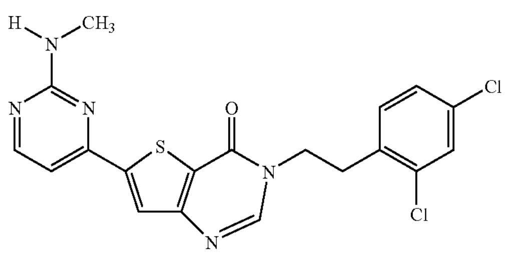 | 432<br>434 | 3-[2-(2,4-dichlorophenyl)ethyl]-6-[2-(methylamino)pyrimidin-4-yl]thieno[3,2-d]pyrimidin-4(3H)-one |
| 147 | 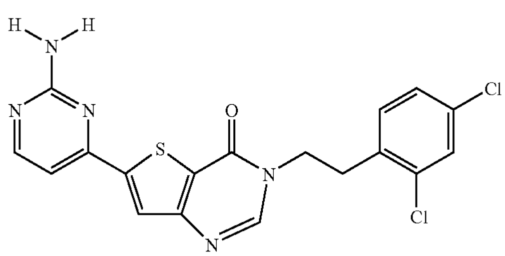 | 418<br>420 | 6-(2-aminopyrimidin-4-yl)-3-[2-(2,4-dichlorophenyl)ethyl]thieno[3,2-d]pyrimidin-4(3H)-one |

TABLE 6-continued

| No. | Structure | MH+ | Name |
|---|---|---|---|
| 148 | 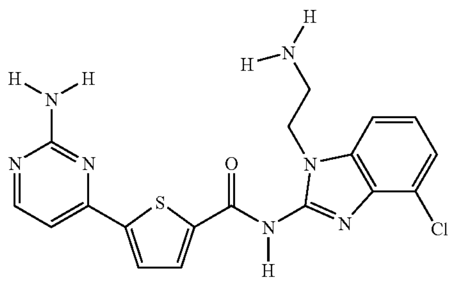 | 414, 416 | N-[1-(2-aminoethyl)-4-chloro-1H-benzimidazol-2-yl]-5-(2-aminopyrimidin-4-yl)thiophene-2-carboxamide |
| 149 | 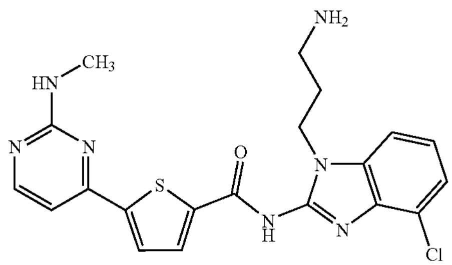 | 442 | N-[1-(3-aminopropyl)-4-chloro-1H-benzimidazol-2-yl]-5-[2-(methylamino)pyrimidin-4-yl]thiophene-2-carboxamide |
| 150 | 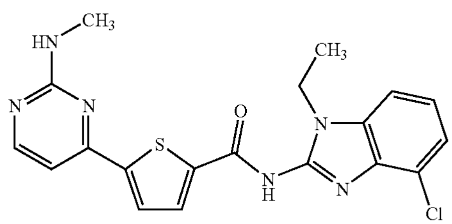 | 413 | N-(4-chloro-1-ethyl-1H-benzimidazol-2-yl)-5-[2-(methylamino)pyrimidin-4-yl]thiophene-2-carboxamide |
| 151 | 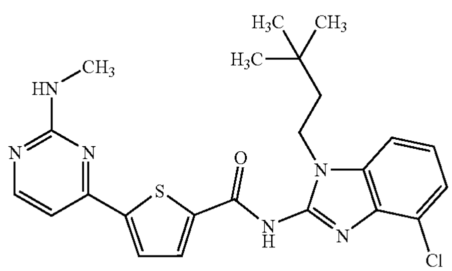 | 469 | N-[4-chloro-1-(3,3-dimethylbutyl)-1H-benzimidazol-2-yl]-5-[2-(methylamino)pyrimidin-4-yl]thiophene-2-carboxamide |
| 152 | 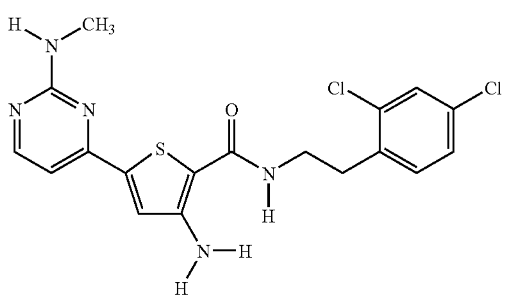 | 422, 424 | 3-amino-N-[2-(2,4-dichlorophenyl)ethyl]-5-[2-(methylamino)pyrimidin-4-yl]thiophene-2-carboxamide |
| 153 | 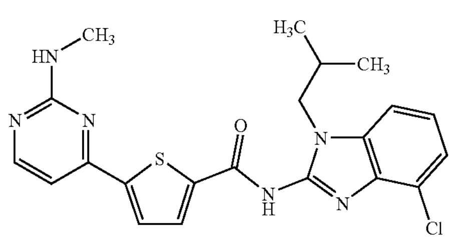 | 441 | N-(4-chloro-1-isobutyl-1H-benzimidazol-2-yl)-5-[2-(methylamino)pyrimidin-4-yl]thiophene-2-carboxamide |

TABLE 6-continued

| No. | Structure | MH+ | Name |
|---|---|---|---|
| 154 | 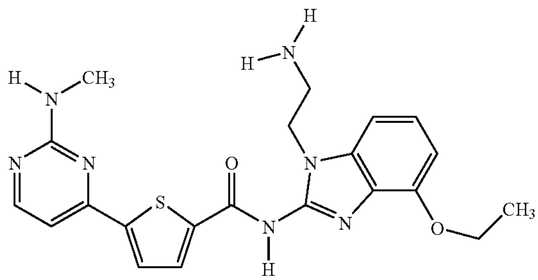 | 438 | N-[1-(2-aminoethyl)-4-ethoxy-1H-benzimidazol-2-yl]-5-[2-(methylamino)pyrimidin-4-yl]thiophene-2-carboxamide |
| 155 | 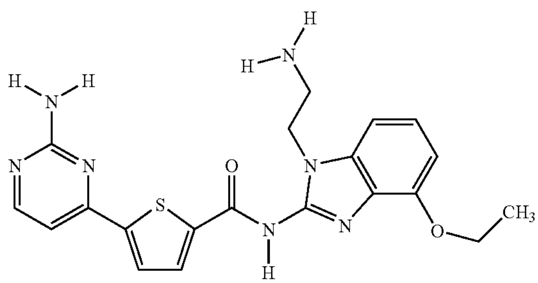 | 424 | N-[1-(2-aminoethyl)-4-ethoxy-1H-benzimidazol-2-yl]-5-(2-aminopyrimidin-4-yl)thiophene-2-carboxamide |
| 156 | 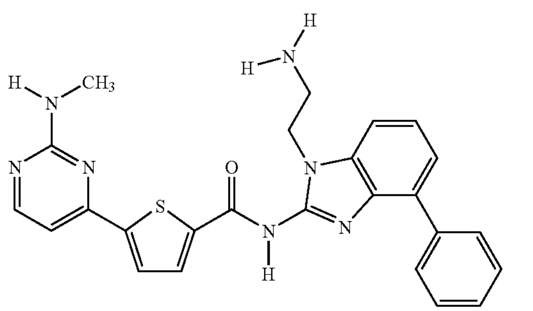 | 470 | N-[1-(2-aminoethyl)-4-phenyl-1H-benzimidazol-2-yl]-5-[2-(methylamino)pyrimidin-4-yl]thiophene-2-carboxamide |
| 157 | 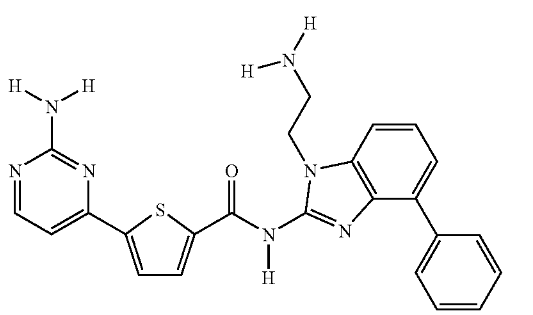 | 456 | N-[1-(2-aminoethyl)-4-phenyl-1H-benzimidazol-2-yl]-5-(2-aminopyrimidin-4-yl)thiophene-2-carboxamide |
| 158 | 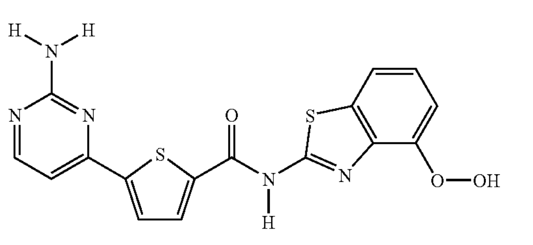 | 370 | 5-(2-aminopyrimidin-4-yl)-N-(4-hydroxy-1,3-benzothiazol-2-yl)thiophene-2-carboxamide |

TABLE 6-continued

| No. | Structure | MH+ | Name |
|---|---|---|---|
| 159 | 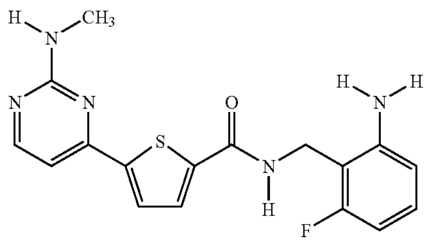 | 358 | N-(2-amino-6-fluorobenzyl)-5-[2-(methylamino)pyrimidin-4-yl]thiophene-2-carboxamide |
| 160 | 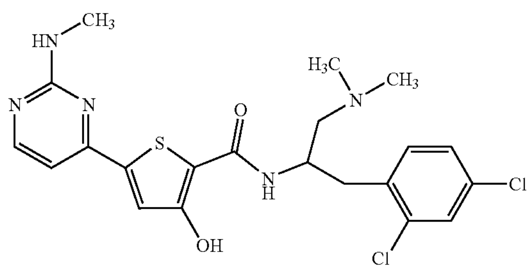 | 480 | N-[1-(2,4-dichlorobenzyl)-2-(dimethylamino)ethyl]-3-hydroxy-5-[2-(methylamino)pyrimidin-4-yl]thiophene-2-carboxamide |
| 161 | 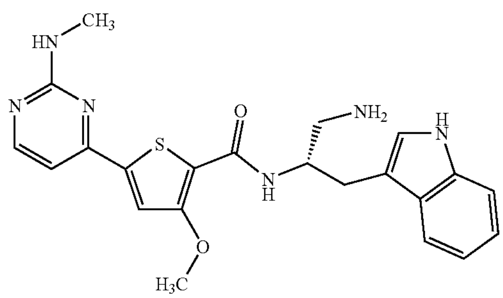 | 437 | N-[(1S)-2-amino-1-(1H-indol-3-ylmethyl)ethyl]-3-methoxy-5-[2-(methylamino)pyrimidin-4-yl]thiophene-2-carboxamide |
| 162 | 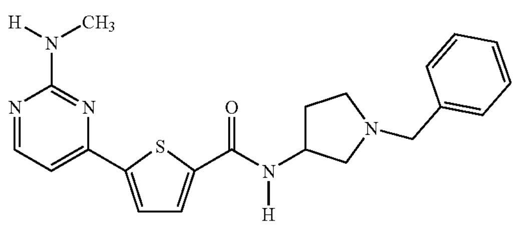 | 394 | N-(1-benzylpyrrolidin-3-yl)-5-[2-(methylamino)pyrimidin-4-yl]thiophene-2-carboxamide |
| 163 | 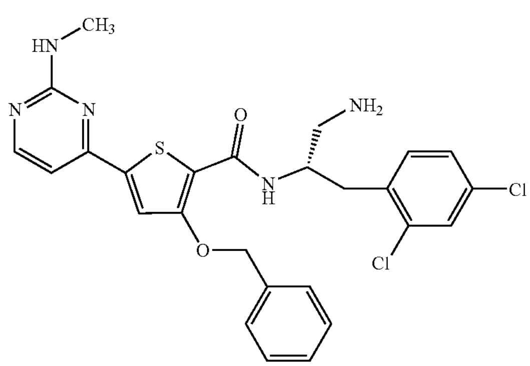 | 542 | N-[(1S)-2-amino-1-(2,4-dichlorobenzyl)ethyl]-3-(benzyloxy)-5-[2-(methylamino)pyrimidin-4-yl]thiophene-2-carboxamide |

TABLE 6-continued

| No. | Structure | MH+ | Name |
|---|---|---|---|
| 164 | 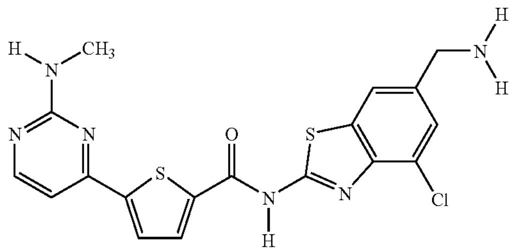 | 431, 433 | N-[6-(aminomethyl)-4-chloro-1,3-benzothiazol-2-yl]-5-[2-(methylamino)pyrimidin-4-yl]thiophene-2-carboxamide |
| 165 | 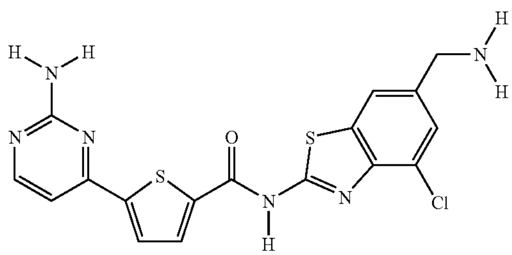 | 417, 419 | N-[6-(aminoethyl)-4-chloro-1,3-benzothiazol-2-yl]-5-(2-aminopyrimidin-4-yl)thiophene-2-carboxamide |
| 166 | 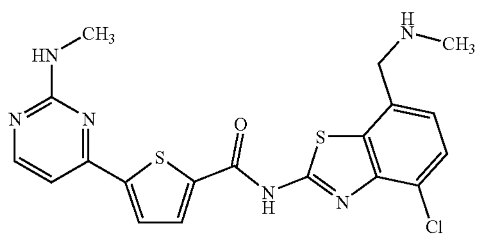 | 445 | N-{4-chloro-7-[(methylamino)methyl]-1,3-benzothiazol-2-yl}-5-[2-(methylamino)pyrimidin-4-yl]thiophene-2-carboxamide |
| 167 | 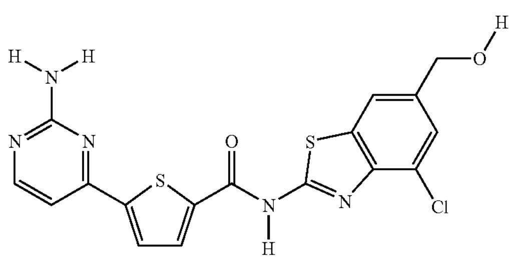 | 418, 420 | 5-(2-aminopyrimidin-4-yl)-N-[4-chloro-6-(hydroxymethyl)-1,3-benzothiazol-2-yl]thiophene-2-carboxamide |
| 168 | 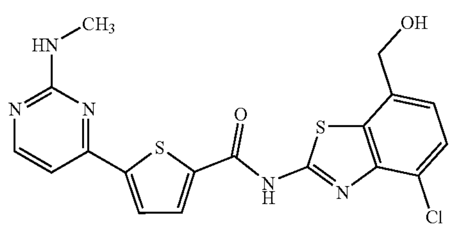 | 432 | N-[4-chloro-7-(hydroxymethyl)-1,3-benzothiazol-2-yl]-5-[2-(methylamino)pyrimidin-4-yl]thiophene-2-carboxamide |
| 169 | 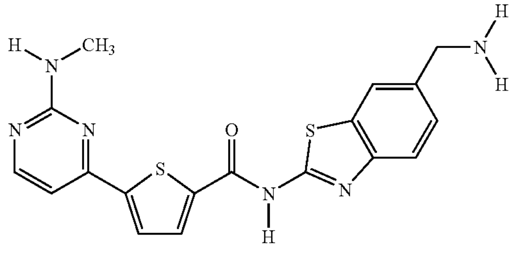 | 397 | N-[6-(aminomethyl)-1,3-benzothiazol-2-yl]-5-[2-(methylamino)pyrimidin-4-yl]thiophene-2-carboxamide |

TABLE 6-continued

| No. | Structure | MH+ | Name |
|---|---|---|---|
| 170 | 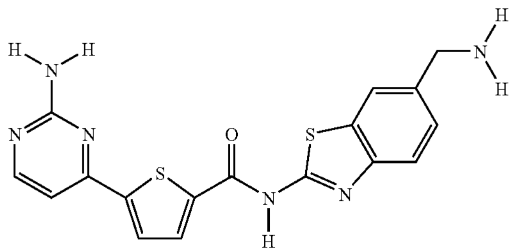 | 383 | N-[6-(aminomethyl)-1,3-benzothiazol-2-yl]-5-(2-aminopyrimidin-4-yl)thiophene-2-carboxamide |
| 171 | 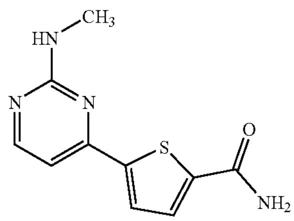 | 235 | 5-[2-(methylamino)pyrimidin-4-yl]thiophene-2-carboxamide |
| 172 | 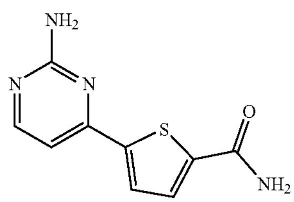 | 221 | 5-(2-aminopyrimidin-4-yl)thiophene-2-carboxamide |
| 173 | 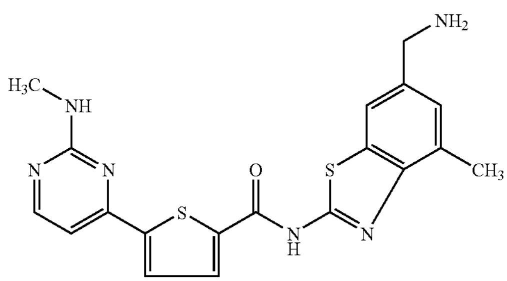 | 411 | N-[6-(aminomethyl)-4-methyl-1,3-benzothiaozl-2-yl]-5-[2-(methylamino)pyrimidin-4-yl]thiophene-2-carboxamide |
| 174 | 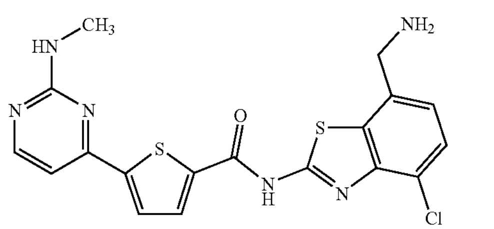 | 431 | N-[7-(aminomethyl)-4-chloro-1,3-benzothiazol-2-yl]-5-[2-(methylamino)pyrimidin-4-yl]thiophene-2-carboxamide |
| 175 | 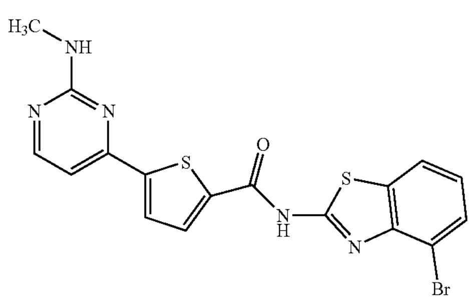 | 548 / 546 | N-(4-bromo-1,3-benzothiazol-2-yl)-5-[2-(methylamino)pyrimidin-4-yl]thiophene-2-carboxamide |

TABLE 6-continued

| No. | Structure | MH+ | Name |
|---|---|---|---|
| 176 | 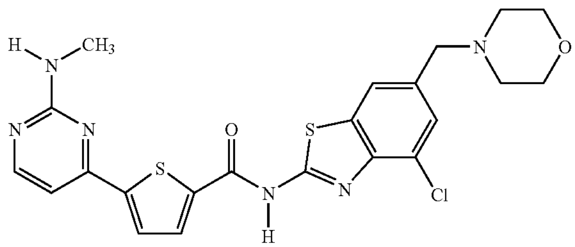 | 501, 503 | N-[4-chloro-6-(morpholin-4-ylmethyl)-1,3-benzothiazol-2-yl]-5-[2-(methylamino)pyrimidin-4-yl]thiophene-2-carboxamide |
| 177 | 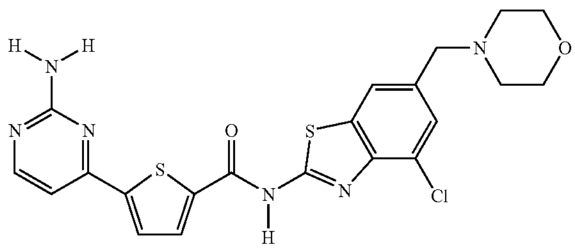 | 487, 489 | 5-(2-aminopyrimidin-4-yl)-N-[4-chloro-6-(morpholin-4-ylmethyl)-1,3-benzothiazol-2-yl]thiophene-2-carboxamide |
| 178 | 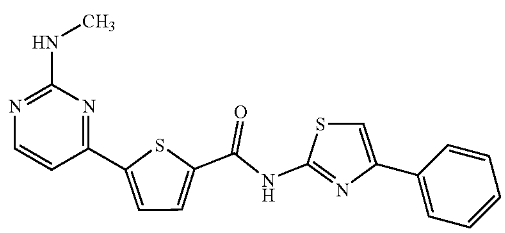 | 394 | 5-[2-(methylamino)pyrimidin-4-yl]-N-(4-phenyl-1,3-thiazol-2-yl)thiophene-2-carboxamide |
| 179 | 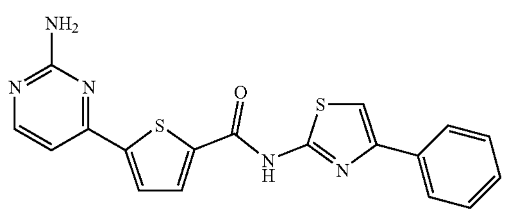 | 380 | 5-(2-aminopyrimidin-4-yl)-N-(4-phenyl-1,3-thiazol-2-yl)thiophene-2-carboxamide |
| 180 | 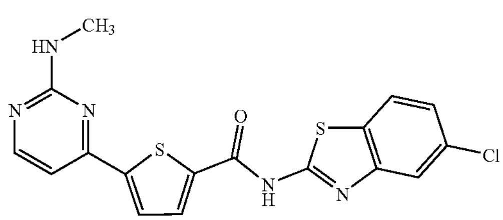 | 402 | N-(5-chloro-1,3-benzothiazol-2-yl)-5-[2-(methylamino)pyrimidin-4-yl]thiophene-2-carboxamide |
| 181 | 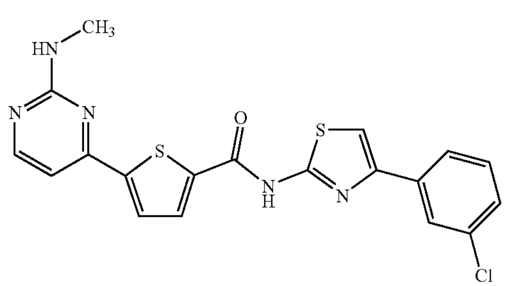 | 428 | N-[4-(3-chlorophenyl)-1,3-thiazol-2-yl]-5-[2-(methylamino)pyrimidin-4-yl]thiophene-2-carboxamide |

TABLE 6-continued

| No. | Structure | MH+ | Name |
|---|---|---|---|
| 182 | 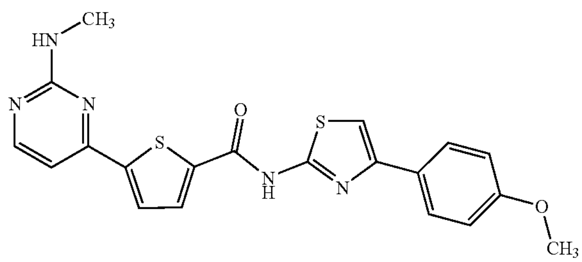 | 424 | N-[4-(4-methoxyphenyl)-1,3-thiazol-2-yl]-5-[2-(methylamino)pyrimidin-4-yl]thiophene-2-carboxamide |
| 183 | 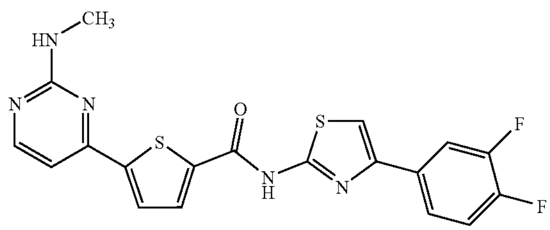 | 430 | N-[4-(3,4-difluorophenyl)-1,3-thiazol-2-yl]-5-[2-(methylamino)pyrimidin-4-yl]thiophene-2-carboxamide |
| 184 | 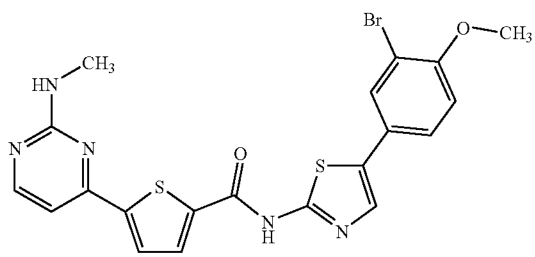 | 502 | N-[5-(3-bromo-4-methoxyphenyl)-1,3-thiazol-2-yl]-5-[2-(methylamino)pyrimidin-4-yl]thiophene-2-carboxamide |
| 185 | 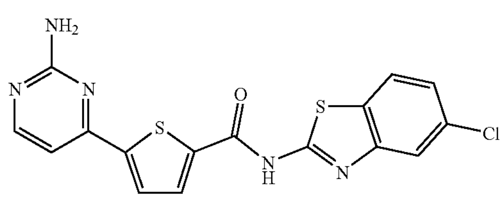 | 388 | 5-(2-aminopyrimidin-4-yl)-N-(5-chloro-1,3-benzothiazol-2-yl)thiophene-2-carboxamide |
| 186 | 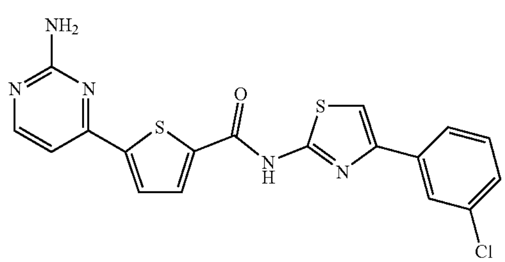 | 414 | 5-(2-aminopyrimidin-4-yl)-N-[4-(3-chlorophenyl)-1,3-thiazol-2-yl]thiophene-2-carboxamide |
| 187 | 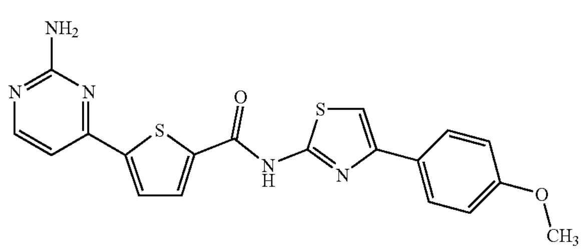 | 410 | 5-(2-aminopyrimidin-4-yl)-N-[4-(4-methoxyphenyl)-1,3-thiazol-2-yl]thiophene-2-carboxamide |

TABLE 6-continued

| No. | Structure | MH+ | Name |
|---|---|---|---|
| 188 | 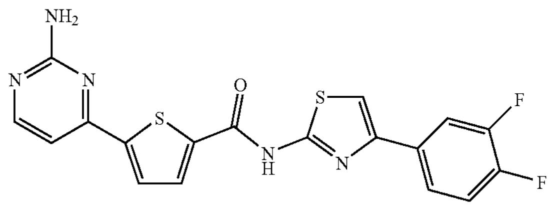 | 416 | 5-(2-aminopyrimidin-4-yl)-N-[4-(3,4-difluorophenyl)-1,3-thiazol-2-yl]thiophene-2-carboxamide |
| 189 | 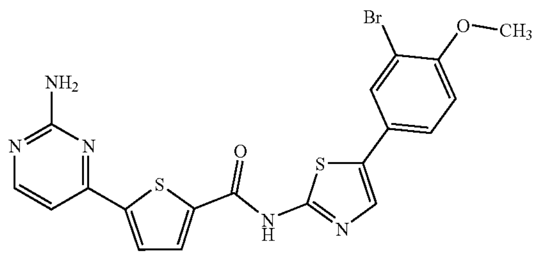 | 488 | 5-(2-aminopyrimidin-4-yl)-N-[5-(3-bromo-4-methoxyphenyl)-1,3-thiazol-2-yl]thiophene-2-carboxamide |
| 190 | 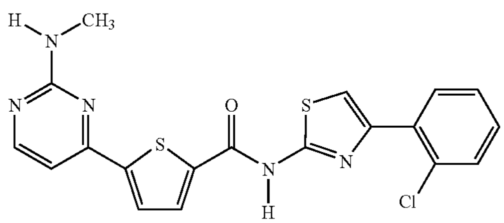 | 428, 430 | N-[4-(2-chlorophenyl)-1,3-thiazol-2-yl]-5-[2-(methylamino)pyrimidin-4-yl]thiophene-2-carboxamide |
| 191 | 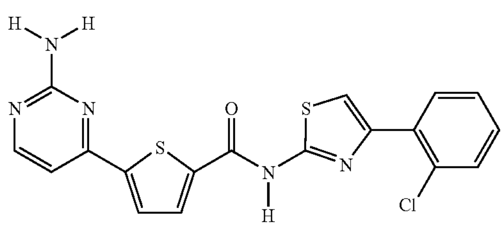 | 414, 416 | 5-(2-aminopyrimidin-4-yl)-N-[4-(2-chlorophenyl)-1,3-thiazol-2-yl]thiophene-2-carboxamide |
| 192 | 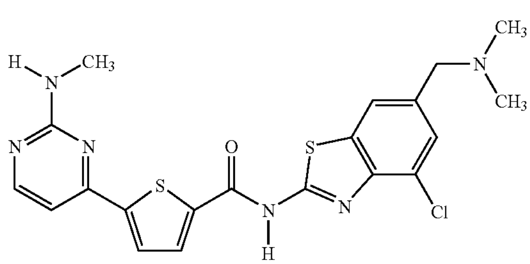 | 459, 461 | N-{4-chloro-6-[(dimethylamino)methyl]-1,3-benzothiazol-2-yl}-5-[2-(methylamino)pyrimidin-4-yl]thiophene-2-carboxamide |
| 193 | 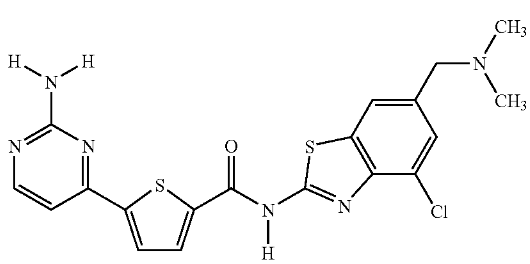 | 445, 447 | 5-(2-aminopyrimidin-4-yl)-N-{4-chloro-6-[(dimethylamino)methyl]-1,3-benzothiazol-2-yl}thiophene-2-carboxamide |

TABLE 6-continued

| No. | Structure | MH+ | Name |
|---|---|---|---|
| 194 | 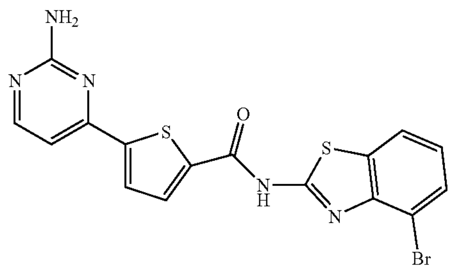 | 434 432 | 5-(2-aminopyrimidin-4-yl)-N-(4-bromo-1,3-benzothiazol-2-yl)thiophene-2-carboxamide |
| 195 | 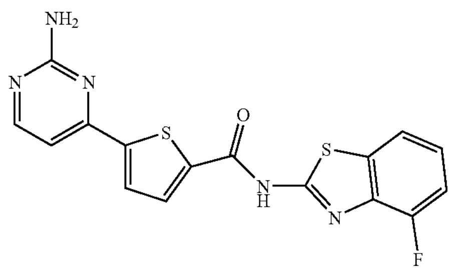 | 372 | 5-(2-aminopyrimidin-4-yl)-N-(4-fluoro-1,3-benzothiazol-2-yl)thiophene-2-carboxamide |
| 196 | 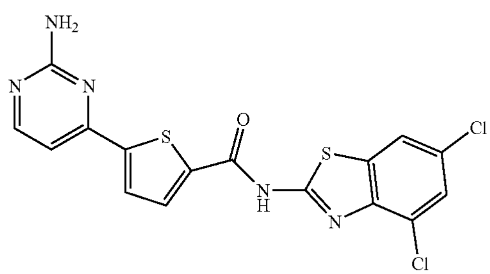 | 422 | 5-(2-aminopyrimidin-4-yl)-N-(4,6-dichloro-1,3-benzothiazol-2-yl)thiophene-2-carboxamide |
| 197 | 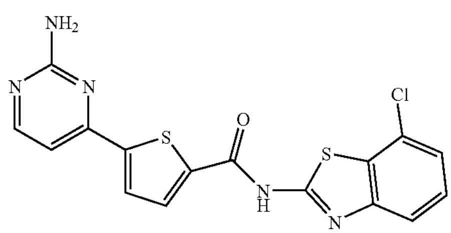 | 389 | 5-(2-aminopyrimidin-4-yl)-N-(7-chloro-1,3-benzothiazol-2-yl)thiophene-2-carboxamide |
| 198 | 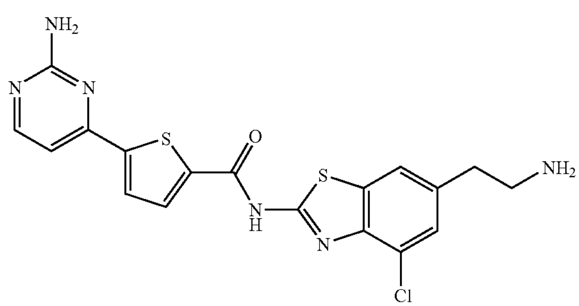 | 432 | N-[6-(2-aminoethyl)-4-chloro-1,3-benzothiazol-2-yl]-5-(2-aminopyrimidin-4-yl)thiophene-2-carboxamide |

TABLE 6-continued

| No. | Structure | MH+ | Name |
|---|---|---|---|
| 199 | 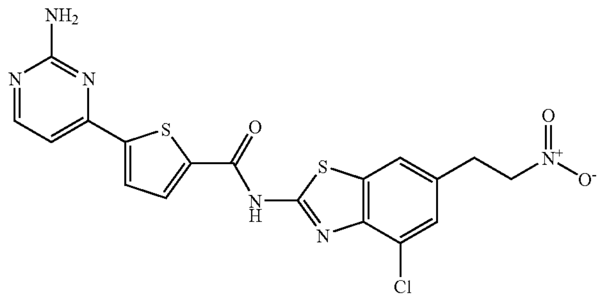 | 462 | 5-(2-aminopyrimidin-4-yl)-N-[4-chloro-6-(2-nitroethyl)-1,3-benzothiazol-2-yl]thiophene-2-carboxamide |
| 200 | 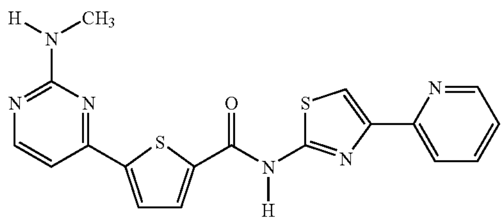 | 395 | 5-[2-(methylamino)pyrimidin-4-yl]-N-(4-pyridin-2-yl-1,3-thiazol-2-yl)thiophene-2-carboxamide |
| 201 | 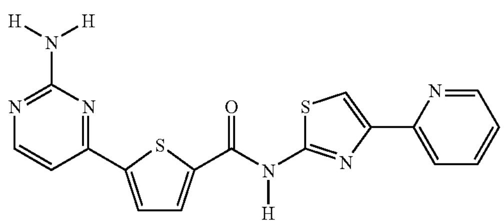 | 381 | 5-(2-aminopyrimidin-4-yl)-N-(4-pyridin-2-yl-1,3-thiazol-2-yl)thiophene-2-carboxamide |
| 202 | 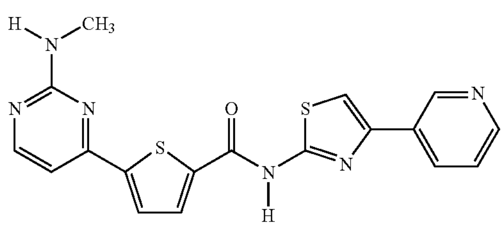 | 395 | 5-[2-(methylamino)pyrimidin-4-yl]-N-(4-pyridin-3-yl-1,3-thiazol-2-yl)thiophene-2-carboxamide |
| 203 | 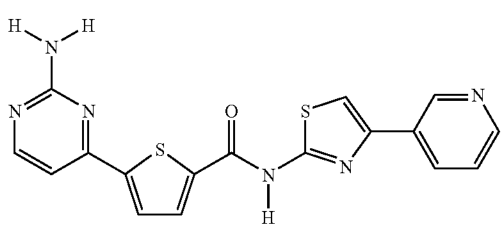 | 381 | 5-(2-aminopyrimidin-4-yl)-N-(4-pyrimidin-3-yl-1,3-thiazol-2-yl)thiophene-2-carboxamide |
| 204 | 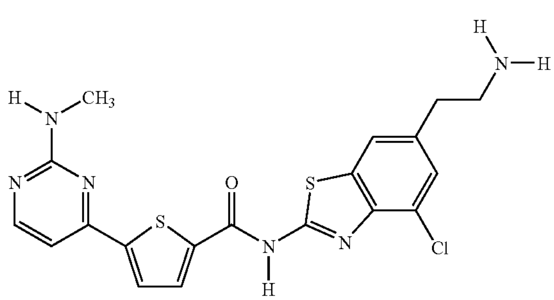 | 445<br>447 | N-[6-(2-aminoethyl)-4-chloro-1,3-benzothiazol-2-yl]-5-[2-(methylamino)pyrimidin-4-yl]thiophene-2-carboxamide |

TABLE 6-continued

| No. | Structure | MH+ | Name |
| --- | --- | --- | --- |
| 205 | 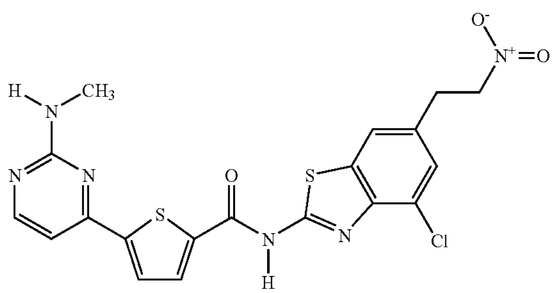 | 475<br>477 | N-[4-chloro-6-(2-nitroethyl)-1,3-benzothiazol-2-yl]-5-[2-(methylamino)pyrimidin-4-yl]thiophene-2-carboxamide |
| 206 | 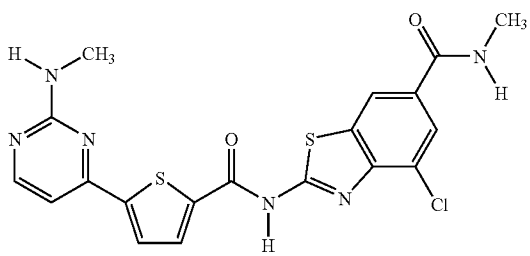 | 459<br>461 | 4-chloro-N-methyl-2-[({5-[2-(methylamino)pyrimidin-4-yl]thien-2-yl}carbonyl)amino]-1,3-benzothiazole-6-carboxamide |
| 207 | 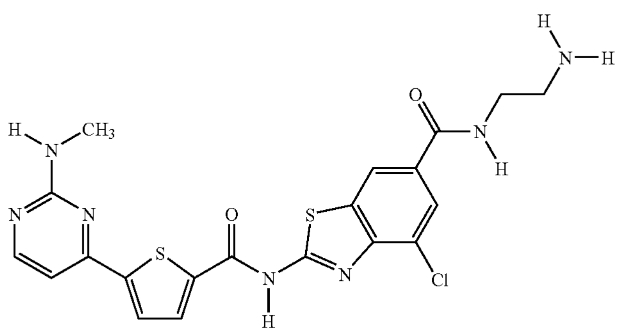 | 488<br>490 | N-(2-aminoethyl)-4-chloro-2-[({5-[2-(methylamino)pyrimidin-4-yl]thien-2-yl}carbonyl)amino]-1,3-benzothiazole-6-carboxamide |
| 208 | 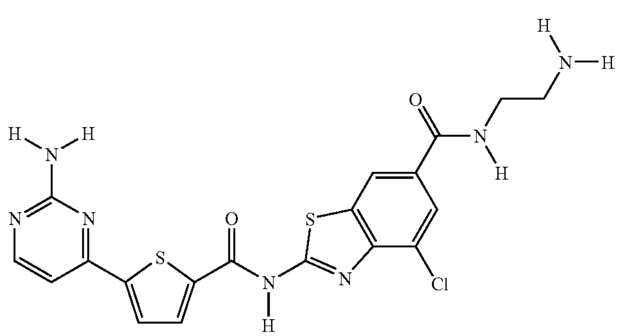 | 474<br>476 | N-(2-aminoethyl)-2-({[5-(2-aminopyrimidin-4-yl)thien-2-yl]carbonyl}amino)-4-chloro-1,3-benzothiazole-6-carboxamide |
| 209 | 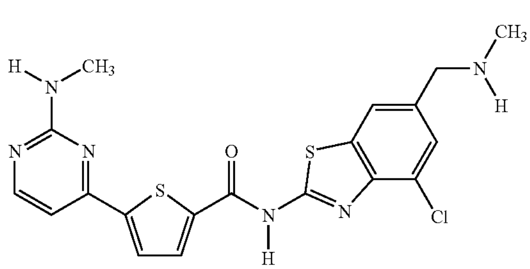 | 445<br>447 | N-{4-chloro-6-[(methylamino)methyl]-1,3-benzothiazol-2-yl}-5-[2-(methylamino)pyrimidin-4-yl]thiophene-2-carboxamide |

TABLE 6-continued

| No. | Structure | MH+ | Name |
|---|---|---|---|
| 210 | 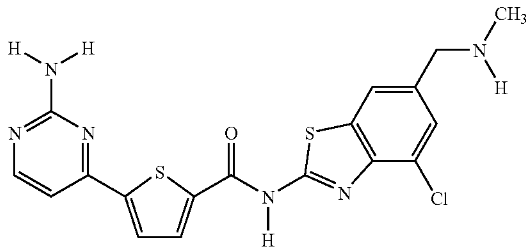 | 431<br>433 | 5-(2-aminopyrimidin-4-yl)-N-{4-chloro-6-[(methylamino)methyl]-1,3-benzothiazol-2-yl}thiophene-2-carboxamide |
| 211 | 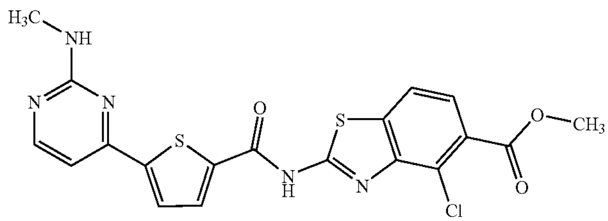 | 460 | methyl 4-chloro-2-[({5-[2-(methylamino)pyrimidin-4-yl]thien-2-yl}carbonyl)amino]-1,3-benzothazole-5-carboxylate |
| 212 | 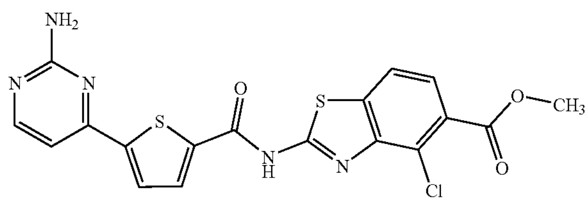 | 446 | methyl 2-({[5-(2-aminopyrimidin-4-yl)thien-2-yl]carbonyl}amino)-4-chloro-1,3-benzothiazole-5-carboxylate |
| 213 | 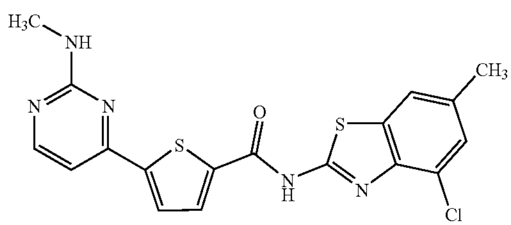 | 416 | N-(4-chloro-6-methyl-1,3-benzothiazol-2-yl)-5-[2-(methylamino)pyrimidin-4-yl]thiophene-2-carboxamide |
| 214 | 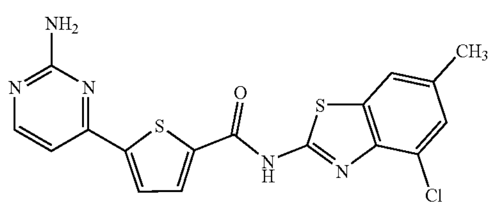 | 402 | 5-(2-aminopyrimidin-4-yl)-N-(4-chloro-6-methyl-1,3-benzothiazol-2-yl)thiophene-2-carboxamide |
| 215 | 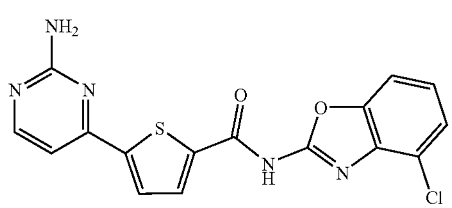 | 372 | 5-(2-aminopyrimidin-4-yl)-N-(4-chloro-1,3-benzoxazol-2-yl)thiophene-2-carboxamide |
| 216 | 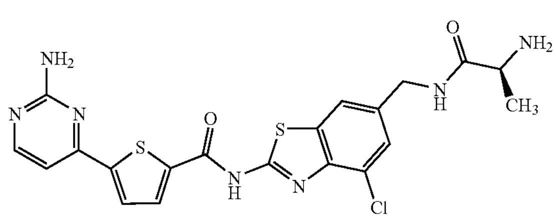 | 488 | N-[6-({[(2S)-2-aminopropanoyl]amino}methyl)-4-chloro-1,3-benzothiazol-2-yl]-5-(2-aminopyrimidin-4-yl)thiophene-2-carboxamide |

TABLE 6-continued

| No. | Structure | MH+ | Name |
|---|---|---|---|
| 217 | 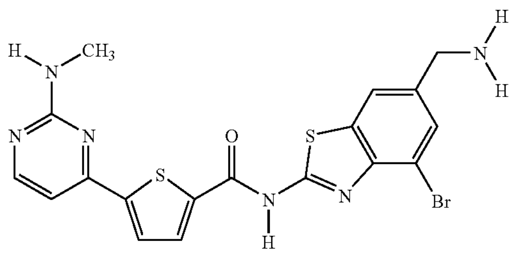 | 475<br>477 | N-[6-(aminomethyl)-4-bromo-1,3-benzothiazol-2-yl]-5-[2-(methylamino)pyrimidin-4-yl]thiophene-2-carboxamide |
| 218 | 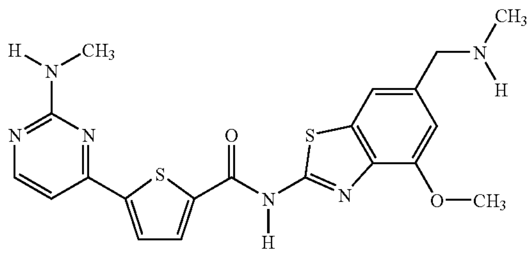 | 441 | N-{4-methoxy-6-[(methylamino)methyl]-1,3-benzothiazol-2-yl}-5-[2-(methylamino)pyrimidin-4-yl]thiophene-2-carboxamide |
| 219 | 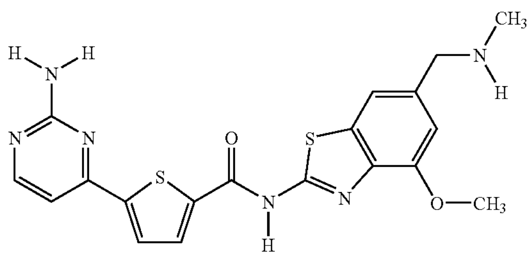 | 427 | 5-(2-aminopyrimidin-4-yl)-N-{4-methoxy-6-[(methylamino)methyl]-1,3-benzothiazol-2-yl}thiophene-2-carboxamide |
| 220 | 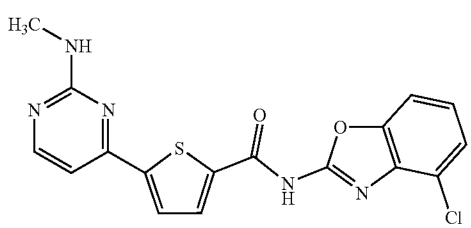 | 386 | N-(4-chloro-1,3-benzoxazol-2-yl)-5-[2-(methylamino)pyrimidin-4-yl]thiophene-2-carboxamide |
| 221 | 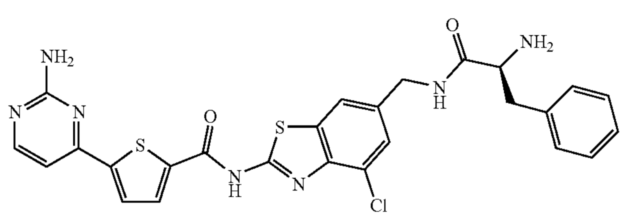 | 564 | N-[6-({[(2S)-2-amino-3-phenylpropanoyl]amino}methyl)-4-chloro-1,3-benzothiazol-2-yl]-5-(2-aminopyrimidin-4-yl)thiophene-2-carboxamide |
| 222 | 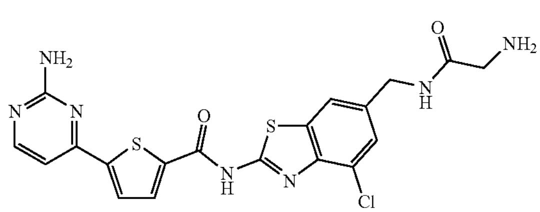 | 474 | N-(6-{[(aminoacetyl)amino]methyl}-4-chloro-1,3-benzothiazol-2-yl)-5-(2-aminopyrimidin-4-yl)thiophene-2-carboxamide |

TABLE 6-continued

| No. | Structure | MH+ | Name |
|---|---|---|---|
| 223 | 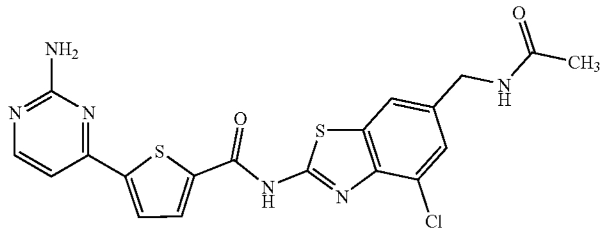 | 459 | N-{6-[(acetylamino)methyl]-4-chloro-1,3-benzothiazol-2-yl}-5-(2-aminopyrimidin-4-yl)thiophene-2-carboxamide |
| 224 | 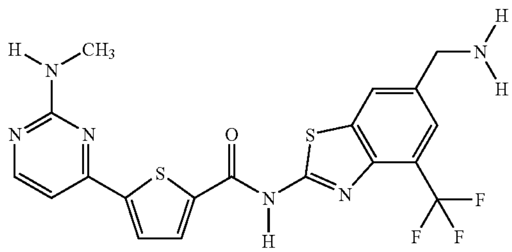 | 465 | N-[6-(aminomethyl)-4-(trifluoromethyl)-1,3-benzothiazol-2-yl]-5-[2-(methylamino)pyrimidin-4-yl]thiophene-2-carboxamide |
| 225 | 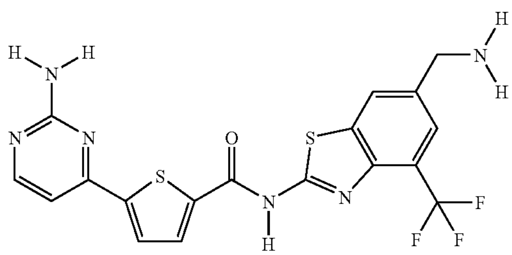 | 451 | N-[6-(aminomethyl)-4-(trifluoromethyl)-1,3-benzothiazol-2-yl]-5-(2-aminopyrimidin-4-yl)thiophene-2-carboxamide |
| 226 | 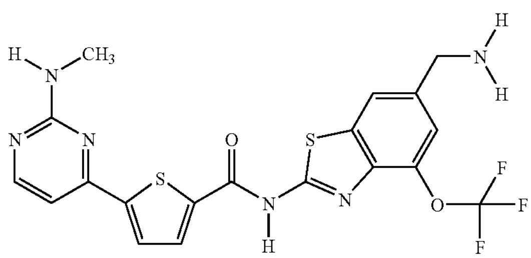 | 481 | N-[6-(aminomethyl)-4-(trifluoromethyl)-1,3-benzothiazol-2-yl]-5-[2-(methylamino)pyrimidin-4-yl]thiophene-2-carboxamide |
| 227 | 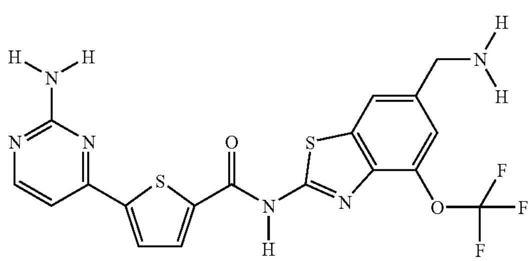 | 467 | N-[6-(aminomethyl)-4-(trifluoromethoxy)-1,3-benzothiazol-2-yl]-5-(2-aminopyrimidin-4-yl)thiophene-2-carboxamide |
| 228 | 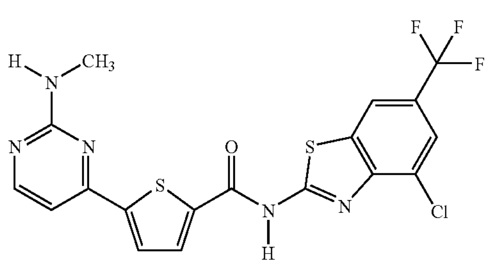 | 470, 472 | N-[4-chloro-6-(trifluoromethyl)-1,3-benzothiazol-2-yl]-5-[2-(methylamino)pyrimidin-4-yl]thiophene-2-carboxamide |

TABLE 6-continued

| No. | Structure | MH+ | Name |
|---|---|---|---|
| 229 | 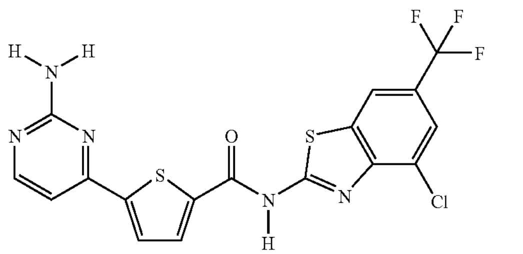 | 456<br>458 | 5-(2-aminopyrimidin-4-yl)-N-[4-chloro-6-(trifluoromethyl)-1,3-benzothiazol-2-yl]thiophene-2-carboxamide |
| 230 | 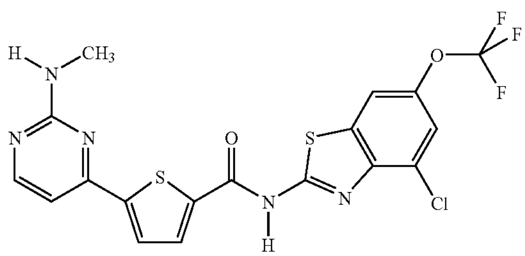 | 486<br>488 | N-[4-chloro-6-(trifluoromethoxy)-1,3-benzothiazol-2-yl]-5-[2-(methylamino)pyrimidin-4-yl]thiophene-2-carboxamide |
| 231 | 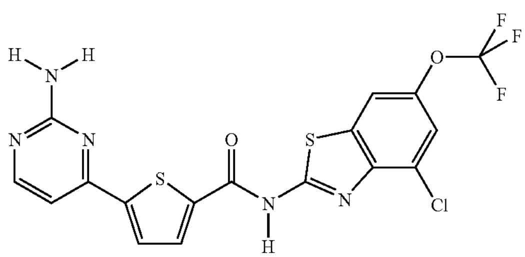 | 472<br>474 | 5-(2-aminopyrimidin-4-yl)-N-[4-chloro-6-(trifluoromethoxy)-1,3-benzothiazol-2-yl]thiophene-2-carboxamide |
| 232 | 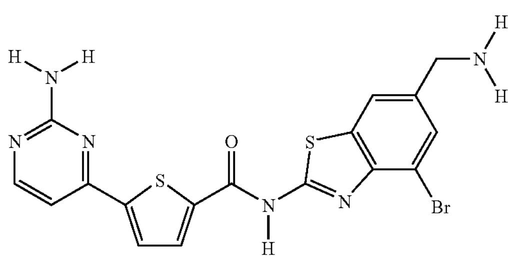 | 457<br>459 | N-[6-(aminomethyl)-4-bromo-1,3-benzothiazol-2-yl]-5-(2-aminopyrimidin-4-yl)thiophene-2-carboxamide |
| 233 | 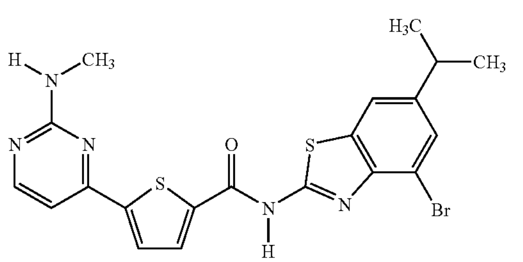 | 488<br>490 | N-(4-bromo-6-isopropyl-1,3-benzothiazol-2-yl)-5-[2-(methylamino)pyrimidin-4-yl]thiophene-2-carboxamide |
| 234 | 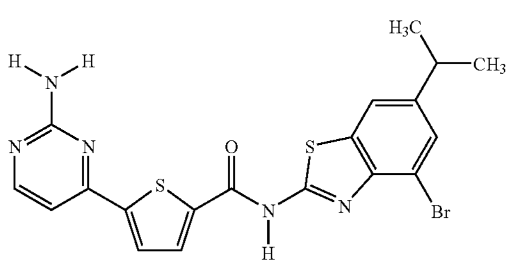 | 474<br>476 | 5-(2-aminopyrimidin-4-yl)-N-(4-bromo-6-isopropyl-1,3-benzothiazol-2-yl)thiophene-2-carboxamide |

TABLE 6-continued

| No. | Structure | MH+ | Name |
|---|---|---|---|
| 235 | 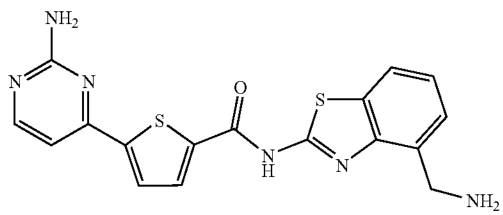 | 383 | N-[4-(aminomethyl)-1,3-benzothiazol-2-yl]-5-(2-aminopyrimidin-4-yl)thiophene-2-carboxamide |
| 236 | 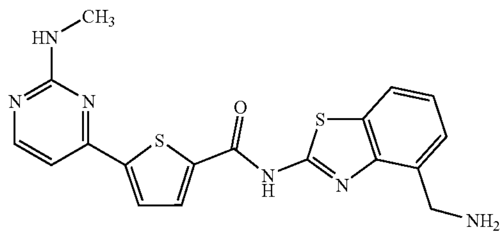 | 397 | N-[4-(aminomethyl)-1,3-benzothiazol-2-yl]-5-[2-(methylamino)pyrimidin-4-yl]thiophene-2-carboxamide |
| 237 | 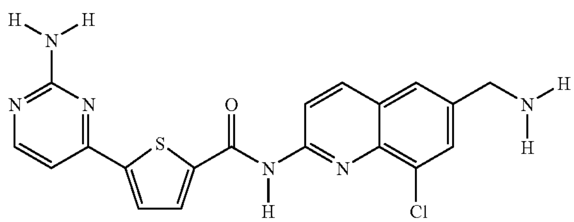 | 411<br>413 | N-[6-(aminomethyl)-8-chloroquinolin-2-yl]-5-(2-aminopyrimidin-4-yl)thiophene-2-carboxamide |
| 238 | 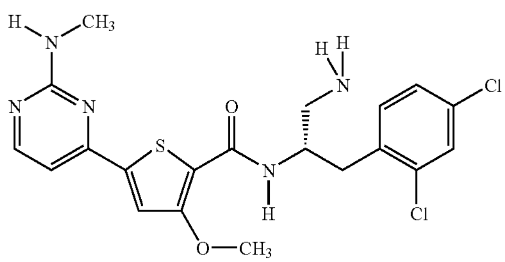 | 466<br>468 | N-[(1S)-2-amino-1-(2,4-dichlorobenzyl)ethyl]-3-methoxy-3-[2-(methylamino)pyrimidin-4-yl]thiophene-2-carboxamide |
| 239 | 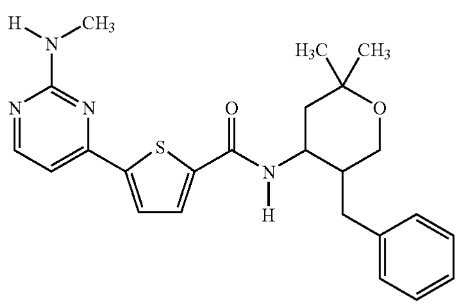 | 437 | N-(5-benzyl-2,2-dimethyltetrahydro-2H-pyran-4-yl)-5-[2-(methylamino)pyrimidin-4-yl]thiophene-2-carboxamide |
| 240 | 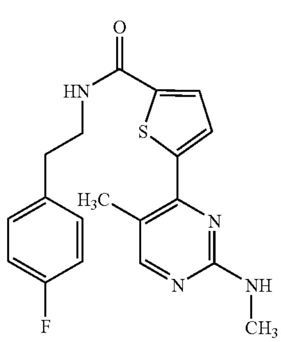 | 371 | N-[2-(4-fluorophenyl)ethyl]-5-[5-methyl-2-(methylamino)pyrimidin-4-yl]thiophene-2-carboxamide |

TABLE 6-continued

| No. | Structure | MH+ | Name |
|---|---|---|---|
| 241 | 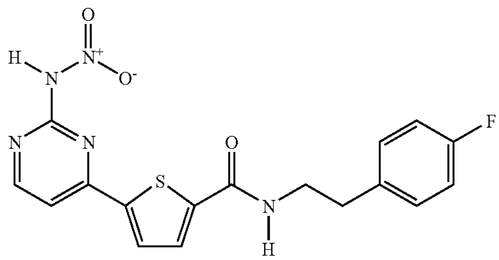 | 388 | N-[2-(4-fluorophenyl)ethyl]-5-[2-(nitroamino)pyrimidin-4-yl]thiophene-2-carboxamide |
| 242 | 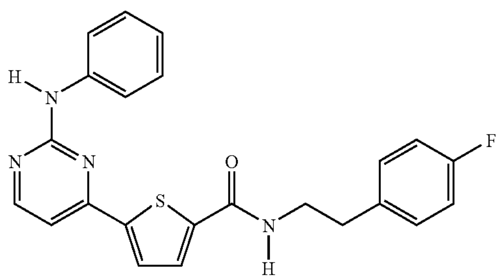 | 419 | 5-(2-anilinopyrimidin-4-yl)-N-[2-(4-fluorophenyl)ethyl]thiophene-2-carboxamide |
| 243 | 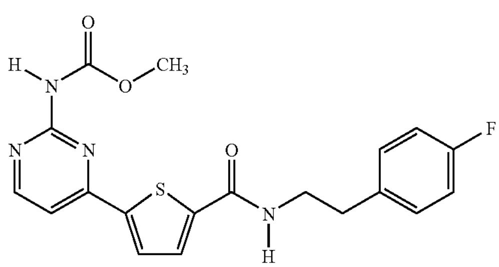 | 401 | methyl 4-[5-({[2-(4-fluorophenyl)ethyl]amino}carbonyl)thien-2-yl]pyrimidin-2-ylcarbamate |
| 244 | 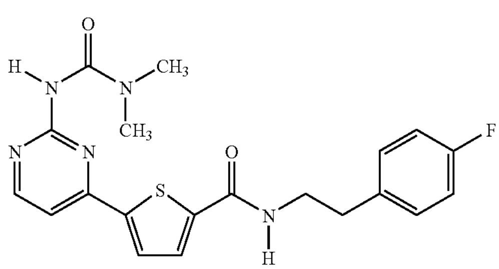 | 414 | 5-(2-{[(dimethylamino)carbonyl]amino}pyrimidin-4-yl)-N-[2-(4-fluorophenyl)ethyl]thiophene-2-carboxamide |
| 245 | 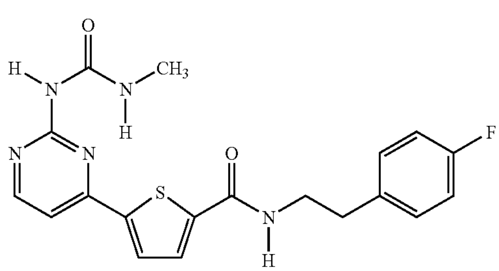 | 400 | N-[2-(4-fluorophenyl)ethyl]-5-(2-{[(methylamino)carbonyl]amino}pyrimidin-4-yl)thiophene-2-carboxamide |

TABLE 6-continued

| No. | Structure | MH+ | Name |
|---|---|---|---|
| 246 | 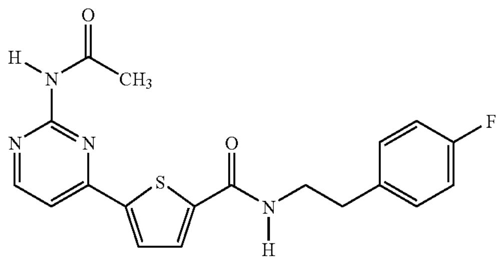 | 385 | 5-[2-(acetylamino)pyrimidin-4-yl]-N-[2-(4-fluorophenyl)ethyl]thiophene-2-carboxamide |
| 247 | 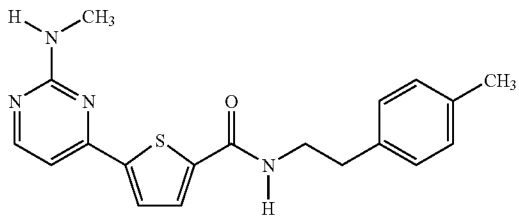 | 353 | 5-[2-(methylamino)pyrimidin-4-yl]-N-[2-(4-methylphenyl)ethyl]thiophene-2-carboxamide |
| 248 | 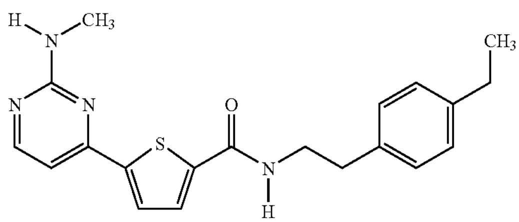 | 367 | N-[2-(4-ethylphenyl)ethyl]-5-[2-(methylamino)pyrimidin-4-yl]thiophene-2-carboxamide |
| 249 | 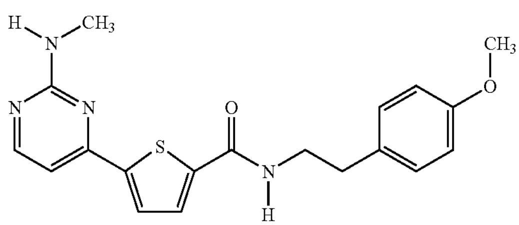 | 369 | N-[2-(4-methoxyphenyl)ethyl]-5-[2-(methylamino)pyrimidin-4-yl]thiophene-2-carboxamide |
| 250 | 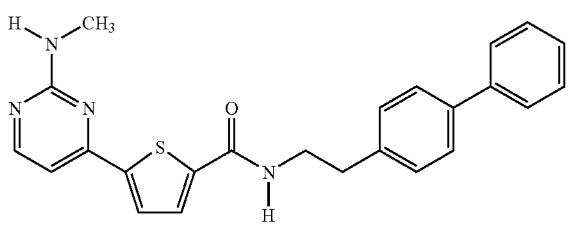 | 415 | N-[2-(1,1'-biphenyl-4-yl)ethyl]-5-[2-(methylamino)pyrimidin-4-yl]thiophene-2-carboxamide |
| 251 | 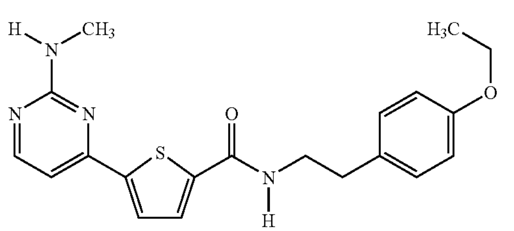 | 383 | N-[2-(4-ethoxyphenyl)ethyl]-5-[2-(methylamino)pyrimidin-4-yl]thiophene-2-carboxamide |

TABLE 6-continued

| No. | Structure | MH+ | Name |
|---|---|---|---|
| 252 | 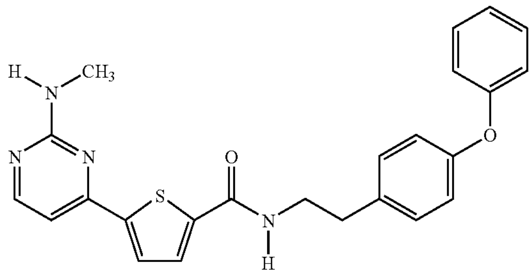 | 431 | 5-[2-(methylamino)pyrimidin-4-yl]-N-[2-(4-phenoxyphenyl)ethyl]thiophene-2-carboxamide |
| 253 | 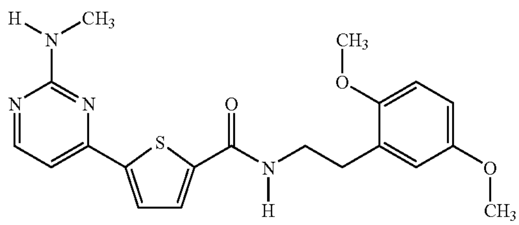 | 399 | N-[2-(2,5-dimethoxyphenyl)ethyl]-5-[2-(methylamino)pyrimidin-4-yl]thiophene-2-carboxamide |
| 254 | 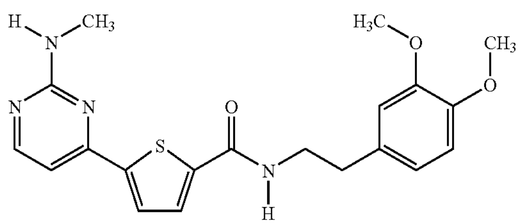 | 399 | N-[2-(3,4-dimethoxyphenyl)ethyl]-5-[2-(methylamino)pyrimidin-4-yl]thiophene-2-carboxamide |
| 255 | 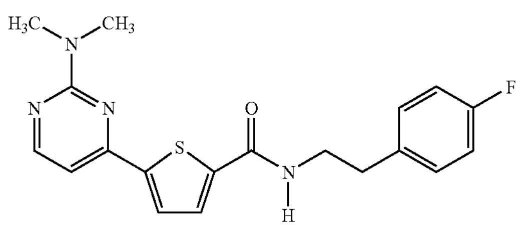 | 371 | 5-[2-(dimethylamino)pyrimidin-4-yl]-N-[2-(4-fluorophenyl)ethyl]thiophene-2-carboxamide |
| 256 | 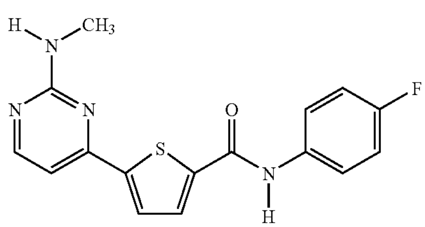 | 329 | N-(4-fluorophenyl)-5-[2-(methylamino)pyrimidin-4-yl]thiophene-2-carboxamide |
| 257 | 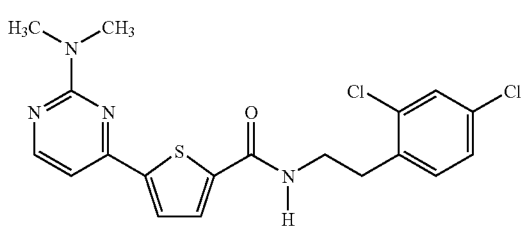 | 421 | N-[2-(2,4-dichlorophenyl)ethyl]-5-[2-(dimethylamino)pyrimidin-4-yl]thiophene-2-carboxamide |

TABLE 6-continued

| No. | Structure | MH+ | Name |
|---|---|---|---|
| 258 | 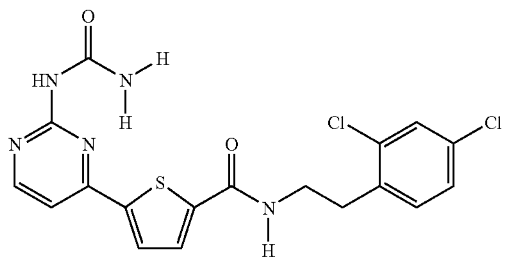 | 436 | 5-{2-[(aminocarbonyl)amino]pyrimidin-4-yl}-N-[2-(2,4-dichlorophenyl)ethyl]thiophene-2-carboxamide |
| 259 | 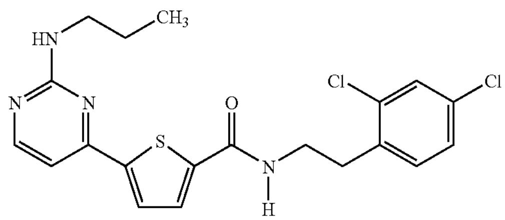 | 435 | N-[2-(2,4-dichlorophenyl)ethyl]-5-[2-(propylamino)pyrimidin-4-yl]thiophene-2-carboxamide |
| 260 | 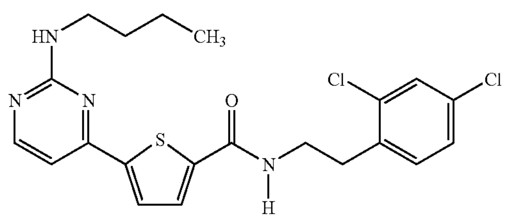 | 449 | 5-[2-(butylamino)pyrimidin-4-yl]-N-[2-(2,4-dichlorophenyl)ethyl]thiophene-2-carboxamide |
| 261 | 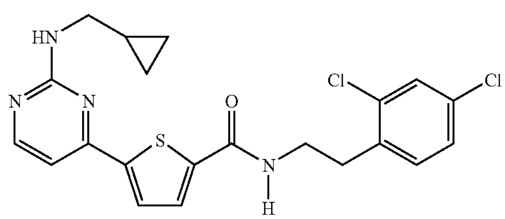 | 447 | 5-{2-[(cyclopropylmethyl)amino]pyrimidin-4-yl}-N-[2-(2,4-dichlorophenyl)ethyl]thiophene-2-carboxamide |
| 262 | 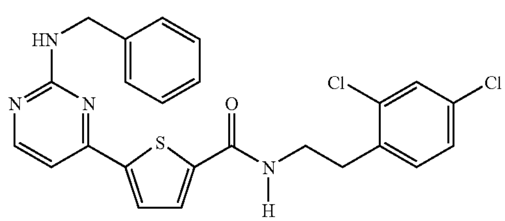 | 483 | 5-[2-(benzylamino)pyrimidin-4-yl]-N-[2-(2,4-dichlorophenyl)ethyl]thiophene-2-carboxamide |
| 263 | 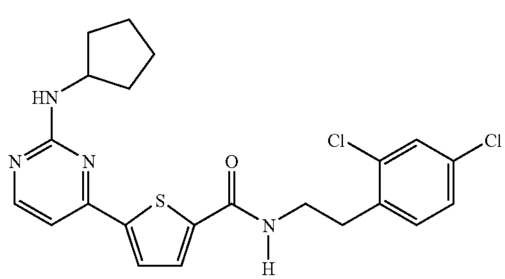 | 461 | 5-[2-(cyclopentylamino)pyrimidin-4-yl]-N-[2-(2,4-dichlorophenyl)ethyl]thiophene-2-carboxamide |

TABLE 6-continued

| No. | Structure | MH+ | Name |
|---|---|---|---|
| 264 | 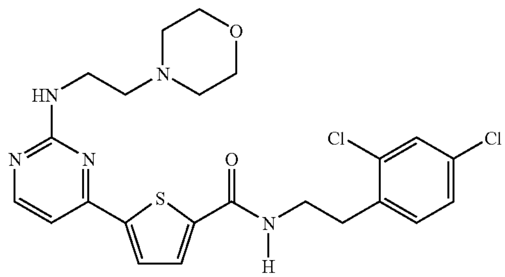 | 506 | N-[2-(2,4-dichlorophenyl)ethyl]-5-{2-[(2-morpholin-4-ylethyl)amino]pyrimidin-4-yl}thiophene-2-carboxamide |
| 265 | 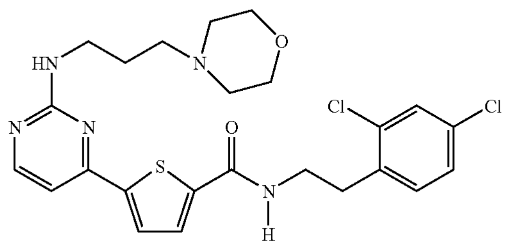 | 520 | N-[2-(2,4-dichlorophenyl)ethyl]-5-{2-[(3-morpholin-4-ylpropyl)amino]pyrimidin-4-yl}thiophene-2-carboxamide |
| 266 | 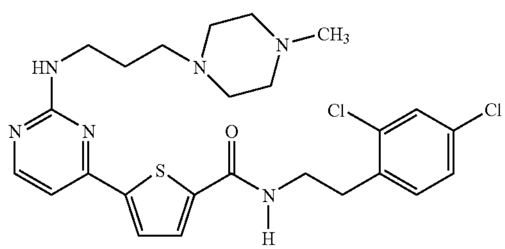 | 533 | N-[2-(2,4-dichlorophenyl)ethyl]-5-(2-{[3-(4-methylpiperazin-1-yl)propyl]amino}pyrimidin-4-yl)thiophene-2-carboxamide |
| 267 | 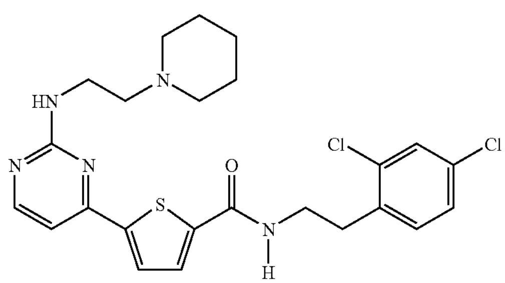 | 504 | N-[2-(2,4-dichlorophenyl)ethyl]-5-{2-[(2-piperidin-1-ylethyl)amino]pyrimidin-4-yl}thiophene-2-carboxamide |
| 268 | 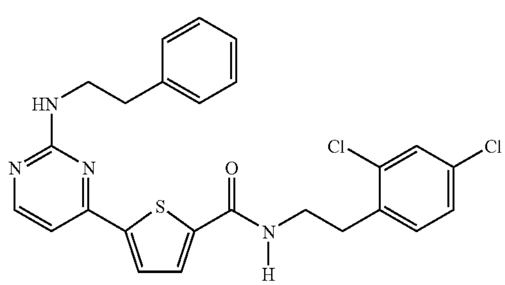 | 497 | N-[2-(2,4-dichlorophenyl)ethyl]-5-{2-[(2-phenylethyl)amino]pyrimidin-4-yl}thiophene-2-carboxamide |
| 269 | 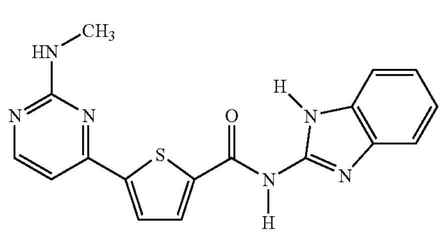 | 351 | N-1H-benzimidazol-2-yl-5-[2-(methylamino)pyrimidin-4-yl]thiophene-2-carboxamide |

TABLE 6-continued

| No. | Structure | MH+ | Name |
|---|---|---|---|
| 270 | 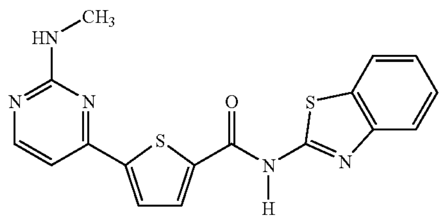 | 368 | N-1,3-benzothiazol-2-yl-5-[2-(methylamino)pyrimidin-4-yl]thiophene-2-carboxamide |
| 271 | 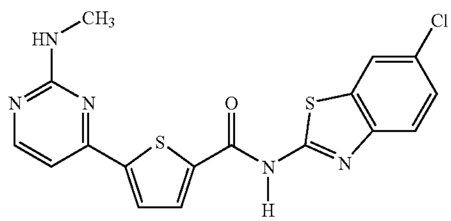 | 402 | N-(6-chloro-1,3-benzothiazol-2-yl)-5-[2-(methylamino)pyrimidin-4-yl]thiophene-2-carboxamide |
| 272 | 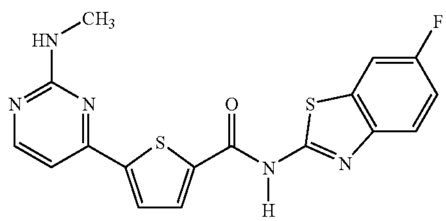 | 386 | N-(6-fluoro-1,3-benzothiazol-2-yl)-5-[2-(methylamino)pyrimidin-4-yl]thiophene-2-carboxamide |
| 273 | 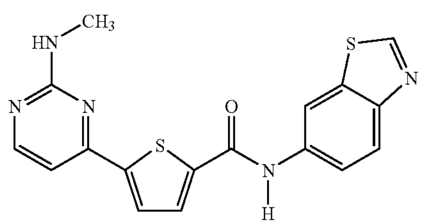 | 368 | N-1,3-benzothiazol-6-yl-5-[2-(methylamino)pyrimidin-4-yl]thiophene-2-carboxamide |
| 274 | 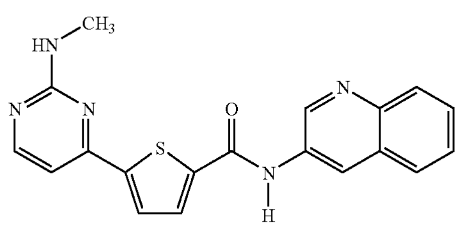 | 362 | 5-[2-(methylamino)pyrimidin-4-yl]-N-quinolin-3-ylthiophene-2-carboxamide |
| 275 | 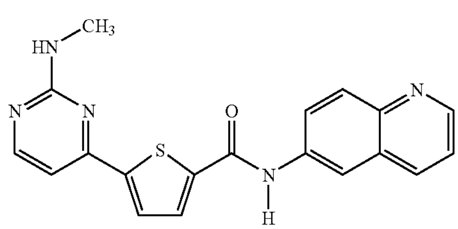 | 362 | 5-[2-(methylamino)pyrimidin-4-yl]-N-quinolin-6-ylthiophene-2-carboxamide |

TABLE 6-continued

| No. | Structure | MH+ | Name |
|---|---|---|---|
| 276 | 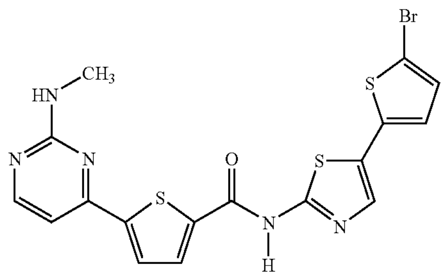 | 478 | N-[5-(5-bromothien-2-yl)-1,3-thiazol-2-yl]-5-[2-(methylamino)pyrimidin-4-yl]thiophene-2-carboxamide |
| 277 | 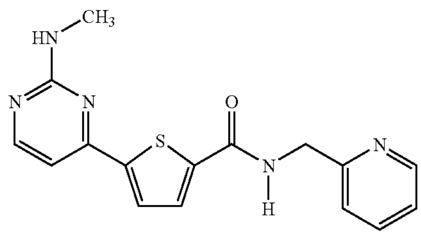 | 326 | 5-[2-(methylamino)pyrimidin-4-yl]-N-(pyridin-2-ylmethyl)thiophene-2-carboxamide |
| 278 | 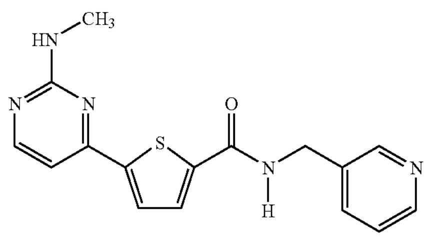 | 326 | 5-[2-(methylamino)pyrimidin-4-yl]-N-(pyridin-2-ylmethyl)thiophene-2-carboxamide |
| 279 | 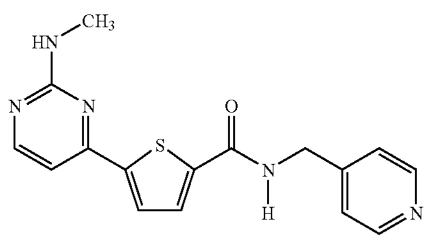 | 326 | 5-[2-(methylamino)pyrimidin-4-yl]-N-(pyridin-4-ylmethyl)thiophene-2-carboxamide |
| 280 | 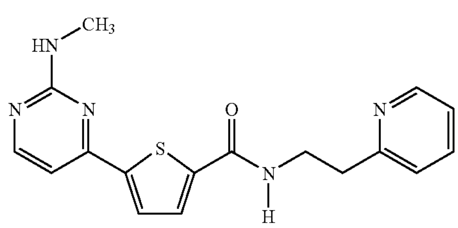 | 340 | 5-[2-(methylamino)pyrimidin-4-yl]-N-(2-pyridin-2-ylethyl)thiophene-2-carboxamide |
| 281 | 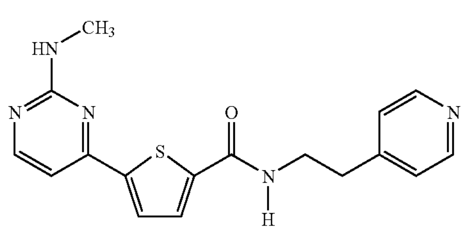 | 340 | 5-[2-(methylamino)pyrimidin-4-yl]-N-(2-pyridin-2-ylethyl)thiophene-2-carboxamide |

TABLE 6-continued

| No. | Structure | MH+ | Name |
|---|---|---|---|
| 282 | 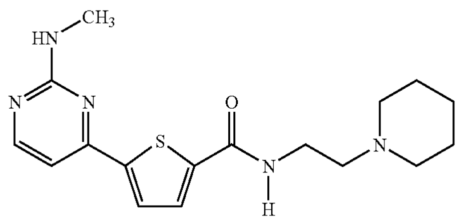 | 346 | 5-[2-(methylamino)pyrimidin-4-yl]-N-(2-piperidin-1-ylethyl)thiophene-2-carboxamide |
| 283 | 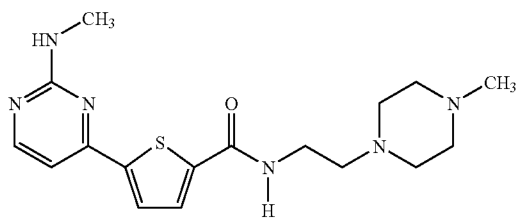 | 361 | 5-[2-(methylamino)pyrimidin-4-yl]-N-[2-(4-methylpiperazin-1-yl)ethyl]thiophene-2-carboxamide |
| 284 | 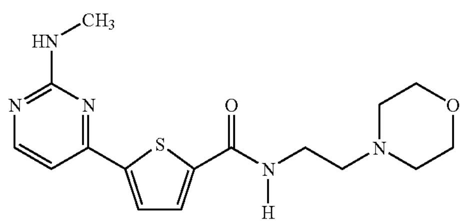 | 348 | 5-[2-(methylamino)pyrimidin-4-yl]-N-(2-morpholin-4-ylethyl)thiophene-2-carboxamide |
| 285 | 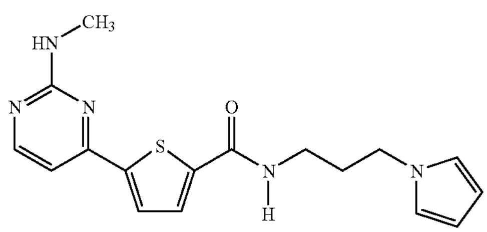 | 342 | 5-[2-(methylamino)pyrimidin-4-yl]-N-[3-(1H-pyrrol-1-yl)propyl]thiophene-2-carboxamide |
| 286 | 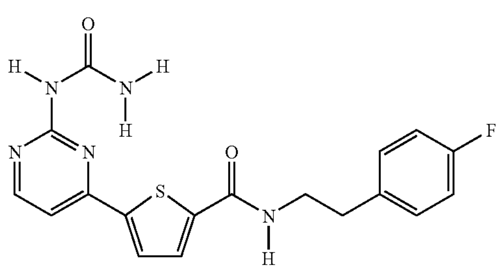 | 386 | 5-{2-[(aminocarbonyl)amino]pyrimidin-4-yl}-N-[2-(4-fluorophenyl)ethyl]thiophene-2-carboxamide |
| 287 | 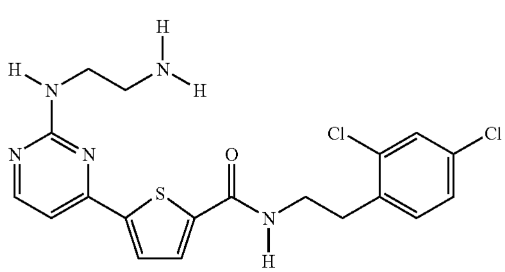 | 436 | 5-{2-[(2-aminoethyl)pyrimidin-4-yl}-N-[2-(2,4-dichlorophenyl)ethyl]thiophene-2-carboxamide |

TABLE 6-continued

| No. | Structure | MH+ | Name |
|---|---|---|---|
| 288 | 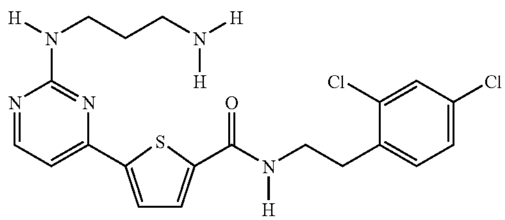 | 450 | 2-{2-[(3-aminopropyl)amino]pyrimidin-4-yl}-N-[2-(2,4-dichlorophenyl)ethyl]thiophene-2-carboxamide |
| 289 | 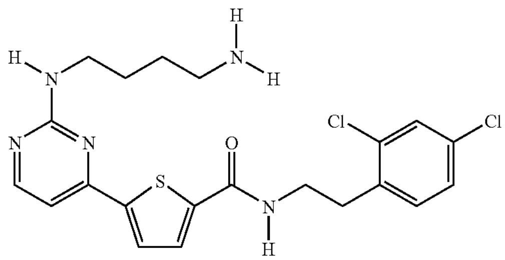 | 464 | 5-{2-[(4-aminobutyl)pyrimidin-4-yl}-N-[2-(2,4-dichlorophenyl)ethyl]thiophene-2-carboxamide |
| 290 | 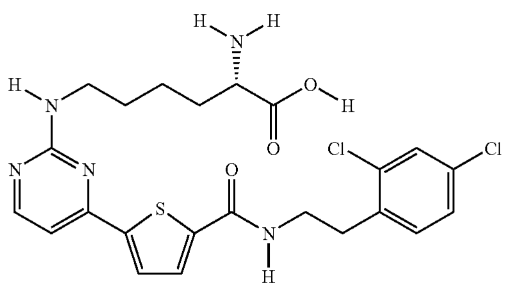 | 522 | N~6~-{4-[5-({[2-(2,4-dichlorophenyl)ethyl]amino}carbonyl)thien-2-yl]pyrimidin-2-yl}-L-lysine |
| 291 | 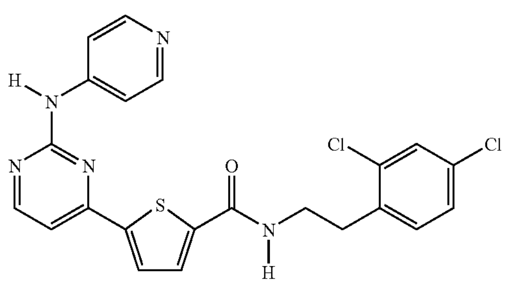 | 470 | N-[2-(2,4-dichlorophenyl)ethyl]-5-[2-(pyridin-4-ylamino)pyrimidin-4-yl]thiophene-2-carboxamide |
| 292 | 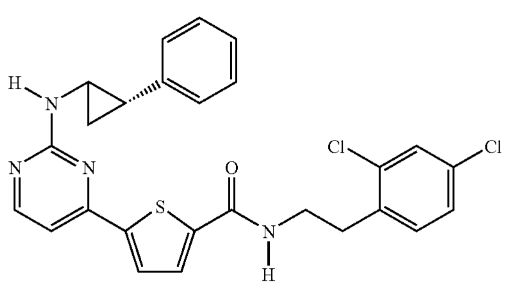 | 509 | N-[2-(2,4-dichlorophenyl)ethyl]-5-(2-{[(2S)-2-phenylcyclopropyl]amino}pyrimidin-4-yl)thiophene-2-carboxamide |
| 293 | 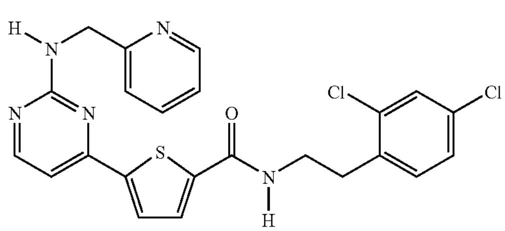 | 484 | N-[2-(2,4-dichlorophenyl)ethyl]-5-{2-[(pyridin-2-ylmethyl)amino]pyrimidin-4-yl}thiophene-2-carboxamide |

TABLE 6-continued

| No. | Structure | MH+ | Name |
|---|---|---|---|
| 294 | 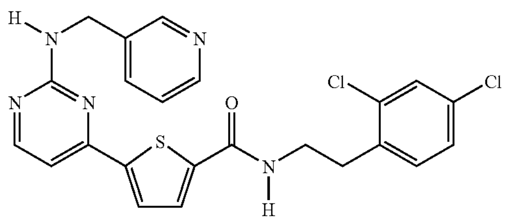 | 484 | N-[2-(2,4-dichlorophenyl)ethyl]-5-{2-[(pyridin-3-ylmethyl)amino]pyrimidin-4-yl}thiophene-2-carboxamide |
| 295 | 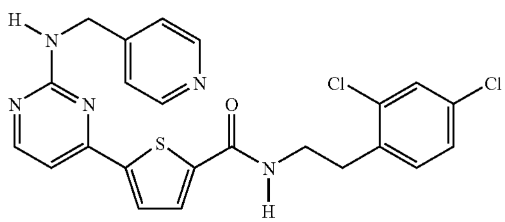 | 484 | N-[2-(2,4-dichlorophenyl)ethyl]-5-{2-[(pyridin-4-ylmethyl)amino]pyrimidin-4-yl}thiophene-2-carboxamide |
| 296 | 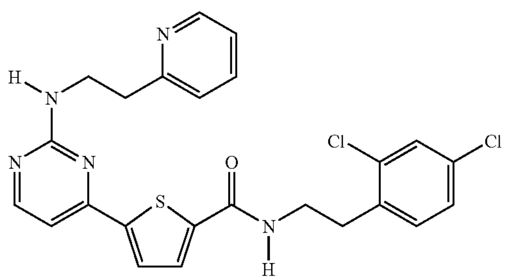 | 498 | N-[2-(2,4-dichlorophenyl)ethyl]-5-{2-[(2-pyridin-2-ylethyl)amino]pyrimidin-4-yl}thiophene-2-carboxamide |
| 297 | 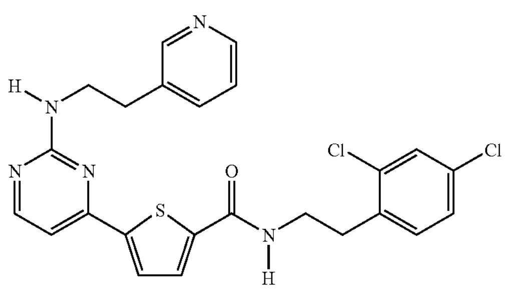 | 498 | N-[2-(2,4-dichlorophenyl)ethyl]-5-{2-[(2-pyridin-3-ylethyl)amino]pyrimidin-4-yl}thiophene-2-carboxamide |
| 298 | 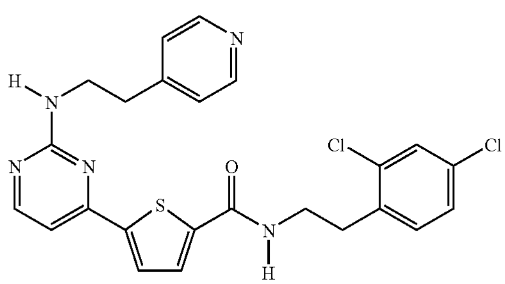 | 498 | N-[2-(2,4-dichlorophenyl)ethyl]-5-{2-[(2-pyridin-4-ylethyl)amino]pyrimidin-4-yl}thiophene-2-carboxamide |
| 299 | 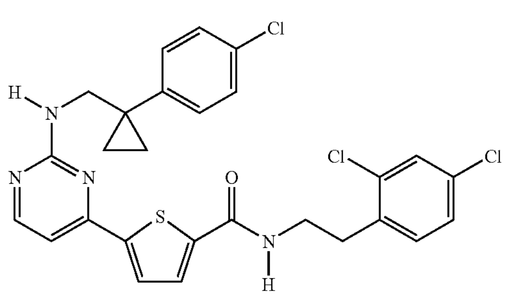 | 557 | 5-[2-({[1-(4-chlorophenyl)cyclopropyl]methyl}amino)pyrimidin-4-yl]-N-[2-(2,4-dichlorophenyl)ethyl]thiophene-2-carboxamide |

TABLE 6-continued

| No. | Structure | MH+ | Name |
|---|---|---|---|
| 300 | 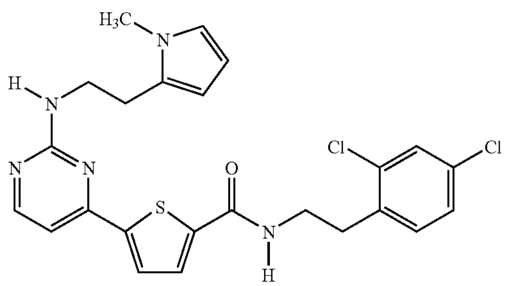 | 500 | N-[2-(2,4-dichlorophenyl)ethyl]-5-(2-{[2-(1-methyl-1H-pyrrol-2-yl)ethyl]amino}pyrimidin-4-yl)thiophene-2-carboxamide |
| 301 | 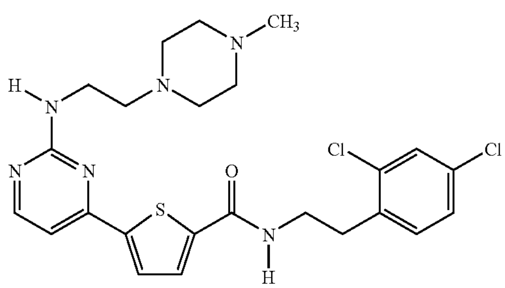 | 519 | N-[2-(2,4-dichlorophenyl)ethyl]-5-(2-{[2-(4-methylpiperazin-1-yl)ethyl]amino}primidin-4-yl)thiophene-2-carboxamide |
| 302 | 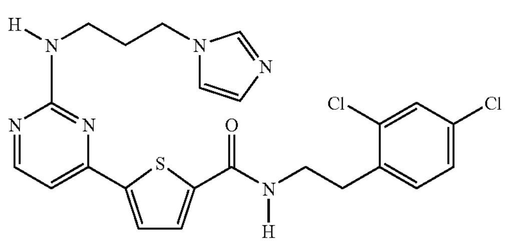 | 501 | N-[2-(2,4-dichlorophenyl)ethyl]-5-(2-{[3-(1H-imidazol-1-yl)propyl]amino}pyrimidin-4-yl)thiophene-2-carboxamide |
| 303 | 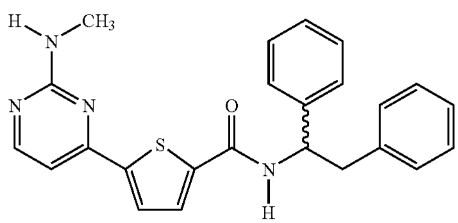 | 415 | N-(1,2-diphenylethyl)-5-[2-(methylamino)pyrimidin-4-yl]thiophene-2-carboxamide |
| 304 | 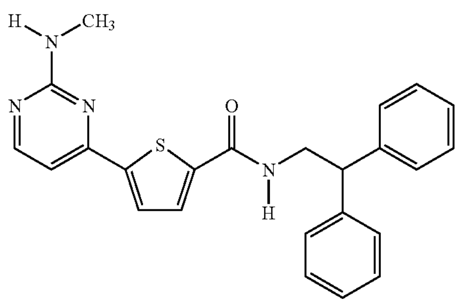 | 415 | N-(2,2-diphenylethyl)-5-[2-(methylamino)pyrimidin-4-yl]thiophene-2-carboxamide |

TABLE 6-continued

| No. | Structure | MH+ | Name |
|---|---|---|---|
| 305 | 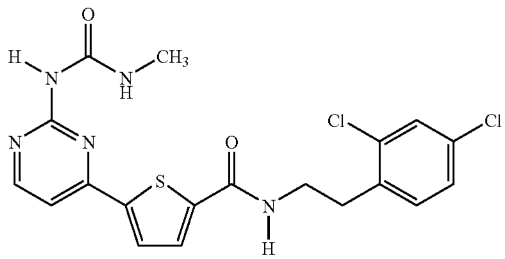 | 450 | N-[2-(2,4-dichlorophenyl)ethyl]-5-(2-{[(methylamino)carbonyl]amino}pyrimidin-4-yl)thiophene-2-carboxamide |
| 306 | 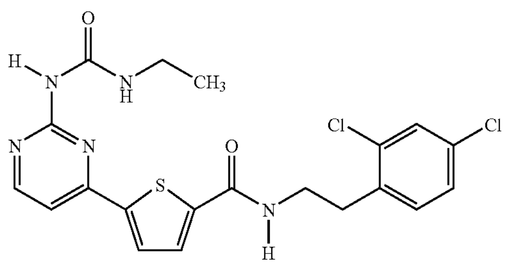 | 464 | N-[2-(2,4-dichlorophenyl)ethyl]-5-(2-{[(ethylamino)carbonyl]amino}pyrimidin-4-yl)thiophene-2-carboxamide |
| 307 | 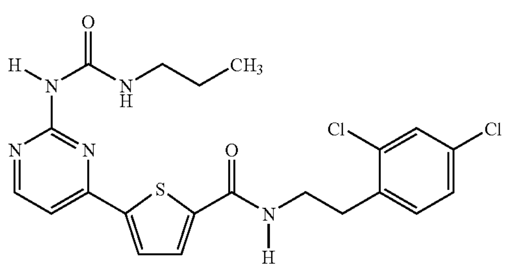 | 478 | N-[2-(2,4-dichlorophenyl)ethyl]-5-(2-{[(propylamino)carbonyl]amino}pyrimidin-4-yl)thiophene-2-carboxamide |
| 308 | 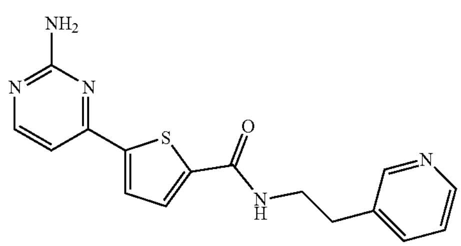 | 326 | 5-(2-aminopyrimidin-4-yl)-N-(2-pyridin-3-ylethyl)thiophen-2-carboxamide |
| 309 | 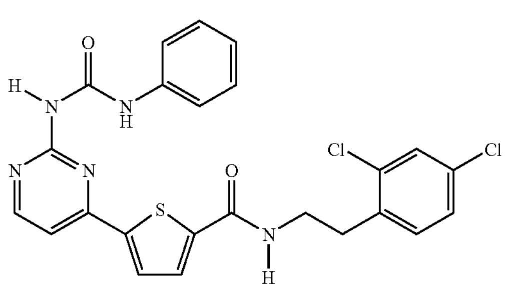 | 512 | 5-{2-[(anilinocarbonyl)amino]pyrimidin-4-yl}-N-[2-(2,4-dichlorophenyl)ethyl]thiophene-2-carboxamide |

TABLE 6-continued

| No. | Structure | MH+ | Name |
|---|---|---|---|
| 310 | 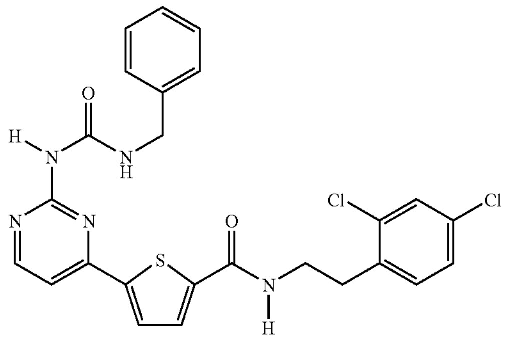 | 526 | 5-(2-{[(benzylamino)carbonyl]amino}pyrimidin-4-yl)-N-[2-(2,4-dichlorophenyl)ethyl]thiophene-2-carboxamide |
| 311 | 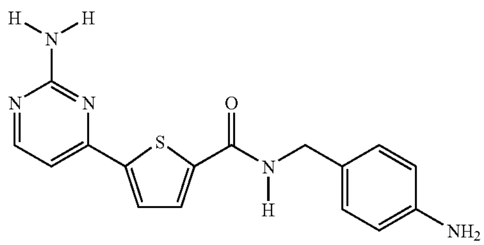 | 326 | N-(4-aminobenzyl)-5-(2-aminopyrimidin-4-yl)thiophene-2-carboxamide |
| 312 | 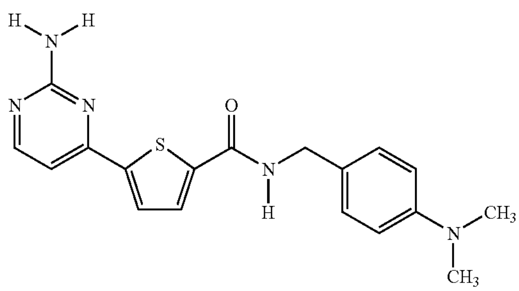 | 354 | 5-(2-aminopyrimidin-4-yl)-N-[4-(dimethylamino)benzyl]thiophene-2-carboxamide |
| 313 | 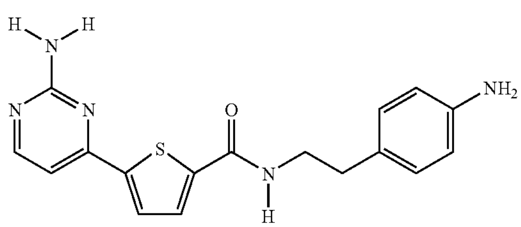 | 340 | N-[2-(4-aminophenyl)ethyl]-5-(2-aminopyrimidin-4-yl)thiophene-2-carboxamide |
| 314 | 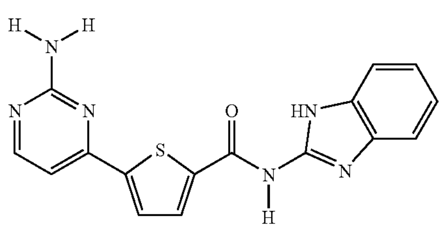 | 337 | 5-(2-aminopyrimidin-4-yl)-N-1H-benzimidazol-2-ylthiophene-2-carboxamide |
| 315 | 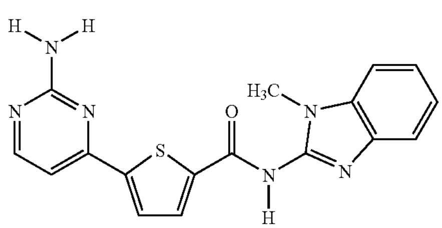 | 351 | 5-(2-aminopyrimidin-4-yl)-N-(1-methyl-1H-benzimidazol-2-yl)thiophene-2-carboxamide |

TABLE 6-continued

| No. | Structure | MH+ | Name |
|---|---|---|---|
| 316 | 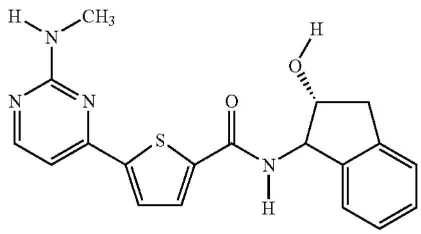 | 367 | N-[(2R)-2-hydroxy-2,3-dihydro-1H-inden-1-yl]-5-[2-(methylamino)pyrimidin-4-yl]thiophene-2-carboxamide |
| 317 | 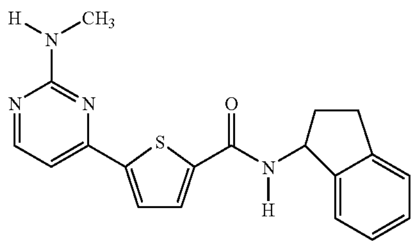 | 351 | N-2,3-dihydro-1H-inden-1-yl-5-[2-(methylamino)pyrimidin-4-yl]thiophene-2-carboxamide |
| 318 | 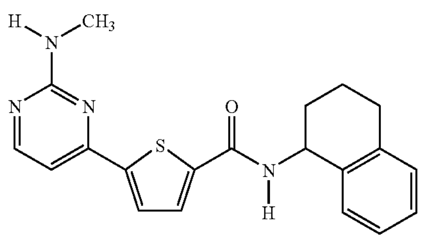 | 365 | 5-[2-(methylamino)pyrimidin-4-yl]-N-1,2,3,4-tetrahydronaphthalen-1-ylthiophene-2-carboxamide |
| 319 | 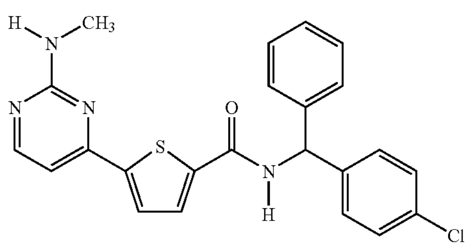 | 435 | N-[(4-chlorophenyl)(phenyl)methyl]-5-[2-(methylamino)pyrimidin-4-yl]thiophene-2-carboxamide |
| 320 | 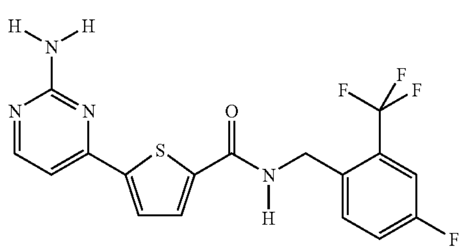 | 397 | 5-(2-aminopyrimidin-4-yl)-N-[4-fluoro-2-(trifluoromethyl)benzyl]thiophene-2-carboxamide |
| 321 | 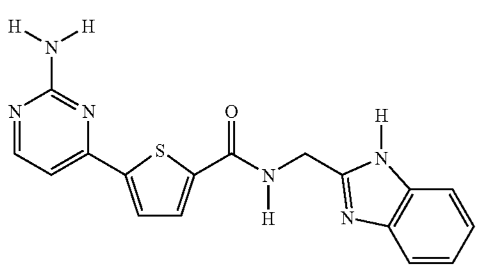 | 351 | 5-(2-aminopyrimidin-4-yl)-N-(1H-benzimidazol-2-ylmethyl)thiophene-2-carboxamide |

TABLE 6-continued

| No. | Structure | MH+ | Name |
|---|---|---|---|
| 322 | 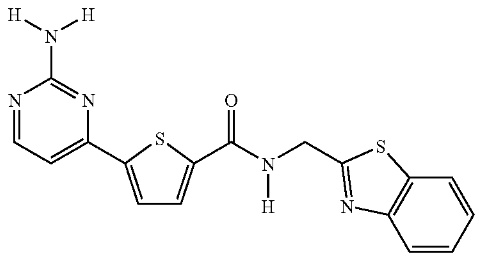 | 367 | 5-(2-aminopyrimidin-4-yl)-N-(1-benzothien-2-ylmethyl)thiophene-2-carboxamide |
| 323 | 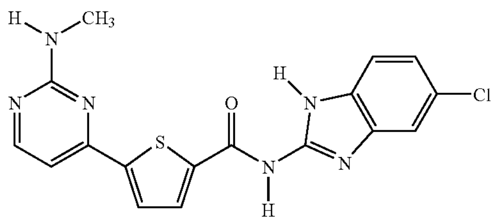 | 385 | N-(5-chloro-1H-benzimidazol-2-yl)-5-[2-(methylamino)pyrimidin-4-yl]thiophene-2-carboxamide |
| 324 | 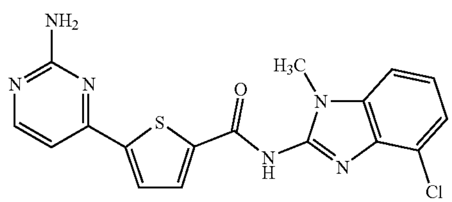 | 385 | 5-(2-aminopyrimidin-4-yl)-N-(4-chloro-1-methyl-1H-benzimidazol-2-yl)thiophene-2-carboxamide |
| 325 | 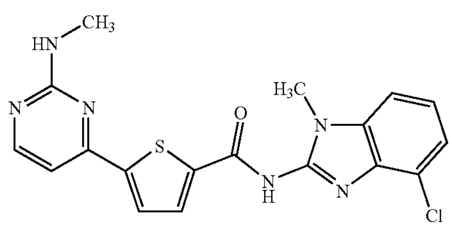 | 399 | N-(4-chloro-1-methyl-1H-benzimidazol-2-yl)-5-[2-(methylamino)pyrimidin-4-yl]thiophene-2-carboxamide |
| 326 | 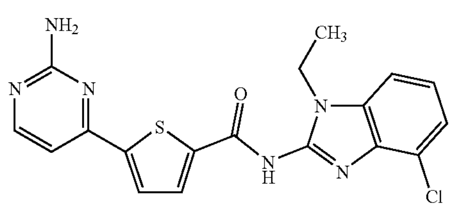 | 399 | 5-(2-aminopyrimidin-4-yl)-N-(4-chloro-1-ethyl-1H-benzimidazol-2-yl)thiophene-2-carboxamide |
| 327 | 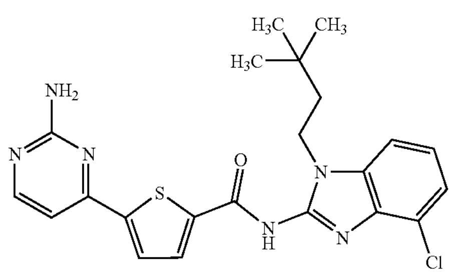 | 455 | 5-(2-aminopyrimidin-4-yl)-N-[4-chloro-1-(3,3-dimethylbutyl)-1H-benzimidazol-2-yl]thiophene-2-carboxamide |

TABLE 6-continued

| No. | Structure | MH+ | Name |
|---|---|---|---|
| 328 | 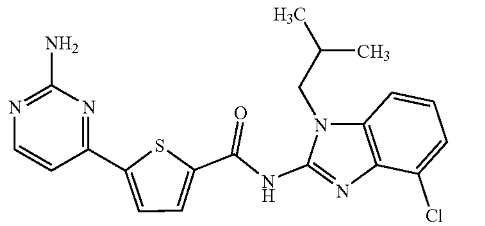 | 427 | 5-(2-aminopyrimidin-4-yl)-N-(4-chloro-1-isobutyl-1H-benzimidazol-2-yl)thiophene-2-carboxamide |
| 329 | 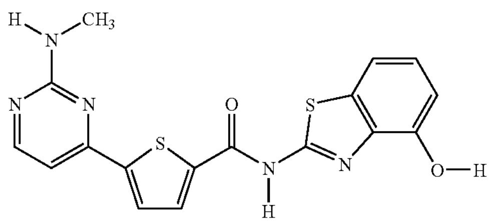 | 384 | N-(4-hydroxy-1,3-benzothiazol-2-yl)-5-[2-(methylamino)pyrimidin-4-yl]thiophene-2-carboxamide |
| 330 | 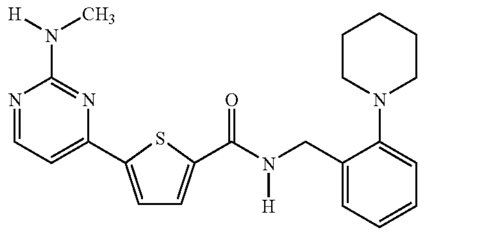 | 408 | 5-[2-(methylamino)pyrimidin-4-yl]-N-(2-piperidin-1-ylbenzyl)thiophene-2-carboxamide |
| 331 | 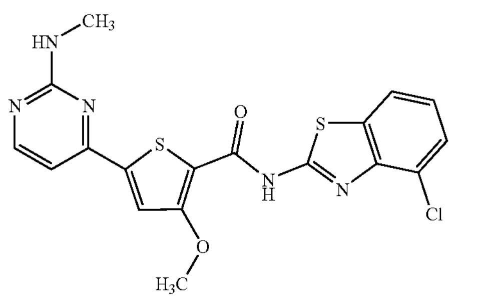 | 432 | N-(4-chloro-1,3-benzothiazol-2-yl)-3-methoxy-5-[2-(methylamino)pyrimidin-4-yl]thiophene-2-carboxamide |
| 332 | 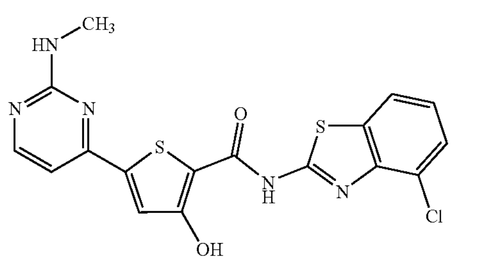 | 418 | N-(4-chloro-1,3-benzothiazol-2-yl)-3-hydroxy-5-[2-(methylamino)pyrimidin-4-yl]thiophene-2-carboxamide |
| 333 | 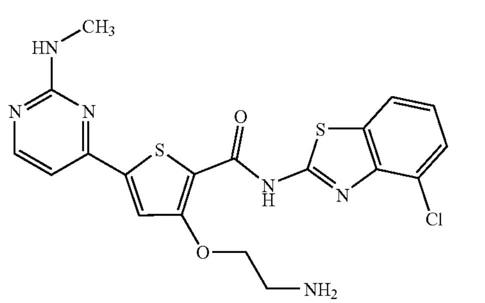 | 461 | 3-(2-aminoethoxy)-N-(4-chloro-1,3-benzothiazol-2-yl)-5-[2-(methylamino)pyrimidin-4-yl]thiophene-2-carboxamide |

TABLE 6-continued

| No. | Structure | MH+ | Name |
|---|---|---|---|
| 334 | 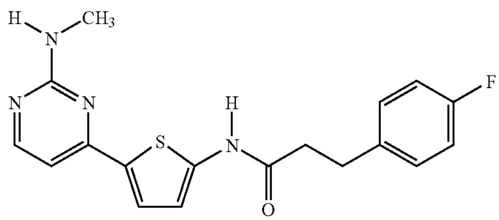 | 357 | 3-(4-fluorophenyl)-N-{5-[2-(methylamino)pyrimidin-4-yl]thien-2-yl}propanamide |
| 335 | 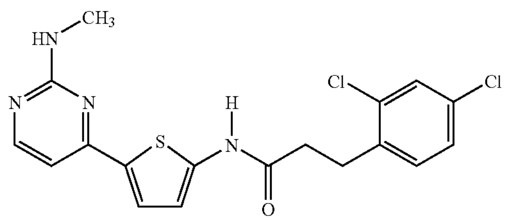 | 407 | 3-(2,4-dichlorophenyl)-N-{5-[2-(methylamino)pyrimidin-4-yl]thien-2-yl}propanamide |
| 336 | 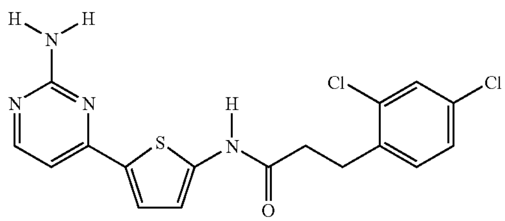 | 393 | N-[5-(2-aminopyrimidin-4-yl)thien-2-yl]-3-(2,4-dichlorophenyl)propanamide |
| 337 | 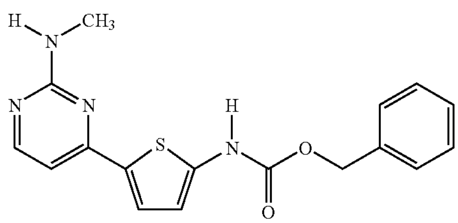 | 341 | benzyl 5-[2-(methylamino)pyrimidin-4-yl]thien-2-ylcarbamate |
| 338 | 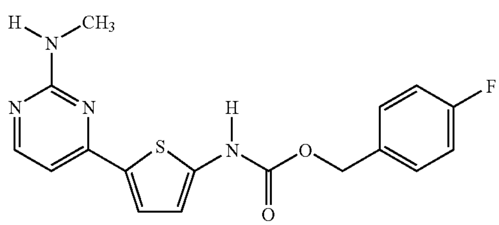 | 359 | 4-fluorobenzyl 5-[2-(methylamino)pyrimidin-4-yl]thien-2-ylcarbamate |
| 339 | 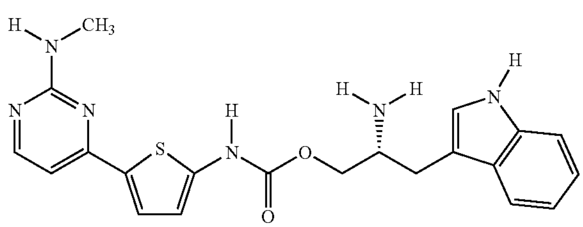 | 423 | (2R)-2-amino-3-(1H-indol-3-yl)propyl 5-[2-(methylamino)pyrimidin-4-yl]thien-2-ylcarbamate |
| 340 | 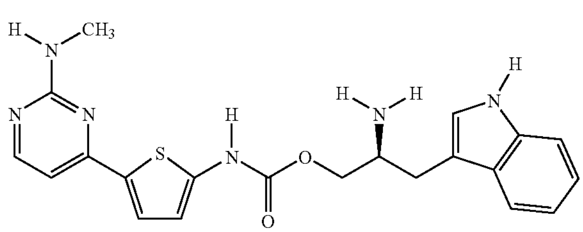 | 423 | (2S)-2-amino-3-(1H-indol-3-yl)propyl 5-[2-(methylamino)pyrimidin-4-yl]thien-2-ylcarbamate |

TABLE 6-continued

| No. | Structure | MH+ | Name |
|---|---|---|---|
| 341 | 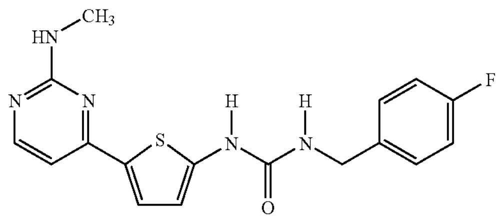 | 358 | N-(4-fluorobenzyl)-N'-{5-[2-(methylamino)pyrimidin-4-yl]thien-2-yl}urea |
| 342 | 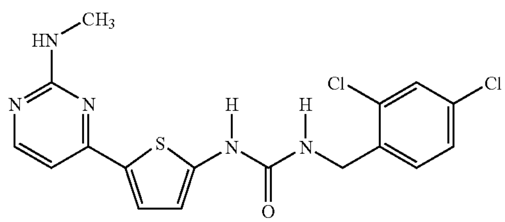 | 408 | N-(2,4-dichlorobenzyl)-N'-{5-[2-(methylamino)pyrimidin-4-yl}thien-2-yl}urea |
| 343 | 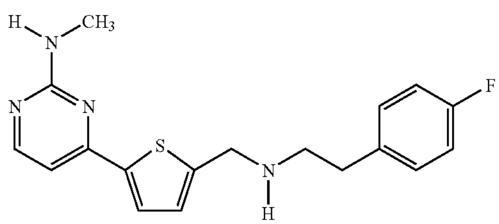 | 343 | N-[5-({[2-(4-fluorophenyl)ethyl]amino}methyl)thien-2-yl]-N-methylpyrimidin-2-amine |
| 344 | 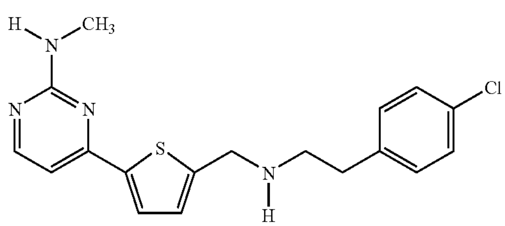 | 359 | 5-[5-({[2-(4-chlorophenyl)ethyl]amino}methyl)thien-2-yl]-N-methylpyrimidin-2-amine |
| 345 | 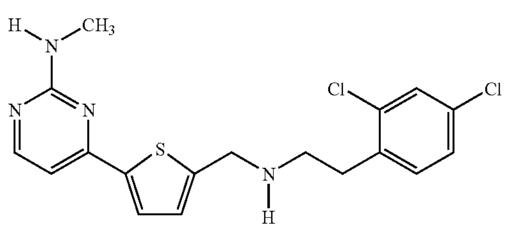 | 393 | 4-[5-({[2-(2,4-dichlorophenyl)ethyl]amino}methyl)thien-2-yl]-N-methylpyrimidin-2-amine |
| 346 | 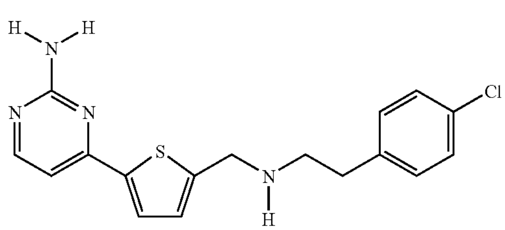 | 345 | 4-[5-({[2-(4-chlorophenyl)ethyl]amino}methyl)thien-2-yl]pyrimidin-2-amine |

TABLE 6-continued

| No. | Structure | MH+ | Name |
|---|---|---|---|
| 347 | 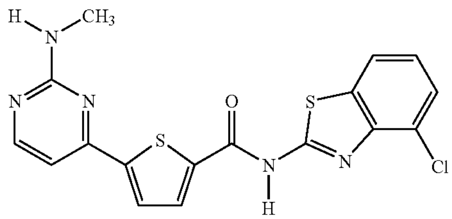 | 388, 390 | 4-chloro-N-({5-[2-(methylamino)pyrimidin-4-yl]thien-2-yl}methyl)-1,3-benzothiazol-2-amine |
| 348 | 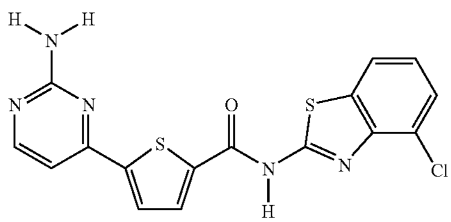 | 374, 376 | N-{[5-(2-aminopyrimidin-4-yl)thien-2-yl]methyl}-4-chloro-1,3-benzothiazol-2-amine |
| 349 | 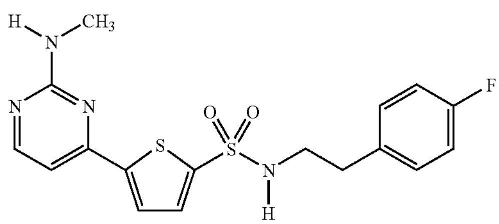 | 393 | N-[2-(4-fluorophenyl)ethyl]-5-[2-(methylamino)pyrimidin-4-yl]thiophene-2-sulfonamide |
| 350 | 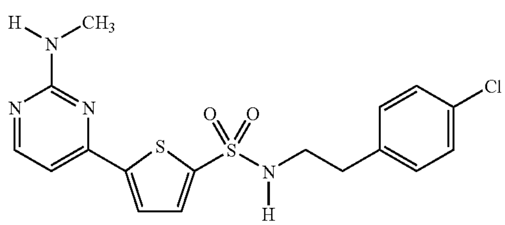 | 409 | N-[2-(4-chlorophenyl)ethyl]-5-[2-(methylamino)pyrimidin-4-yl]thiophene-2-sulfonamide |
| 351 | 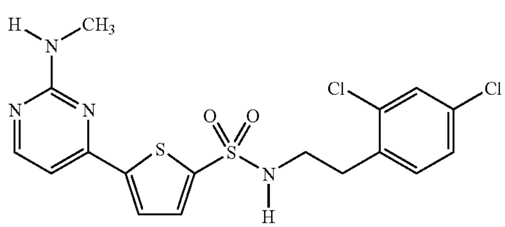 | 443 | N-[2-(2,4-dichlorophenyl)ethyl]-5-[2-(methylamino)pyrimidin-4-yl]thiophene-2-sulfonamide |
| 352 | 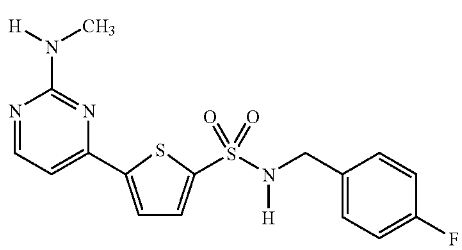 | 379 | N-(4-fluorobenzyl)-5-[2-(methylamino)pyrimidin-4-yl]thiophene-2-sulfonamide |

TABLE 6-continued

| No. | Structure | MH+ | Name |
|---|---|---|---|
| 353 | 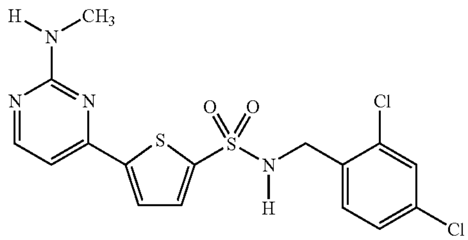 | 429 | N-(2,4-dichlorobenzyl)-5-[2-(methylamino)pyrimidin-4-yl]thiophene-2-sulfonamide |
| 354 | 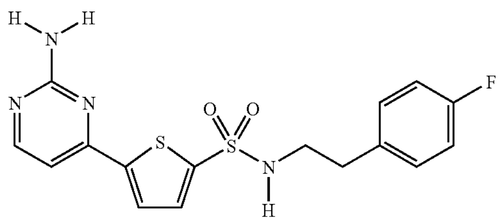 | 379 | 5-(2-aminopyrimidin-4-yl)-N-[2-(4-fluorophenyl)ethyl]thiophene-2-sulfonamide |
| 355 | 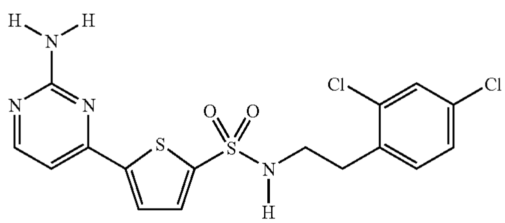 | 429 | 5-(2-aminopyrimidin-4-yl)-N-[2-(2,4-dichlorophenyl)ethyl]thiophene-2-sulfonamide |
| 356 | 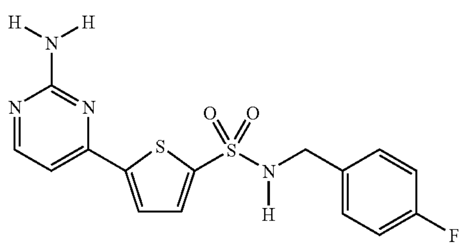 | 365 | 5-(2-aminopyrimidin-4-yl)-N-(4-fluorobenzyl)thiophene-2-sulfonamide |
| 357 | 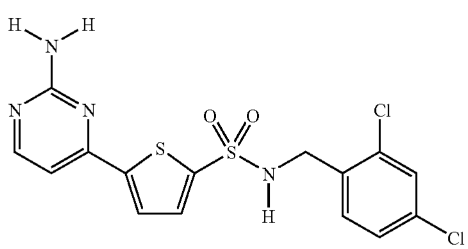 | 415 | 5-(2-aminopyrimidin-4-yl)-N-(2,4-dichlorobenzyl)thiophene-2-sulfonamide |
| 358 | 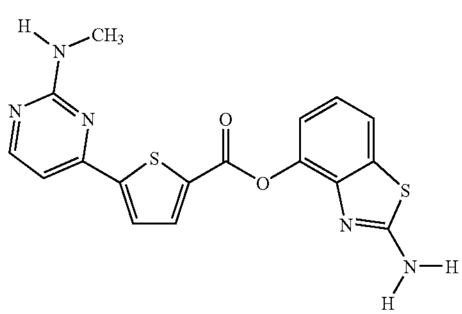 | 384 | 2-amino-1,3-benzothiazol-4-yl 5-[2-(methylamino)pyrimidin-4-yl]thiophene-2-carboxylate |

TABLE 6-continued

| No. | Structure | MH+ | Name |
|---|---|---|---|
| 359 | 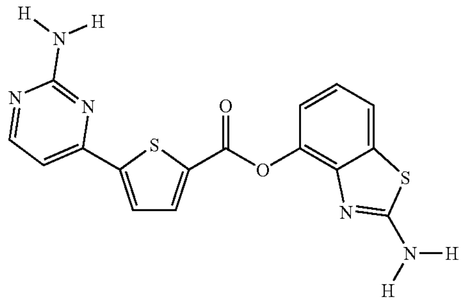 | 370 | 2-amino-1,3-benzothiazol-4-yl 5-(2-aminopyrimidin-4-yl)thiophene-2-carboxylate |
| 360 | 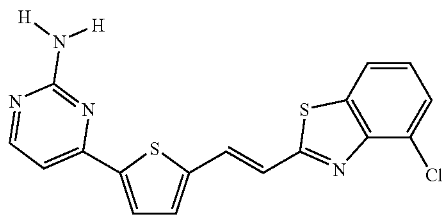 | 371<br>373 | 4-{5-[(E)-2-(4-chloro-1,3-benzothiazol-2-yl)vinyl]thien-2-yl}pyrimidin-2-amine |
| 361 | 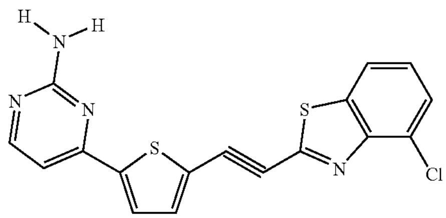 | 369<br>371 | 4-{5-[(4-chloro-1,3-benzothiazol-2-yl)ethynyl]thien-2-yl}pyrimidin-2-amine |
| 362 | 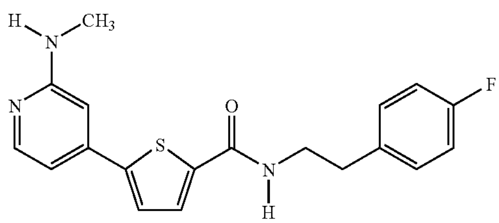 | 356 | N-[2-(4-fluorophenyl)ethyl]-5-[2-(methylamino)pyridin-4-yl]thiophene-2-carboxamide |
| 363 | 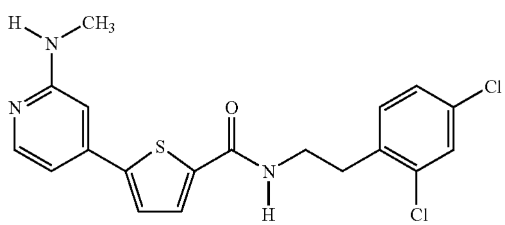 | 407 | N-[2-(2,4-dichlorophenyl)ethyl]-5-[2-(methylamino)pyridin-4-yl]thiophene-2-carboxamide |
| 364 | 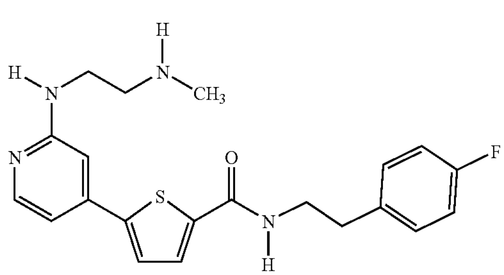 | 399 | N-[2-(4-fluorophenyl)ethyl]-5-(2-{[2-(methylamino)ethyl]amino}pyridin-4-yl)thiophene-2-carboxamide |

TABLE 6-continued

| No. | Structure | MH+ | Name |
|---|---|---|---|
| 365 | 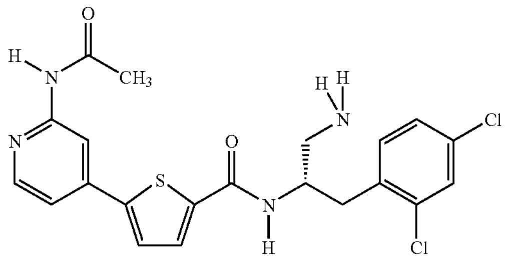 | 463, 465 | 5-[2-(acetylamino)pyrimidin-4-yl]-N-[(1S)-2-amino-1-(2,4-dichlorophenyl)ethyl]thiophene-2-carboxamide |
| 366 | 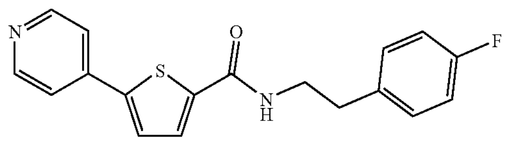 | 327 | N-[2-(4-fluorophenyl)ethyl]-5-pyridin-4-ylthiophene-2-carboxamide |
| 367 | 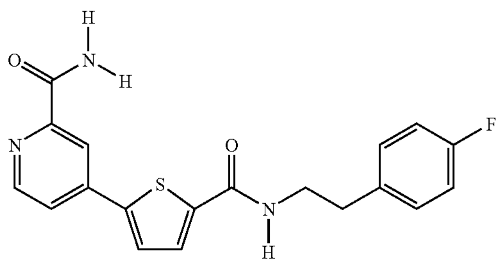 | 370 | 4-[5-({[2-(4-fluorophenyl)ethyl]amino}carbonyl)thien-2-yl]pyridine-2-carboxamide |
| 368 | 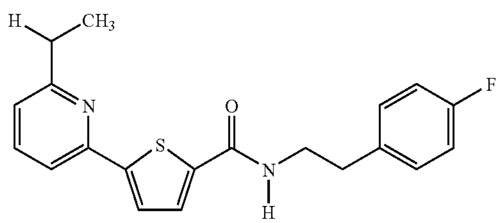 | 356 | N-[2-(4-fluorophenyl)ethyl]-5-[6-(methylamino)pyridin-2-yl]thiophene-2-carboxamide |
| 369 | 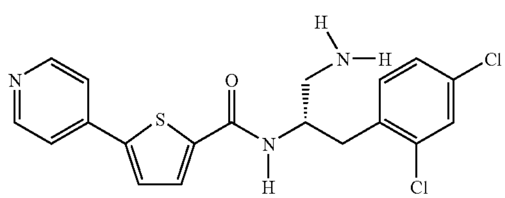 | 406, 408 | N-[(1S)-2-amino-1-(2,4-dichlorobenzyl)ethyl]-5-pyridin-4-ylthiophene-2-carboxamide |
| 370 | 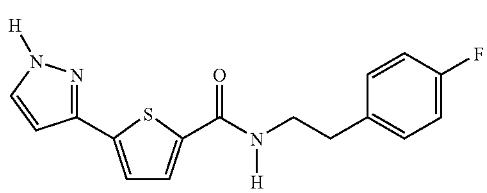 | 316 | N-[2-(4-fluorphenyl)ethyl]-5-(1H-pyrazol-3-yl)thiophene-2-carboxamide |
| 371 | 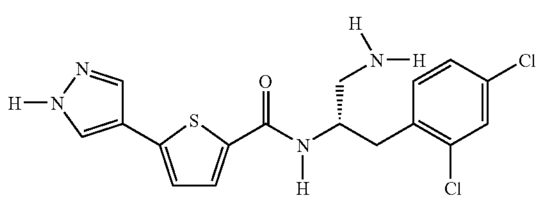 | 395, 397 | N-[(1S)-2-amino-1-(2,4-dichlorobenzyl)ethyl]-5-(1H-pyrazol-4-yl)thiophene-2-carboxamide |

TABLE 6-continued

| No. | Structure | MH+ | Name |
|---|---|---|---|
| 372 | 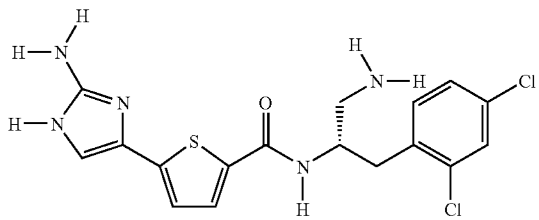 | 410<br>412 | N-[(1S)-2-amino-1-(2,4-dichlorobenzyl)ethyl]-5-(2-amino-1H-imidazol-4-yl)thiophene-2-carboxamide |
| 373 | 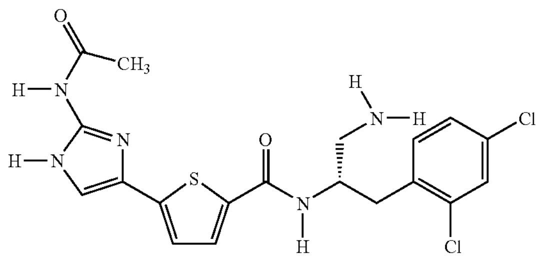 | 452<br>454 | 5-[2-(acetylamino)-1H-imidazol-4-yl]-N-[(1S)-2-amino-1-(2,4-dichlorobenzyl)ethyl]thiophene-2-carboxamide |
| 374 | 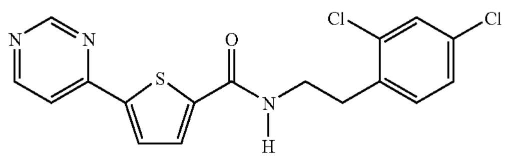 | 378<br>380 | N-[2-(2,4-dichlorophenyl)ethyl]-5-pyrimidin-4-ylthiophene-2-carboxamide |

Example 22

Akt3 kinase activity assays

Akt3 kinase activity was measured using either a [γ$^{33}$P]-ATP-based radiometric assay or an antibody-based, time-resolved fluorescence assay, which measure the level of phosphorylation of a biotin-labeled peptide in the presence of Akt3 kinase. The reagents used in these assays, and the procedures for performing the assays, are described below.

The following reagents were used in the assays:
Recombinant human Akt3: Histag full length Akt3 protein was expressed in insect cells and purified on Ni affinity resin.
Biotin-peptide substrate: Biotin-Gly-Gly-Gly-Gly-Arg-Pro-Arg-Ala-Ala-Thr-Phe-NH$_2$ (American Peptide Company, Sunnyvale, Calif.); SEQ ID NO:2
Affinity purified, rabbit anti-phospho-peptide antibody
DELFIA Eu-N1 labeled anti-rabbit antibody (PerkinElmer, Foster City, Calif.)
DELFIA Enhancement Solution (PerkinElmer, Foster City, Calif.)
[γ$^{33}$P]-ATP (PerkinElmer, Foster City, Calif.)
Assay buffer: (50 mM Tris-HCl (pH 7.5), 10 mM MgCl$_2$, 5 mM MnCl$_2$, 5 mM BGP, 2 mM DTT, and 0.01% BSA)

Time Resolved Fluorescence Assay

Test compounds were diluted in DMSO to 50 times the final assay concentration. 2 µl of each diluted test compound were then transferred to a 96-well plate and diluted with freshly prepared assay buffer to a final volume of 25 µl. 50 µl assay buffer comprising, 3 nM Akt3 enzyme and 1 µM biotin-peptide substrate, were then added to the diluted test compounds. The reaction was started by the addition of 25 µl of 800 nM ATP in assay buffer, resulting in final concentrations of 1.5 nM enzyme, 0.5 µM biotin-peptide substrate, and 200 nM ATP.

The reactions were allowed to proceed for 60 minute then stopped by the addition of EDTA to a final concentration of 30 mM. 100 ill of each reaction was transferred to a black 96-well Neutravidin plate (Pierce Biotechnology, Rockford, Ill.). The plates were washed after 1 hour, and anti-phospho-peptide primary antibody was added. After a 1 hour incubation, the plates were again washed, followed by the addition of DELFIA Eu-N1-labeled anti-rabbit antibody for 1 hour. A final wash was followed by the addition of 100 µl DELFIA Enhancement Solution (PerkinElmer, Foster City, Calif.), accompanied by 3-5 minutes of shaking. Time resolved fluorescence was then measured using a Wallac Victor 2 instrument (PerkinElmer).

[γ$^{33}$P]-ATP-based Radiometric Assay

Radiometric assays were performed using conditions similar to those described for the time resolved fluorescence assay, except that [γ$^{33}$P]-ATP was added at the start of each reaction to a final concentration of 5 µCi/ml. The reactions were stopped by the addition of EDTA and 100 µl of each reaction was transferred to 96-well, streptavidin-coated Flashplates (PerkinElmer), to capture the biotin-peptide substrate. After 1 hour, the plates were washed, sealed, and the amount of incorporated $^{33}$P was determined using a Wallac MicroBeta Trilux plate counter.

Compounds of the invention inhibit CDC7, Akt and/or PKA. To test the inhibitory properties, the compounds are assayed as outlined in the preceding example for Akt, Example 23 for PKA and Example 24 or 25 for CDC7. One measure of inhibition is IC$_{50}$, defined as the concentration of the composition at which the activity of the kinase, either CDC7, Akt and/or PKA, is decreased by fifty percent. Preferred compounds have $IC_{50}$ values of less than about 1 mM, with preferred embodiments having $IC_{50}$ values of less than about 25 µM, with particularly preferred embodiments having $IC_{50}$ values of less than about 1000 nM, and with the most preferred embodiments having $IC_{50}$ values of less than about 100 nM.

Example 23

PKA Activity Assays

The compounds are tested in cell-free kinase assays using commercially available PKA (Upstate #14-440) at a final enzyme concentration of 0.1 nM and a biotinylated substrate for PKA (Upstate #12-394) at a final concentration of 0.5 µM in a buffer containing 30 mM Tris-HCl pH 7.5, 30 mM $MgCl_2$, 1.4 mM DTT, 7 mM EGTA, 25 mM beta glycerol phosphate, and 0.035% BSA. The final reaction volume is 150 µl, with a final DMSO concentration of 1%.

The reactions are made 1 µM in unlabeled ATP and 1.6 nM in $\gamma[^{33}P]$-ATP, then are incubated for one hour at room temperature. The phosphorylated substrate is captured onto a white, streptavidin coated, 96-well plate for one hour, which is then washed four times. Scintillation fluid is added and the plates are sealed and counted using a scintillation counter.

As stated above, the compounds of the present invention may also inhibit PKA. To test the inhibitory properties, the compounds are tested as outlined in the preceding example. Preferred compounds have $IC_{50}$ values of less than about 1 mM, with preferred embodiments having $IC_{50}$ values of less than about 25 µM, with particularly preferred embodiments having $IC_{50}$ values of less than about 1000 nM, and with the most preferred embodiments having $IC_{50}$ values of less than about 100 nM.

Example 24

Assay to Screen for CDC7 Inhibitors

The following reagents were used directly in the assay or used to prepare the solutions described, below:
CDC7/DBF4 enzyme,
Biotin-MCM2 substrate,
1 M Hepes pH 7.2-7.5,
1 M $MgCl_2$,
1 M DTT,
1 M PBS,
100 mg/ml Leupeptin,
10 mg/ml (1%) BSA in PBS,
100 mM ATP,
1 M Tris pH 7.5,
4 M NaCl,
0.5 M EDTA,
Tween 20,
Rx-MCM2 pSer108 BL1539 antibody (1 mg/ml) (1:4000 Dilution) (Bethyl, A300-094A),
AlphaScreen Protein A 500 Point Detection Kit (PerkinElmer, 6760671C),
White Opaque 384-well Microplates (PerkinElmer, 6007290),
Buffer (10 mg/ml (1%) BSA/distilled $H_2O$),
20% Tween 20,
Assay Buffer (50 mM Hepes, 10 mM $MgCl_2$, 1 mM DTT, 10 ug/mL Leupeptin, and 0.2 mg/mL BSA), and
Detection Buffer (25 mM Tris, 400 mM NaCl, 100 mM EDTA, 0.3% BSA in PBS, 0.05% Tween 20).

40× stock solutions of the compounds to be tested for CDC7 inhibitor activity and stock solutions of staurosporine, a naturally occurring kinase inhibitor, were prepared in buffer for use in the assay. Various known concentrations of staurosporine were prepared.

0.5 µl of each stock solution of test compound was transferred to "Test wells" of a 384-well assay plate. 1 µl of each staurosporine solution was similarly transferred to the "Staurosporine-control wells."

5 µl of a solution of 0.5 M EDTA and 4% DMSO was transferred to "Background wells." 1 µl of a solution containing 30% DMSO was transferred to the "Total wells."

10 µL of a solution containing the CDC7/DBF4 enzyme (0.2 µg/ml) and biotin-MCM2 substrate (0.125 µg/ml) was transferred to each well. 10 µL of 0.5 µM ATP was then transferred to each well to start the reactions. The plates were then incubated for 1 hour on the plate shaker.

Detection Mixture was freshly prepared and maintained under low light conditions by diluting streptavidin-coated donor beads and protein A conjugated acceptor Beads to 54 µg/ml in Detection Buffer along with pSer108-specific antibody at a 1:4,000 dilution. At the end of the 1 hour incubation, 10 µL of Detection Mixture was transferred to each well, under low light conditions, to stop the reaction.

The plates were further incubated in the dark for 4 hours, then read with a Perkin Elmer Fusion Instrument to determine the relative amounts of phosphorylated biotin-MCM2 substrate resulting from CDC7/DBF4 enzyme activity. The amount of inhibition produced by the various test compounds was compared to the amount of inhibition produced by the various, known concentrations, of staurosporine, to determine the relative inhibitory activity of each test compound. Background signal produced by small amounts of DMSO (present in the reagents supplied in the detection kit) was determined based on the "Background wells," described above, and substacted, accordingly.

In this manner, the amount of CDC7 kinase inhibition by each of the compounds tested was determined.

Example 25

Assay to Screen for CDC7 Inhibitors

The following reagents were used directly in the assay or used to prepare the solutions described, below:
CDC7/DBF4 enzyme,
Biotin-MCM2 substrate,
1 M Hepes pH 7.2-7.5,
1 M $MgCl_2$,
1 M DTT,
1 M PBS,
100 mg/ml Leupeptin,
10 mg/ml (1%) BSA in PBS,
100 mM ATP,
1 M Tris pH 7.5,
4 M NaCl,
0.5 M EDTA,
Tween 20,
Rx-MCM2 pSer108 BL1539 antibody (1 mg/ml) (1:4000 Dilution) (Bethyl, A300-094A),
AlphaScreen Protein A 500 Point Detection Kit (PerkinElmer, 6760671C), White Opaque 384-well Microplates (PerkinElmer, 6007290), Buffer (10 mg/ml (1%) BSA/distilled H$_2$O), 20% Tween 20, Assay Buffer (50 mM Hepes, 10 mM MgCl$_2$, 1 mM DTT, 10 ug/mL Leupeptin, and 0.2 mg/mL BSA), and Detection Buffer (25 mM Tris, 400 mM NaCl, 100 mM EDTA, 0.3% BSA in PBS, 0.05% Tween 20).

40× stock solutions of the compounds to be tested for CDC7 inhibitor activity and stock solutions of staurosporine, a naturally occurring kinase inhibitor, were prepared in buffer for use in the assay. Various known concentrations of staurosporine were prepared.

0.5 μl of each stock solution of test compound was transferred to "Test wells" of a 384-well assay plate. 1 μl of each staurosporine solution was similarly transferred to the "Staurosporine-control wells."

5 μl of a solution of 0.5 M EDTA and 4% DMSO was transferred to "Background wells." 1 μl of a solution containing 30% DMSO was transferred to the "Total wells."

10 μL of a solution containing the CDC7/DBF4 enzyme (0.2 μg/ml) and biotin-MCM2 substrate (0.125 μg/ml) was transferred to each well. 10 μL of 0.5 μM ATP was then transferred to each well to start the reactions. The plates were then incubated for 1 hour on the plate shaker.

Detection Mixture was freshly prepared and maintained under low light conditions by diluting streptavidin-coated donor beads and protein A conjugated acceptor Beads to 54 μg/ml in Detection Buffer along with a phosphoylated threonine-specific antibody (Cell Signalling, 9381) at a 1:4,000 dilution. At the end of the 1 hour incubation, 10 μL of Detection Mixture was transferred to each well, under low light conditions, to stop the reaction.

The plates were further incubated in the dark for 4 hours, then read with a Perkin Elmer Fusion Instrument to determine the relative amounts of phosphorylated biotin-MCM2 substrate resulting from CDC7/DBF4 enzyme activity. The amount of inhibition produced by the various test compounds was compared to the amount of inhibition produced by the various, known concentrations, of staurosporine, to determine the relative inhibitory activity of each test compound. Background signal produced by small amounts of DMSO (present in the reagents supplied in the detection kit) was determined based on the "Background wells," described above, and substacted, accordingly.

In this manner, the amount of CDC7 kinase inhibition by each of the compounds tested was determined.

As stated above, the compounds of the present invention may also inhibit CDC7. To test the inhibitory properties, the compounds are tested as outlined in the two preceding examples. Preferred compounds have IC$_{50}$ values of less than about 1 mM, with preferred embodiments having IC$_{50}$ values of less than about 25 μM, with particularly preferred embodiments having IC$_{50}$ values of less than about 1000 nM, and with the most preferred embodiments having IC$_{50}$ values of less than about 100 nM.

From the foregoing description, various modifications and changes in the composition and method will occur to those skilled in the art. All such modifications coming within the scope of the appended claims are intended to be included therein.

What is claimed is:

1. A compound represented by the formula

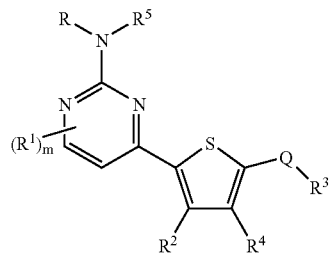

wherein:
R is selected from the group consisting of:
   a) hydrogen,
   b) hydroxy,
   c) optionally substituted alkyl substituted with a substituent selected from the group
      consisting of hydroxy, cycloalkyl, substituted cycloalkyl, phenyl, heterocycle,
      substituted heterocycle, heteroaryl, substituted heteroaryl, amino, substituted
      amino, carboxyl, and 4-chlorophenyl,
   d) cycloalkyl,
   e) substituted cycloalkyl,
   f) —SO$_2$R$^7$ where R$^7$ is C$_1$ to C$_5$ alkyl or substituted alkyl,
   g) alkoxy,
   h) carboxyl,
   i) carboxyl ester,
   j) nitro,
   k) aryl,
   l) substituted aryl,
   m) heteroaryl,
   n) substituted heteroaryl,
   o) acylamino, and
   p) acyl;
R$^5$ is selected from the group consisting of:
   a) hydrogen, and
   b) alkyl
each R$^5$ is independently selected from the group consisting of:
   a) halo,
   b) cyano,
   c) nitro,
   d) hydroxy,
   e) thiol,
   f) amino,
   g) substituted amino,
   h) alkoxy,
   i) substituted alkoxy,
   j) aryloxy,
   k) substituted aryloxy,
   l) heteroaryloxy,
   m) substituted heteroaryloxy,
   n) alkylthio,
   o) substituted alkylthio,
   p) —C(=O)NR$^8$R$^8$ wherein each R$^8$ is independently selected from the group consisting of hydrogen, alkyl, substituted alkyl, aryl, substituted aryl, heteroaryl, substituted heteroaryl, heterocyclyl, substituted heterocyclyl, or each R$^8$ can be optionally joined together with the nitrogen atom pendent thereto to form a heterocyclyl or substituted heterocyclyl, q) —NHC(=O)—$R^9$, wherein $R^9$ is selected from the group consisting of hydrogen, alkyl, substituted alkyl, aryl, substituted aryl, heteroaryl, substituted heteroaryl, heterocyclyl, substituted heterocyclyl,
r) aryl or heteroaryl, each of which may be optionally substituted with optionally substituted alkyl or aryl,
s) heterocyclyl, each of which may be optionally substituted with optionally substituted alkyl or aryl, and
t) $C_1$ to $C_5$ alkyl optionally substituted with 1 to 3 substituents selected from halo, hydroxy, amino, aryl, $C_1$ to $C_5$ alkyl monosubstituted amino, and $C_1$ to $C_5$ alkyl disubstituted amino wherein each alkyl group is independent from the other alkyl group;

m is an integer equal to 0, 1 or 2;

$R^2$ and $R^4$ are independently selected from the group consisting of:
  a) hydrogen,
  b) cycloalkyl,
  c) substituted cycloalkyl,
  d) heterocyclyl,
  e) substituted heterocyclyl,
  f) aryl,
  g) substituted aryl,
  h) heteroaryl,
  i) substituted heteroaryl,
  j) $C_1$ to $C_5$ alkyl optionally substituted with 1 to 3 substituents selected from halo, hydroxy, amino, $C_1$ to $C_5$ alkyl monosubstituted amino, and $C_1$ to $C_5$ alkyl disubstituted amino wherein each alkyl group is independent from the other alkyl group,
  k) optionally substituted $C_2$ to $C_5$ alkenyl,
  l) optionally substituted $C_2$ to $C_5$ alkynyl,
  m) optionally substituted $C_1$ to $C_5$ alkoxy,
  n) hydroxy,
  o) amino,
  p) $C_1$ to $C_5$ alkyl monosubstituted amino, and
  q) $C_1$ to $C_5$ alkyl disubstituted amino wherein each alkyl group is independent from the other alkyl group,
  with the proviso that when one of $R^2$ or $R^4$ is cycloalkyl, substituted cycloalkyl, heterocyclyl, substituted heterocyclyl, aryl substituted aryl, heteroaryl, substituted heteroaryl, then the other of $R^2$ or $R^4$ is hydrogen;

$R^3$ is selected from the group consisting of:
  a) hydrogen,
  b) $C_1$ to $C_5$ alkyl, and
  c) —($C_1$ to $C_5$ alkylene)$_p$-Z optionally substituted on the alkylene chain with 1 to 2 substituents selected from the group consisting of:
    i. $C_1$ to $C_5$ alkyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group,
    ii. $C_2$ to $C_5$ alkenyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group with the proviso that said hydroxy substitution is not pendent to a vinyl carbon atom of the substituted alkenyl,
    iii. $C_2$ to $C_5$ alkynyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group with the proviso that said hydroxyl substitution is not pendent to a acetylene carbon atom of the substituted alkynyl,
    iv. $C_3$ to $C_6$ cycloalkyl,
    v. $C_3$ to $C_6$ spirocycloalkyl,
    vi. carboxyl,
    vii. carboxyl esters,
    viii. halo,
    ix. hydroxy,
    x. $C_1$ to $C_5$ alkoxy,
    xi. amino,
    xii. $C_1$ to $C_5$ alkyl monosubstituted amino,
    xiii. $C_1$ to $C_5$ alkyl disubstituted amino,
    xiv. aryl, and
    xv. heterocyclyl;

Z is selected from the group consisting of:
  a) alkyl,
  b) substituted alkyl,
  c) alkylamino,
  d) alkoxy,
  e) substituted alkoxy,
  f) cycloalkyl,
  g) heterocyclyl,
  h) substituted heterocyclyl,
  i) aryl,
  j) substituted aryl,
  k) heteroaryl,
  l) substituted heteroaryl,
  m) amino, and
  n) dialkylamino;

p is an integer selected from zero or one;

Q is selected from the group consisting of:
  a) —$CH_2NR^6$—,
  b) —$NR^6C(X{-})$—,
  c) —$NR^6C(X{-})O$—,
  d) —$NR^6C(X{-})NR^6$—,
  e) —$OC(X{-})NR^6$—,
  f) —$C(X')O$—,
  g) —$CR^6CR^6$—,
  h) —C≡C—, and
  i) —$S(O)NR^6$—,
where X' is selected from the group consisting of oxygen and sulfur and each $R^6$ is independently selected from the group consisting of hydrogen and $C_1$-$C_3$ alkyl and $C_1$-$C_3$ substituted alkyl,
or $R^6$ together with Q and the carbon atom attached thereto and together with $R^4$ and the carbon atom attached thereto join to form a heterocyclyl or substituted heterocyclyl,
or pharmaceutically acceptable salts, esters or prodrugs thereof.

2. The compound of claim 1, wherein R is selected from the group consisting of hydrogen, alkyl, substituted alkyl, cycloalkyl, substituted cycloalkyl, acylamino, heteroaryl, nitro, aryl, and —$SO_2R^7$ wherein $R^7$ is selected from the group consisting of hydrogen, methyl, carboxyl ester, and acyl.

3. The compound of claim 2, wherein R is selected from the group consisting of:
  2-(methylamino)eth-1-yl,
  2-(N-methylpiperazin-N'-yl)eth-1-yl,
  2-(N-methylpyrrol-2-yl)eth-1-yl,
  2-(N-morpholino)eth-1-yl,
  2-(piperidin-N-yl)eth-1-yl,
  2-(pyridin-2-yl)eth-1-yl,
  2-(pyridin-3-yl)eth-1-yl,
  2-(pyridin-4-yl)eth-1-yl, 2-(S)-phenylcyclopropyl,
2-aminoeth-1-yl,
2-hydroxyeth-1-yl,
2-phenyleth-1-yl,
2-spirocyclopropyl-2-(4-chlorophenyl)eth-1-yl,
3-(imidazol-N-yl)prop-1-yl,
3-(N-methylpiperazin-N'-yl)prop-1-yl,
3-(N-morpholino)prop-1-yl,
3-aminobut-1-yl,
3-aminoprop-1-yl,
5-carboxy-4-(R,S)-aminopent-1-yl, aminocarbonyl,
benzyl,
benzylaminocarbonyl,
butyl,
cyclobutyl,
cyclopentyl,
cyclopropyl,
cyclopropylmethyl,
dimethylaminocarbonyl,
ethylaminocarbonyl,
hydrogen,
ethyl,
methyl,
methoxycarbonyl,
methylaminocarbonyl,
methylcarbonyl,
neopentyl,
nitro,
phenyl,
phenylaminocarbonyl,
propyl,
propylaminocarbonyl,
pyridin-2-ylmethyl,
pyridin-3-ylmethyl,
pyridin-4-yl,
pyridin-4-ylmethyl, and
$SO_2CH_3$.

4. The compound of claim 1, wherein $R^5$ is hydrogen or methyl.

5. The compound of claim 1, wherein $R^1$ is selected from the group consisting of $C_{1-5}$ alkyl, —C(=O)$NR^8R^8$, and —NHC(=O)—$R^9$.

6. The compound of claim 5, wherein $R^2$ is selected from the group consisting of methyl, aminocarbonyl, and methylcarbonylamino.

7. The compound of claim 1, wherein $R^2$ and $R^4$ are independently selected from the group consisting of hydrogen, hydroxy, amin, and $C_1$ to $C_5$ alkoxy optionally substituted with aryl or amino.

8. The compound of claim 7, wherein $R^2$ and $R^4$ are selected from the group consisting of hydrogen, hydroxy, amino, methoxy, benzyloxy, and 2-aminoethoxy.

9. The compound of claim 1, wherein $R^3$ is hydrogen.

10. The compound of claim 1, where $R^3$ is —($C_1$ to $C_5$ alkylene)$_p$-Z wherein p is 0 or 1.

11. The compound of claim 10, wherein p is 1 and the alkylene chain is unsubstituted or substituted with a substituent selected from the group consisting of $C_1$ to $C_5$ alkyl, $C_1$ to $C_5$ alkyl substituted with hydroxy, amino, monosubstituted amino, or disubstituted amino, $C_2$ to $C_5$ alkenyl, $C_2$ to $C_5$ alkynyl, $C_3$ to $C_6$ spirocycloalkyl, carboxyl, carboxyl esters, hydroxy, amino, heterocyclyl and aryl.

12. The compound of claim 10, wherein the alkylene chain is unsubstituted or substituted with a substituent selected from the group consisting of:
   2-aminoethyl,
   2-dimethylaminoethyl,
   2-hydroxyethyl,
   2-methylaminoethyl,
   3-methylaminopropyl,
   amino,
   aminomethyl,
   carboxyl,
   dimethylamino,
   dimethylaminomethyl,
   ethyl,
   methyl,
   methylcarboxyl,
   morpholino,
   hydroxymethyl,
   phenyl,
   prop-2-enyl,
   prop-2-ynyl,
   propyl,
   spirocyclobutyl, and
   spirocyclopropyl.

13. The compound of claim 10, wherein Z is selected from the group consisting of cycloalkyl, substituted cycloalkyl, heterocyclyl, substituted heterocyclyl, aryl, substituted aryl, heteroaryl, substituted heteroaryl, alkyl, amino, alkylamino, and dialkylamino.

14. The compound of claim 1, wherein $R^3$ is selected from the group consisting of:
   (2-fluoro-4-methoxyphenyl)eth-1-yl,
   (2-fluoro-4-methylphenyl)eth-1-yl,
   [1-(4-chlorophenyl)cyclobut-1-yl]methyl,
   [1-(4-chlorophenyl)cycloprop-1-yl]methyl,
   1-(1-aminoethyl)-4-chloro-1H-benzoimidazol-2-yl,
   1-(2-aminoethyl)-1H-benzoimidazol-2-yl,
   1-(2-aminoethyl)-4-chloro-1H-benzimidazol-2-yl,
   1-(2-aminoethyl)-4-methoxy-1H-benzimidazol-2-yl,
   1-(2-aminoethyl)-4-phenyl-1H-benzimidazol-2-yl,
   1-(2-aminoethyl)-7-chloro-1H-benzimidazol-2-yl,
   1-(2-methylpropyl)-4-chloro-1H-benzimidazol-2-yl,
   1-(3,3-dimethylbutyl)-4-chloro-1H-benzimidazol-2-yl,
   1-(3-aminopropyl)-4-chloro-1H-benzimidazol-2-yl,
   1-(4-chlorophenyl)-3-(N-methylamino)prop-1-yl,
   1-(4-chlorophenyl)-3-(N,N-dimethylamino)prop-1-yl,
   1-(4-chlorophenyl)-3-hydroxyprop-1-yl,
   1-(aminomethyl)-2-(2,4-dichlorophenyl)eth-1-yl,
   1-(R)-1-(2,4-dichlorobenzyl)-4-(dimethylamino)but-2-yl,
   1-(R)-1-(2,4-dichlorobenzyl)-4-(methylamino)but-2-yl,
   1-(R)-1-(2,4-dichlorobenzyl)-4-aminobut-2-yl,
   1-(R)-2-(2,4-dichlorophenyl)-1-methyleth-1-yl,
   1-(R)-4-fluorophenyl)eth-1-yl,
   1-(R)-amino-1-(2,4-dichlorobenzyl)eth-1-yl,
   1-(R)-aminomethyl-2-(2,4-dichlorophenyl)eth-1-yl,
   1-(R)-hydroxymethyl-2-(4-chlorophenyl)eth-1-yl,
   1-(R,S)-carboxyl-2-(2,4-dichlorophenyl)eth-1-yl,
   1-(R,S)-hydroxymethyl-1-phenylmethyl,
   1-(R,S)-hydroxymethyl-2-(2,4-dichlorophenyl)eth-1-yl,
   1-(R,S)-hydroxymethyl-2-phenyleth-1-yl,
   1-(R,S)-methylcarboxyl-2-(2,4-dichlorophenyl)eth-1-yl,
   1-(R,S)-phenyl-2-phenyleth-1-yl,
   1-(S)-1-(2,4-dichlorobenzyl)-4-(dimethylamino)but-2-yl,
   1-(S)-1-(2,4-dichlorobenzyl)-4-(methylamino)but-2-yl,
   1-(S)-1-(2,4-dichlorobenzyl)-4-amino-but-2-yl,
   1-(S)-amino-1-(2,4-dichlorobenzyl)eth-1-yl,
   1-(S)-aminomethyl-2-(1H-indol-3y1)eth-1-yl,
   1-(S)-aminomethyl-2-(2,4-dichlorophenyl)eth-1-yl,
   1-(S)-aminomethyl-2-(indol-3-yl)eth-1-yl,
   1-(S)-dimethylamino-2-(2,4-dichlorophenyl)eth-1-yl,
   1-(S)-dimethylaminomethyl-2-(2,4-dichlorophenyl)eth-1-yl, 1,2,3,4-tetrahydronaphthalen-1-yl,
1-aminoethyl-4-methoxybenzoimidazol-2-yl,
1-aminomethyl-2-(2,4-dichlorophenyl)eth-1-yl,
1-aminomethyl-2-(4-chlorophenyl)eth-1-yl,
1-aminomethyl-4-chloro-1H-benzimidazole-2-yl,
1-benzylpyrrolidin-3-yl,
1-dimethylamino-3-(2,4-dichlorophenyl)prop-2-yl,
1-ethyl-4-chlorobenzoimidazol-2-yl,
1-hydroxymethyl-2-(2,4-dichlorophenyl)eth-1-yl,
1-hydroxymethyl-2-methylprop-1-yl,
1-isobutyl-4-chlorobenzoimidazol-2-yl,
1-methyl-2-hydroxyeth-1-yl,
1-methyl-4-chlorobenzoimidazol-2-yl,
1-methylbenzoimidazol-2-yl,
1-phenyl-1-(4-chlorophenyl)methyl,
1-phenyl-2-hydroxyeth-1-yl,
2-(2,4-dichlorophenyl)but-1-yl,
2-(2,4-dichlorophenyl)eth-1-yl,
2-(2,4-dichlorophenyl)pent-1-yl,
2-(2,4-dichlorophenyl)pent-4-eth-1-yl,
2-(2,4-dichlorophenyl)pent-4-yn-1-yl,
2-(2,4-dichlorophenyl)prop-1-yl,
2-(2,5-dimethoxyphenyl)eth-1-yl,
2-(2,6-dichlorophenyl)eth-1-yl,
2-(2-chlorophenyl)eth-1-yl,
2-(3,4-dichlorophenyl)eth-1-yl,
2-(3,4-dimethoxyphenyl)eth-1-yl,
2-(3-chlorophenyl)eth-1-yl,
2-(3-fluorophenyl)eth-1-yl,
2-(3-methoxyphenyl)eth-1-yl,
2-(4-aminophenyl)eth-1-yl,
2-(4-aminosulfonylphenyl)eth-1-yl,
2-(4-biphenyl)eth-1-yl,
2-(4-bromophenyl)eth-1-yl,
2-(4-chlorophenyl)eth-1-yl,
2-(4-ethoxyphenyl)eth-1-yl,
2-(4-ethylphenyl)eth-1-yl,
2-(4-fluorophenyl)eth-1-yl,
2-(4-methoxyphenyl)eth-1-yl,
2-(4-methylphenyl)eth-1-yl,
2-(4-phenoxyphenyl)eth-1-yl,
2-(N-methylpiperazin-N'-yl)eth-1-yl,
2-(N-methylpyrrol-2-yl)eth-1-yl,
2-(N-morpholino)eth-1-yl,
2-(piperidin-1-yl)eth-1-yl,
2-(piperidin-3-yl)eth-1-yl,
2-(pyridin-2-yl)eth-1-yl,
2-(pyridin-4-yl)eth-1-yl,
2-(R)-(N-morpholino)-2-phenyleth-1-yl,
2-(R)-amino-3-(indol-3-yl)prop.-1-yl,
2-(R)-hydroxyindan-1-yl,
2-(R)-methyl-2-phenyleth-1-yl,
2-(R,S)-amino-2-phenyleth-1-yl,
2-(R,S)-hydroxy-2-(4-chlorophenyl)eth-1-yl,
2-(R,S)-methyl-2-phenyleth-1-yl,
2-(S)-amino-3-(indol-3-yl)prop-1-yl,
2-(S)-methyl-2-phenyleth-1-yl,
2-(trifluoromethyl)-4-fluorophenylmethyl,
2,4-dichlorobenzyl,
2,4-dichlorophenylmethyl,
2,2-dimethyl-5-benzyltetrahydropyran-4-yl,
2,2-diphenyleth-1-yl,
2,4-dichlorobenzyl,
2,4-difluorobenzyl,
2,5-difluorobenzyl,
2-aminobenzothiazol-4-yl,
2-aminoeth-1-yl,
2-chlorobenzyl,
2-dimethylaminoeth-1-yl,
2-fluoro-4-chlorobenzyl,
2-fluoro-6-aminobenzyl,
2-methoxybenzyl,
2-methyl-4-chlorophenylmethyl,
2-methylbenzyl,
2-phenethyl,
2-phenylbenzyl,
2-piperidin-N-ylbenzyl,
3-(4-fluorophenyl)prop-1-yl,
3-(pyrrol-N-yl)prop-1-yl,
3,4-dichlorobenzyl,
3,5-dichlorobenzyl,
3,5-difluorobenzyl,
3-amino-i-(4-chlorophenyl)prop-1-yl,
3-bromobenzyl,
3-chlorobenzyl,
3-methoxybenzyl,
4-(2-chlorophenyl)thiazol-2-yl,
4-(3,4-difluorophenyl)thiazol-2-yl,
4-(3-chlorophenyl)thiazol-2-yl,
4-(4-methoxyphenyl)thiazol-2-yl,
4-(aminomethyl)benzothiazol-2-yl,
4-(pyridin-2-yl)thiazol-2-yl,
4-(pyridin-3-yl)thiazol-2-yl,
4-(trifluoromethoxy)-6-(aminomethyl)benzothiazol-2-yl,
4-(trifluoromethyl)-6-(aminomethyl)benzothiazol-2-yl,
4,6-dichlorobenzothiazol-2-yl,
4,6-difluorobenzothiazol-2-yl,
4-amino-2-(4-chlorophenyl)but-1-yl,
4-aminobenzyl,
4-aminosulfonylbenzyl,
4-bromo-6-(aminomethyl)benzothiazol-2-yl,
4-bromo-6-isopropyl-benzothiazol-2-yl,
4-bromobenzothiazol-2-yl,
4-bromobenzyl,
4-chloro-[2-(S)-2-(aminopropanoyl)aminomethyl]benzothiazol-2yl,
4-chloro-1,3-benzothiazol-2-yl,
4-chloro-5-methylcarboxyl-benzothiazol-2-yl,
4-chloro-6-({[2-(S)-2-amino-3-phenylpropanoyl]amino}methyl)benzolhiazol-2-yl,
4-chloro-6-(2-aminoethyl)benzothiazol-2-yl,
4-chloro-6-(2-nitroethyl)benzothiazol-2-yl,
4-chloro-6-(dimethylaminomethyl)benzothiazol-2-yl,
4-chloro-6-(methylaminomethyl)benzothiazol-2-yl,
4-chloro-6-(methylcarbonylaminomethyl)benzothiazol-2yl,
4-chloro-6-(trifluoromethoxy)benzothiazol-2-yl,
4-chloro-6-(trifluoromethyl)benzothiazol-2-yl,
4-chloro-6-[(2-amino)ethylaminocarbonyl]benzothiazol-2-yl,
4-chloro-6-{[(aminomethylcarbonyl)amino]methyl}benzothiaozl-2-yl,
4-chloro-6-aminomethylbenzothiazol-2-yl,
4-chloro-6-hydroxymethylbenzothiazol-2-yl,
4-chloro-6-methylaminomethylbenzothiazol-2-yl,
4-chloro-6-methyhhiazol-2-yl,
4-chloro-6-N-morpholinomethyl-benzothiazol-2-yl,
4-chloro-7-aminomethyl-benzothiazol-2-yl,
4-chloro-7-hydroxymethyl-benzothiazol-2-yl,
4-chlorobenzothiazol-2-yl,
4-chlorobenzoxazol-2-yl,
4-chlorobenzyl,
4-dimethylaminobenzyl,
4-fluorobenzyl, 4-fluorobenzothiazol-2-yl,
4-fluorobenzyl,
4-fluorophenyl,
4-fluorophenylmethyl,
4-hydroxy-2-(4-chlorophenyl)but-1-yl,
4-hydroxybenzothiazol-2-yl,
4-hydroxybenzothiazol-4-yl,
4-methoxy-6-(methylaminomethyl)benzothiazol-1-yl,
4-methoxybenzothiazol-2-yl,
4-methoxythiazol-2-yl,
4-methyl-6-aminomethyl-benzothiazol-2-yl,
4-methylbenzyl,
4-methylthiazol-2-yl,
4-phenylthiazol-2-yl,
5-(2-bromothiophen-5-yl)thiazol-2-yl,
5-(3-bromo-4-methoxyphenyl)thiazol-2-yl,
5-chlorobenzoimidazol-2-yl,
5-chlorobenzothiazol-2-yl,
6-aminomethyl-8-chloroquinolin-2-yl,
6-aminomethyl-benzothiazol-2-yl,
6-chlorobenzothiazol-2-yl,
6-fluorobenzothiazol-2-yl,
7-chlorobenzothiazol-2-yl,
benzoimidazol-2-yl,
benzothiazol-2-yl,
benzothiazol-6-yl,
benzothiophen-2-yl,
benzyl,
indan-1-yl,
naphthalen-1-ylmethyl,
pyridin-2-ylmethyl,
pyridin-3-ylmethyl,
pyridin-4-ylmethyl,
pyrimidin-3-yl,
pyrrolidin-3-yl,
quinolin-2-yl,
quinolin-3-yl,
quinolin-6-yl, and
thiophen-2-ylmethyl.

15. The compound of claim 1, wherein Q is selected from the group consisting of —C(O)NH—, —NH—C(O)—, —NH—C(O)NH—, —NHC(O)O—, —CH$_2$NH—, —C(O)N(CH$_2$CH$_2$NH$_2$)—, —C(O)N(CH$_3$)—, —C(O)O—, —CH═CH—, and —C≡C—.

16. The compound of claim 1, wherein R$^6$ together with Q and the carbon atom attached thereto and together with R$^4$ and the carbon atom attached thereto join to form a substituted heterocyclyl.

17. The compound of claim 16, wherein the substituted heterocyclyl is 5,6-dihydropyrimidin-4-one.

18. The compound of claim 1, wherein R$^6$ is hydrogen or C$_{1-3}$ alkyl optionally substituted with amino.

19. The compound of claim 5, wherein R$^1$ is selected from the group consisting of methyl, aminocarbonyl, and methylcarbonylamino.

20. A pharmaceutical composition comprising a compound of claim 1 or a mixture thereof and a pharmaceutically acceptable carrier and/or excipient.

21. A compound selected from the group consisting of:
3-(4-fluorophenyl)-N-{5-[2-(methylamino)pyrimidin-4-yl]thien-2-yl}propanamide;
3-(2,4-dichlorophenyl)-N-{5-[2-(methylamino)pyrimidin-4-yl]thien-2-yl}propanamide;
N-[5-(2-aminopyrimidin-4-yl)thien-2-yl]-3-(2,4-dichlorophenyl)propanamide;
benzyl 5-[2-(methylamino)pyrimidin-4-yl]thien-2-ylcarbamate;
4-fluorobenzyl 5-[2-(methylamino)pyrimidin-4-yl]thien-2-ylcarbamate;
(2R)-2-amino-3-(1H-indol-3-yl)propyl 5-[2-(methylamino)pyrimidin-4-yl]thien-2-ylcarbamate;
(2S)-2-amino-3-(1H-indol-3-yl)propyl 5-[2-(methylamino)pyrimidin-4-yl]thien-2-ylcarbamate;
N-(4-fluorobenzyl)-N'-{5-[2-(methylamino)pyrimidin-4-yl]thien-2-yl}urea;
N-(2,4-dichlorobenzyl)-N'-{5-[2-(methylamino)pyrimidin-4-yl]thien-2yl}urea;
4-[5-({[2-(4-fluorophenyl)ethyl]amino}methyl)thien-2-yl]-N-methylpyrimidin-2-amine;
4-[5-({[2-(4-chlorophenyl)ethyl]amino}methyl)thien-2-yl]-N-methylpyrimidin-2-amine;
4-[5-({[2-(2,4-dichlorophenyl)ethyl]amino}methyl)thien-2-yl]-N-methylpyrimidin-2-amine;
4-[5-({[2-(4-chlorophenyl)ethyl]amino}methyl)thien-2-yl]pyrimidin-2-amine;
4-chloro-N-({5-[2-(methylamino)pyrimidin-4-yl]thien-2-yl}methyl)-1,3-benzothiazol-2-amine;
N-{[5-(2-aminopyrimidin-4-yl)thien-2-yl]methyl}-4-chloro-1,3-benzothiazol-2-amine;
N-[2-(4-fluorophenyl)ethyl]-5-[2-(methylamino)pyrimidin-4-yl]thiophene-2-sulfonamide;
N-[2-(4-chlorophenyl)ethyl]-5-[2-(methylamino)pyrimidin-4-yl]thiophene-2-sulfonamide;
N-[2-(2,4-dichlorophenyl)ethyl]-5-[2-(methylamino)pyrimidin-4-yl]thiophene-2-sulfonamide;
N-(2,4-dichlorobenzyl)-5-[2-(methylamino)pyrimidin-4-yl]thiophene-2-sulfonamide;
5-(2-aminopyrimidin-4-yl)-N-[2-(4-fluorophenyl)ethyl]thiophene-2-sulfonamide;
5-(2-aminopyrimidin-4-yl)-N-[2-(2,4-dichlorophenyl)ethyl]thiophene-2-sulfonamide;
5-(2-aminopyrimidin-4-yl)-N-(4-fluorobenzyl)thiophene-2-sulfonamide;
5-(2-aminopyrimidin-4-yl)-N-(2,4-dichlorobenzyl)thiophene-2-sulfonamide;
2-amino-1,3-benzothiazol-4-yl 5-[2-(methylamino)pyrimidin-4-yl]thiophene-2-carboxylate;
2-amino-1,3-benzothiazol-4-yl 5-(2-aminopyrimidin-4-yl)thiophene-2-carboxylate;
4-{5-[(E)-2-(4-chloro-1,3-benzothiazol-2-yl)vinyl]thien-2-yl}pyrimidin-2-amine; and
4-{5-[(4-chloro-1,3-benzothiazol-2-y1)ethynyl]thien-2-yl}pyrimidin-2-amine;
or pharmaceutically acceptable salts, esters or prodrugs thereof.

22. A compound represented by the formula

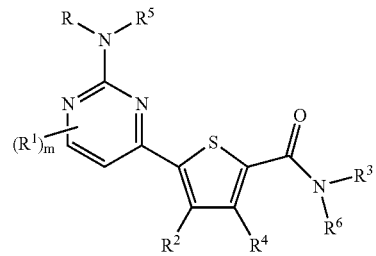

wherein:
R is selected from the group consisting of:
a) hydrogen,
b) hydroxy, c) optionally substituted alkyl substituted with a substituent selected from the group consisting of hydroxy, cycloalkyl, substituted cycloalkyl, phenyl, hetervycle, substituted heterocycle, heteroaryl, substituted heteroaryl, amino, substituted amino, carboxyl, and 4-chlorophenyl,
d) cycloalkyl,
e) substituted cycloalkyl,
f) —$SO_2R^7$ where $R^7$ is $C_1$ to $C_5$ alkyl or substituted alkyl,
g) alkoxy,
h) carboxyl,
i) carboxyl ester,
j) nitro,
k) aryl,
l) substituted aryl,
m) heteroaryl,
n) substituted heteroaryl,
o) acylamino, and
p) acyl;

$R^5$ is selected from the group consisting of:
a) hydrogen, and
b) alkyl, and
c) substituted alkyl;

each $R^1$ is independently selected from the group consisting of:
a) halo,
b) cyano,
c) nitro,
d) hydroxy,
e) thiol,
f) amino,
g) substituted amino,
h) alkoxy,
i) substituted alkoxy,
j) aryloxy,
k) substituted aryloxy,
l) heteroaryloxy,
m) substituted heteroaryloxy,
n) alkylthio,
o) substituted alkylthio,
p) —C(=O)$NR^8R^8$, wherein each $R^8$ is independently selected from the group consisting of hydrogen, alkyl, substituted alkyl, aryl, substituted aryl, heteroaryl, substituted heteroaryl, heterocyclyl, substituted heterocyclyl, or each $R^8$ can be optionally joined together with the nitrogen atom pendent thereto to form a heterocyclyl or substituted heterocyclyl,
q) —NHC(=O)—$R^9$, wherein $R^9$ is selected from the group consisting of hydrogen, alkyl, substituted alkyl, aryl, substituted aryl, heteroaryl, substituted heteroaryl, heterocyclyl, substituted heterocyclyl,
r) aryl or heteroaryl, each of which may be optionally substituted with optionally substituted alkyl or aryl,
s) heterocyclyl, each of which may be optionally substituted with optionally substituted alkyl or aryl, and
t) $C_1$ to $C_5$ alkyl optionally substituted with 1 to 3 substituents selected from halo, hydroxy, amino, aryl, $C_1$ to $C_5$ alkyl monosubstituted amino, and $C_1$ to $C_5$ alkyl disubstituted amino wherein each alkyl group is independent from the other alkyl group;

m is an integer equal to 0, 1 or 2;

$R^2$ and $R^4$ are independently selected from the group consisting of:
a) hydrogen,
b) cycloalkyl,
c) substituted cycloalkyl,
d) heterocyclyl,
e) substituted heterocyclyl,
f) aryl,
g) substituted aryl,
h) heteroaryl,
i) substituted heteroaryl,
j) $C_1$ to $C_5$ alkyl optionally substituted with 1 to 3 substituents selected from halo, hydroxy, amino, $C_1$ to $C_5$ alkyl monosubstituted amino, and $C_1$ to $C_5$ alkyl disubstituted amino wherein each alkyl group is independent from the other alkyl group,
k) optionally substituted $C_2$ to $C_5$ alkenyl,
l) optionally substituted $C_2$ to $C_5$ alkynyl,
m) optionally substituted $C_1$ to $C_5$ alkoxy,
n) hydroxy,
) amino,
p) $C_1$ to $C_5$ alkyl monosubstituted amino, and
q) $C_1$ to $C_5$ alkyl disubstituted amino wherein each alkyl group is independent from the other alkyl group, with the proviso that when one of $R^2$ or $R^4$ is cycloalkyl, substituted cycloalkyl, heterocyclyl, substituted heterocyclyl, aryl substituted aryl, heteroaryl, substituted heteroaryl, then the other of $R^2$ or $R^4$ is hydrogen;

$R^3$ selected from the group consisting of:
a) hydrogen,
b) $C_1$ to $C_5$ alkyl, and
c) ($C_1$ to $C_5$ alkylene)$_p$-Z optionally substituted on the alkylene chain with 1 to 2 substituents selected from the group consisting of:
   i. $C_1$ to $C_5$ alkyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group,
   ii. $C_2$ to $C_5$ alkenyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group with the proviso that said hydroxy substitution is not pendent to a vinyl carbon atom of the substituted alkenyl,
   ii. $C_2$ to $C_5$ alkynyl optionally substituted with 1 to 3 substituents selected from hydroxy, carboxyl, carboxyl esters, amino, $C_1$ to $C_5$ alkyl monosubstituted amino, and $C_1$ to $C_5$ alkyl disubstituted amino wherein each alkyl group is independent from the other alkyl group with the proviso that said hydroxyl substitution is not pendent to a acetylene carbon atom of the substituted alkynyl,
   iv. $C_3$ to $C_6$ cycloalkyl,
   v. $C_3$ to $C_6$ spirocycloalkyl,
   vi. carboxyl,
   vii. carboxyl esters,
   viii. halo,
   viii. hydroxy,
   ix. $C_1$ to $C_5$ alkoxy,
   x. amino,
   xi. $C_1$ to $C_5$ alkyl monosubstituted amino,
   xii. $C_1$ to $C_5$ alkyl disubstituted amino,
   xiii. aryl, and
   ix. heterocyclyl;

Z is selected from the group consisting of:
a) alkyl,
b) substituted alkyl,
c) alkylamino, d) alkoxy,
e) substituted alkoxy,
f) cycloalkyl,
g) heterocyclyl,
h) substituted heterocyclyl,
i) aryl,
j) substituted aryl,
k) heteroaryl,
l) substituted heteroaryl,
m) amino, and
n) dialkylamino;

p is an integer selected from zero or one;

$R^6$ is independently selected from the group consisting of hydrogen and $C_1$-$C_3$ alkyl and $C_1$-$C_3$ substituted alkyl or $R^6$ together with the nitrogen atom attached thereto and together with $R^4$ and the carbon atom attached thereto join to form a heterocyclyl or substituted heterocyclyl, with the proviso that $R^3$ is not $C_2$ alkyl further substituted with at least a —C(O) group at the beta position to the —C(O)NH—, with the further proviso that $R^4$ is not aryl or heteroaryl;

or pharmaceutically acceptable salts, esters or prodrugs thereof.

23. The compound of claim 22, wherein R is selected from the group consisting of hydrogen, alkyl, substituted alkyl, cycloalkyl, substituted cycloalkyl, acylamino, heteroaryl, nitro, aryl, and —$SO_2R^7$ wherein $R^7$ is selected from the group consisting of hydrogen, methyl, carboxyl ester, and acyl.

24. The compound of claim 23, wherein R is selected from the group consisting of:
2-(methylamino)eth-1-yl,
2-(N-methylpiperazin-N'-yl)eth-1-yl,
2-(N-methylpyrrol-2-yl)eth-1-yl,
2-(N-morpholino)eth-1-yl,
2-(piperidin-N-yl)eth-1-yl,
2-(pyridin-2-yl)eth-1-yl,
2-(pyridin-3-yl)eth-1-yl,
2-(pyridin-4-yl)eth-1-yl,
2-(S)-phenylcyclopropyl,
2-aminoeth-1-yl,
2-hydroxyeth-1-yl,
2-phenyleth-1-yl,
2-spirocyclopropyl-2-(4-chlorophenyl)eth-1-yl,
3-(imidazol-N-yl)prop-1-yl,
3-(N-methylpiperazin-N'-yl)prop-1-yl,
3-(N-morpholino)prop-1-yl,
3-aminobut-1-yl,
3-aminoprop-1-yl,
5-carboxy-4-(R,S)-aminopent-1-yl,
aminocarbonyl,
benzyl,
benzylaminocarbonyl,
butyl,
cyclobutyl,
cyclopentyl,
cyclopropyl,
cyclopropylmethyl,
dimethylaminocarbonyl,
ethylaminocarbonyl,
hydrogen,
ethyl,
methyl,
methoxycarbonyl,
methylaminocarbonyl,
methylcarbonyl,
neopentyl,
nitro,
phenyl,
henylaminocarbonyl,
propyl,
propylaminocarbonyl,
pyridin-2-ylmethyl,
pyridin-3-ylmethyl,
pyridin-4-yl,
pyridin-4-ylmethyl, and
$SO_2CH_3$.

25. The compound of claim 22, wherein $R^5$ is hydrogen or methyl.

26. The compound of claim 22, wherein $R^1$ is selected from the group consisting of $C_{1-5}$ alkyl, —C(=O)$NR^8R^8$, and —NHC(=O)—$R^9$.

27. The compound of claim 22, wherein $R^2$ and $R^4$ are independently selected from the group consisting of hydrogen, hydroxy, amino, and $C_1$ to $C_5$ alkoxy optionally substituted with aryl or amino.

28. The compound of claim 27, wherein $R^2$ and $R^4$ are selected from the group consisting of hydrogen, hydroxy, amino, methoxy, benzyloxy, and 2-aminoethoxy.

29. The compound of claim 22, wherein $R^3$ is hydrogen.

30. The compound of claim 22, where $R^3$ is —($C_1$ to $C_5$ alkylene)$_p$-Z wherein p is 0 or 1.

31. The compound of claim 30, wherein p is 1 and the aLkylene chain is unsubstituted or substituted with a substituent selected from the group consisting of $C_1$ to $C_5$ alkyl, $C_1$ to $C_5$ alkyl substituted with hydroxy, amino, monosubstituted amino, or disubstituted amino, $C_2$ to $C_5$ alkenyl, $C_2$ to $C_5$ alkynyl, $C_3$ to $C_6$ spirocycloalkyl, carboxyl, carboxyl esters, hydroxy, amino, heterocyclyl and aryl.

32. The compound of claim 30, wherein the alkylene chain is unsubstituted or substituted with a substituent selected from the group consisting of:
2-aminoethyl,
2-dimethylaminoethyl,
2-hydroxyethyl,
2-methylaminoethyl,
3-methylaminopropyl,
amino,
aminomethyl,
carboxyl,
dimethylamino,
dimethylaminomethyl,
ethyl,
ethyl,
methylcarboxyl,
morpholino,
hydroxymethyl,
phenyl,
prop-2-enyl,
prop-2-ynyl,
propyl,
pirocyclobutyl, and
spirocyclopropyl.

33. The compound of claim 30, wherein Z is selected from the group consisting of cycloalkyl, substituted cydoalkyl, heterocyclyl, substituted heterocyclyl, aryl, substituted aryl, heteroaryl, substituted heteroaryl, alkyl, amino, alkylamino, and dialkylamino.

34. The compound of claim 30, wherein $R^3$ is selected from the group consisting of:
(2-fluoro-4-methoxyphenyl)eth-1-yl,
(2-fluoro-4-methylphenyl)eth-1-yl,
[1-(4-chlorophenyl)cyclobut-1-yl]methyl,
[1-(4-chlorophenyl)cycloprop-1-yl]methyl, 1-(1-aminoethyl)-4-chloro-1H-benzoimidazol-2-yl,
1-(2-aminoethyl)-1H-benzoimidazol-2-yl,
1-(2-aminoethyl)-4-chloro-1H-benzimidazol-2-yl,
1-(2-aminoethyl)-4-methoxy-1H-benzimidazol-2-yl,
1-(2-aminoethyl)-4-phenyl-1H-benzimidazol-2-yl,
1-(2-aminoethyl)-7-chloro-1H-benzimidazol-2-yl,
1-(2-methylpropyl-4-chloro-1H-benzimidazol-2-yl,
1-(3,3-dimethylbutyl)-4-chloro-1H-benzimidazol-2-yl,
1-(3-aminopropyl)-4-chloro-1H-benzimidazol-2-yl,
1-(4-chlorophenyl)-3-(N-methylamino)prop-1-yl,
1-(4-chlorophenyl)-3-(N,N-dimethylamino)prop-1-yl,
1-(4-chlorophenyl)-3-hydroxyprop-1-yl,
1-(aminomethyl)-2-(2,4-dichlorophenyl)eth-1-yl,
1-(R)-1-(2,4-dichlorobenzyl)-4-(dimethylamino)but-2-yl,
1-(R)-1-(2,4-dichlorobenzyl)-4-(methylamino)but-2-yl,
1-(R)-1-(2,4-dichlorobenzyl)-4-aminobut-2-yl,
1-(R)-2-(2,4-dichlorophenyl)-1-methyleth-1-yl,
1-(R)-4-fluorophenyl)eth-1-yl,
1-(R)-amino-1-(2,4-dichlorobenzyl)eth-1-yl,
1-(R)-aminomethyl-2-(2,4-dichlorophenyl)eth-1-yl,
1-(R)-hydroxymethyl-2-(4-chlorophenyl)eth-1-yl,
1-(R,S)-carboxyl-2-(2,4-dichlorophenyl)eth-1-yl,
1-(R,S)-hydroxymethyl-1-phenylmethyl,
1-(R,S)-hydroxymethyl-2-(2,4-dichlorophenyl)eth-1-yl,
1-(R,S)-hydroxymethyl-2-phenyleth-1-yl,
1-(R,S)-methylcarboxyl-2-(2,4-dichlorophenyl)eth-1-yl,
1-(R,S)-phenyl-2-phenyleth-1-yl,
1-(S)-1-(2,4-dichlorobenzyl)-4-(dimethylamino)but-2-yl,
1-(S)-1-(2,4-dichlorobenzyl)-4-(methylamino)but-2-yl,
1-(S)-1-(2,4-dichlorobenzyl)-4-amino-but-2-yl,
1-(S)-amino-1-(2,4-dichlorobenzyl)eth-1-yl,
1-(S)-aminomethyl-2-(1H-indol-3y1)eth-1-yl,
1-(S)-aminomethyl-2-(2,4-dichlorophenyl)eth-1-yl,
1-(S)-aminomethyl-2-(indol-3-yl)eth-1-yl,
1-(S)-dimethylamino-2-(2,4-dichlorophenyl)eth-1-yl,
1-(S)-dimethylaminomethyl-2-(2,4-dichlorophenyl)eth-1-yl,
1,2,3,4-tetrahydronaphthalen-1-yl,
1-aminoethyl-4-methoxybenzoimidazol-2-yl,
1-aminomethyl-2-(2,4-dichlorophenyl)eth-1-yl,
1-aminomethyl-2-(4-chlorophenyl)eth-1-yl,
1-aminomethyl-4-chloro-1H-benzimidazole-2-yl,
1-benzylpyrrolidin-3-yl,
1-dimethylamino-3-(2,4-dichlorophenyl)prop-2-yl,
1-ethyl-4-chlorobenzoimidazol-2-yl,
1-hydroxymethyl-2-(2,4-dichlorophenyl)eth-1-yl,
1-hydroxymethyl-2-methylprop-1-yl,
1-isobutyl-4-chlorobenzoimidazol-2-yl,
1-methyl-2-hydroxyeth-1-yl,
1-methyl-4-chlorobenzoimidazol-2-yl,
1-methylbenzoimidazol-2-yl,
1-phenyl-1-(4-chlorophenyl)methyl,
1-phenyl-2-hydroxyeth-1-yl,
2-(2,4-dichlorophenyl)but-1-yl,
2-(2,4-dichlorophenyl)eth-1-yl,
2-(2,4-dichlorophenyl)pent-1-yl,
2-(2,4-dichlorophenyl)pent-4-en-1-yl,
2-(2,4-dichlorophenyl)pent-4-yn-1-yl,
2-(2,4-dichlorophenyl)prop-1-yl,
2-(2,5-dimethoxyphenyl)eth-1-yl,
2-(2,6-dichlorophenyl)eth-1-yl,
2-(2-chlorophenyl)eth-1-yl,
2-(3,4-dichlorophenyl)eth-1-yl,
2-(3,4-dimethylphenyl)eth-1-yl,
2-(3-chlorophenyl)eth-1-yl,
2-(3-fluorophenyl)eth-1-yl,
2-(3-methoxyphenyl)eth-1-yl,
2-(4-aminophenyl)eth-1-yl,
2-(4-aminosulfonylphenyl)eth-1-yl,
2-(4-biphenyl)eth-1-yl,
2-(4-bromophenyl)eth-1-yl,
2-(4-chlorophenyl)eth-1-yl,
2-(4-ethoxyphenyl)eth-1-yl,
2-(4-ethylphenyl)eth-1-yl,
2-(4-fluorophenyl)eth-1-yl,
2-(4-methoxyphenyl)eth-1-yl,
2-(4-methylphenyl)eth-1-yl,
2-(4-phenoxyphenyl)eth-1-yl,
2-(N-methylpiperazin-N'-yl)eth-1-yl,
2-(N-methylpyrrol-2-yl)eth-1-yl,
2-(N-morpholino)eth-1-yl,
2-(piperidin-1-yl)eth-1-yl,
2-(piperidin-3-yl)eth-1-yl,
2-(pyridin-2-yl)eth-1-yl,
2-(pyridin-4-yl)eth-1-yl,
2-(R)-(N-morpholino)-2-phenyleth-1-yl,
2-(R)-amino-3-(indol-3-yl)prop-1-yl,
2-(R)-hydroxyindan-1-yl,
2-(R)-methyl-2-phenyleth-1-yl,
2-(R,S)-amino-2-phenyleth-1-yl,
2-(R,S)-hydroxy-2-(4-chlorophenyl)eth-1-yl,
2-(R,S)-methyl-2-phenyleth-1-yl,
2-(S)-amino-3-(indol-3-yl)prop-1-yl,
2-(S)-methyl-2-phenyleth-1-yl,
2-(trifluoromethyl)-4-fluorophenylmethyl,
2,4-dichlorobenzyl,
2,4-dichlorophenylmethyl,
2,2-dimethyl-5-benzyltetrahydropyran-4-yl,
2,2-diphenyleth-1-yl,
2,4-dichlorobenzyl,
2,4-.difluorobenzyl,
2,5-difluorobenzyl,
2-aminobenzothiazol-4-yl,
2-aminoeth-1-yl,
2-chlorobenzyl,
2-dimethylaminoeth-1-yl,
2-fluoro-4-chlorobenzyl,
2-fluoro-6-aminobenzyl,
2-methoxybenzyl,
2-methyl-4-chlorophenylmethyl,
2-methylbenzyl,
2-phenethyl,
2-phenylbenzyl,
2-piperidin-N-ylbenzyl,
3-(4-fluorophenyl)prop-1-yl,
3-(pyrrol-N-yl)prop-1-yl,
3,4-dichlorobenzyl,
3,5-dichlorobenzyl,
3,5-difluorobenzyl,
3-amino-i -(4-chlorophenyl)prop-1-yl,
3-bromobenzyl,
3-chlorobenzyl,
3-methoxybenzyl,
4-(2-chlorophenyl)thiazol-2-yl,
4-(3,4-difluorophenyl)thiazol-2-yl,
4-(3-chlorophenyl)thiazol-2-yl,
4-(4-methoxyphenyl)thiazol-2-yl,
4-(aminomethyl)benzothiazol-2-yl,
4-(pyridin-2-yl)thiazol-2-yl,
4-(pyridin-3-yl)thiazol-2-yl,
4-(trifluoromethoxy)-6-(aminomethyl)benzothiazol-2-yl,
4-(trifluoromethyl)-6-(aminomethyl)benzothiazol-2-yl,
4,6-dichlorobenzothiazol-2-yl,
4,6-difluorobenzothiazol-2-yl, 4-amino-2-(4-chlorophenyl)but-1-yl,
4-aminobenzyl,
4-aminosulfonylbenzyl,
4-bromo-6-(aminomethyl)benzothiazol-2-yl,
4-bromo-6-isopropyl-benzothiazol-2-yl,
4-bromobenzothiazol-2-yl,
4-bromobenzyl,
4-chloro-[2-(S)-2-(aminopropanoyl)aminomethyl]benzothiazol-2-yl,
4-chloro-1,3-benzothiazol-2-yl,
4-chloro-5-methylcarboxyl-benzothiazol-2-yl,
4-chloro-6-({[2-(S)-2-amino-3-phenylpropanoyl]amino}methyl)benzothiazol-2-yl,
4-chloro-6-(2-aminoethyl)benzothiazol-2-yl,
4-chloro-6-(2-nitroethyl)benzothiazol-2-yl,
4-chloro-6-(dimethylaminomethyl)benzothiazol-2-yl,
4-chloro-6-(methylaminomethyl)benzothiazol-2-yl,
4-chloro-6-(methylcarbonylaminomethyl)benzothiazol-2-yl,
4-chloro-6-(trifluoromethoxy)benzothiazol-2-yl,
4-chloro-6-(trifluoromethyl)benzothiazol-2-yl,
4-chloro-6-[(2-amino)ethylaminocarbonyl]benzothiazol-2-yl,
4-chloro-6-{[(aminomethylcarbonyl)amino]methyl}benzothiaozl-2-yl,
4-chloro-6-aminomethylbenzothiazol-2-yl,
4-chloro-6-hydroxymethylbenzothiazol-2-yl,
4-chloro-6-methylaminomethylbenzothiazol-2-yl,
4-chloro-6-methyhhiazol-2-yl,
4-chloro-6-N-morpholinomethyl-benzothiazol-2-yl,
4-chloro-7-aminomethyl-benzothiazol-2-yl,
4-chloro-7-hydroxymethyl-benzothiazol-2-yl,
4-chlorobenzothiazol-2-yl,
4-chlorobenzoxazol-2-yl,
4-chlorobenzyl,
4-dimethylaminobenzyl,
4-fluorobenzyl,
4-fluorobenzothiazol-2-yl,
4-fluorobenzyl,
4-fluorophenyl,
4-fluorophenylmethyl,
4-hydroxy-2-(4-chlorophenyl)but-1-yl,
4-hydroxybenzothiazol-2-yl,
4-hydroxybenzothiazol-4-yl,
4-methoxy-6-(methylaminomethyl)benzothiazol-1-yl,
4-methoxybenzothiazol-2-yl,
4-methoxythiazol-2-yl,
4-methyl-6-aminomethyl-benzothiazol-2-yl,
4-methylbenzyl,
4-methylthiazol-2-yl,
4-phenylthiazol-2-yl,
5-(2-bromothiophen-5-yl)thiazol-2-yl,
5-(3-bromo-4-methoxyphenyl)thiazol-2-yl,
5-chlorobenzoimidazol-2-yl,
5-chlorobenzothiazol-2-yl,
6-aminomethyl-8-chloroquinolin-2-yl,
6-aminomethyl-benzothiazol-2-yl,
6-chlorobenzothiazol-2-yl,
6-fluorobenzothiazol-2-yl,
7-chlorobenzothiazol-2-yl,
benzoimidazol-2-yl,
benzothiazol-2-yl,
benzothiazol-6-yl,
benzothiophen-2-yl,
benzyl,
indan-1-yl,
naplithalen-1-ylmethyl,
pyridin-2-ylmethyl,
pyridin-3-ylmethyl,
pyridin-4-ylmethyl,
pyrimidin-3-yl,
pyrrolidin-3-yl,
quinolin-2-yl,
quinolin-3-yl,
quinolin-6-yl, and
thiophen-2-ylmethyl.

35. The compound of claim 22, wherein $R^6$ is hydrogen or $C_{1-3}$ alkyl, optionally substituted with amino.

36. The compound of claim 22, wherein $R^6$ together with the atoms bound thereto and together with $R^4$ and the carbon atom attached thereto join to form a substituted heterocyclyl.

37. The compound of claim 36, wherein the substituted heterocyclyl is 5,6-dihydropyrimidin-4-one.

38. A compound selected from the group consisting of:
N-[2-(4-fluorophenyl)ethyl]-5-[2-(methylamino)pyrimidin-4-yl]thiophene-2-carboxamide;
5-[2-(methylamino)pyrimidin-4-yl]-N-(2-phenylethyl)thiophene-2-carboxamide;
N-(4-fluorobenzyl)-5-[2-(methylamino)pyrimidin-4-yl]thiophene-2-carboxamide;
N-[2-(4-fluorophenyl)ethyl]-5-{2-[(methylsulfonyl)amino]pyrimidin-4-yl}thiophene-2-carboxamide;
N-[2-(4-chlorophenyl)ethyl]-5-[2-(methylamino)pyrimidin-4-yl]thiophene-2-carboxamide;
N-[2-(4-bromophenyl)ethyl1-5-[2-(methylamino)pyrimidin-4-yl]thiophene-2-carboxamide;
N-{2-[4-(aminosulfonyl)phenyl]ethyl}-5-[2-(methylamino)pyrimidin-4-yl]thiophene-2-carboxamide;
N-[2-(2-fluorophenyl)ethyl]-5-[2-(methylamino)pyrimidin-4-yl]thiophene-2-carboxamide;
N-[2-(2-methoxyphenyl)ethyl]-5-[2-(methylamino)pyrimidin-4-yl]thiophene-2-carboxamide;
N-[2-(3-fluorophenyl)ethyl]-5-[2-(methylamino)pyrimidin-4-yl]thiophene-2-carboxamide;
N-[2-(3-methoxyphenyl)ethyl]-5-[2-(methylamino)pyrimidin-4-yl]thiophene-2-carboxamide;
5-[2-(methylamino)pyrimidin-4-yl]-N-[(2S)-2-phenylpropyl]thiophene-2-carboxamide;
N-[2-(2,4-dichlorophenyl)ethyl]-5-[2-(methylamino)pyrimidin-4-yl]thiophene-2-carboxamide;
N-[2-(2,6-dichlorophenyl)ethyl]-5-[2-(methylamino)pyrimidin-4-yl]thiophene-2-carboxamide;
N-[2-(3,4-dichlorophenyl)ethyl]-5-[2-(methylamino)pyrimidin-4yl]thiophene-2-carboxamide;
N-[3-(4-fluorophenyl)propyl]-5-[2-(methylamino)pyrimidin-4-yl]thiophene-2-carboxamide;
N-[2-(2,4-dichlorophenyl)ethyl]-5-[2-(ethylamino)pyrimidin-4-yl]thiophene-2-carboxamide;
5-(2-aminopyrimidin-4-yl)-N-[2-(2,4-dichlorophenyl)ethyl]thiophene-2-carboxamide;
N-[2-(2,4-dichlorophenyl)ethyl]-5-[2-(neopentylamno)pyrimidin4yl]thiophene-2-carboxamide;
5-[2-(cyclopropylamino)pyrimidin-4-yl]-N-[2-(2,4dichlorophenyl)ethyl]thiophene-2-carboxamide;
5-[2-(cyclobutylamino)pyrin-4yl]-N-[2-(2,4-dichloropheny)ethyl]thiophene-2-carboxamide;
N-(4-chloro-1,3-benzothiazol-2-yl)-5-[2-(methylamino)pyrimidin-4-yl]thiophene-2-carboxamide;
N-[4-(aminosulfonyl)benzyl]-5-[2-(methylamino)pyrimidin-4-yl]thiophene-2-carboxamide;
5-[2-(methylamino)pyrimidin-4-yl]-N-(thien-2-ylmethyl)thiophene-2-carboxamide;
N-{[1-(4-chlorophenyl)cyclopropyl]methyl}-5-[2-(methylamino)pyrimidin-4-yl]thiophene-2-carboxamide;

5-[2-(methylamino)pyrimidin-4-yl]-N-[2-(1-methyl-1H-pyrrol-2-yl)ethyl]thiophene-2-carboxamide;
N-[2-(2,4-dichlorophenyl)ethyl]-5-{2-[(2-hydroxyethyl)amino]pyrimidin-4-yl}thiophene-2-carboxamide;
N-[2-(4-fluorophenyl)ethyl]-5-[5-methyl-2-(methylamino)pyrimidin-4-yl]thiophene-2-carboxamide;
N-[1-(4-fluorophenyl)ethyl]-5-[2-(methylamino)pyrimidin-4-yl]thiophene-2-carboxamide;
N-(2-chlorobenzyl)-5-[2-(methylamino)pyrimidin-4-yl]thiophene-2-carboxamide;
N-(3-chlorobenzyl)-5-[2-(methylamino)pyrimidin-4-yl]thiophene-2-carboxamide;
N-(4-chlorobenzyl)-5-[2-(methylamino)pyrimidin-4-yl]thiophene-2-carboxamide;
N-(2,4-difluorobenzyl)-5-[2-(methylamino)pyrimidin-4-yl]thiophene-2-carboxamide;
N-(2,4-dichlorobenzyl)-5-[2-(methylamino)pyrimidin4yl]thiophene-2carboxamide;
5-[2-(methylamino)pyrimidin-4-yl]-N-(2-morpholin-4-yl-2-phenylethyl)thiophene-2-carboxamide;
5-[2-(methylamino)pyrimidin-4-yl]-N-(1-naphthylmethyl)thiophene-2-carboxamide;
5-2-(methylamino)pyrimidin-4-yl]-N-(2-phenylpropyl)thiophene-2-carboxamide;
N-[2-(2-chlorophenyl)ethyl]-5-[2-(methylamino)pyrimidin-4-yl]thiophene-2-carboxamide;
N-[2-(3-chlorophenyl)ethyl]-5-[2-(methylamino)pyrimidin-4-yl]thiophene-2-carboxamide;
N-[1-(4-chlorobenzyl)-2-hydroxyethyl]-5-[2-(methylamino)pyrimidin-4-yl]thiophene-2-carboxamide;
5-[2-(methylamino)pyrimidin-4-yl]-N-[(2R)-2-phenylpropyl]thiophene-2-carboxamide;
N-[(2S)-2-amino-2-phenylethyl]-5-[2-(methylamino)pyrimidin-4-yl]thiophene-2-carboxamide;
5-(2-aminopyrimidin-4-yl)-N-(2-chlorobenzyl)thiophene-2-carboxamide;
5-(2-aminopyrimidin-4-yl)-N-(3-chlorobenzyl)thiophene-2-carboxamide;
5-(2-aminopyrimidin-4-yl)-N-(4-chlorobenzyl)thiophene-2-carboxamide;
5-(2-aminopyrimidin-4-yl)-N-(2,4-difluorobenzyl)thiophene-2-carboxamide;
5-(2-aminopyrimidin-4-yl)-N-(2,5-difluorobenzyl)thiophene-2-carboxamide;
5-(2-aminopyrimidin-4-yl)-N-(3,5-difluorobenzyl)thiophene-2-carboxamide;
5-(2-aminopyrimidin-4-yl)-N-(4-chloro-2-fluorobenzyl)thiophene-2-carboxamide;
5-(2-aminopyrimidin-4-yl)-N-(2,4-dichlorobenzyl)thiophene-2-carboxamide;
5-(2-aminopyrimidin-4-yl)-N-(3,4-dichlorobenzyl)thiophene-2-carboxamide;
5-(2-aminopyrimidin-4-yl)-N-(3,5-dichlorobenzyl)thiophene-2-carboxamide;
5-(2-aminopyrimidin-4-yl)-N-[2-(2-chlorophenyl)ethyl]thiophene-2-carboxamide;
5-(2-aminopyrimidin-4-yl)-N-[2-(3-chlorophenyl)ethyl]thiophene-2-carboxamide;
5-(2-aminopyrimidin-4-yl)-N-[2-(4-chlorophenyl)ethyl]thiophene-2-carboxamide;
5-(2-aminopyrimidin-4-yl)-N-[2-(3,4-dichlorophenyl)ethyl]thiophene-2-carboxamide;
5-(2-aminopyrimidin-4-yl)-N-[2-(2,6-dichlorophenyl)ethyl]thiophene-2carboxamide;
5-(2-aminopyrimidin-4-yl)-N-[(2R)-2-phenylpropyl]thiophene-2-carboxamide;
5-(2-aminopyrimidin-4-yl)-N-[(2S)-2-phenylpropyl]thiophene-2-carboxamide;
5-(2-aminopyrimidin-4-yl)-N-(2-phenylpropyl)thiophene-2-carboxamide;
5-(2-aminopyrimidin-4-yl)-N-{[1-(4-chlorophenyl)cyclopropyl]methyl}thiophene-2-carboxamide;
5-(2-aminopyrimidin-4-yl)-N-[2-(1-methyl-1H-pyrrol-2-yl)ethyl]thiophene-2-carboxamide;
N-[(1S)-1-(2,4-dichlorobenzyl)-2-hydroxyethyl]-5-[2-(methylamino)pyrimidin-4-yl]thiophene-2-carboxamide;
N-[2-(4-chlorophenyl)-4-hydroxybutyl]-5-[2-(methylamino)pyrimidin-4-yl]thiophene-2-carboxamide;
N-[(2S)-2-amino-2-phenylethyl]-5-(2-aminopyrimidin-4-yl)thiophene-2-carboxamide;
5-(2-aminopyrimidin-4-yl)-N-(2-methylbenzyl)thiophene-2-carboxamide;
5-(2-aminopyrimidin-4-yl)-N-(4-methylbenzyl)thiophene-2-carboxamide;
5-(2-aminopyrimidin-4-yl)-N-(2-methoxybenzyl)thiophene-2-carboxamide;
5-(2-aminopyrimidin-4-yl)-N-(3-methoxybenyl)thiophene-2-carboxamide;
5-(2-aminopyrimidin-4-yl)-N-(3-bromobenzyl)thiophene-2-carboxamide;
5-(2-aminopyrimidin-4-yl)-N-(4-bromobenzyl)thiophene-2-carboxamide;
5-(2-aminopyrimidin-4-yl)-N-(2-hydroxy-1-phenylethyl)thiophene-2-carboxamide;
5-(2-aminopyrimidin-4-yl)-N-[2-(2-fluoro-4-methylphenyl)ethyl]thiophene-2-carboxamide;
5-(2-aminopyrimidin-4-yl)-N-[2-(2-fluoro-4-methoxyphenyl)ethyl]thiophene-2-carboxamide;
5-(2-aminopyrimidin-4-yl)-N-[(2R)-2-(4-chlorophenyl)-2-hydroxyethyl]thiophene-2-carboxamide;
5-(2-aminopyrimidin-4-yl)-N-[2-(2,4-dichlorophenyl)propyl]thiophene-2-carboxamide;
5-(2-aminopyrimidin-4-yl)-N-[2-(2,4-dichlorophenyl)butyl]thiophene-2-carboxamide;
5-(2-aminopyrimidin-4-yl)-N-[2-(2,4-dichlorophenyl)pentyl]thiophene-2-carboxamide;
5-(2-aminopyrimidin-4-yl)-N-[2-(2,4-dichlorophenyl)pent-4-enyl]thiophene-2-carboxamide;
5-(2-aminopyrimidin-4-yl)-N-[2-(2,4-dichlorophenyl)pent-4-ynyl]thiophene-2-carboxamide;
5-(2-aminopyrimidin-4-yl)-N-1,3-benzothiazol-2-ylthiophene-2-carboxamide;
5-(2-aminopyrimidin-4-yl)-N-(4-chloro-1,3-benzothiazol-2-yl)thiophene-2-carboxamide;
5-(2-aminopyrimidin-4-yl)-N-{[1-(4-chlorophenyl)cyclobutyl]methyl}thiophene-2-carboxamide;
5-(2-aminopyrimidin-4-yl)-N-[(1S)-1-(2,4-dichlorobenzyl)-2-hydroxyethyl]thiophene-2-carboxamide;
methyl 2,4-dichloro-N-({5-[2-(methylamino)pyrimidin-4-yl]thien-2-yl}carbonyl)-L-phenylalaninate;
N-[(1S)-1-benzyl-2-hydroxyethyl]-5-[2-(methylamino)pyrimidin-4-yl]thiophene-2-carboxamide;
N-[(1S)-2-hydroxy-1-phenylethyl]-5-[2-(methylamino)pyrimidin-4-yl]thiophene-2-carboxamide;
N-[4-amino-2-(4-chlorophenyl)butyl]-5-[2-(methylamino)pyrimidin-4-yl]thiophene-2-carboxamide;
N-[1-(4-chlorophenyl)-3-hydroxypropyl]-5-[2-(methylamino)pyrimidin-4-yl]thiophene-2-carboxamide;
N-[1-(2,4-dichlorobenzyl)-2-hydroxyethyl]-5-[2-(methylamino)pyrimidin-4-yl]thiophene-2-carboxamide;
5-(2-aminopyrimidin-4-yl)-N-[1-(2,4-dichlorobenzyl)-2-hydroxyethyl]thiophene-2-carboxamide;

2,4-dichloro-N-({5-[2-(methylamino)pyrimidin-4-yl]
thien-2-yl}carbonyl)-L-phenylalanine;
N-(4-chloro-2-methylbenzyl)-5-[2-(methylamino)pyrimi-
din-4-yl]thiophene-2-carboxamide;
5-(2-aminopyrimidin-4-yl)-N-(4-chloro-2-methylbenzyl)
thiophene-2-carboxamide;
N-[2-amino-1-(4-chlorobenzyl)ethyl]-5-[2-(methy-
lamino)pyrimidin-4-yl]thiophene-2-carboxamide;
N-[1-(4-chlorophenyl)-3-(dimethylamino)propyl]-5-[2-
(methylamino)pyrimidin-4-yl]thiophene-2-carboxam-
ide;
5-(2-aminopyrimidin-4-yl)-N-[1-(4-chlorophenyl)-3-
(methylamino)propyl]thiophene-2-carboxamide;
5-(2-aminopyrimidin-4-yl)-N-[1-(4-chlorophenyl)-3-
(dimethylamino)propyl]thiophene-2-carboxamide;
5-(2-aminopyrimidin-4-yl)-N-(1,1'-biphenyl-2-ylmethyl)
thiophene-2-carboxamide;
N-[3-amino-1-(4-chlorophenyl)propyl]-5-(2-aminopyri-
midin-4-yl)thiophene-2-carboxamide;
N-[2-amino-1-(2,4-dichlorobenzyl)ethyl]-5-[2-(methy-
lamino)pyrimidin-4-yl]thiophene-2-carboxamide;
5-[2-(methylamino)pyrimidin-4-yl]-N-(4-methyl-1,3-
benzothiazol-2-yl)thiophene-2-carboxamide;
N-(4-methoxy-1,3-benzothiazol-2-yl)-5-[2-(methy-
lamino)pyrimidin-4-yl]thiophene-2-carboxamide;
5-(2-aminopyrimidin-4-yl)-N-[2-(4-fluorophenyl)ethyl]
thiophene-2-carboxamide;
5-[2-(ethylamino)pyrimidin-4-yl]-N-[2-(4-fluorophenyl)
ethyl]thiophene-2-carboxamide;
N-[2-(4-fluorophenyl)ethyl]-N-methyl-5-[2-(methy-
lamino)pyrimidin-4-yl]thiophene-2-carboxamide;
N-[(1R)-2-(2,4-dichlorophenyl)-1-methylethyl]-5-[2-
(methylamino)pyrimidin-4-yl]thiophene-2-carboxam-
ide;
N-[1-(2-aminoethyl)-1H-benzimidazol-2-yl]-5-[2-(me-
thylamino)pyrimidin-4-yl]thiophene-2-carboxamide;
N-[1-(2-aminoethyl)-7-chloro-1H-benzimidazol-2-yl]-5-
[2-(methylamino)pyrimidin-4-yl]thiophene-2-carboxa-
mide;
N-[(1R)-2-amino-1-(2,4-dichlorobenzyl)ethyl]-5-[2-(me-
thylamino)pyrimidin-4-yl]thiophene-2-carboxamide;
N-[(1S)-2-amino-1-(2,4-dichlorobenzyl)ethyl]-5-[2-(me-
thylamino)pyrimidin4-yl]thiophene-2-carboxamide;
N-[(1R)-1-(2,4-dichlorobenzy1)-3-(methylamino)pro-
pyl]-5-[2-(methylamino)pyrimidin4-yl]thiophene-2-
carboxamide;
N-[(1R)-1-(2,4-dichlorobenzyl)-3-(dimethylamino)pro-
pyl]-5-[2-(methylamino)pyrimidin-4-yl]thiophene-2-
carboxamide;
N-[(1S)-1-(2,4-dichlorobenzyl)-3-(methylamino)propyl]-
5-[2-(methylamino)pyrimidin-4-yl]thiophene-2-car-
boxamide;
N-[(1S)-1-(2,4-dichlorobenzyl)-3-(dimethylamino)pro-
pyl]-5-[2-(methylamino)pyrimidin-4-yl]thiophene-2-
carboxamide;
N-[(1R)-3-amino-1-(2,4-dichlorobenzyl)propyl]-5-[2-
(methylamino)pyrimidin-4-yl]thiophene-2-carboxam-
ide;
N-[(1S)-3-amino-1-(2,4-dichlorobenzyl)propyl]-5-[2-
(methylamino)pyrimidin-4-yl]thiophene-2-carboxamide;
N-(2-aminoethyl)-N-(4-chloro-1,3-benzothiazol-2-yl)-5-
[2-(methylamino)pyrimidin-4-yl]thiophene-2-carboxa-
mide;
N-[1-(2-aminoethyl)-4-chloro-1H-benzimidazol-2-yl]-5-
[2-(methylamino)pyrimidin-4-yl]thiophene-2-carboxa-
mide;
N-[(1S)-2-amino-1-(2,4-dichlorobenzyl)ethyl]-5-[2-(me-
thylamino)pyrimidin-4-yl]thiophene-2-carboxamide;
N-[(1R)-2-amino-1-(2,4-dichlorobenzyl)ethyl]-5-[2-(me-
thylamino)pyrimidin-4-yl]thiophene-2-carboxamide;
N-[(1S)-1-(2,4-dichlorobenzyl)-2-(dimethylamino)
ethyl]-5-[2-(methylamino)pyrimidin-4-yl]thiophene-2-
carboxamide;
5-(2-aminopyrimidin-4-yl)-N-[(1S)-1-(2,4-dichloroben-
zyl)-2-(dimethylamino)ethyl]thiophene-2-carboxam-
ide;
N-(4-chloro-1,3-benzothiazol-2-yl)-N-methyl-5-[2-(me-
thylamino)pyrimidin-4-yl]thiophene-2-carboxamide;
N-(4,6-difluoro-1,3-benzothiazol-2-yl)-5-[2-(methy-
lamino)pyrimidin-4-yl]thiophene-2-carboxamide;
5-(2-aminopyrimidin-4-yl)-N-(4,6-difluoro-1,3-ben-
zothiazol-2-yl)thiophene-2-carboxamide;
N-[1-(3-aminopropyl)-4-chloro-1H-benzimidazol-2-yl]-
5-(2-aminopyrimidin-4-yl)thiophene-2-carboxamide;
N-[1-(2-aminoethyl)-4-methoxy-1H-benzimidazol-2-yl]-
5-[2-(methylamino)pyrimidin-4-yl]thiophene-2-car-
boxamide;
N-[1-(2-aminoethyl)-4-methoxy-1H-benzimidazol-2-yl]-
5-(2-aminopyrimidin-4-yl)thiophene-2-carboxamide;
5-[2-(methylamino)pyrimidin-4-yl]-N-quinolin-2-ylth-
iophene-2-carboxamide;
5-(2-aminopyrimidin-4-yl)-N-(4-methoxy-1,3-benzothia-
zol-2-yl)thiophene-2-carboxamide;
3-amino-N-[(1S)-1-(2,4-dichlorobenzyl)-2-(dimethy-
lamino)ethyl]-5-[2-(methylamino)pyrimidin-4-yl]
thiophene-2-carboxamide;
N-[(1S)-1-(2,4-dichlorobenzyl)-2-(dimethylamino)
ethyl]-3-methoxy-5-[2-(methylamino)pyrimidin-4-yl]
thiophene-2-carboxamide;
5-(2-aminopyrimidin-4-yl)-N-(4-methoxy-1,3-benzothia-
zol-2-yl)thiophene-2-carboxamide;
3-amino-N-(4-chloro-1,3-benzothiazol-2-yl)-5-[2-(me-
thylamino)pyrimidin-4-yl]thiophene-2-carboxamide;
N-[1-(hydroxymethyl)-2-methylpropyl]-5-[2-(methy-
lamino)pyrimidin-4-yl]thiophene-2-carboxamide;
N-(2-hydroxy-1-methylethyl)-5-[2-(methylamino)pyri-
midin-4-yl]thiophene-2 -carboxamide;
N-[2-(dimethylamino)ethyl]-5-[2-(methylamino)pyrimi-
din-4-yl]thiophene-2-carboxamide;
N-(2-aminoethyl)-5-[2-(methylamino)pyrimidin-4-yl]
thiophene-2-carboxamide;
5-[2-(methylamino)pyrimidin-4-yl]-N-pyrrolidin-3-ylth-
iophene-2-carboxamide;
5-[2-(methylamino)pyrimidin-4-yl]-N-piperidin-3-ylth-
iophene-2-carboxamide;
N-[(2S)-2-amino-3-(1H-indol-3-yl)propyl]-5-[2-(methy-
lamino)pyrimidin-4-yl]thiophene-2-carboxamide;
N-[(1S)-2-amino-1-(1H-indol-3-ylmethyl)ethyl]-5-[2-
(methylamino)pyrimidin-4-yl]thiophene-2-carboxam-
ide;
N-[2-(2,4-dichlorophenyl)ethyl]-5-[4-(methylamino)-1,3,
5-triazin-2-yl]thiophene-2-carboxamide;
3-[2-(2,4-dichlorophenyl)ethyl]-6-[2-(methylamino)pyri-
midin-4-yl]thieno[3,2-d]pyrimidin-4(3H)-one;
6-(2-aminopyrimidin-4-yl)-3-[2-(2,4-dichlorophenyl)
ethyl]thieno[3,2-d]pyrimidin-4(3H)-one;
N-[1-(2-aminoethyl)-4-chloro-1H-benzimidazol-2-yl]-5-
(2-aminopyrimidin-4-yl)thiophene-2-carboxamide;
N-[1-(3-aminopropyl)-4-chloro-1H-benzimidazol-2-yl]-
5-[2-(methylamino)pyrimidin-4-yl]thiophene-2-car-
boxamide;
N-(4-chloro-1-ethyl-1H-benzimidazol-2-yl)-5-[2-(methy-
lamino)pyrimidin-4-yl]thiophene-2-carboxamide;

N-[4-chloro-1-(3,3-dimethylbutyl)-1H-benzimidazol-2-yl]-5-[2-(methylamino)pyrimidin-4-yl]thiophene-2-carboxamide;

3-amino-N-[2-(2,4-dichlorophenyl)ethyl]-5-[2-(methylamino)pyrimidin-4-yl]thiophene-2-carboxamide;

N-(4-chloro-1-isobutyl-1H-benzimidazol-2-yl)-5-[2-(methylamino)pyrimidin-4-yl]thiophene-2-carboxamide;

N-[1-(2-aminoethyl)-4-ethoxy-1H-benzimidazol-2-yl]-5-[2-(methylamino)pyrimidin-4-yl]thiophene-2-carboxamide;

N-[1-(2-aminoethyl)-4-ethoxy-1H-benzimidazol-2-yl]-5-(2-aminopyrimidin-4-yl)thiophene-2-carboxamide;

N-[1-(2-aminoethyl)-4-phenyl-1H-benzimidazol-2-yl[-5-]2-(methylamino)pyrimidin-4-yl]thiophene-2-carboxamide;

N-[1-(2-aminoethyl)-4-phenyl-1H-benzimidazol-2-yl]-5-(2-aminopyrimidin-4-yl)thiophene-2-carboxamide;

5-(2-aminopyrimidin-4-yl)-N-(4-hydroxy-1,3-benzothiazol-2-yl)thiophene-2-carboxamide;

N-(2-amino-6-fluorobenzyl)-5-[2-(methylamino)pyrimidin-4-yl]thiophene-2-carboxamide;

N-[1-(2,4-dichlorobenzyl)-2-(dimethylamino)ethyl]-3-hydroxy-5-[2-(methylamino)pyrimidin-4-yl]thiophene-2-carboxamide;

N-[(1S)-2-amino-1-(1H-indol-3-ylmethyl)ethyl]-3-methoxy-5-[2-(methylamino)pyrimidin-4-yl]thiophene-2-carboxamide;

N-(1-benzylpyrrolidin-3-yl)-5-[2-(methylamino)pyrimidin-4-yl]thiophene-2-carboxamide;

N-[(1S)-2-amino-1-(2,4-dichlorobenzyl)ethyl]-3-(benzyloxy)-5-[2-(methylamino)pyrimidin-4-yl]thiophene-2-carboxamide;

N-[6-(aminomethyl)-4-chloro-1,3-benzothiazol-2-yl]-5-[2-(methylamino)pyrimidin-4-yl]thiophene-2-carboxamide;

N-[6-(aminomethyl)-4-chloro-1,3-benzothiazol-2-yl]-5-(2-aminopyrimidin-4-yl)thiophene-2-carboxamide;

N-{4-chloro-7-[(methylamino)methyl]-1,3-benzothiazol-2-yl}-5-[2-(methylamino)pyrimidin-4-yl]thiophene-2-carboxamide;

5-(2-aminopyrimidin-4-yl)-N-[4-chloro-6-(hydroxymethyl)-1,3-benzothiazol-2-yl]thiophene-2-carboxamide;

N-[4-chloro-7-(hydroxymethyl)-1,3-benzothiazol-2-yl]-5-[2-(methylamino)pyrimidin-4-yl]thiophene-2-carboxamide;

N-[6-(aminomethyl)-1,3-benzothiazol-2-yl]-5-[2-(methylamino)pyrimidin-4-yl]thiophene-2-carboxamide;

N-[6-(aminomethyl)-1,3-benzothiazol-2-yl]-5-(2-aminopyrimidin-4-yl)thiophene-2-carboxamide;

5-[2-(methylamino)pyrimidin-4-yl]thiophene-2-carboxamide;

5-(2-aminopyrimidin-4-yl)thiophene-2-carboxamide;

N-[6-(aminomethyl)-4-methyl-1,3-benzothiazol-2-yl]-5-[2-(methylamino)pyrimidin-4-yl]thiophene-2-carboxamide;

N-[7-(aminomethyl)-4-chloro-1,3-benzothiazol-2-yl]-5-[2-(methylamino)pyrimidin-4-yl]thiophene-2-carboxamide;

N-(4-bromo-1,3-benzothiazol-2-yl)-5-[2-(methylamino)pyrimidin-4-yl]thiophene-2-carboxamide;

N-[4-chloro-6-(morpholin-4-ylmethyl)-1,3-benzothiazol-2-yl]-5-[2-(methylamino)pyrimidin-4-yl]thiophene-2-carboxamide;

5-(2-aminopyrimidin-4-yl)-N-[4-chloro-6-(morpholin-4-ylmethyl)-1,3-benzothiazol-2-yl]thiophene-2-carboxamide;

5-[2-(methylamino)pyrimidin-4-yl]-N-(4-phenyl-1,3-thiazol-2-yl)thiophene-2-carboxamide;

5-(2-aminopyrimidin-4-yl)-N-(4-phenyl-1,3-thiazol-2-yl)thiophene-2-carboxamide;

N-(5-chloro-1,3-benzothiazol-2-yl)-5-[2-(methylamino)pyrimidin-4-yl]thiophene-2-carboxamide;

N-[4-(3-chlorophenyl)-1,3-thiazol-2-yl]-5-[2-(methylamino)pyrimidin-4-yl]thiophene-2-carboxamide;

N-[4-(4-methoxyphenyl)-1,3-thiazol-2-yl]-5-[2-(methylamino)pyrimidin-4-yl]thiophene-2-carboxamide;

N-[4-(3,4-difluorophenyl)-1,3-thiazol-2-yl]-5-[2-(methylamino)pyrimidin-4-yl]thiophene-2-carboxamide;

N-[5-(3-bromo-4-methoxyphenyl)-1,3-thiazol-2-yl]-5-[2-(methylamino)pyrimidin-4-yl]thiophene-2-carboxamide;

5-(2-aminopyrimidin-4-yl)-N-(5-chloro-1,3-benzothiazol-2-yl)thiophene-2-carboxamide;

5-(2-aminopyrimidin-4-yl)-N-[4-(3-chlorophenyl)-1,3-thiazol-2-yl]thiophene-2-carboxamide;

5-(2-aminopyrimidin-4-yl)-N-[4-(4-methoxyphenyl)-1,3-thiazol-2-yl]thiophene-2-carboxamide;

5-(2-aminopyrimidin-4-yl)-N-[4-(3,4-difluorophenyl)-1,3-thiazol-2-yl]thiophene-2-carboxamide;

5-(2-aminopyrimidin-4-yl)-N-[5-(3-bromo-4-methoxyphenyl)-1,3-thiazol-2-yl]thiophene-2-carboxamide;

N-[4-(2-chlorophenyl)-1,3-thiazol-2-yl]-5-[2-(methylamino)pyrimidin-4-yl]thiophene-2-carboxamide;

5-(2-aminopyrimidin-4-yl)-N-[4-(2-chlorophenyl)-1,3-thiazol-2-yl]thiophene-2-carboxamide;

N-{4-chloro-6-[(dimethylamino)methyl]-1,3-benzothiazol-2-yl}-5-[2-(methylamino)pyrimidin-4-yl]thiophene-2-carboxamide;

5-(2-aminopyrimidin-4-yl)-N-{4-chloro-6-[(dimethylamino)methyl]-1,3-benzothiazol-2-yl}thiophene-2-carboxamide;

5-(2-aminopyrimidin-4-yl)-N-(4-bromo-1,3-benzothiazol-2-yl)thiophene-2-carboxamide;

5-(2-aminopyrimidin-4-yl)-N-(4-fluoro-1,3-benzothiazol-2-yl)thiophene-2-carboxamide;

5-(2-aminopyrimidin-4-yl)-N-(4,6-dichloro-1,3-benzothiazol-2-yl)thiophene-2-carboxamide;

5-(2-aminopyrimidin-4-yl)-N-(7-chloro-1,3-benzothiazol-2-yl)thiophene-2-carboxamide;

N-[6-(2-aminoethyl)-4-chloro-1,3-benzothiazol-2-yl]-5-(2-aminopyrimidin-4-yl)thiophene-2-carboxamide;

5-(2-aminopyrimidin-4-yl)-N-[4-chloro-6-(2-nitroethyl)-1,3-benzothiazol-2-yl]thiophene-2-carboxamide;

5-[2-(methylamino)pyrimidin-4-yl]-N-(4-pyridin-2-yl-1,3-thiazol-2-yl)thiophene-2-carboxamide;

5-(2-aminopyrimidin-4-yl)-N-(4-pyridin-2-yl-1,3-thiazol-2-yl)thiophene-2-carboxamide;

5-[2-(methylamino)pyrimidin-4-yl]-N-(4-pyridin-3-yl-1,3-thiazol-2-yl)thiophene-2-carboxamide;

5-(2-aminopyrimidin-4-yl)-N-(4-pyridin-3-yl-1,3-thiazol-2-yl)thiophene-2-carboxamide;

N-[6-(2-aminoethyl)-4-chloro-1,3-benzothiazol-2-yl]-5-[2-(methylamino)pyrimidin-4-yl]thiophene-2-carboxamide;

N-[4-chloro-6-(2-nitroethyl)-1,3-benzothiazol-2-yl]-5-[2-(methylamino)pyrimidin-4-yl]thiophene-2-carboxamide;

4-chloro-N-methyl-2-[({5-[2-(methylamino)pyrimidin-4-yl]thien-2-yl}carbonyl)amino]-1,3-benzothiazole-6-carboxamide;

N-(2-aminoethyl)-4-chloro-2[({5-[2-(methylamino)pyrimidin-4-yl]thien-2-yl}carbonyl)amino]-1,3-benzothiazole-6-carboxamide;

N-(2-aminoethyl)-2-({[5-(2-aminopyrimidin-4-yl)thien-2-yl[carbony}amino)-4-chloro-1,3-benzothiazole-6-carboxamide;

N-{4-chloro-6-[(methylamino)methyl]-1,3-benzothiazol-2-yl}-5-[2-(methylamino)pyrimidin-4-yl]thiophene-2-carboxamide;

5-(2-aminopyrimidin-4-yl)-N-{4-chloro-6-[(methylamino)methyl]-1,3-benzothiazol-2-yl}thiophene-2-carboxamide;

methyl 4-chloro-2-[({5-[2-(methylamino)pyrimidin-4-yl]thien-2-yl}carbonyl)amino]-1,3-benzothiazole-5-carboxylate;

methyl 2-({[5-(2-aminopyrimidin-4-yl)thien-2-yl]carbonyl}amino)-4-chloro-1,3-benzothiazole-5-carboxylate;

N-(4-chloro-6-methyl-1,3-benzothiazol-2-yl)-5-[2-(methylamino)pyrimidin-4-yl]thiophene-2-carboxamide;

5-(2-aminopyrimidin-4-yl)-N-(4-chloro-6-methyl-1,3-benzothiazol-2-yl)thiophene-2-carboxamide;

5-(2-aminopyrimidin-4-yl)-N-(4-chloro-1,3-benzoxazol-2-yl)thiophene-2-carboxamide;

N-[6-({[(2S)-2-aminopropanoyl]amino}methyl)-4-chloro-1,3-benzothiazol-2-yl]-5-(2-aminopyrimidin-4-yl)thiophene-2-carboxamide;

N-[6-(aminomethyl)-4-bromo-1,3-benzothiazol-2-yl]-5-[2-(methylamino)pyrimidin-4-yl]thiophene-2-carboxamide;

N-{4-methoxy-6-[(methylamino)methyl]-1,3-benzothiazol-2-yl}-5-[2-(methylamino)pyrimidin-4-yl]thiophene-2-carboxamide;

5-(2-aminopyrimidin-4-yl)-N-{4-methoxy-6-[(methylamino)methyl]-1,3-benzothiazol-2-yl}thiophene-2-carboxamide;

N-(4-chloro-1,3-benzoxazol-2-yl)-5-[2-(methylamino)pyrimidin-4-yl]thiophene-2 -carboxamide;

N-[6-({[(2S)-2-amino-3-phenylpropanoyl]amino}methyl)-4-chloro-1,3-benzothiazol-2-yl]-5-(2-aminopyrimidin-4-yl)thiophene-2-carboxamide;

N-(6-{[(aminoacetyl)amino]methyl}-4-chloro-1,3-benzothiazol-2-yl)-5-(2-aminopyrimidin-4-yl)thiophene-2-carboxamide;

N-{6-[(acetylamino)methyl]-4-chloro-1,3-benzothiazol-2-yl}-5-(2-aminopyrimidin-4-yl)thiophene-2-carboxamide;

N-[6-(aminomethyl)-4-(trifluoromethyl)-1,3-benzothiazol-2-yl]-5-[2-(methylamino)pyrimidin-4-yl]thiophene-2-carboxamide;

N-[6-(aminomethyl)-4-(trifluoromethyl)-1,3-benzothiazol-2-yl]-5-(2-aminopyrimidin-4-yl)thiophene-2-carboxamide;

N-[6-(aminomethyl)-4-(trifluoromethoxy)-1,3-benzothiazol-2-yl]-5-[2-(methylamino)pyrimidin-4-yl]thiophene-2-carboxamide;

N-[6-(aminomethyl)-4-(trifluoromethoxy)-1,3-benzothiazol-2-yl]-5-(2-aminopyrimidin-4-yl)thiophene-2-carboxamide;

N-[4-chloro-6-(trifluoromethyl)-1,3-benzothiazol-2-yl]-5-[2-(methylamino)pyrimidin-4-yl]thiophene-2-carboxamide;

5-(2-aminopyrimidin-4-yl)-N-[4-chloro-6-(trifluoromethyl)-1,3-benzothiazol-2-yl]thiophene-2-carboxamide;

N-[4-chloro-6-(trifluoromethoxy)-1,3-benzothiazol-2-yl]-5-[2-(methylamino)pyrimidin-4-yl]thiophene-2-carboxamide;

5-(2-aminopyrimidin-4-yl)-N-[4-chloro-6-(trifluoromethoxy)-1,3-benzothiazol-2-yl]thiophene-2-carboxamide;

N-[6-(aminomethyl)-4-bromo-1,3-benzothiazol-2-yl]-5-(2-aminopyrimidin-4-yl)thiophene-2-carboxamide;

N-(4-bromo-6-isopropyl-1,3-benzothiazol-2-yl)-5-[2-(methylamino)pyrimidin-4-yl]thiophene-2-carboxamide;

5-(2-aminopyrimidin-4-yl)-N-(4-bromo-6-isopropyl-1,3-benzothiazol-2-yl)thiophene-2-carboxamide;

N-[4-(aminomethyl)-1,3-benzothiazol-2-yl]-5-(2-aminopyrimidin-4-yl)thiophene-2-carboxamide;

N-[4-(aminomethyl)-1,3-benzothiazol-2-yl]-5-[2-(methylamino)pyrimidin-4-yl]thiophene-2-carboxamide;

N-[6-(aminomethyl)-8-chloroquinolin-2-yl]-5-(2-aminopyrimidin-4-yl)thiophene-2-carboxamide;

N-[(1S)-2-amino-1-(2,4-dichlorobenzyl)ethyl]-3-methoxy-5-[2-(methylamino)pyrimidin-4-yl]thiophene-2-carboxamide;

N-(5-benzyl-2,2-dimethyltetrahydro-2H-pyran-4-yl)-5-[2-(methylamino)pyrimidin-4-yl]thiophene-2-carboxamide;

N-[2-(4-fluorophenyl)ethyl]-5-[5-methyl-2-(methylamino)pyrimidin-4-yl]thiophene-2-carboxamide;

N-[2-(4-fluorophenyl)ethyl]-5-[2-(nitroamino)pyrimidin-4-yl]thiophene-2-carboxamide;

5-(2-anilinopyrimidin-4-yl)-N-[2-(4-fluorophenyl)ethyl]thiophene-2-carboxamide;

methyl 4-[5-({[2-(4-fluorophenyl)ethyl]amino}carbonyl)thien-2-yl]pyrimidin-2-ylcarbamate;

5-(2-{[(dimethylamino)carbonyl]amino}pyrimidin-4-yl)-N-[2-(4-fluorophenyl)ethyl]thiophene-2-carboxamide;

N-[2-(4-fluorophenyl)ethyl]-5-(2-{[(methylamino)carbonyl]amino}pyrimidin-4-yl)thiophene-2-carboxamide;

5-[2-(acetylamino)pyrimidin-4-yl]-N-[2-(4-fluorophenyl)ethyl]thiophene-2-carboxamide;

5-[2-(methylamino)pyrimidin-4-yl]-N-[2-(4-methylphenyl)ethyl]thiophene-2-carboxamide;

N-[2-(4-ethylphenyl)ethyl]-5-[2-(methylamino)pyrimidin-4-yl]thiophene-2-carboxamide;

N-[2-(4-methoxyphenyl)ethy]-5-[2-(methylamino)pyrimidin-4-yl]thiophene-2-carboxamide;

N-[2-(1,1'-biphenyl-4-yl)ethyl]-5-[2-(methylamino)pyrimidin-4-yl]thiophene-2-carboxamide;

N-[2-(4-ethoxyphenyl)ethyl]-5-[2-(methylamino)pyrimidin-4-yl]thiophene-2-carboxamide;

5-[2-(methylamino)pyrimidin-4-yl]-N-[2-(4-phenoxyphenyl)ethyl]thiophene-2-carboxamide;

N-[2-(2,5-dimethoxyphenyl)ethyl]-5-[2-(methylamino)pyrimidin-4-yl]thiophene-2-carboxamide;

N-[2-(3,4-dimethoxyphenyl)ethyl]-5-[2-(methylamino)pyrimidin-4-yl]thiophene-2-carboxamide;

5-[2-(dimethylamino)pyrimidin-4-yl]-N-[2-(4-fluorophenyl)ethyl]thiophene-2-carboxamide;

N-(4-fluorophenyl)-5-[2-(methylamino)pyrimidin-4-yl]thiophene-2-carboxamide;

N-[2-(2,4-dichlorophenyl)ethyl]-5-[2-(dimethylamino)pyrimidin-4-yl]thiophene-2-carboxamide;

5-{2-[(aminocarbonyl)amino]pyrimidin-4-yl}-N-[2-(2,4-dichlorophenyl)ethyl]thiophene-2-carboxamide;

N-[2-(2,4-dichlorophenyl)ethyl]-5-[2-(propylamino)pyrimidin-4-yl]thiophene-2-carboxamide;

5-[2-(butylamino)pyrimidin-4-yl]-N-[2-(2,4-dichlorophenyl)ethyl]thiophene-2-carboxamide;

5-{2-[(cyclopropylmethyl)amino]pyrimidin-4-yl}-N-[2-(2,4-dichlorophenyl)ethyl]thiophene-2-carboxamide;

5-[2-(benzylamino)pyrimidin-4-yl]-N-[2-(2,4-dichlorophenyl)ethyl]thiophene-2-carboxamide;
5-[2-(cyclopentylamino)pyrimidin-4-yl]-N-[2-(2,4-dichlorophenyl)ethyl]thiophene-2-carboxamide;
N-[2-(2,4-dichlorophenyl)ethyl]-5-{2-[(2-morpholin-4-ylethyl)amino]pyrimidin-4-yl}thiophene-2-carboxamide;
N-[2-(2,4-dichlorophenyl)ethyl]-5-{2-[(3-morpholin-4-ylpropyl)amino]pyrimidin-4-yl}thiophene-2-carboxamide;
N-[2-(2,4-dichlorophenyl)ethyl]-5-(2-{[3-(4-methylpiperazin-1-yl)propyl]amino}pyrimidin-4-yl)thiophene-2-carboxamide;
N-[2-(2,4-dichlorophenyl)ethyl]-5-{2-[(2-piperidin-1-ylethyl)amino]pyrimidin-4-yl}thiophene-2-carboxamide;
N-[2-(2,4-dichlorophenyl)ethyl]-5-{2-[(2-phenylethyl)amino]pyrimidin-4-yl}thiophene-2-carboxamide;
N-1H-benzimidazol-2-yl-5-[2-(methylamino)pyrimidin-4-yl]thiophene-2-carboxamide;
N-1,3-benzothiazol-2-yl-5-[2-(methylamino)pyrimidin-4-yl]thiophene-2-carboxamide;
N-(6-chloro-1,3-benzothiazol-2-yl)-5-[2-(methylamino)pyrimidin-4-yl]thiophene-2-carboxamide;
N-(6-fluoro-1,3-benzothiazol-2-yl)-5-[2-(methylamino)pyrimidin-4-yl]thiophene-2-carboxamide;
N-1,3-benzothiazol-6-yl-5-[2-(methylamino)pyrimidin-4-yl]thiophene-2-carboxamide;
5-[2-(methylamino)pyrimidin-4-yl]-N-quinolin-3-ylthiophene-2-carboxamide;
5-[2-(methylamino)pyrimidin-4-yl]-N-quinolin-6-ylthiophene-2-carboxamide;
N-[5-(5-bromothien-2-yl)-1,3-thiazol-2-yl]-5-[2-(methylamino)pyrimidin-4-yl]thiophene-2-carboxamide;
5-[2-(methylamino)pyrimidin-4-yl]-N-(pyridin-3-ylmethyl)thiophene-2-carboxamide;
5-[2-(methylamino)pyrimidin-4-yl]-N-(2-pyridin-2-ylethyl)thiophene-2-carboxamide;
5-[2-(methylamino)pyrimidin-4-yl]-N-(2-piperidin-1-ylethyl)thiophene-2-carboxamide;
5-[2-(methylamino)pyrimidin-4-yl]-N-[2-(4-methylpiperazin-1-yl)ethyl]thiophene-2-carboxamide;
5-[2-(methylamino)pyrimidin-4-yl]-N-(2-morpholin-4-ylethyl)thiophene-2-carboxamide;
5-[2-(methylamino)pyrimidin-4-yl]-N-[3-(1H-pyrrol-1-yl)propyl]thiophene-2-carboxamide;
5-{2-[(aminocarbonyl)amino]pyrimidin-4-yl}-N-[2-(4-fluorophenyl)ethyl]thiophene-2-carboxamide;
5-{2-[(2-aminoethyl)amino]pyrimidin-4-yl}-N-[2-(2,4-dichlorophenyl)ethyl]thiophene-2-carboxamide;
5-{2-[(3-aminopropyl)amino]pyrimidin-4-yl}-N-[2-(2,4-dichlorophenyl)ethyl]thiophene-2-carboxamide;
5-{2-[(4-aminobutyl)amino]pyrimidin-4-yl}-N-[2-(2,4-dichlorophenyl)ethyl]thiophene-2-carboxamide;
N~6~-{4-[5-({[2-(2,4-dichlorophenyl)ethyl]amino}carbonyl)thien-2-yl]pyrimidin-2-yl}-L-lysine;
N-[2-(2,4-dichlorophenyl)ethyl]-5-[2-(pyridin-4-ylamino)pyrimidin-4-yl]thiophene-2-carboxamide;
N-[2-(2,4-dichlorophenyl)ethyl]-5-(2-{[(2S)-2-phenylcyclopropyl]amino}pyrimidin-4-yl)thiophene-2-carboxamide;
N-[2-(2,4-dichlorophenyl)ethyl]-5-{2-[(pyridin-2-ylmethyl)amino]pyrimidin-4-yl}thiophene-2-carboxamide;
N-[2-(2,4-dichlorophenyl)ethyl]-5-{2-[(pyridin-3-ylmethyl)amino]pyrimidin-4-yl}thiophene-2-carboxamide;
N-[2-(2,4-dichlorophenyl)ethyl]-5-{2-[(pyridin-4-ylmethyl)amino]pyrimidin-4-yl}thiophene-2-carboxamide;
N-[2-(2,4-dichlorophenyl)ethyl]-5-{2-[(2-pyridin-2-ylethyl)amino]pyrimidin-4-yl}thiophene-2-carboxamide;
N-[2-(2,4-dichlorophenyl)ethyl]-5-{2-[(2-pyridin-3-ylethyl)amino]pyrimidin-4-yl}thiophene-2-carboxamide;
N-[2-(2,4-dichlorophenyl)ethyl]-5-{2-[(2-pyridin-4-ylethyl)amino]pyrimidin-4-yl}thiophene-2-carboxamide;
5-[2-({[1-(4-chlorophenyl)cyclopropyl]methyl}amino)pyrimidin-4-yl]-N-[2-(2,4-dichlorophenyl)ethyl]thiophene-2-carboxamide;
N-[2-(2,4-dichlorophenyl)ethyl]-5-(2-{[2-(1-methyl-1H-pyrrol-2-yl)ethyl]amino}pyrimidin-4-yl)thiophene-2-carboxamide;
N-[2-(2,4-dichlorophenyl)ethyl]-5-(2-{[2-(4-methylpiperazin-1-yl)ethyl]amino}pyrimidin-4-yl)thiophene-2-carboxamide;
N-[2-(2,4-dichlorophenyl)ethyl]-5-(2-{[3-(1H-imidazol-1-yl)propyl]amino}pyrimidin-4-yl)thiophene-2-carboxamide;
N-(1,2-diphenylethyl)-5-[2-(methylamino)pyrimidin-4-yl]thiophene-2-carboxamide;
N-(2,2-diphenylethyl)-5-[2-(methylamino)pyrimidin-4-yl]thiophene-2-carboxamide;
N-[2-(2,4-dichlorophenyl)ethyl]-5-(2-{[(methylamino)carbonyl]amino}pyrimidin-4-yl)thiophene-2-carboxamide;
N-[2-(2,4-dichlorophenyl)ethyl]-5-(2-{[(ethylamino)carbonyl]amino}pyrimidin-4-yl)thiophene-2-carboxamide;
N-[2-(2,4-dichlorophenyl)ethyl]-5-(2-{[(propylamino)carbonyl]amino}pyrimidin-4-yl)thiophene-2-carboxamide;
5-(2-aminopyrimidin-4-yl)-N-(2-pyridin-3-ylethyl)thiophene-2-carboxamide;
5-{2-[(anilinocarbonyl)amino]pyrimidin-4-yl}-N-[2-(2,4-dichlorophenyl)ethyl]thiophene-2-carboxamide;
5-(2-{[(benzylamino)carbonyl]amino}pyrimidin-4-yl)-N-[2-(2,4-dichlorophenyl)ethyl]thiophene-2-carboxamide;
N-(4-aminobenzyl)-5-(2-aminopyrimidin-4-yl)thiophene-2-carboxamide;
5-(2-aminopyrimidin-4-yl)-N-[4-(dimethylamino)benzyl]thiophene-2-carboxamide;
N-[2-(4-aminophenyl)ethyl]-5-(2-aminopyrimidin-4-yl)thiophene-2-carboxamide;
5-(2-aminopyrimidin-4-yl)-N-1H-benzimidazol-2-ylthiophene-2-carboxamide;
5-(2-aminopyrimidin-4-yl)-N-(1-methyl-1H-benzimidazol-2-yl)thiophene-2-carboxamide;
N-[(2R)-2-hydroxy-2,3-dihydro-1H-inden-1-yl]-5-[2-(methylamino)pyrimidin-4-yl]thiophene-2-carboxamide;
N-2,3-dihydro-1H-inden-1-yl-5-[2-(methylamino)pyrimidin-4-yl]thiophene-2-carboxamide;
5-[2-(methylamino)pyrimidin-4-yl]-N-1,2,3,4-tetrahydronaphthalen-1-ylthiophene-2-carboxamide;
N-[(4-chlorophenyl)(phenyl)methyl]-5-[2-(methylamino)pyrimidin-4-yl]thiophene-2-carboxamide;
5-(2-aminopyrimidin-4-yl)-N-[4-fluoro-2-(trifluoromethyl)benzyl]thiophene-2-carboxamide;
5-(2-aminopyrimidin-4-yl)-N-(1H-benzimidazol-2-ylmethyl)thiophene-2-carboxamide;

5-(2-aminopyrimidin-4-yl)-N-(1-benzothien-2-ylmethyl)thiophene-2-carboxamide;

N-(5-chloro-1H-benzimidazol-2-yl)-5-[2-(methylamino)pyrimidin4-yl]thiophene-2-carboxamide;

5-(2-aminopyrimidin-4-yl)-N-(4-chloro-1-methyl-1H-benzimidazol-2-yl)thiophene-2-carboxamide;

N-(4-chloro-1-methyl-1H-benzimidazol-2-yl)-5-[2-(methylamino)pyrimidin-4-yl]thiophene-2-carboxamide;

5-(2-aminopyrimidin-4-yl)-N-(4-chloro-1-ethyl-1H-benzimidazol-2-yl)thiophene-2-carboxamide;

5-(2-aminopyrimidin-4-yl)-N-[4-chloro-1-(3,3-dimethylbutyl)-1H-benzimidazol-2-yl]thiophene-2-carboxamide;

5-(2-aminopyrimidin-4-yl)-N-(4-chloro-1-isobutyl-1H-benzimidazol-2-yl)thiophene-2-carboxamide;

N-(4-hydroxy-1,3-benzothiazol-2-yl)-5-[2-(methylamino)pyrimidin-4-yl]thiophene-2-carboxamide;

5-[2-(methylamino)pyrimidin-4-yl]-N-(2-piperidin-1-ylbenzyl)thiophene-2-carboxamide;

N-(4-chloro-1,3-benzothiazol-2-yl)-3-methoxy-5-[2-(methylamino)pyrimidin-4-yl]thiophene-2-carboxamide;

N-(4-chloro-1,3-benzothiazol-2-yl)-3-hydroxy-5-[2-(methylamino)pyrimidin-4-yl]thiophene-2-carboxamide;

3-(2-aminoethoxy)-N-(4-chloro-1,3-benzothiazol-2-yl)-5-[2-(methylamino)pyrimidin-4-yl]thiophene-2-carboxamide; and N-[2-(2,4-dichlorophenyl)ethyl]-5-pyrimidin-4-ylthiophene-2-carboxamide;

or pharmaceutically acceptable salts, esters or prodrugs thereof.

* * * * *

UNITED STATES PATENT AND TRADEMARK OFFICE
CERTIFICATE OF CORRECTION

| | | |
|---|---|---|
| PATENT NO. | : 7,470,701 B2 | |
| APPLICATION NO. | : 11/095993 | |
| DATED | : December 30, 2008 | |
| INVENTOR(S) | : Xiaodong Lin et al. | |

It is certified that error appears in the above-identified patent and that said Letters Patent is hereby corrected as shown below:

In Column 230, Claim 1, Line 44, please replace the term "each $R^5$" with

-- each $R^1$ --.

In Column 237, Claim 15, Lines 41-44, please replace the phrase

"the group consisting of —C(O)NH—, —NH—C(O)—,

—NH—C(O)NH—, —NHC(O)O—, —CH$_2$NH—, —C(O)N(CH$_2$CH$_2$NH$_2$)—,

—C(O)N(CH$_3$)—, —C(O)O—, —CH=CH—, and —C≡C—." with

-- the group consisting of —NH—C(O)—, —NH—C(O)NH—,

—NHC(O)O—, —CH$_2$NH—, —C(O)O—, —CH=CH—, and —C≡C—. --.

Signed and Sealed this

Twenty-ninth Day of September, 2009

David J. Kappos
*Director of the United States Patent and Trademark Office*